US012532601B2

(12) United States Patent
Eum et al.

(10) Patent No.: US 12,532,601 B2
(45) Date of Patent: Jan. 20, 2026

(54) ORGANIC COMPOUND AND ORGANIC ELECTROLUMINESCENT DEVICE COMPRISING SAME

(71) Applicant: SOLUS ADVANCED MATERIALS CO., LTD., Iksan-si (KR)

(72) Inventors: Minsik Eum, Yongin-si (KR); Hoemoon Kim, Yongin-si (KR); Jinwoong Kim, Yongin-si (KR); Hwasoon Jung, Yongin-si (KR); Hyungchan Bae, Yongin-si (KR); Hojun Son, Yongin-si (KR); Hyosuk Son, Yongin-si (KR)

(73) Assignee: SOLUS ADVANCED MATERIALS CO., LTD., Iksan-si (KR)

( * ) Notice: Subject to any disclaimer, the term of this patent is extended or adjusted under 35 U.S.C. 154(b) by 953 days.

(21) Appl. No.: 17/768,579

(22) PCT Filed: Oct. 6, 2020

(86) PCT No.: PCT/KR2020/013567

§ 371 (c)(1),
(2) Date: Apr. 13, 2022

(87) PCT Pub. No.: WO2021/075775

PCT Pub. Date: Apr. 22, 2021

(65) Prior Publication Data

US 2024/0138173 A1 Apr. 25, 2024

(30) Foreign Application Priority Data

Oct. 14, 2019 (KR) ........................ 10-2019-0127012

(51) Int. Cl.

| | |
|---|---|
| ***H10K 50/12*** | (2023.01) |
| ***C07D 239/26*** | (2006.01) |
| ***C07D 405/04*** | (2006.01) |
| ***C09K 11/06*** | (2006.01) |
| ***H10K 50/16*** | (2023.01) |
| ***H10K 85/60*** | (2023.01) |

(52) U.S. Cl.

CPC ........... *H10K 50/12* (2023.02); *C07D 239/26* (2013.01); *C07D 405/04* (2013.01); *C09K 11/06* (2013.01); *H10K 50/16* (2023.02); *H10K 85/654* (2023.02); *H10K 85/6574* (2023.02)

(58) Field of Classification Search

None

See application file for complete search history.

(56) References Cited

U.S. PATENT DOCUMENTS

| | | | |
|---|---|---|---|
| 2016/0093808 | A1 | 3/2016 | Adamovich et al. |
| 2017/0025618 | A1 | 1/2017 | Zheng et al. |

FOREIGN PATENT DOCUMENTS

| | | | |
|---|---|---|---|
| KR | 10-2015-0115622 | A | 10/2015 |
| KR | 10-2015-0129282 | A | 11/2015 |
| KR | 10-2016-0006633 | A | 1/2016 |
| WO | 2016/012075 | A1 | 1/2016 |
| WO | 2019/022455 | A1 | 1/2019 |

OTHER PUBLICATIONS

Extended European Search Report issued Sep. 27, 2023 in European Application No. 20875884.7.

International Search Report for PCT/KR2020/013567, dated Jan. 22, 2021.

Written Opinion for PCT/KR2020/013567, dated Jan. 22, 2021.

*Primary Examiner* — Jay Yang

(74) *Attorney, Agent, or Firm* — Sughrue Mion, PLLC

(57) ABSTRACT

A novel compound having excellent carrier transport ability, light-emitting ability, and thermal stability, and its uses are disclosed. An organic electroluminescent device containing the novel compound in one or more organic material layers is disclosed. The organic electroluminescent device shows improved characteristics such as luminous efficiency, driving voltage, and lifespan.

17 Claims, No Drawings

ORGANIC COMPOUND AND ORGANIC ELECTROLUMINESCENT DEVICE COMPRISING SAME

CROSS REFERENCE TO RELATED APPLICATIONS

This application is a National Stage of International Application No. PCT/KR2020/013567 filed Oct. 6, 2020, claiming priority based on Korean Patent Application No. 10-2019-0127012 filed Oct. 14, 2019.

TECHNICAL FIELD

The present invention relates to a novel organic light-emitting compound and an organic electroluminescent device using the same, and more particularly, to an organic electroluminescent device including a compound having excellent carrier transport ability and light-emitting ability in one or more organic layers, thereby having improved characteristics such as luminous efficiency, driving voltage, and lifespan.

DISCUSSION OF RELATED ART

Starting from Bernanose's observation of light emission from organic thin films in the 1950s, the study of organic electroluminescent devices (hereinafter, "EL devices") led to blue electroluminescence using anthracene monocrystals in 1965, and Tang suggested in 1987 an organic EL device in a stack structure which may be divided into functional layers of hole layers and light-emitting layers. Then, in order to develop high efficiency, long lifespan organic EL devices, organic layers each having distinctive characteristics have been introduced in the EL devices, leading to the development of specialized materials used therein.

In organic EL devices, upon application of voltage between two electrodes, holes are injected from an anode (e.g., positive electrode) to an organic layer and electrons are injected from a cathode (e.g., negative electrode) into an organic layer. Injected holes and electrons meet each other to form excitons, and light emission occurs when the excitons fall to a ground state. In this case, materials used for the organic layer may be classified into, for example, light-emitting materials, hole injection materials, hole transport materials, electron transport materials and electron injection materials depending on their function.

Light-emitting materials may be classified into blue, green and red light-emitting materials depending on their emission colors. The light-emitting materials may be further classified into yellow and orange light-emitting materials for realizing better natural colors. In addition, a host/dopant system may be employed in the light-emitting material to increase color purity and luminous efficiency through energy transition. Dopant materials may be classified into fluorescent dopants using organic materials and phosphorescent dopants using metal complex compounds which include heavy atoms such as Ir and Pt. In such a case, the developed phosphorescent materials may improve the luminous efficiency theoretically up to four times as compared to fluorescent materials, so attention is given to phosphorescent dopants as well as phosphorescent host materials.

To date, NPB, BCP and $Alq_3$, for example, are widely known as materials used in a hole injection layer, a hole transport layer, a hole blocking layer and an electron transport layer, and anthracene derivatives have been reported as fluorescent dopant/host materials for light-emitting materials. Particularly, metal complex compounds including Ir, such as Firpic, $Ir(ppy)_3$, and $(acac)Ir(btp)_2$, which are known to have advantages in terms of efficiency improvement among light-emitting materials, are used as blue, green and red phosphorescent dopant materials. To date, CBP exhibits excellent characteristics as a phosphorescent host material.

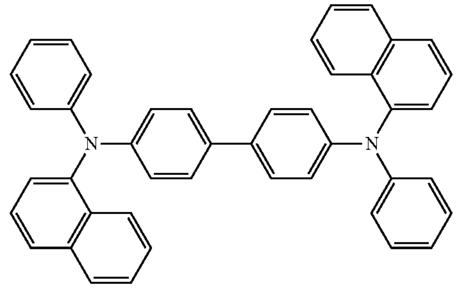

NPB

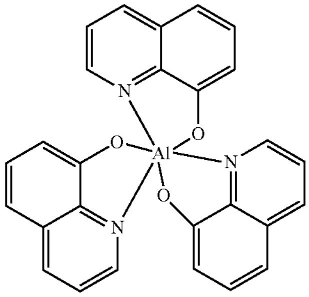

Alq3

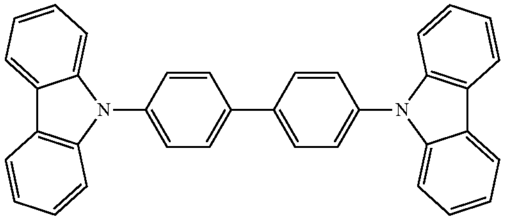

CBP

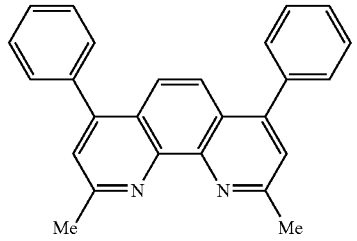

BCP

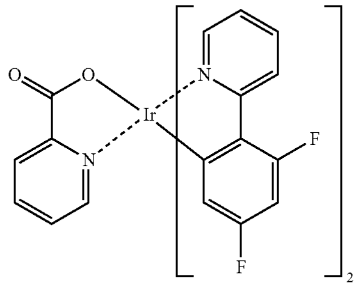

Firpic

-continued

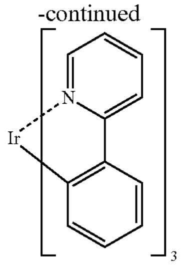

Ir(ppy)3

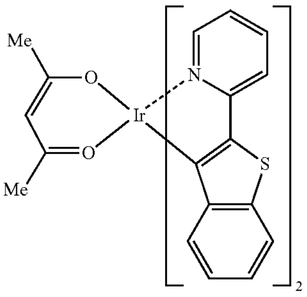

(acac)Ir(btp)2

However, although conventional materials for organic layers are advantages in terms of luminous properties, they have low glass transition temperatures, thus having poor thermal stability, and accordingly, organic EL devices do not exhibit satisfactory lifespan characteristics.

DESCRIPTION OF THE INVENTION

Technical Objectives

The present invention is directed to a novel compound having improved characteristics such as electron injection and transport ability and excellent light-emitting ability, thereby being applicable as an organic layer material of an organic electroluminescent device, specifically a light-emitting layer material, an electron transport layer material, an electron transport auxiliary layer material, or the like.

The present invention is further directed to an organic electroluminescent device including the novel compound, thereby having characteristics such as low driving voltage, high luminous efficiency, and long lifespan.

Technical Solution to the Problem

According to an embodiment of the present invention, a compound is represented by the following Chemical Formula 1:

[Chemical Formula 1]

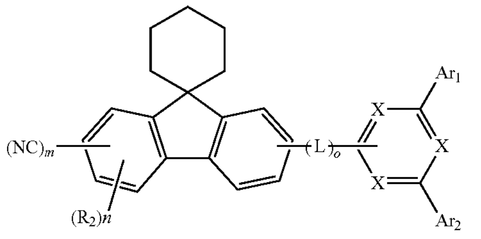

where in Chemical Formula 1, a plurality of X are the same as or different from each other, each independently being $C(R_1)$ or N, wherein at least two of the plurality of X are N, $R_1$ and $R_2$ are the same as or different from each other, each independently being selected from: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ monoarylphosphinyl group, a $C_6$ to $C_{60}$ diarylphosphinyl group, a $C_6$ to $C_{60}$ arylamine group, a $C_5$ to $C_{60}$ arylheteroarylamine group, and a heteroarylamine group having 5 to 60 nuclear atoms, m is an integer in a range from 0 to 2, n is an integer in a range from 0 to 4, L is a single bond, or is selected from: a $C_6$ to $C_{18}$ arylene group and a heteroarylene group having 5 to 18 nuclear atoms, o is an integer in a range from 0 to 3, $Ar_1$ and $Ar_2$ are the same as or different from each other, each independently being selected from: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphinyl group, a $C_6$ to $C_{60}$ monoarylphosphinyl group, a $C_6$ to $C_{60}$ diarylphosphinyl group, a $C_6$ to $C_{60}$ arylamine group, a $C_5$ to $C_{60}$ arylheteroarylamine group, and a heteroarylamine group having 5 to 60 nuclear atoms, and the arylene group and the heteroarylene group of L; the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $Ar_1$ to Are and $R_1$ to $R_2$ are each independently substituted or unsubstituted with one or more substituents of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, a $C_6$ to $C_{60}$ arylamine group, a $C_5$ to $C_{60}$ arylheteroarylamine group, and a heteroarylamine group having 5 to 60 nuclear atoms, and when the substituents are plural in number, the substituents are the same as or different from each other, and m is 1 or more; or at least one of the substituent of $Ar_1$ and the substituent of Are has a cyano group (—CN).

In some embodiments, the compound represented by Chemical Formula 1 may be applicable as a light-emitting layer material (e.g., a phosphorescent light-emitting material), an electron transport layer material, or an electron transport auxiliary layer material.

According to an embodiment, an organic electroluminescent device includes an anode; a cathode; and one or more organic layers disposed between the anode and the cathode, where at least one of the one or more organic layers includes the compound represented by Chemical Formula 1.

In some embodiments, the organic layer including the compound is selected from: a light-emitting layer, a light-emitting auxiliary layer, an electron transport layer, and an electron transport auxiliary layer.

Effects of the Invention

According to an embodiment of the present invention, the compound represented by Chemical Formula 1 has excellent characteristics such as carrier transport ability, light-emitting ability and thermal stability, thereby being applicable as an organic layer material of an organic electroluminescent device.

In particular, an organic electroluminescent device including the compound of the present invention as a phosphorescent host material, an electron transport layer material or an electron transport auxiliary layer material is greatly improved in terms of high thermal stability, low driving voltage, fast mobility, high current efficiency and long lifespan characteristics, thereby being effectively applicable to a full color display panel with improved performance and lifespan.

DETAILED DESCRIPTION OF THE INVENTION

Hereinafter, the present invention will be described in detail.

<Organic Compound>

The present invention provides a novel organic compound improved in terms of electron injection and transport ability and having excellent thermal stability and light-emitting ability.

Specifically, a compound represented by Chemical Formula 1 includes, as a core, a structure in which an aliphatic ring group, such as a cyclohexyl group in the form of a hexagonal ring, is substituted at a 9-th position of fluorene, and two electron withdrawing groups (EWG) having excellent electron transport ability, for example, a nitrogen-containing heteroaromatic ring (e.g., azines such as pyrimidine and triazine) and a cyano group (—CN) are bonded with the core to form a basic skeleton.

The cyclohexyl fluorene-based core may be substituted with a chemically and physically stable cycloalkyl group to increase stability of a molecular structure, thereby contributing to high efficiency and long lifespan. Accordingly, as compared to the conventional structure in which an alkyl group or an aryl group is substituted at a 9-th position of fluorene, structural and thermal stability may be further secured, and accordingly, a glass transition temperature (Tg) is excellent. In addition, since an aliphatic ring group such as a cyclohexyl group has a chair form, it forms a uniform morphology and has excellent device properties.

The compound of Chemical Formula 1 has a dual EWG-type structure [e.g., EWG1-L-EWG2] in which a fluorene-based core having electron donating group (EDG) properties is bonded through a linker (L) to a nitrogen-containing heteroaromatic ring (e.g., X-containing ring) which is an electron withdrawing group (EWG1) having high electron absorbing properties, and a cyano group (—CN) that is a strong electron withdrawing group (EWG2) is directly bonded with a phenyl ring on another side of the fluorene-based core. As such, by including at least two or more azine groups and cyano groups having such strong electron withdrawing ability, electron migration speed may be improved, thereby providing a structure with physicochemical properties more suitable for electron injection and electron transport. When the compound of Chemical Formula 1 is applied as a material for the electron transport layer or the electron transport auxiliary layer, electrons from the cathode may be well accepted, such that the electrons may be smoothly transferred to the light-emitting layer, a driving voltage of the device may be lowered, and high efficiency and long life may be induced, thereby maximizing performance of a full color organic light-emitting panel. Accordingly, when the compound of Chemical Formula 1 is applied to an organic electroluminescent device, excellent thermal stability and carrier transport ability (especially, electron transport ability and light-emitting ability) may be expected, while enhancing driving voltage, efficiency, lifespan, and the like of the device, and accordingly, excellent efficiency increase may be exhibited due to triplet-triplet fusion (TTF) effects by virtue of a state-of-the-art ETL material with high triplet energy (T1).

Since the compound represented by Chemical Formula 1 of the present invention is bonded through a linker (L) to a fluorene-based core structure that is directly bonded with at least one cyano group (—CN) having a strong electron withdrawing ability, a wider band gap value may be acquired, and it is easy to adjust HOMO and LUMO energy levels according to direction or position of a substituent. An organic electroluminescent device using such a compound may exhibit high electron transport properties.

In addition, since the compound represented by Chemical Formula 1 of the present invention has a high triplet energy (T1), it is possible to prevent excitons generated in the light-emitting layer from diffusing (migrating) into an adjacent electron transport layer or hole transport layer. Accordingly, the number of excitons contributing to light emission in the light-emitting layer may be increased, thus improving luminous efficiency of the device, and durability and stability of the device may be improved, such that the lifespan of the device may be effective increased. Most of the developed materials allow low-voltage operation, thereby exhibiting physical characteristics with improved lifespan.

Furthermore, in the present invention, at least one dibenzo-based moiety [e.g., a fluorene group, a carbazolylene group, dibenzofuran (DBF), or dibenzothiophene (DBT)] having amphoteric physicochemical properties for holes and electrons may be included as a substituent (e.g., $Ar_1$ to $Ar_2$) introduced to the linker (L) and/or the nitrogen-containing aromatic ring. It may be applied as a green phosphorescent material with excellent luminous efficiency characteristics through combination of such a dibenzo-based moiety and a nitrogen-containing heteroaromatic ring (e.g., pyrimidine, pyrazine, and triazine) which is a strong EWG. In addition, it may be operated at a low voltage to exhibit an effect of increasing lifespan, and have thermal stability, high glass transition temperature characteristics, and uniform morphology, thereby having excellent device characteristics.

As described above, the compound represented by Chemical Formula 1 of the present invention may be applicable as an organic layer material of an organic electroluminescent device, preferably a light-emitting layer material (a blue phosphorescent host material), an electron transport/injection layer material, a light-emitting auxiliary layer material, or an electron transport auxiliary layer material, and more preferably a light-emitting layer material, an electron transport layer material, or an electron transport auxiliary layer material. In addition, the organic electroluminescent device including the compound of the above chemical formula may be greatly improved in terms of the performance and lifespan characteristics, and the performance a full color organic electroluminescent panel to which the organic electroluminescent device is applied may also be maximized.

In the compound represented by Chemical Formula 1 according to the present invention, two electron withdrawing groups (EWG) having excellent electron transport ability are introduced to a core structure in which a cyclohexyl group is introduced at a 9-th position of fluorene, and specifically, a nitrogen-containing heteroaromatic ring (e.g., an X-containing ring) is directly bonded or connected through a linker (L) to a phenyl ring on one side of the cyclohexyl fluorene-based core, and a cyano group is directly bonded with a phenyl ring on another side of the fluorene-based core, thereby forming a basic skeleton.

In Chemical Formula 1, at least one cyano group (—CN) and at least one $R_2$ may each be introduced to a fluorene core to which an aliphatic ring group, specifically, a cyclohexyl group in the form of a hexagonal ring, is introduced. Herein, at least one $R_2$ may be the same as or different from each other, each independently being selected from: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphinyl group, a $C_6$ to $C_{60}$ monoarylphosphinyl group, a $C_6$ to $C_{60}$ diarylphosphinyl group, a $C_6$ to $C_{60}$ arylamine group, a $C_5$ to $C_{60}$ arylheteroarylamine group, and a heteroarylamine group having 5 to 60 nuclear atoms, or bonded with an adjacent group (e.g., another $R_2$) to form a fused ring (e.g., a condensed ring). Specifically, it is preferable that at least one $R_2$ are the same as or different from each other, and are each independently selected from: hydrogen, a $C_1$ to $C_{40}$ alkyl group, a $C_6$ to $C_{60}$ aryl group, and a heteroaryl group having 5 to 60 nuclear atoms.

Herein, n may be an integer in a range from 0 to 4. In such a case, when n is 0, $R_2$ is hydrogen, and when n is in a range from 1 to 4, $R_2$ may have the aforementioned substituents except for hydrogen.

In an embodiment, the number (m) of the substituted cyano group in the cyclohexyl fluorene-based core is not particularly limited, and may be, for example, an integer in a range from 0 to 2, specifically 0 or 1. In this case, when m is 0, at least one of substituents $Ar_1$ and $Ar_2$ to be described below has a cyano group.

In an embodiment of the present invention, the cyclohexyl fluorene-based core may be embodied into the following structural formulas in terms of a substitution position of the cyano group.

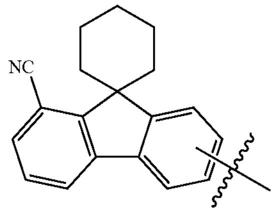

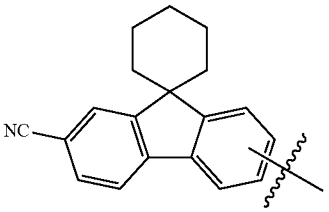

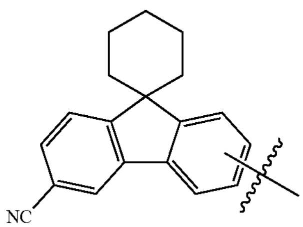

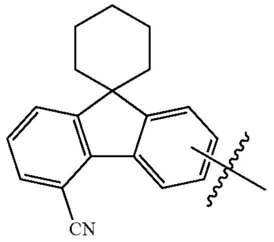

In another embodiment of the present invention, the cyclohexyl fluorene-based core may be embodied into the following structural formulas according to a bonding position with a linker (e.g., L) to be described below.

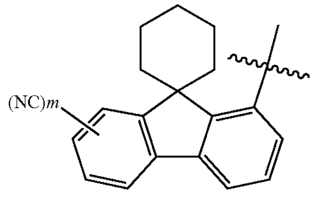

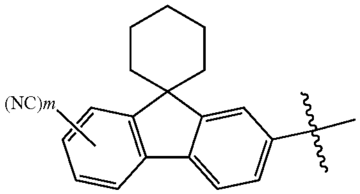

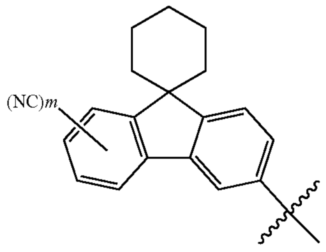

-continued

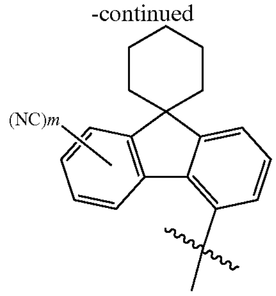

In the above formula, the wavy part means a site where a bond is made with the linker (L) in Chemical Formula 1 above. In addition, although not specifically illustrated in the above structural formula, at least one $R_2$ described above may be introduced, and a polycyclic structure in which fluorene and $R_2$ are fused (e.g., condensed) also falls within the scope of the present invention.

In Chemical Formula 1 of the present invention, L may be a conventional divalent linker known in the art. For example, L may each independently be a single bond, or may each independently be selected from: a $C_6$ to $C_{18}$ arylene group and a heteroarylene group having 5 to 18 nuclear atoms. The number of L (e.g., o) may be in a range from 0 to 3. Here, when o is 0, it may be a single bond, and when o is in a range from 1 to 3, the plurality of L may be the same as or different from each other.

In an embodiment, L may be a single bond, or may include at least one of: an arylene group moiety of the following Chemical Formula 2 and a dibenzo-based moiety of the following Chemical Formula 3:

[Chemical Formula 2]

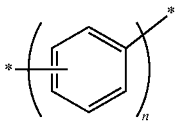

[Chemical Formula 3]

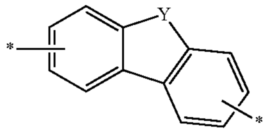

where in Chemical Formula 2 or 3,

* may mean a site in which a bond with Chemical Formula 1 is made,

Y may be selected from: $C(R_3)_2$, $NR_3$, O, S and Se, $R_3$ may be the same as or different from each other, each independently being selected from: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphinyl group, a $C_6$ to $C_{60}$ monoarylphosphinyl group, a $C_6$ to $C_{60}$ diarylphosphinyl group, a $C_6$ to $C_{60}$ arylamine group, a $C_5$ to $C_{60}$ arylheteroarylamine group, and a heteroarylamine group having 5 to 60 nuclear atoms, and n may be an integer in a range from 1 to 3.

The moiety of Chemical Formula 2 may be an arylene-group linker known in the art, and specific examples thereof may include a phenylene group, a biphenylene group, a naphthylene group, an anthracenylene group, an indenylene group, a pyrantrenylene group, a carbazolylene group, a thiophenylene group, an indolylene group, a purinylene group, a quinolinylene group, a pyrrolylene group, an imidazolylene group, an oxazolylene group, a thiazolylene group, a pyridinylene group, a pyrimidinylene group, and the like. More specifically, the linker (L) represented by Chemical Formula 2 is preferably a phenylene group or a biphenylene group.

In an embodiment of the present invention, the linker of Chemical Formula 2 may be a linker selected from the following structural formulas.

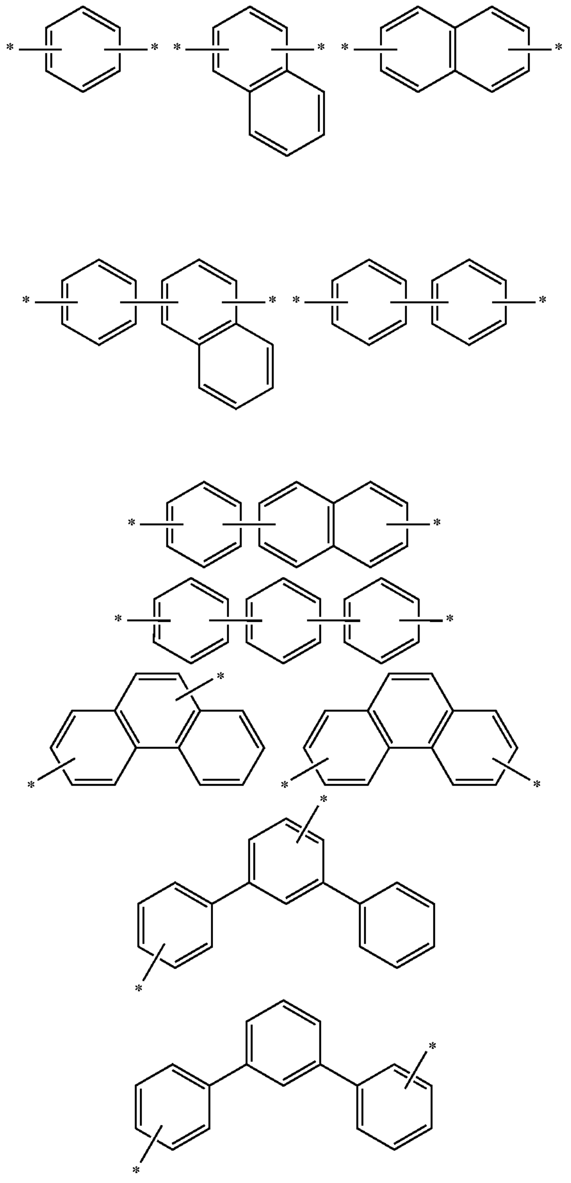

-continued

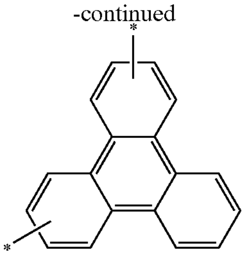

In an embodiment, the linker of Chemical Formula 3 may be a dibenzo-based moiety known in the art. For example, it may include a fluorene group (Y═$CR_3R_3$), a carbazolylene group (Y═$NR_3$), a dibenzofuran-based (Y═O) moiety, a dibenzothiophene-based (Y═S) moiety, and/or a dibenzo-selenophenone-based (Y═Se) moiety.

The dibenzo-based moiety represented by Chemical Formula 3 may be more specifically embodied into the following structural formula:

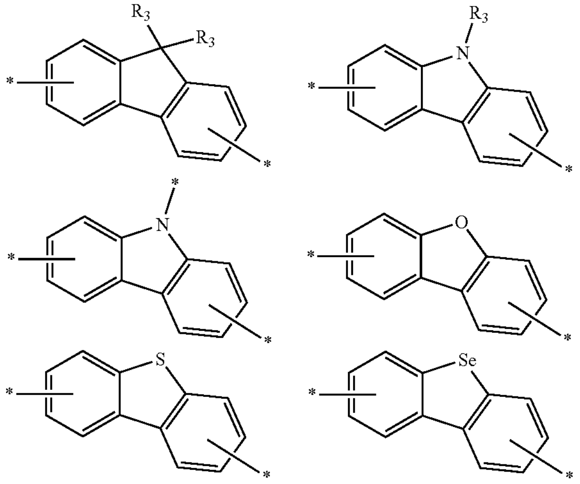

in the above formula,

* may mean a site in which a bond with Chemical Formula 1 is made, $R_3$ may be the same as or different from each other, each independently being selected from: hydrogen, a $C_1$ to $C_{40}$ alkyl group, a $C_6$ to $C_{60}$ aryl group, a heteroaryl group having to 60 nuclear atoms, and a $C_6$ to $C_{60}$ arylamine group. Specifically, $R_3$ may be the same as or different from each other, and may each independently be a $C_6$ to $C_{60}$ aryl group or a heteroaryl group having 5 to 60 nuclear atoms.

The linker (L) represented by the above Chemical Formulas 2 and 3, although not specifically illustrated in the Chemical Formulas, may be substituted with at least one or more substituents known in the art (e.g., $R_2$).

In the compound represented by Chemical Formula 1 of the present invention, a nitrogen-containing heteroaromatic ring (e.g., X-containing ring) which is a type of an electron withdrawing group (EWG) having excellent electron transport ability is directly bonded or bonded through a linker (L) to a phenyl ring on one side of a fluorene-based core in which a cyclohexyl group is introduced at a 9-th position.

In Chemical Formula 1, the plurality of X are the same as or different from each other, each independently representing $C(R_1)$ or N, and at least two of the plurality of X are N. Specifically, the number of nitrogen (N) included in the plurality of X may be in a range from 2 to 3. Since each of such triazines and pyrimidines is a type of 6-membered hetero ring having excellent electron withdrawing group (EWG) properties, they have strong electron-receiving properties.

$Ar_1$ and $Ar_2$ may be the same as or different from each other, each independently being selected from: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphinyl group, a $C_6$ to $C_{60}$ monoarylphosphinyl group, a $C_6$ to $C_{60}$ diarylphosphinyl group, a $C_6$ to $C_{60}$ arylamine group, a $C_5$ to $C_{60}$ arylheteroarylamine group, and a heteroarylamine group having 5 to 60 nuclear atoms. Specifically, it is preferable that $Ar_1$ and $Ar_2$ are the same as or different from each other, and are each independently selected from: a $C_6$ to $C_{60}$ aryl group and a heteroaryl group having 5 to 60 nuclear atoms. More specifically, at least one of $Ar_1$ and $Ar_2$ is a $C_6$ to $C_{18}$ aryl group, and the aryl group may be substituted with a heteroaromatic ring containing at least one nitrogen. Here, the number of nitrogens contained in the heteroaromatic ring is not particularly limited, and may be, for example, in a range from 1 to 3.

Such a nitrogen-containing heteroaromatic ring (e.g., an X-containing ring) may be embodied into any one of the following Chemical Formulas A-1 to A-3:

A-1

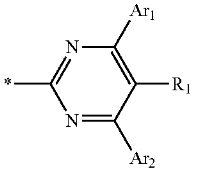

A-2

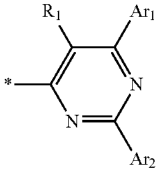

A-3

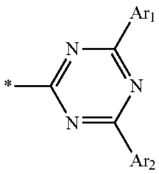

in A-1 to A-3 above, $R_1$, $Ar_1$ and $Ar_2$ are each as defined in Chemical Formula 1. In addition to the aforementioned A-1 to A-3, polycyclic structures in which these are fused also fall within the scope of the present invention.

In the above Chemical Formula 1, the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $Ar_1$ to $Ar_2$ and $R_1$ to $R_2$ may each independently be substituted or unsubstituted with one or more substituents of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, a $C_6$ to $C_{60}$ arylamine group, a $C_5$ to $C_{60}$ arylheteroarylamine group, and a heteroarylamine group having 5 to 60 nuclear atoms, and when the substituents are plural in number, the substituents may be the same as or different from each other.

In an embodiment of the present invention, the compound represented by Chemical Formula 1 may be more specifically embodied into any one of Chemical Formulas 4 to 7, according to a bonding position of the cyano group (—CN) directly bonded with the cyclohexyl fluorene-based core. However, the present invention is not limited thereto.

[Chemical Formula 4]

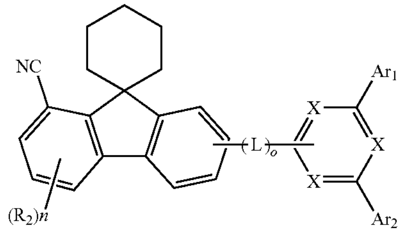

[Chemical Formula 5]

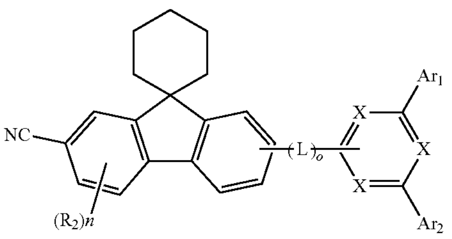

[Chemical Formula 6]

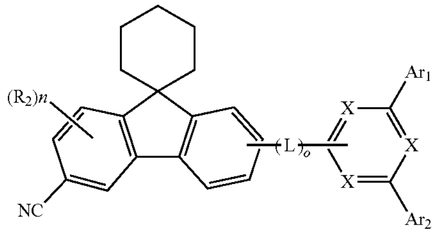

-continued

[Chemical Formula 7]

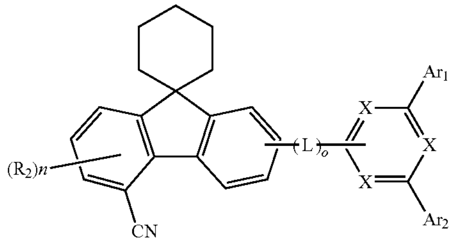

In Chemical Formulas 4 to 7,

X, L, $Ar_1$, $Ar_2$, $R_2$, n and o are each as defined in Chemical Formula 1.

In another embodiment of the present invention, the compound represented by Chemical Formula 1 may be more specifically embodied into any one of the following Chemical Formulas 8 to 11 according to a bonding position of the linker (L) bonded with the cyclohexyl fluorene-based core. However, the present invention is not limited thereto.

[Chemical Formula 8]

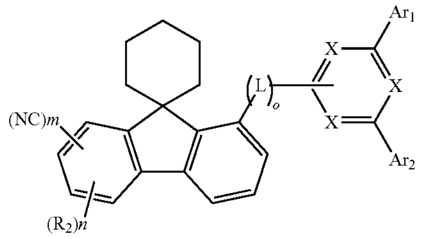

[Chemical Formula 9]

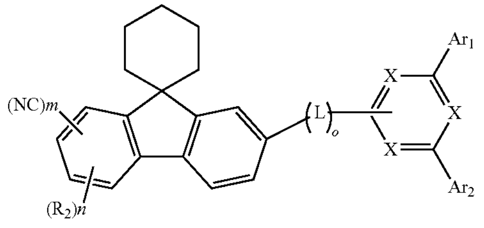

[Chemical Formula 10]

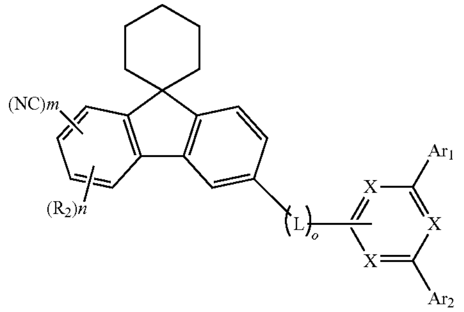

-continued

[Chemical Formula 11]

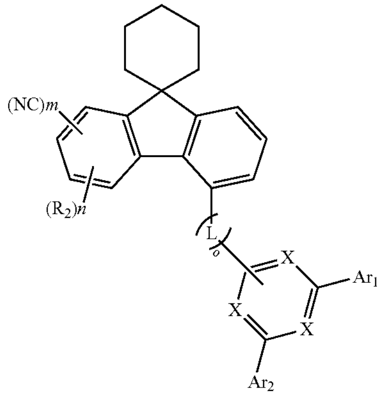

In Chemical Formulas 8 to 11,

X, L, $Ar_1$, $Ar_2$, $R_2$, m, n and o are each as defined in Chemical Formula 1.

For a preferred embodiment of the compound represented by any one of Chemical Formulas 4 to 11, two to three of the plurality of X are N, $Ar_1$ and $Ar_2$ are the same or different from each other, each independently being selected from a $C_6$ to $C_{60}$ aryl group and a heteroaryl group having 5 to 60 nuclear atoms.

L is a single bond or is selected from: a $C_6$ to $C_{18}$ arylene group and a heteroarylene group having 5 to 18 nuclear atoms, and o is an integer in a range from 0 to 3.

$R_1$ and $R_2$ are the same as or different from each other, and are each independently selected from: hydrogen, a $C_6$ to $C_{60}$ aryl group, and a heteroaryl group having 5 to 60 nuclear atoms, m is 0 or 1, and n is an integer in a range from 0 to 4.

Here, the arylene group and the heteroarylene group of L; and the alkyl group, the aryl group, the heteroaryl group of $R_1$ to $R_2$ may each independently be substituted or unsubstituted with at least one of: hydrogen, deuterium (D), halogen, a cyano group, a nitro group, a $C_1$ to $C_{40}$ alkyl group, a $C_6$ to $C_{60}$ aryl group, a heteroaryl group having 5 to 60 nuclear atoms, and a $C_6$ to $C_{60}$ arylamine group, and when the substituents are plural in number, they may be the same as or different from each other.

In another embodiment of the present invention, the compound represented by Chemical Formula 1 may be more specifically embodied into any one of the following Chemical Formulas 12 to 15 according to a type of the linker (L); and $Ar_1$ and $Ar_2$ introduced to the nitrogen-containing aromatic ring.

[Chemical Formula 12]

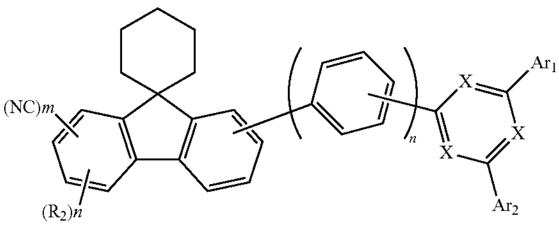

-continued

[Chemical Formula 13]

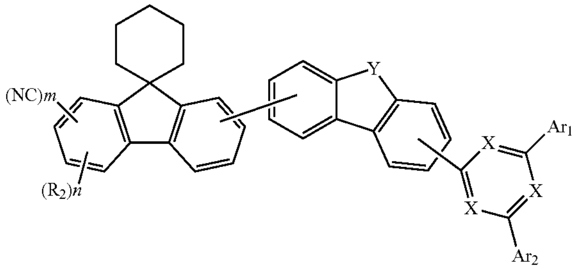

[Chemical Formula 14]

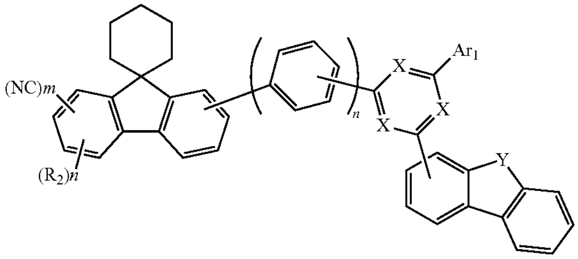

[Chemical Formula 15]

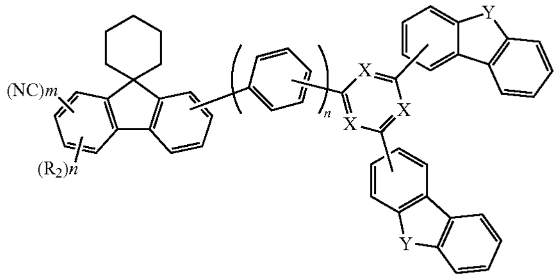

In Chemical Formulas 12 to 15,

X, Y, $Ar_1$, $Ar_2$, $R_2$, m and n are each as defined in Chemical Formulas 1 and 3.

In an embodiment, the compound represented by any one of the above Chemical Formulas 12 to 15 may include at least one cyano group (—CN) as a substituent of the cyclohexyl fluorene-based core; and/or as a substituent of the nitrogen-containing heteroaromatic ring (e.g., an X-containing ring).

As a preferred example of a compound in which a cyano group is substituted in the cyclohexyl fluorene-based core, it may be more specifically embodied into any one of the following Chemical Formulas 12A to 15A:

[Chemical Formula 12A]

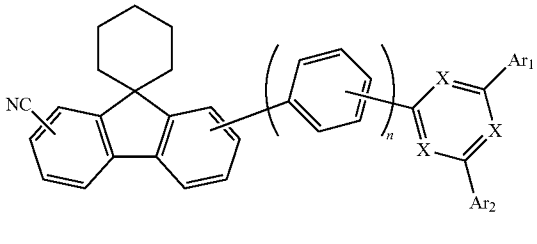

-continued

[Chemical Formula 13A]

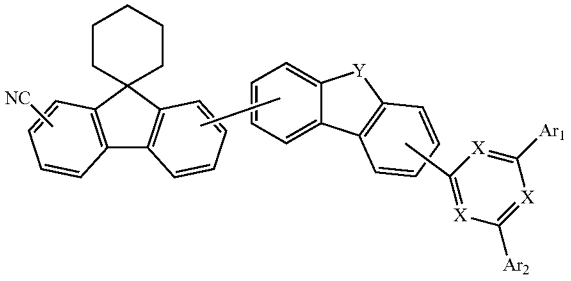

[Chemical Formula 14A]

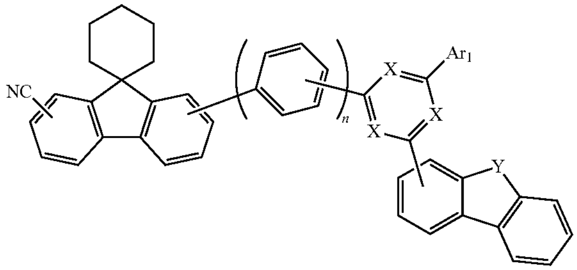

[Chemical Formula 15A]

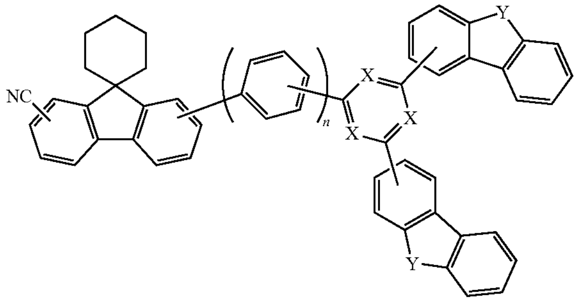

where in the above Chemical Formulas 12A to 15A,

X, Y, $Ar_1$, $Ar_2$ and n are each as defined in Chemical Formulas 1 and 3.

A preferred example of a compound in which a cyano group is substituted in at least one of $Ar_1$ and $Ar_2$ of the nitrogen-containing heteroaromatic ring (e.g., an X-containing ring) may be embodied into any one of the following Chemical Formulas 16 to 18:

[Chemical Formula 16]

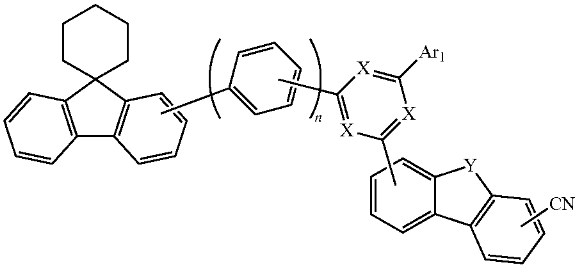

-continued

[Chemical Formula 17]

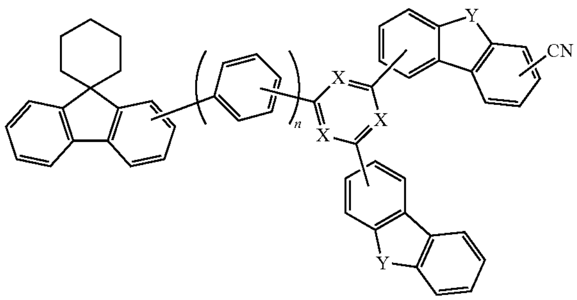

[Chemical Formula 18]

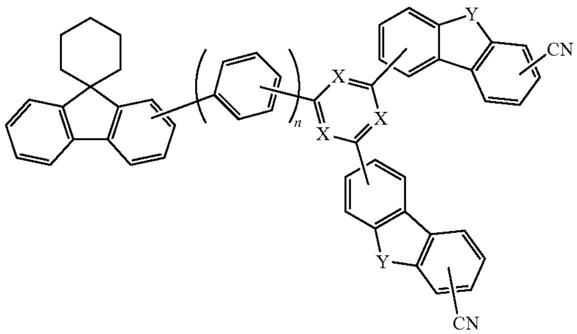

where in Chemical Formulas 16 to 18,

X, Y, $Ar_1$, and n are each as defined in Chemical Formulas 1 and 3.

in a preferred example of a compound represented by any one of the above Chemical Formulas 12A to 15A and Chemical Formulas 16 to 18, two to three of the plurality of X are N, Y is selected from: $C(R_3)_2$, $NR_3$, O, S and Se, and $R_3$ is selected from: hydrogen, a $C_1$ to $C_6$ alkyl group, a $C_6$ to $C_{18}$ aryl group, a heteroaryl group having 5 to 13 nuclear atoms, and n is in a range from 0 to 3.

In addition, although not specifically illustrated in the above chemical formula, the alkyl group, the aryl group and the heteroaryl group of $R_3$ may each independently be substituted or unsubstituted with one or more substituents of: hydrogen, deuterium (D), halogen, a cyano group, a nitro group, a $C_1$ to $C_{40}$ alkyl group, a $C_6$ to $C_{60}$ aryl group, a heteroaryl group having 5 to 60 nuclear atoms, and a $C_6$ to $C_{60}$ arylamine group.

According to an embodiment of the present invention, a structure in which a cyano group is substituted in any one of the cyclohexyl fluorene-based core and the nitrogen-containing heteroaromatic ring has been specifically described. However, the present invention is not limited thereto, and compounds in which a plurality of cyano groups are substituted in both the cyclohexyl fluorene-based core and the nitrogen-containing heteroaromatic ring are also within the scope of the present invention.

The compound represented by Chemical Formula 1 of the present invention described above may be further embodied into a compound exemplified below, for example, compounds represented by A-1 to C-117. However, the compound represented by Chemical Formula 1 of the present invention is not limited by those exemplified below.

-continued
A-1
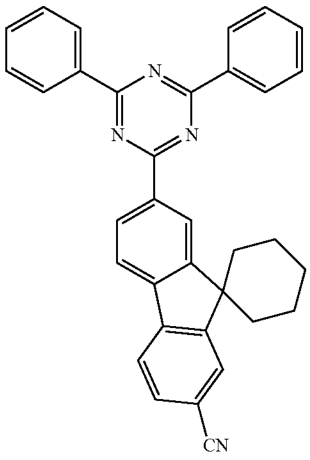
A-2
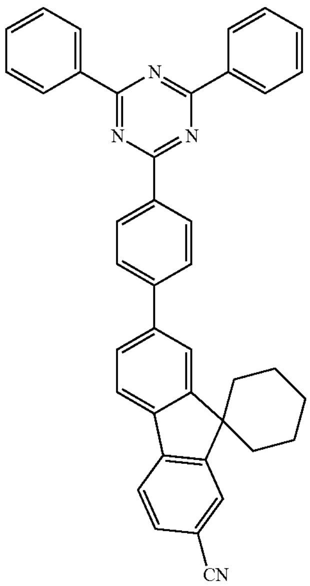
A-3
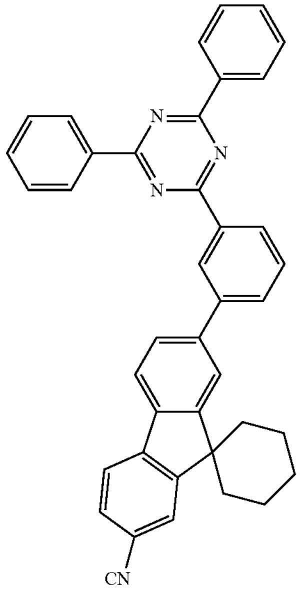
A-4
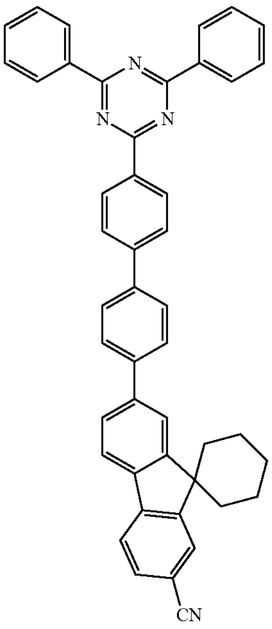
A-5
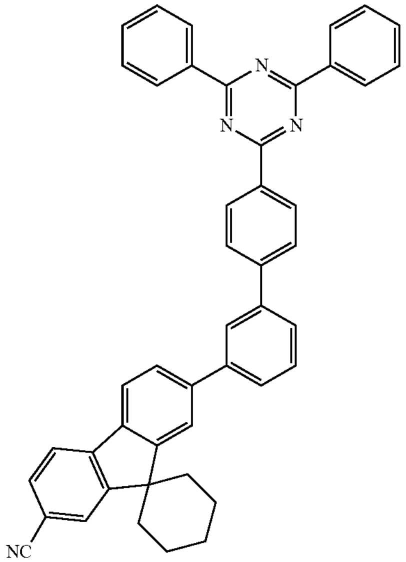

-continued
A-6
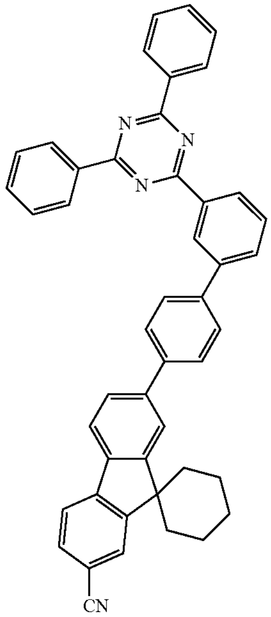
-continued
A-8
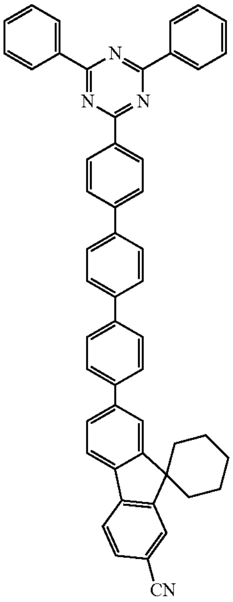
A-7
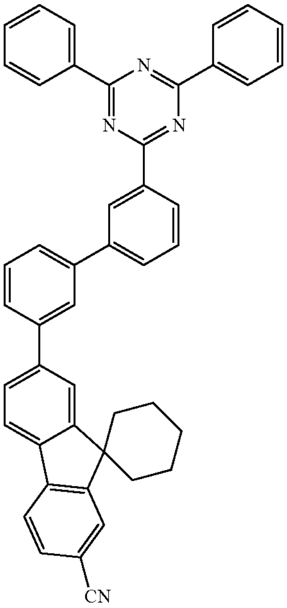
A-9
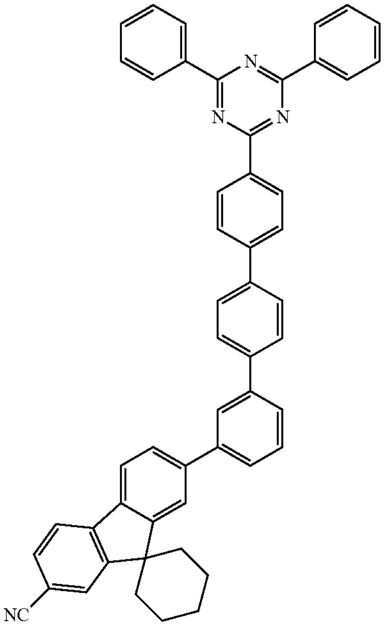

-continued
A-10
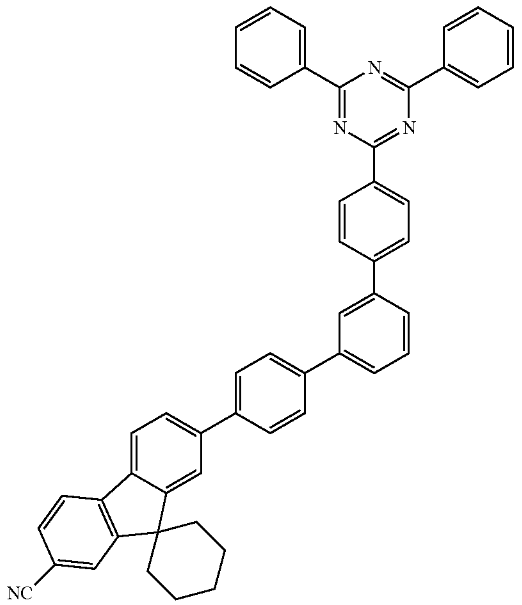
A-11
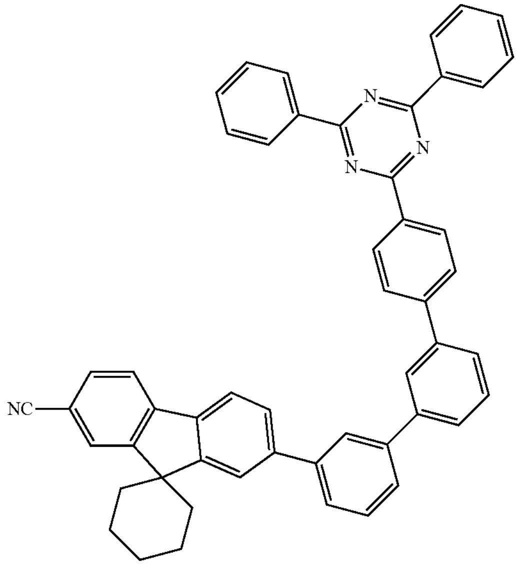
-continued
A-12
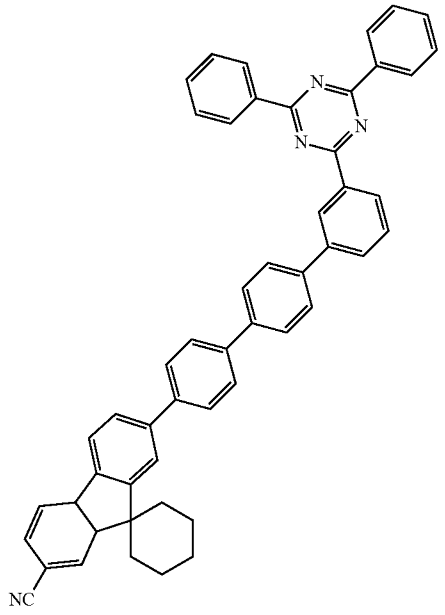
A-13
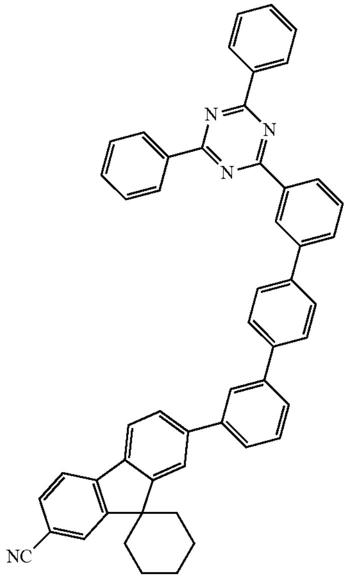

-continued
A-14
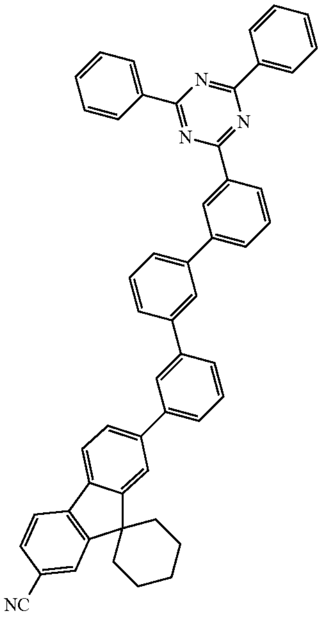
A-15
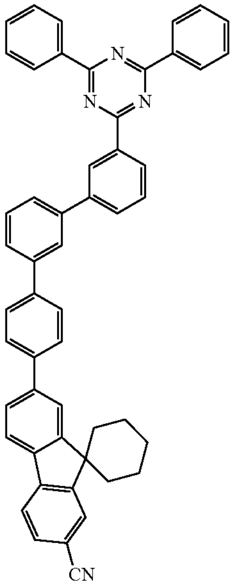
-continued
A-16
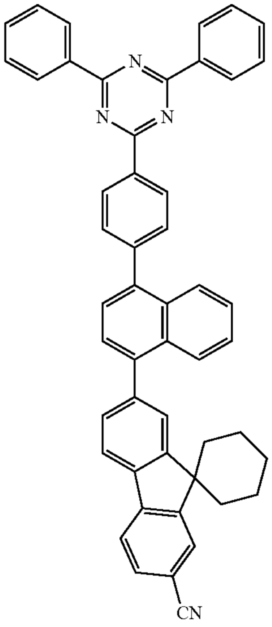
A-17
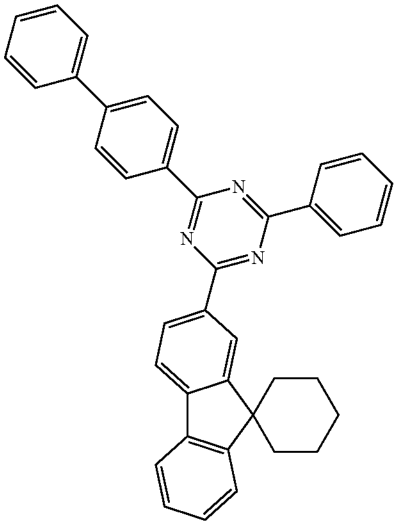

-continued
A-18
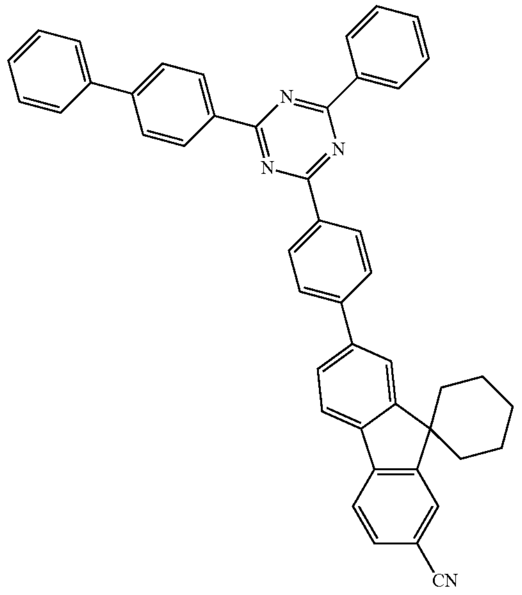
A-19
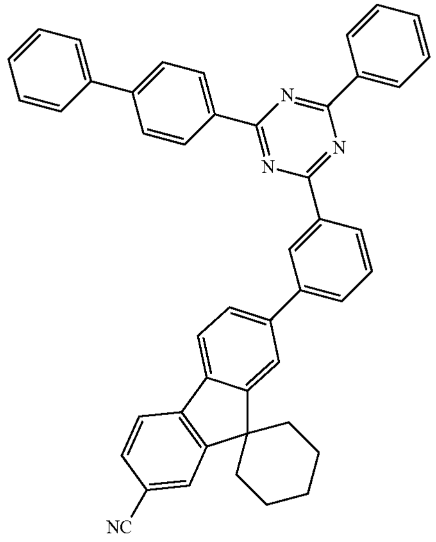
-continued
A-20
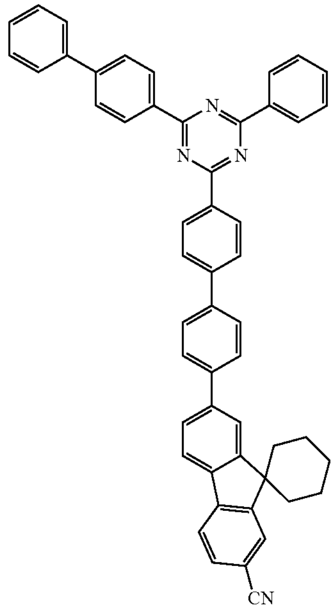
A-21
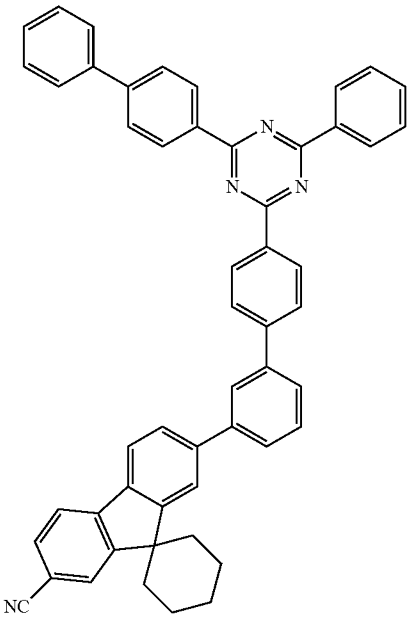

-continued
A-22
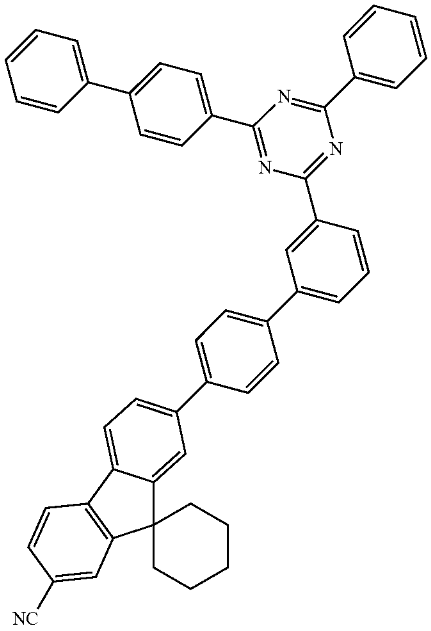
-continued
A-24
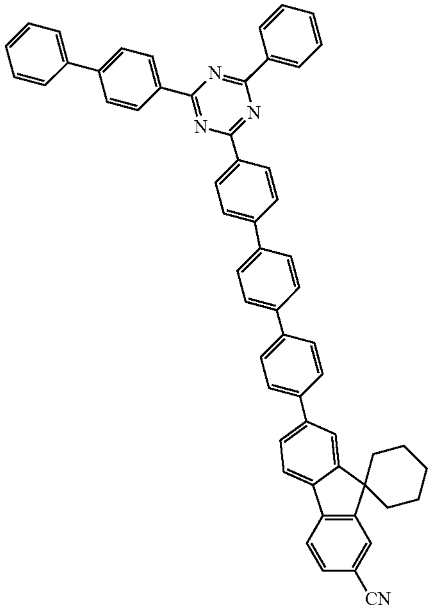
A-23
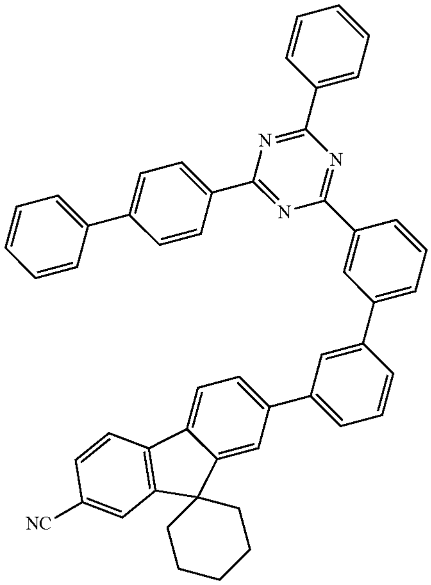
A-25
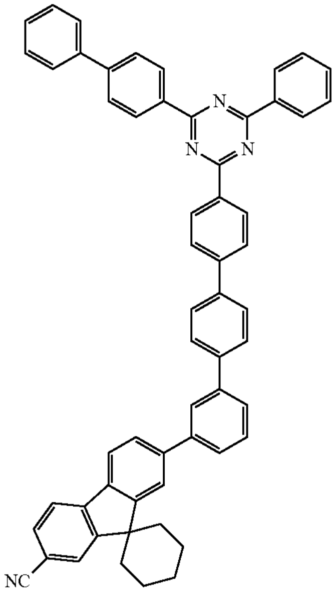

-continued
A-26
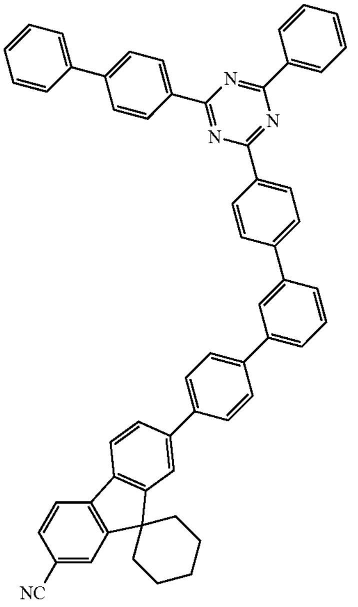
A-27
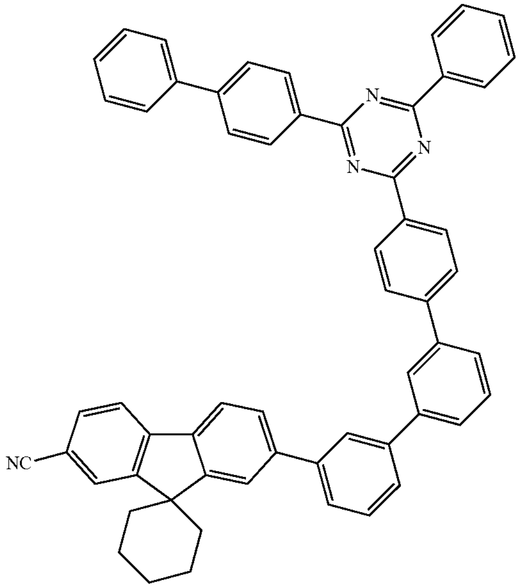
-continued
A-28
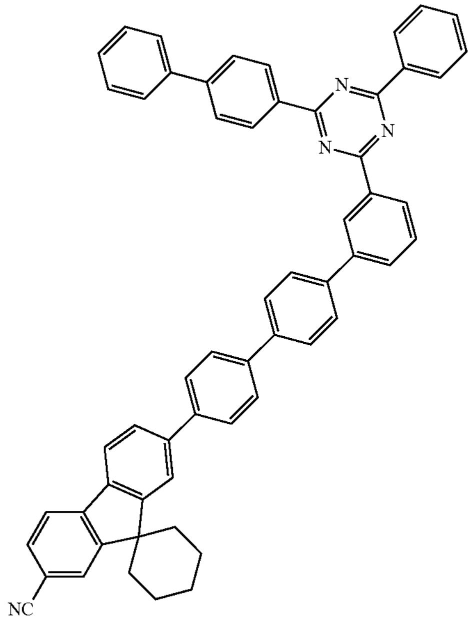
A-29
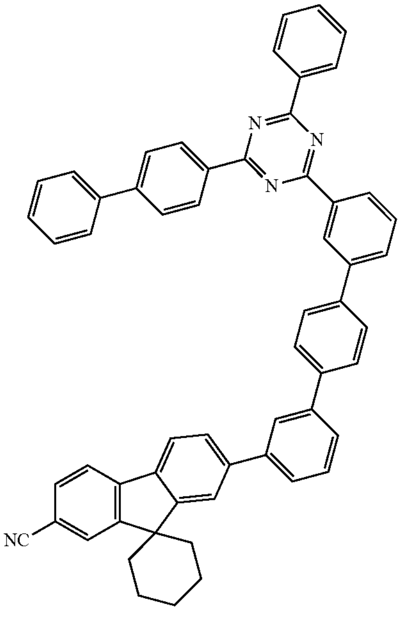

-continued
A-30
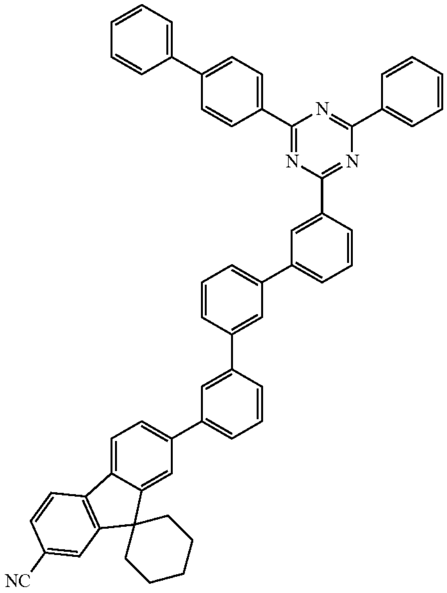
A-31
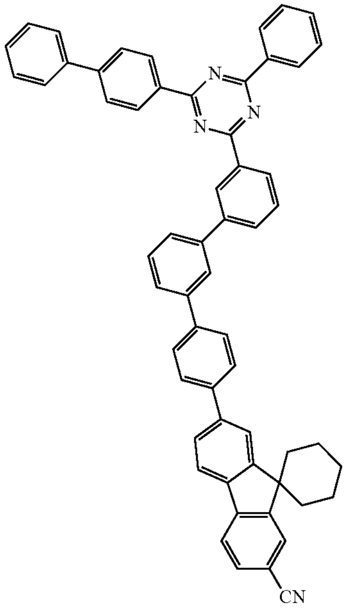
-continued
A-32
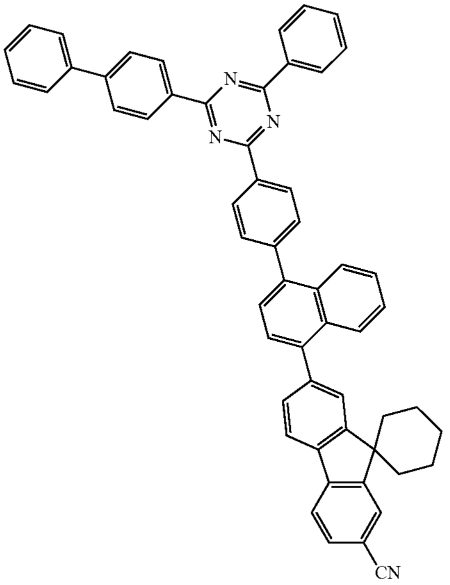
A-33
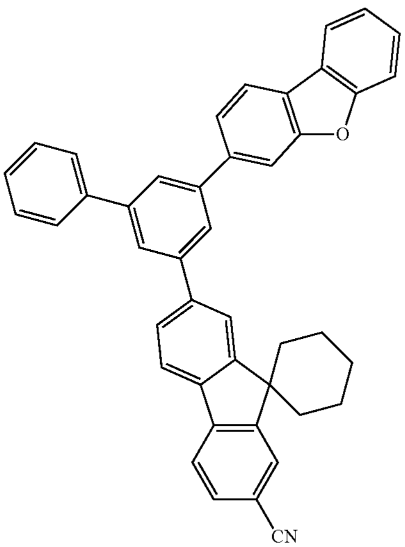

-continued
A-34
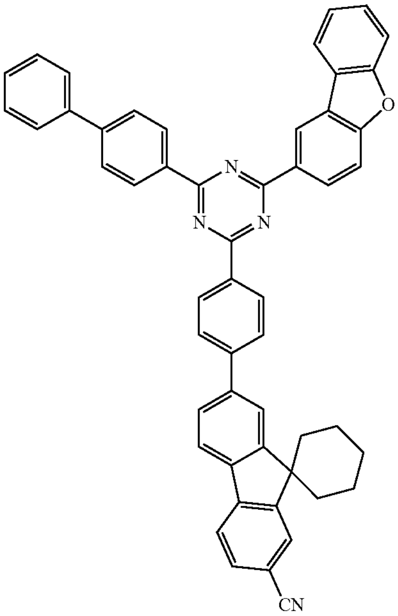
A-35
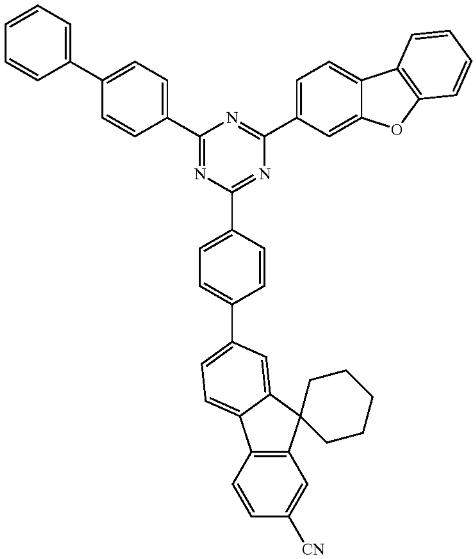
-continued
A-36
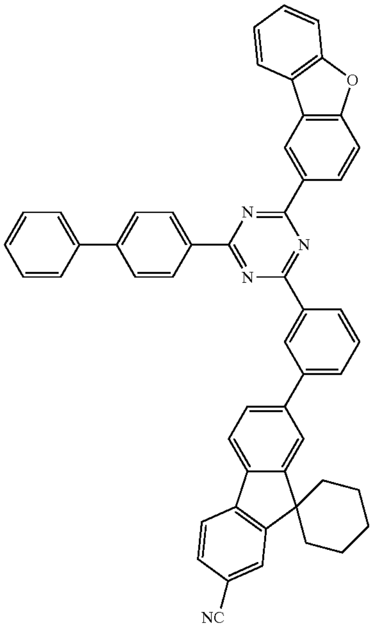
A-37
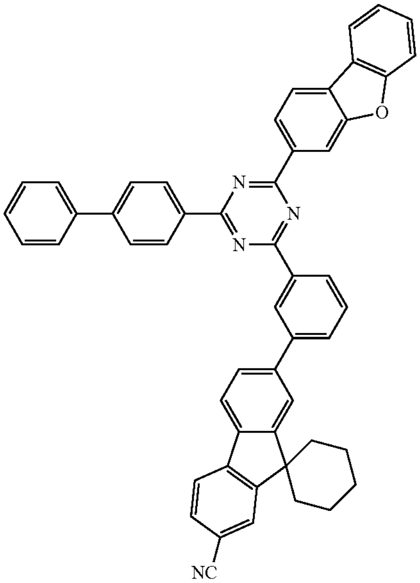

-continued
A-38
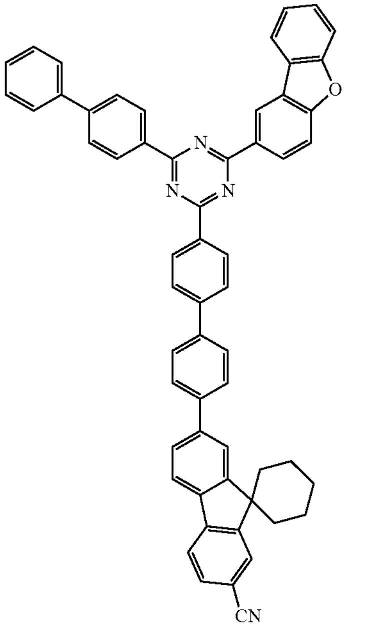
A-39
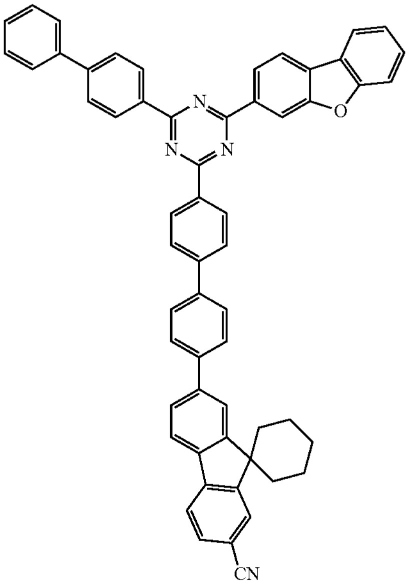
-continued
A-40
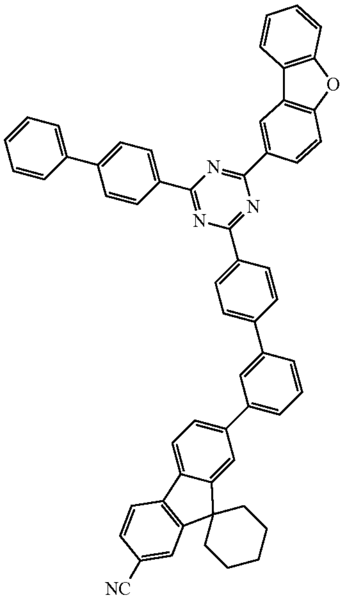
A-41
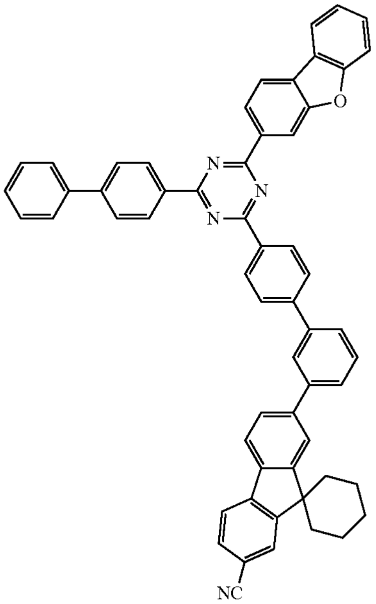

-continued
A-42
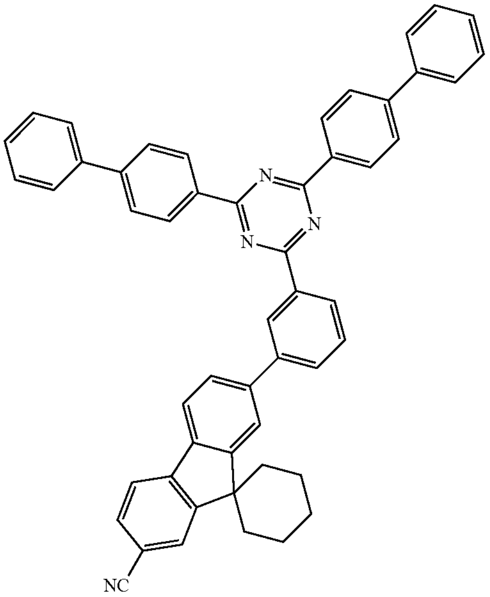
A-43
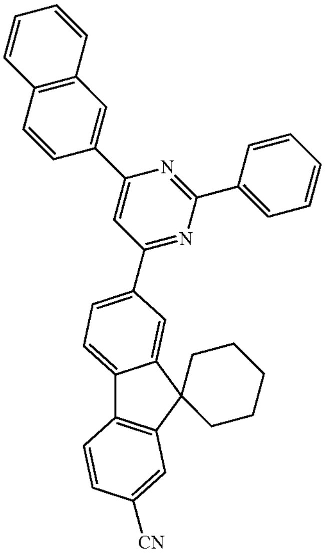
-continued
A-44
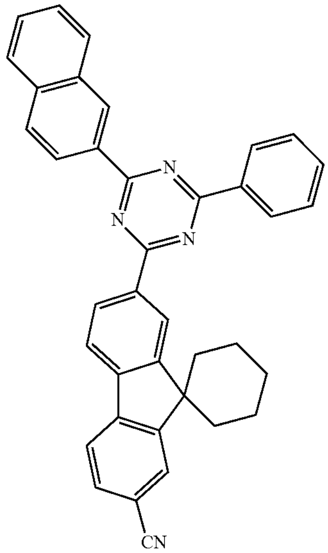
A-45
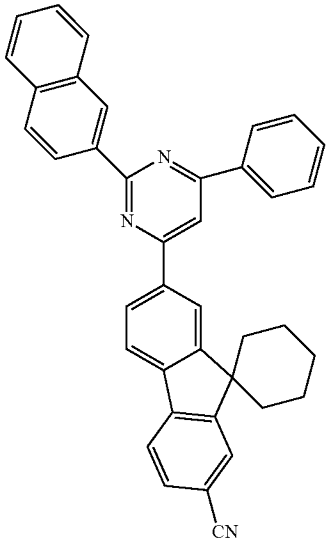
A-4
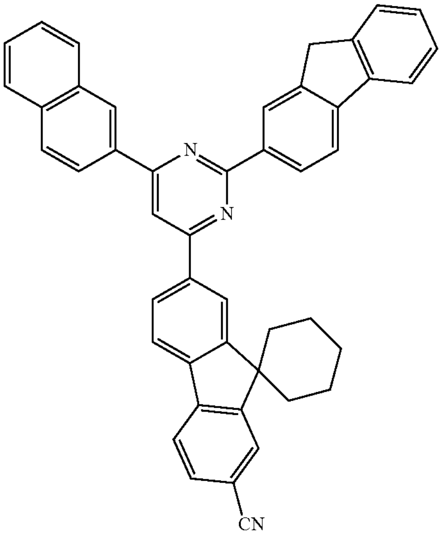

-continued
A-47
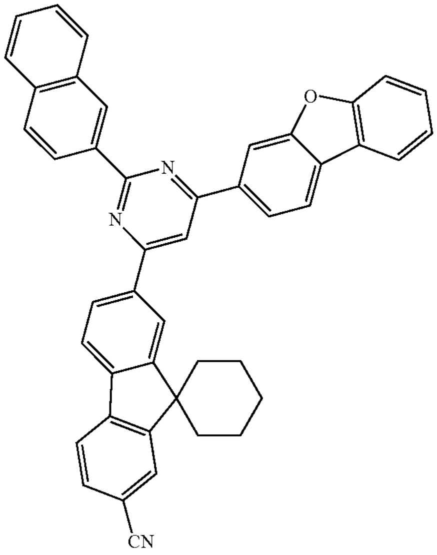
A-48
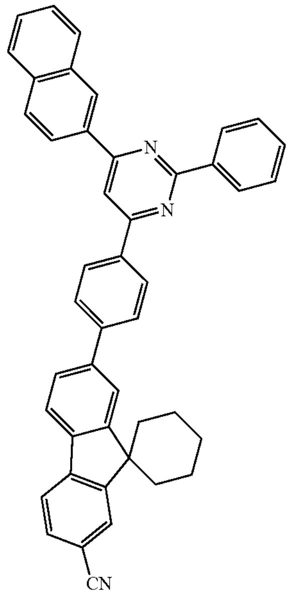
-continued
A-49
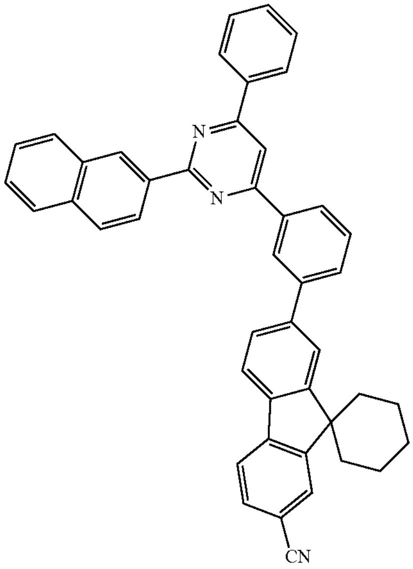
A-50
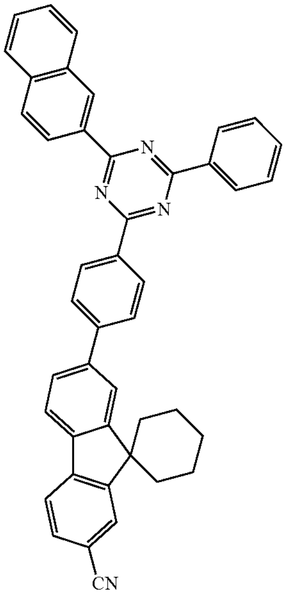

-continued
A-51
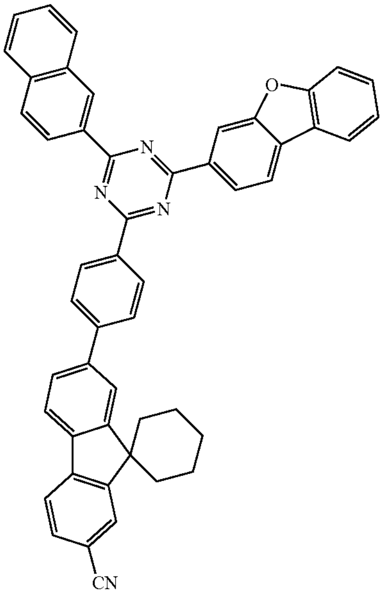
A-52
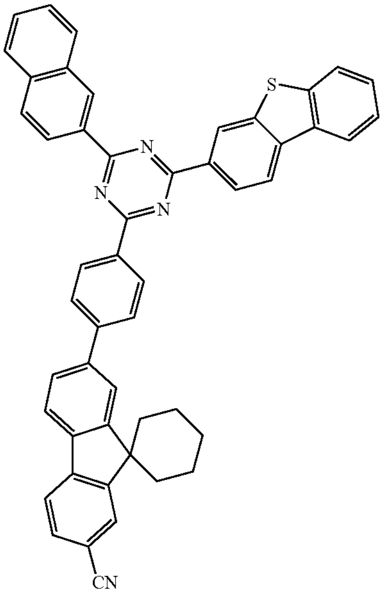
-continued
A-53
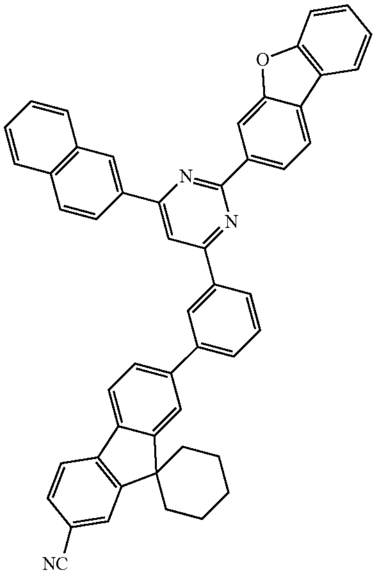
A-54
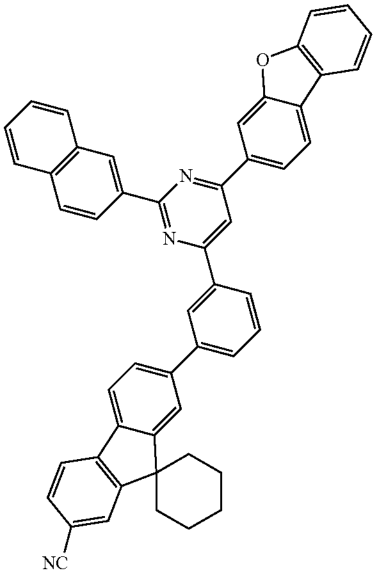

-continued
A-55
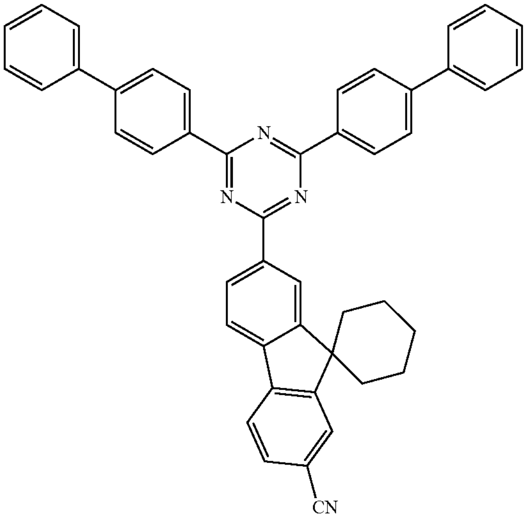
A-56
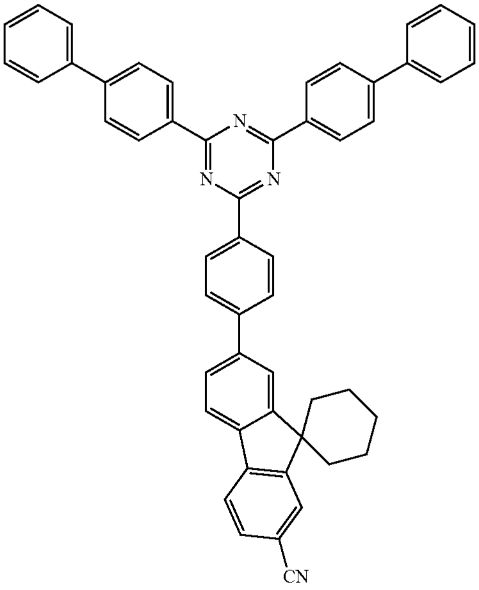
-continued
A-57
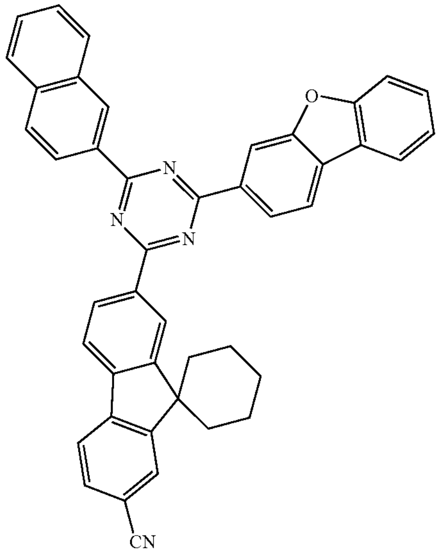
A-58
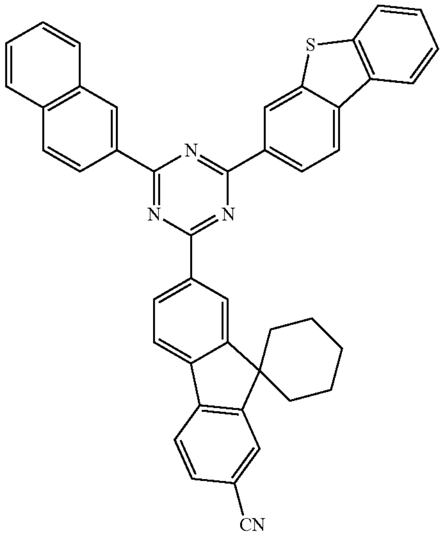
A-59
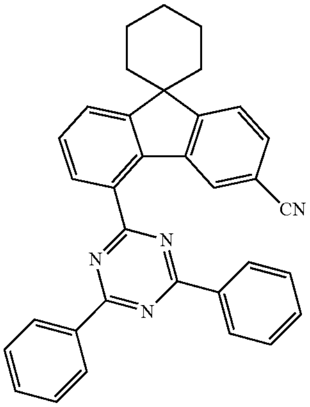

-continued
A-60
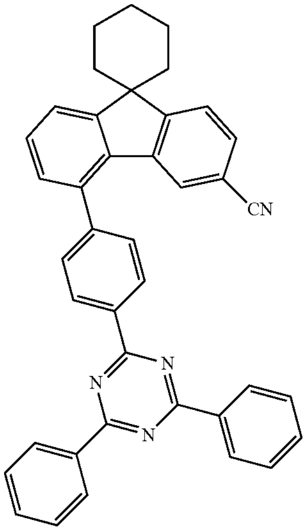
A-61
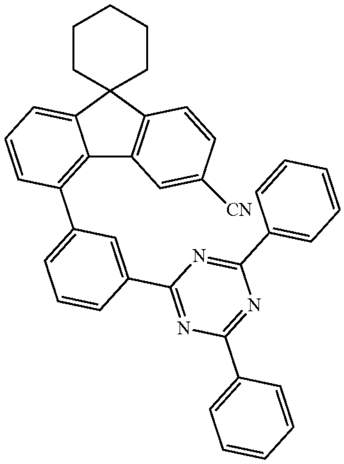
A-62
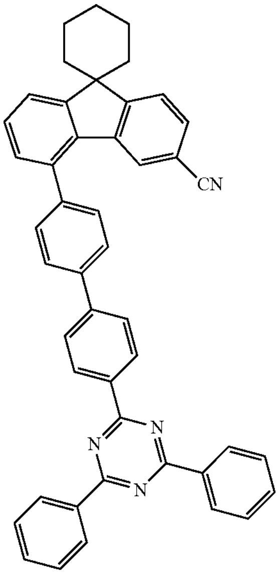
-continued
A-63
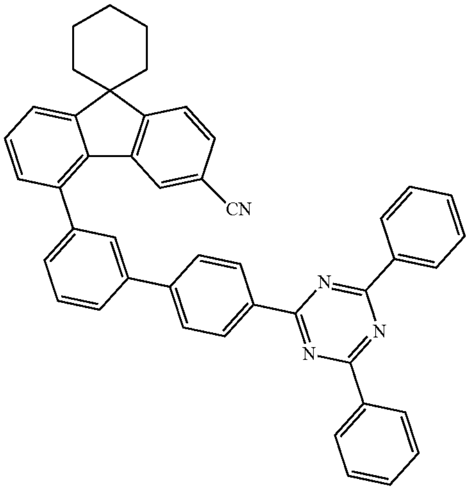
A-64
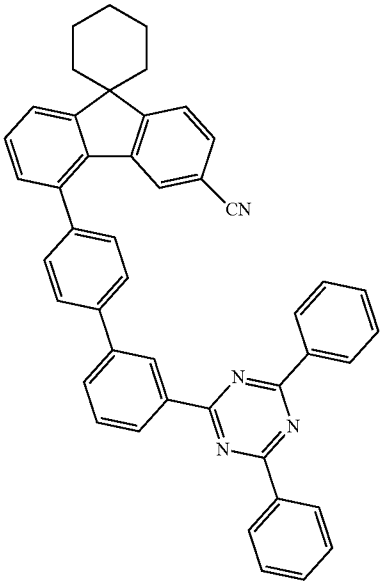

-continued
A-65
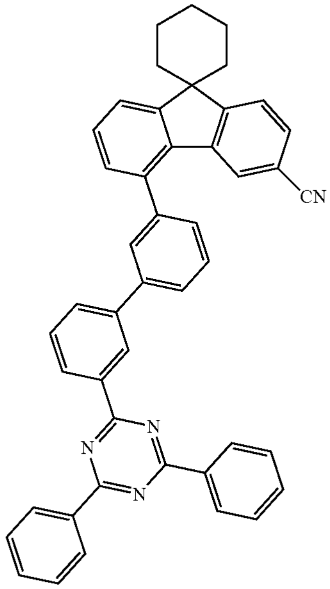
A-66
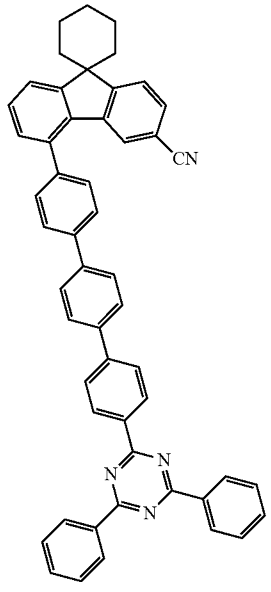
-continued
A-67
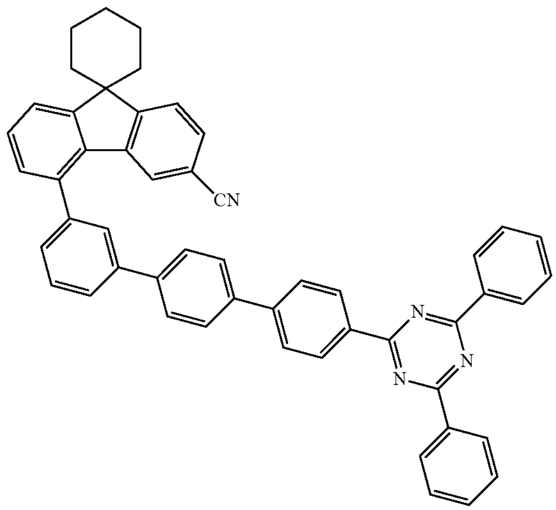
A-68
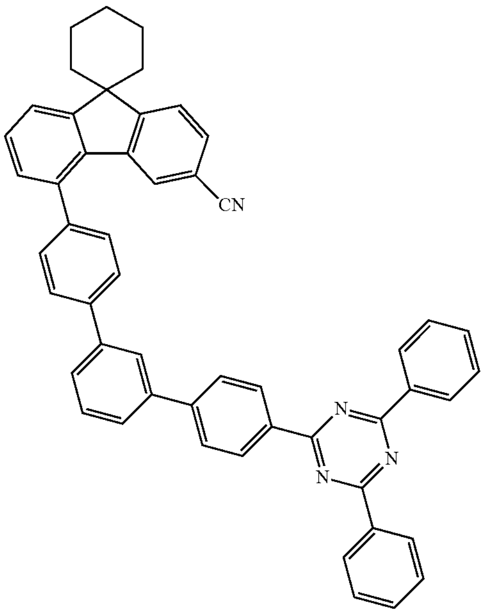
A-69
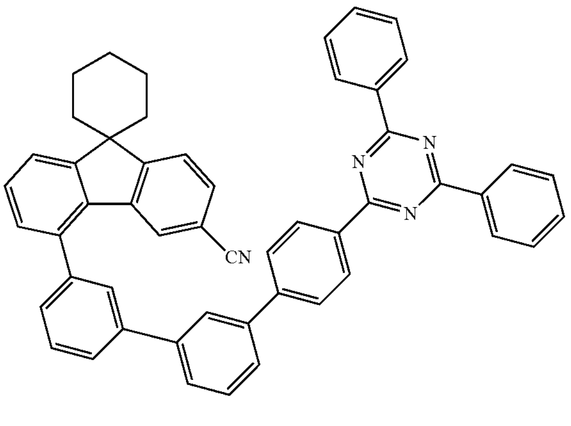

-continued
A-70
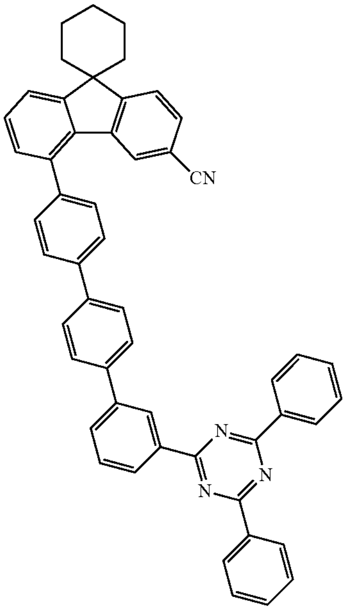
A-71
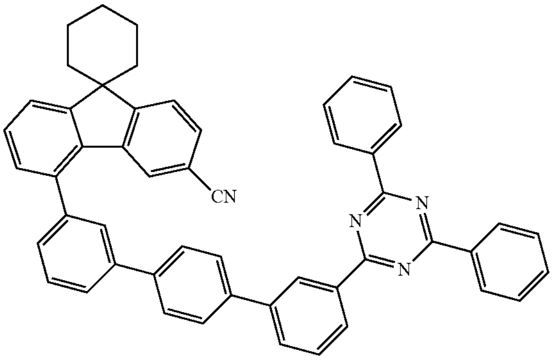
A-72
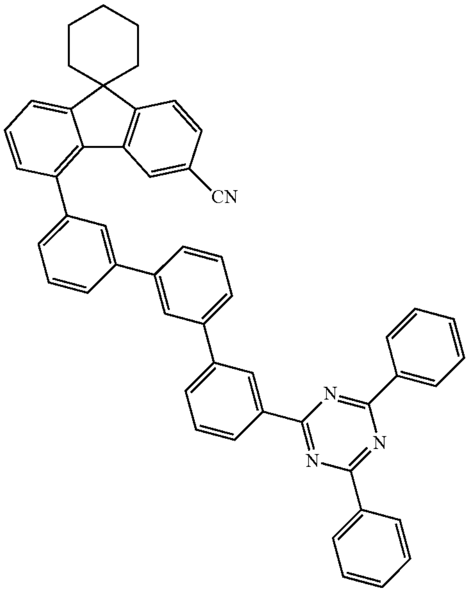
-continued
A-73
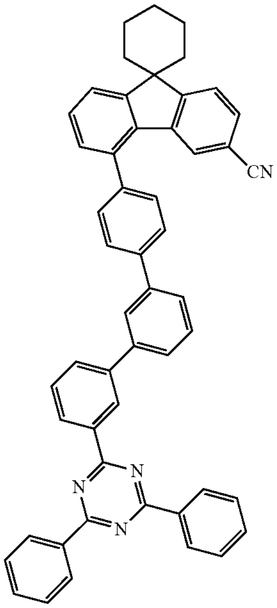
A-74
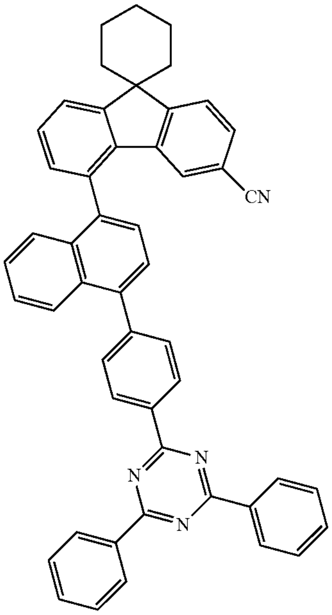
A-75
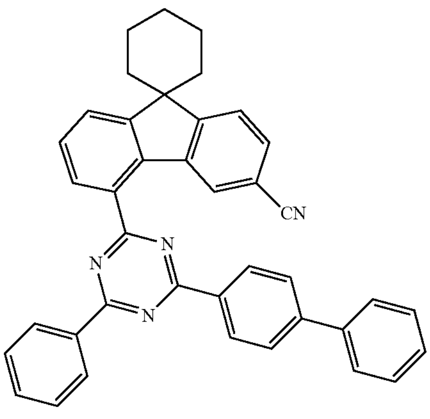

-continued
A-76
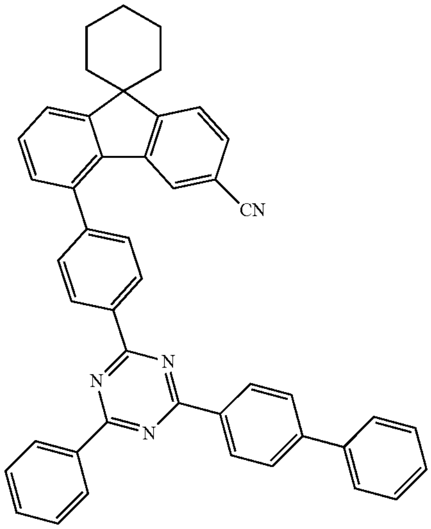
A-77
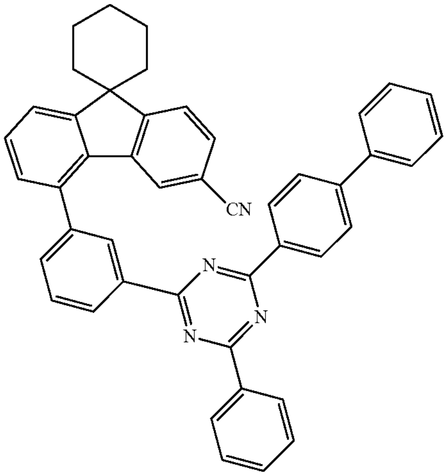
A-78
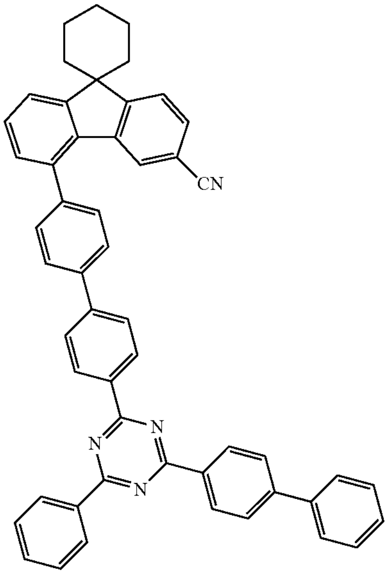
-continued
A-79
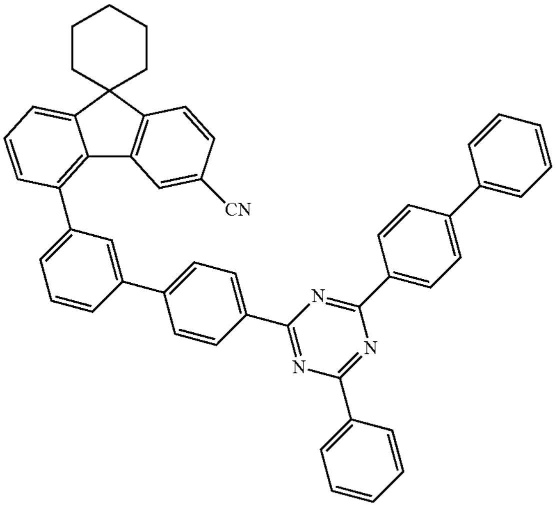
A-80
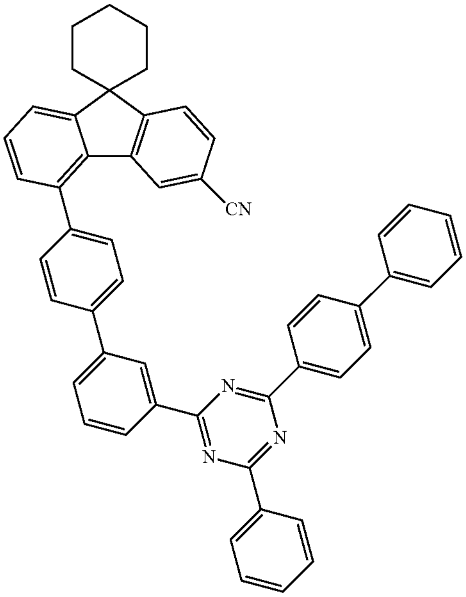
A-81
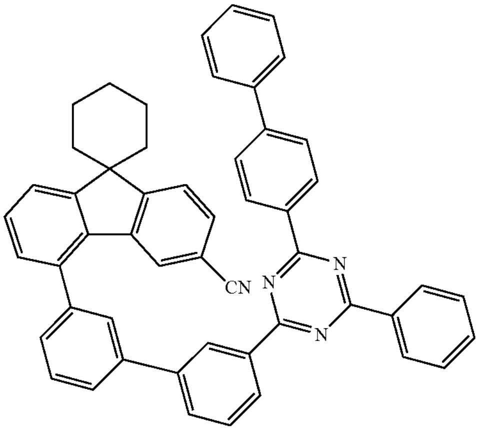

-continued
A-82
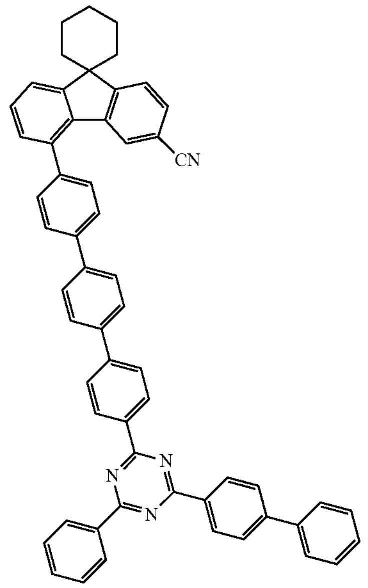
A-83
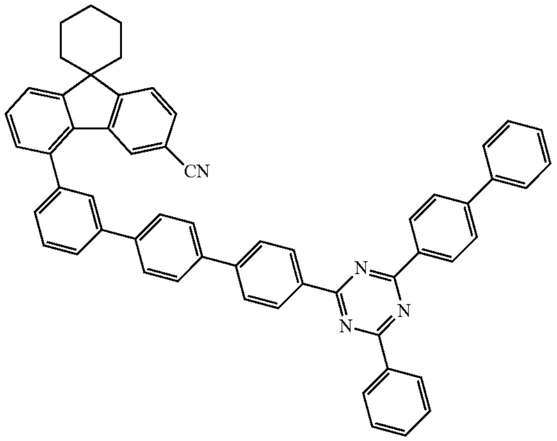
A-84
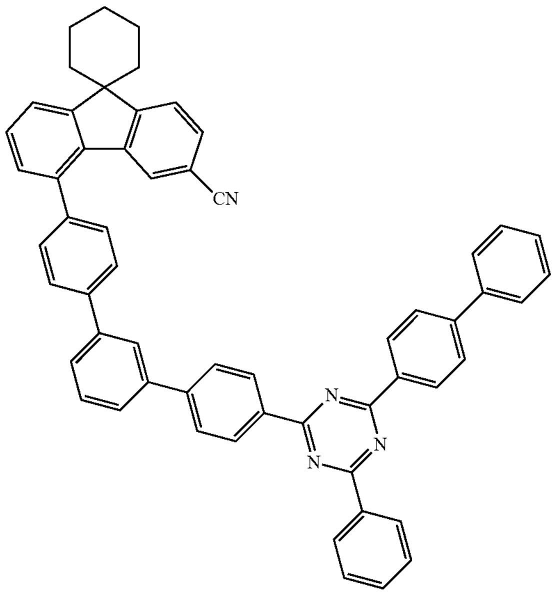
-continued
A-85
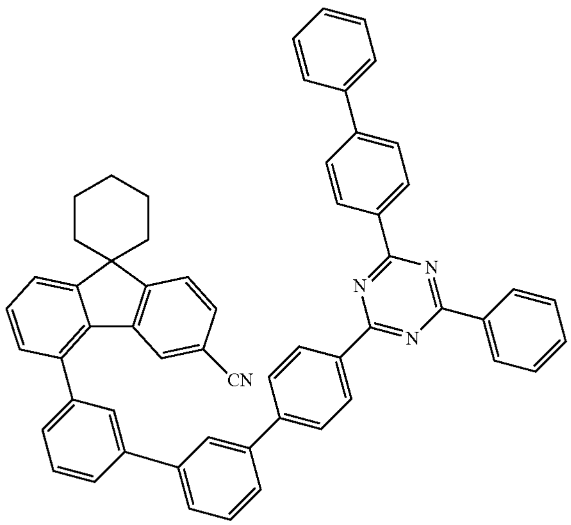
A-86
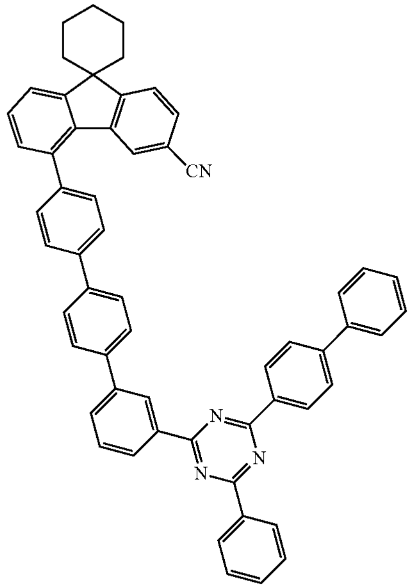
A-87
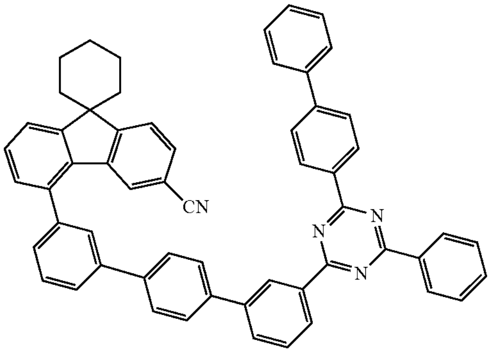

-continued
A-88
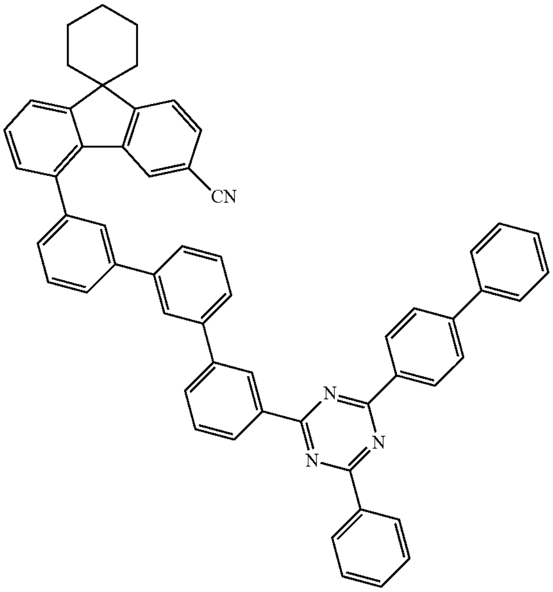
A-89
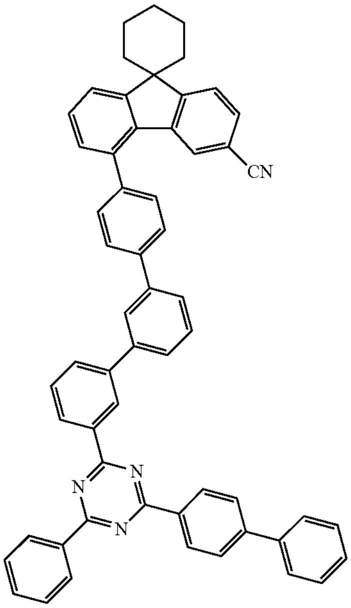
-continued
A-90
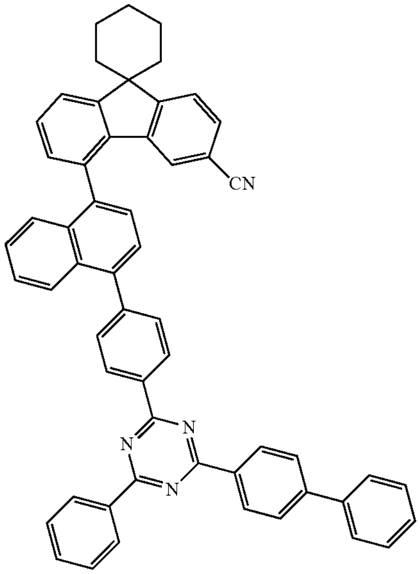
A-91
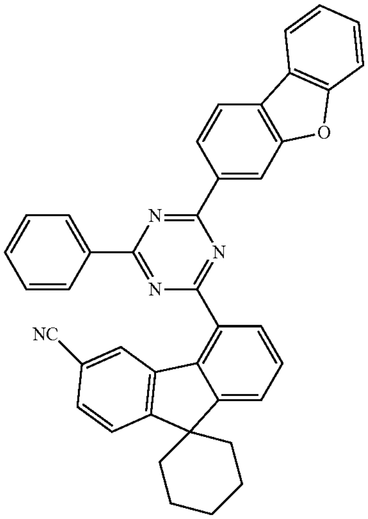

-continued
A-92
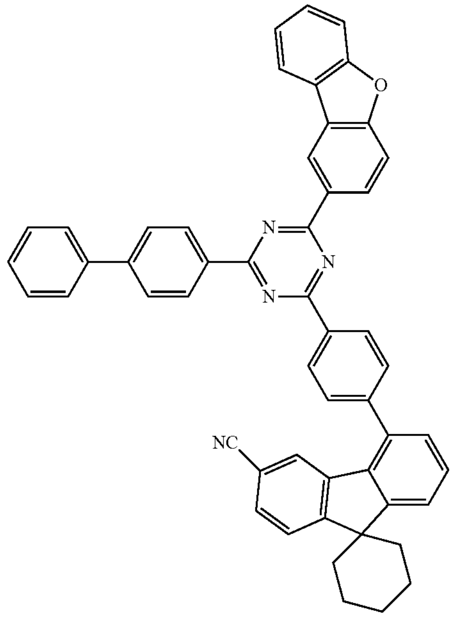
A-93
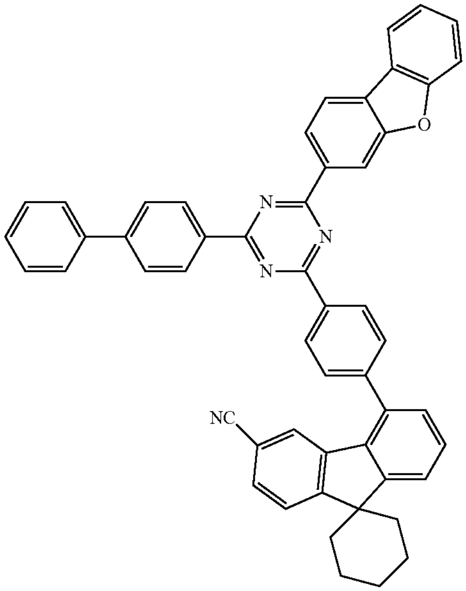
-continued
A-94
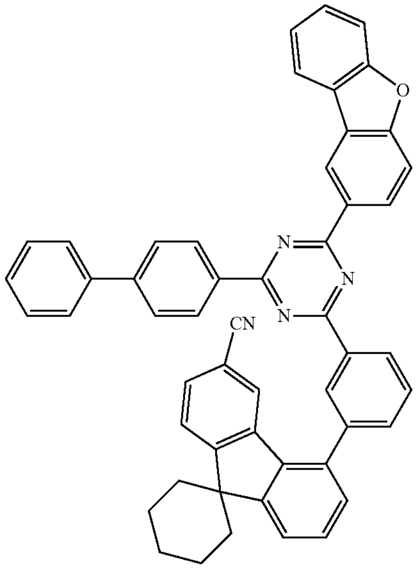
A-95
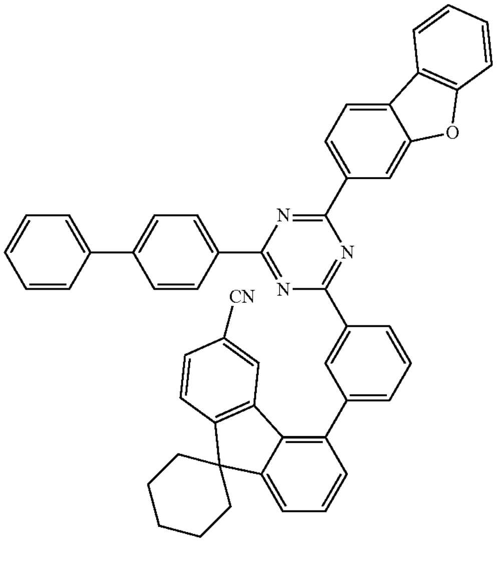

-continued
A-96
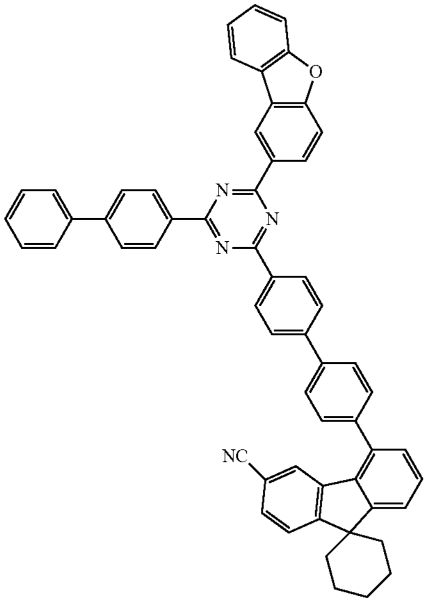
A-97
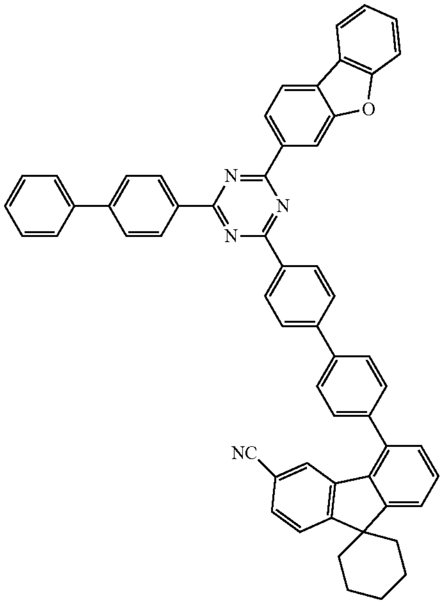
-continued
A-98
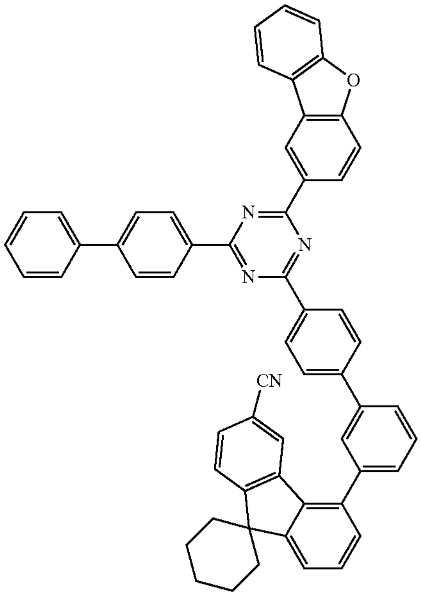
A-99
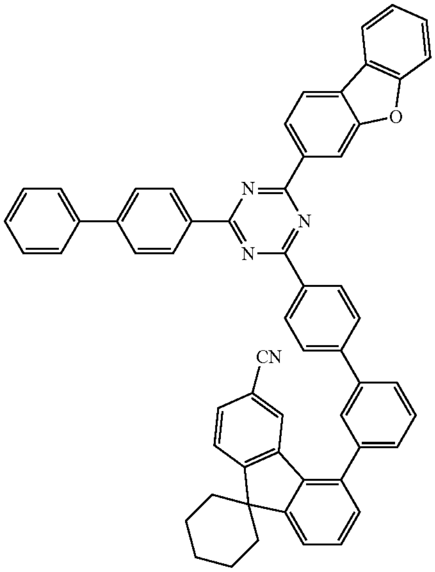

-continued
A-100
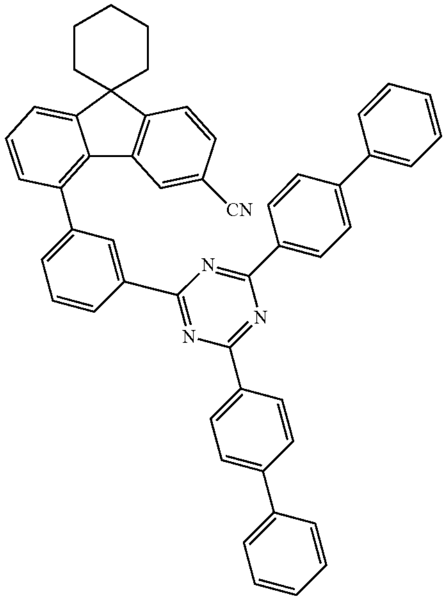
A-101
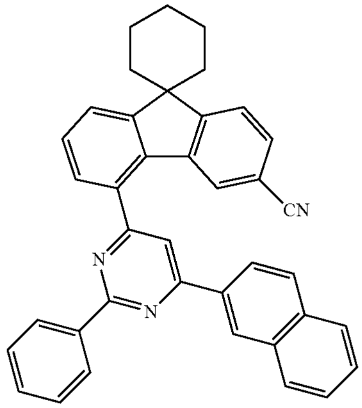
A-102
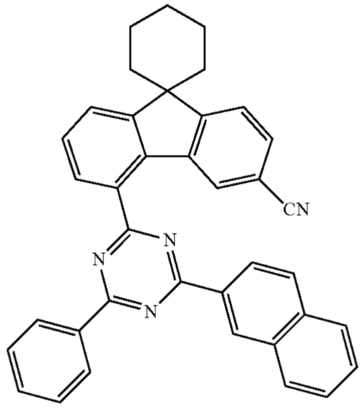
-continued
A-103
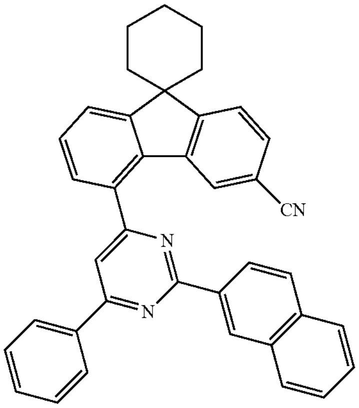
A-104
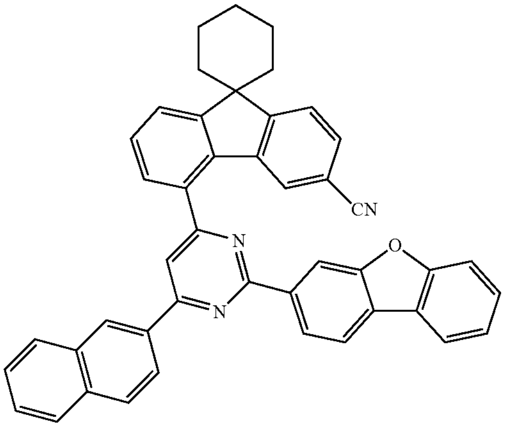
A-105
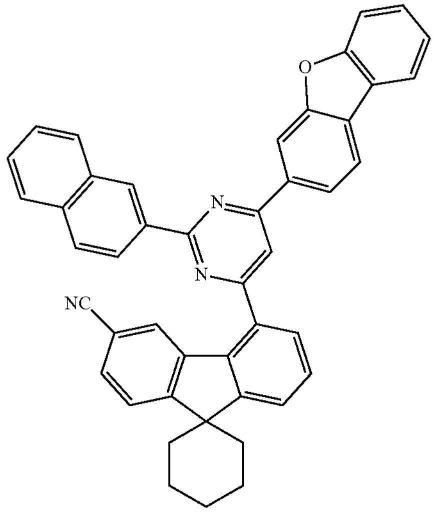

-continued
A-106
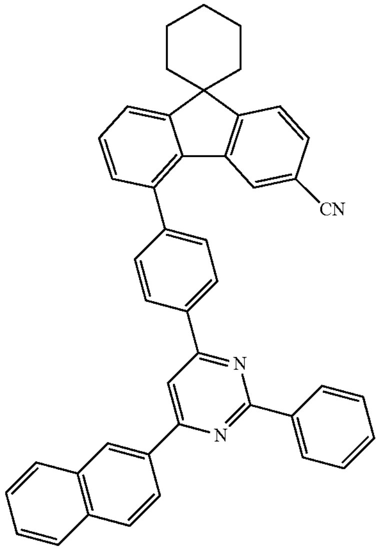
A-107
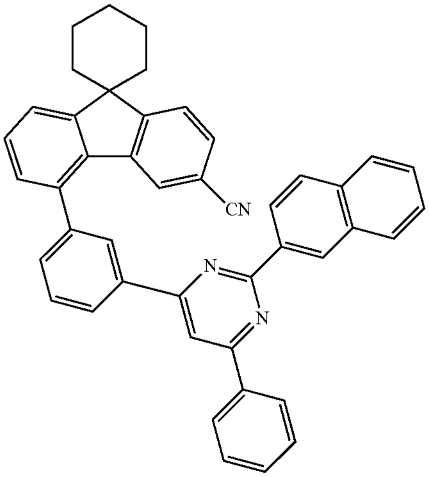
A-108
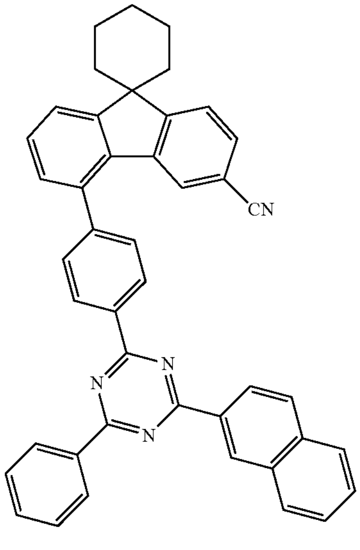
-continued
A-109
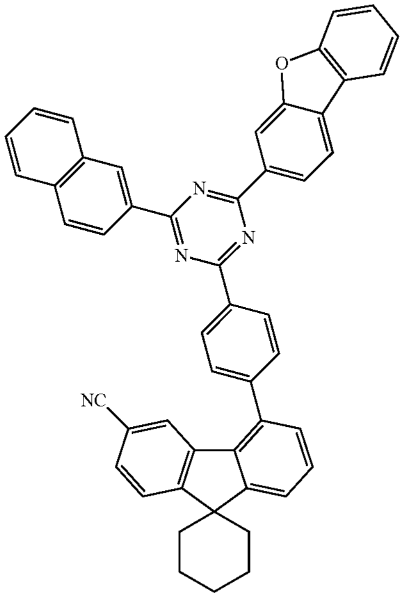
A-110
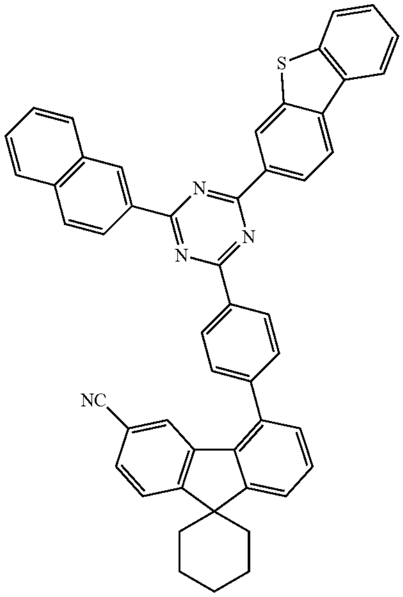

-continued
A-111
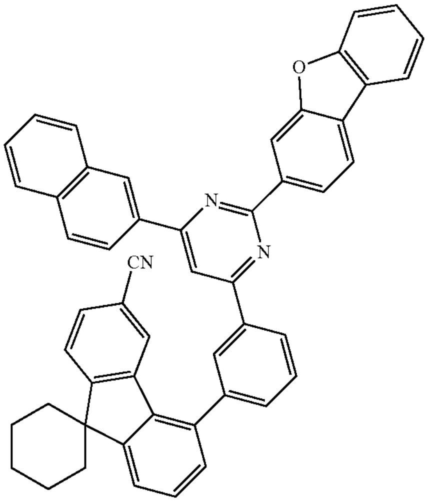
A-112
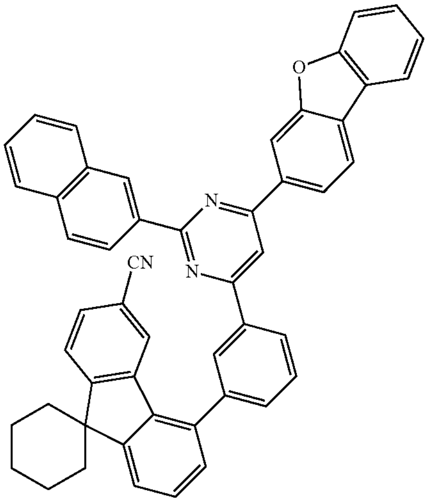
A-113
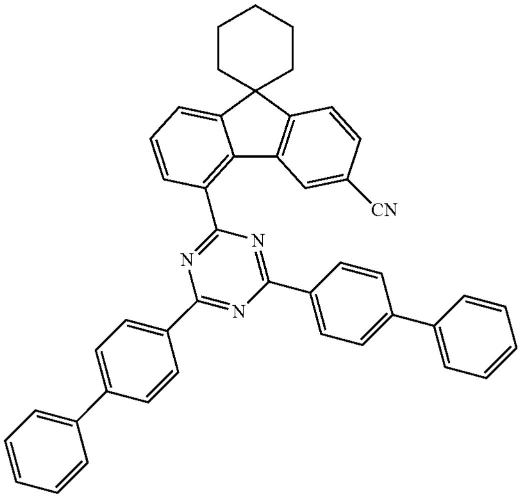
-continued
A-114
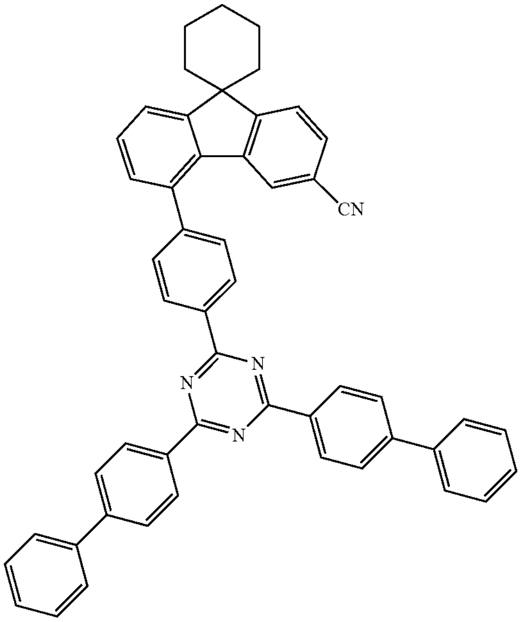
A-115
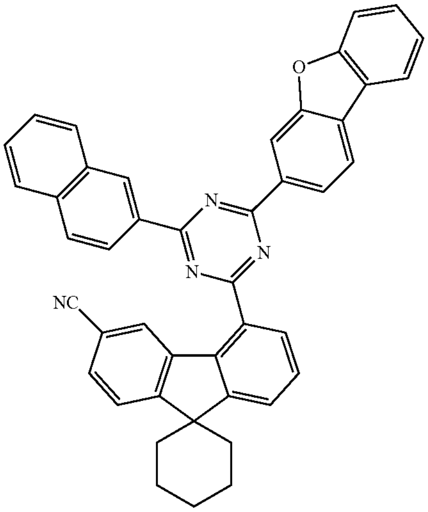
A-116
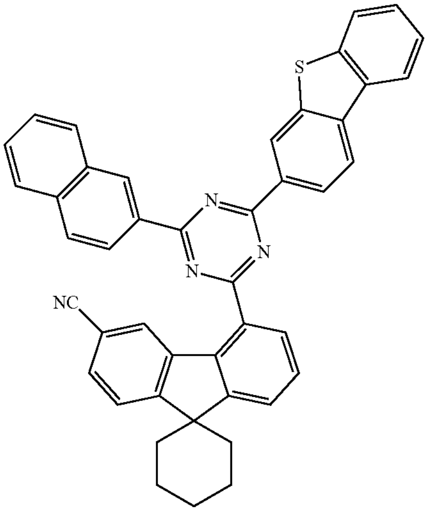

-continued
A-117
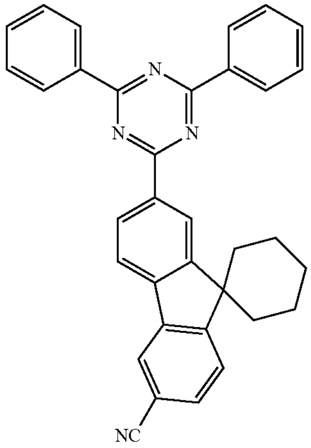
A-118
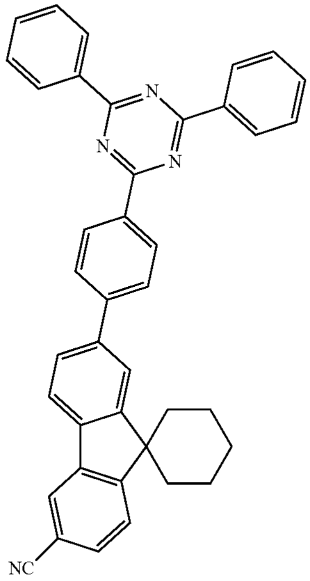
A-119
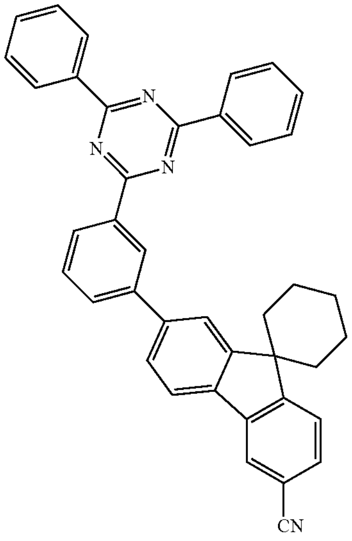
-continued
A-120
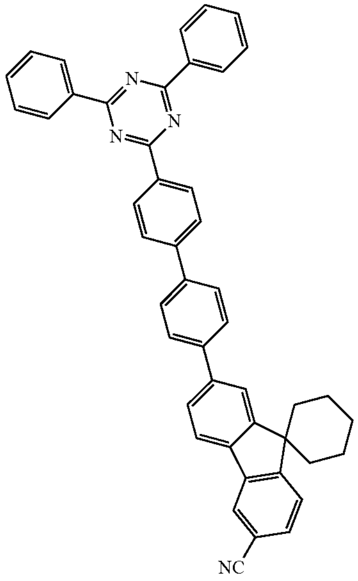
A-121
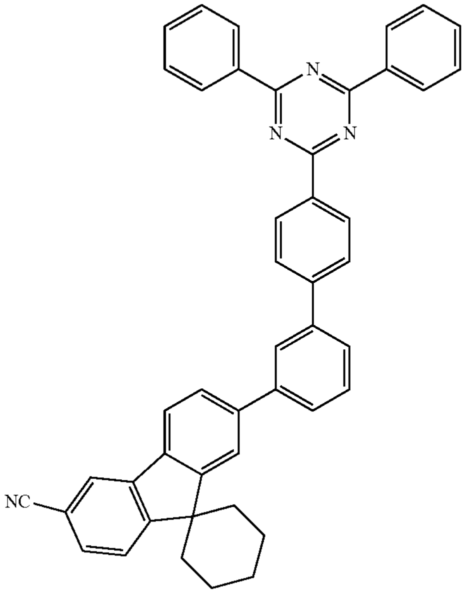

-continued
A-122
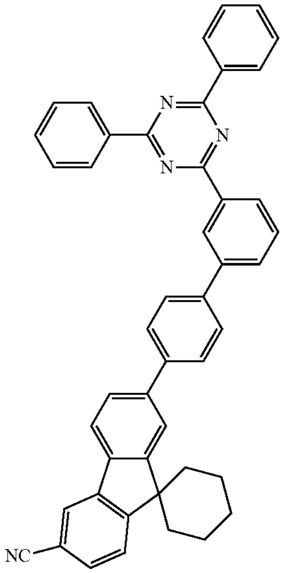
A-123
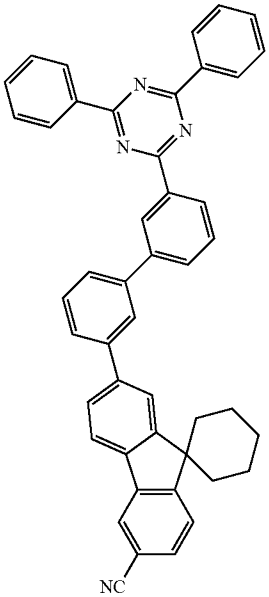
-continued
A-124
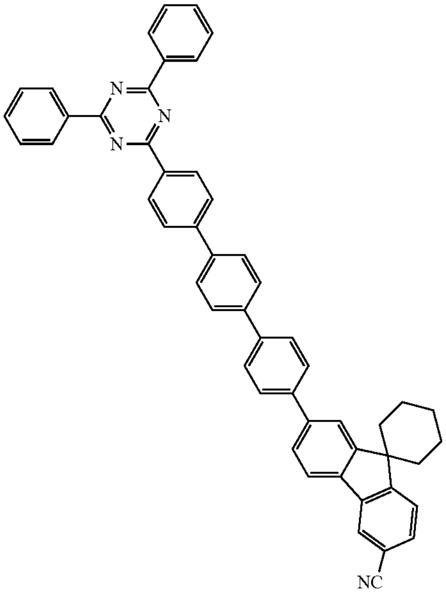
A-125
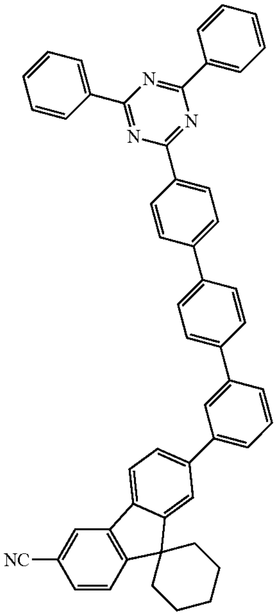

-continued
A-126
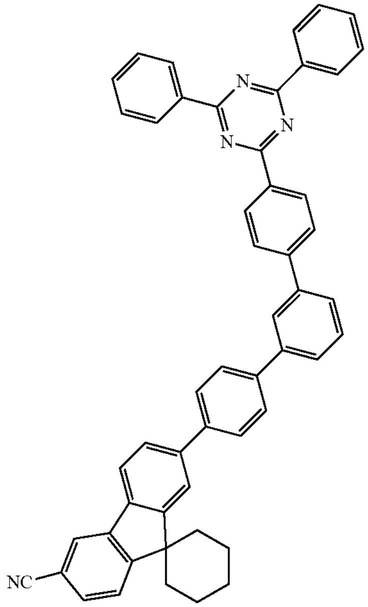
A-127
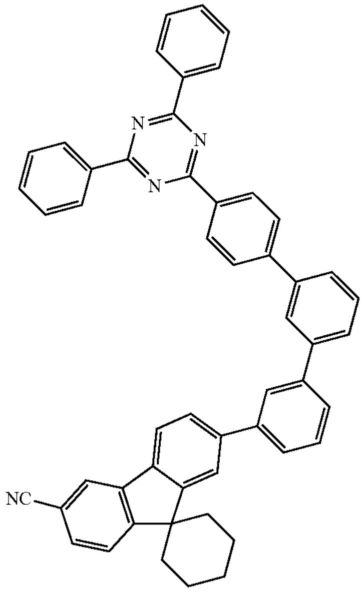
-continued
A-128
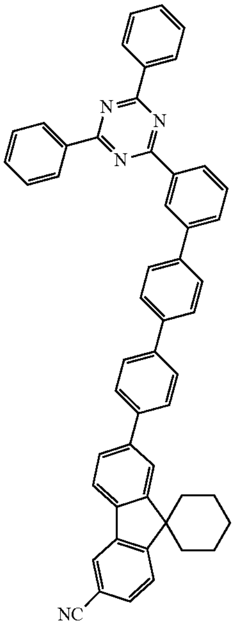
A-129
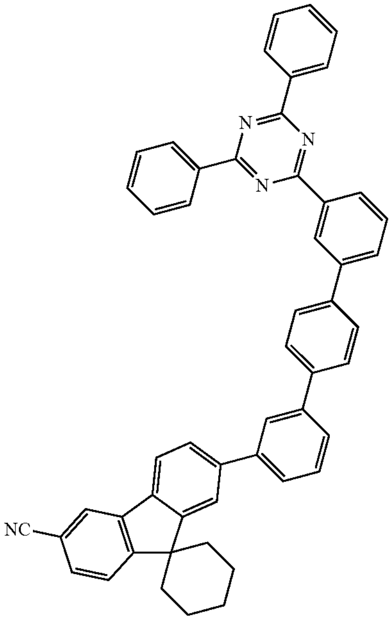

-continued
A-130
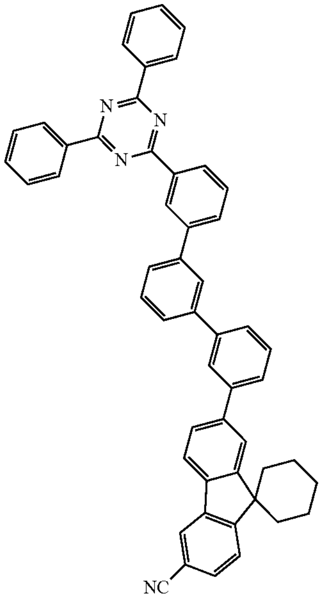
A-131
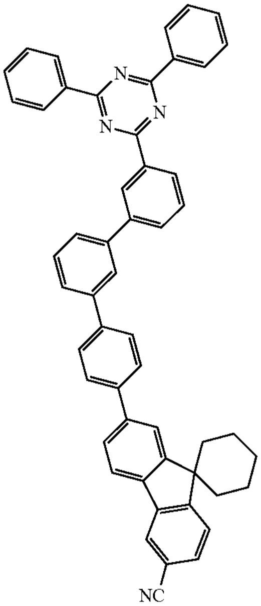
-continued
A-132
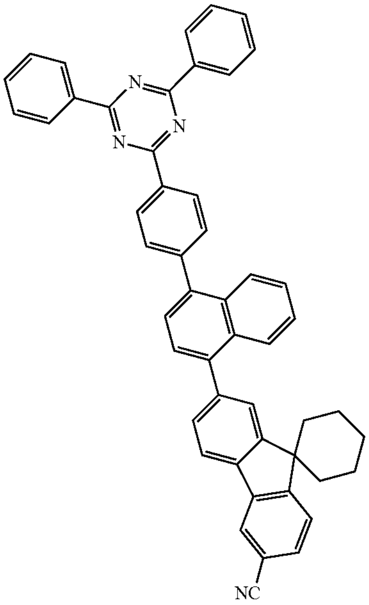
A-133
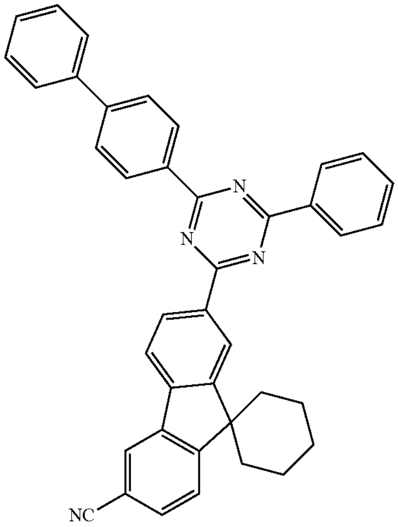

-continued
A-134
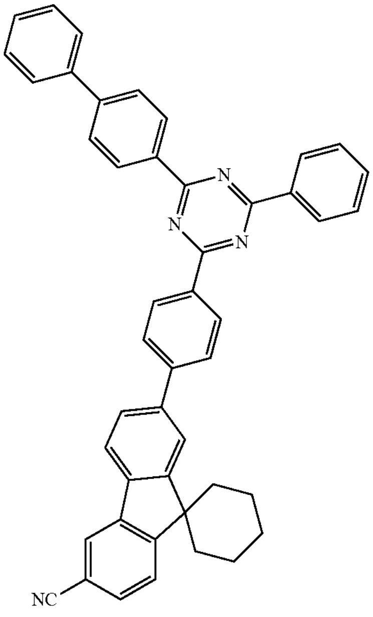
A-135
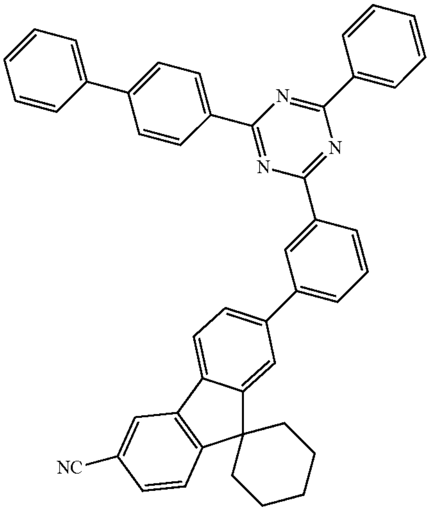
-continued
A-136
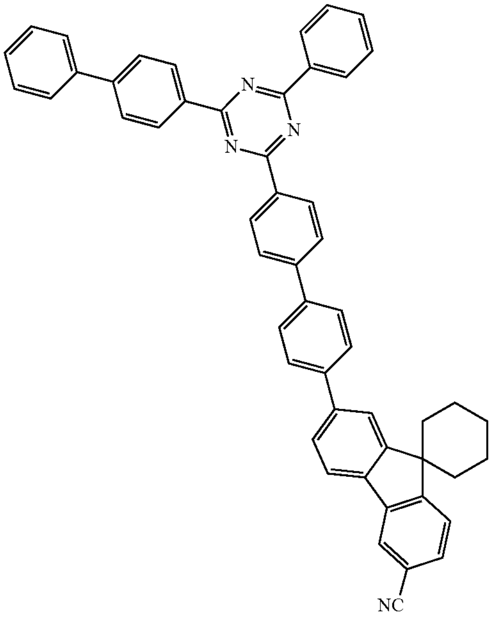
A-137
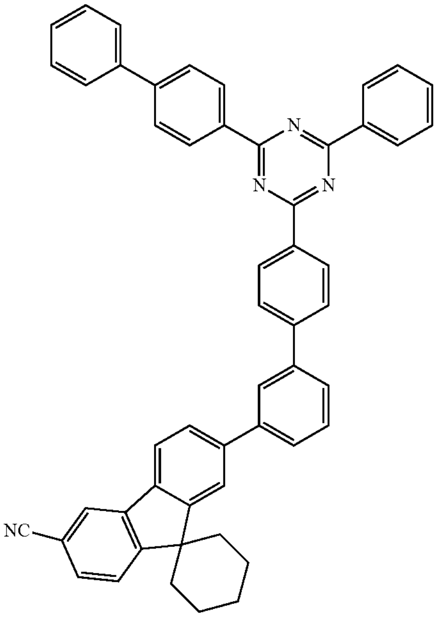

-continued
A-138
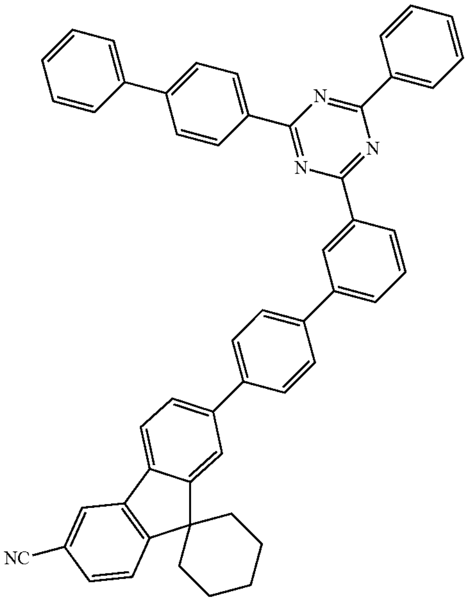
A-139
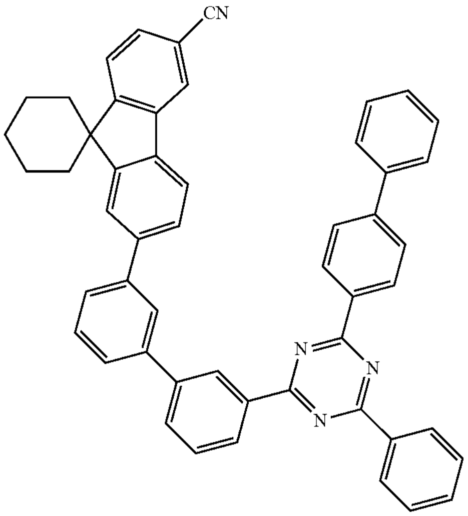
-continued
A-140
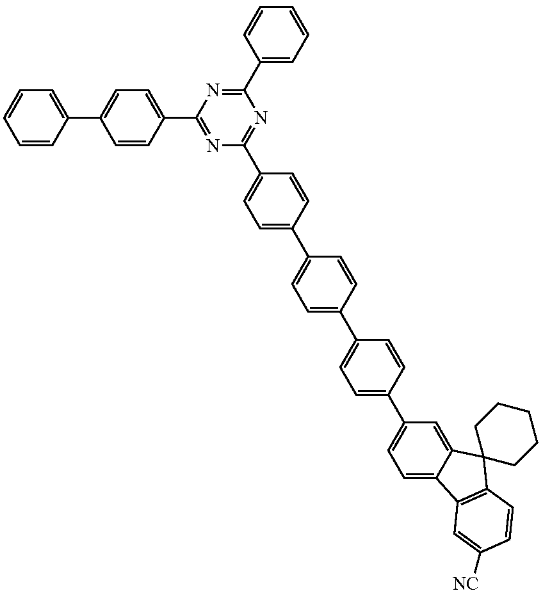
A-141
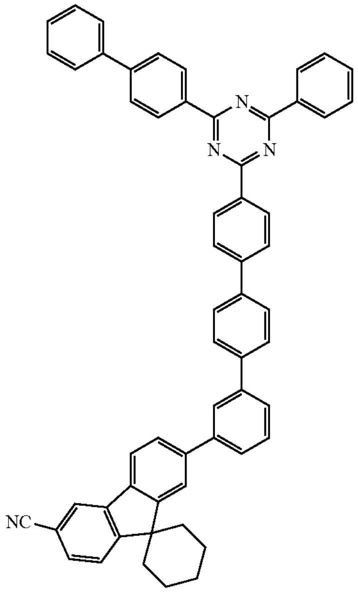

-continued
A-142
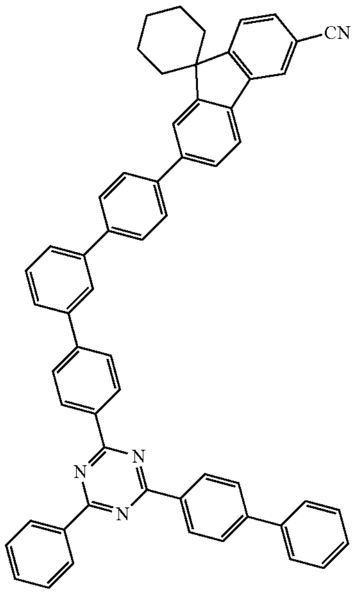
A-143
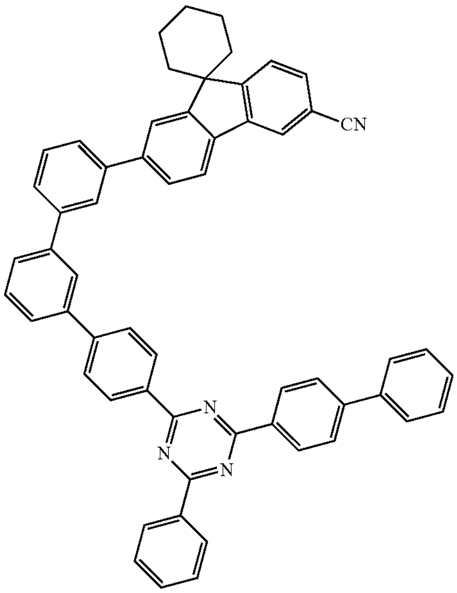
-continued
A-144
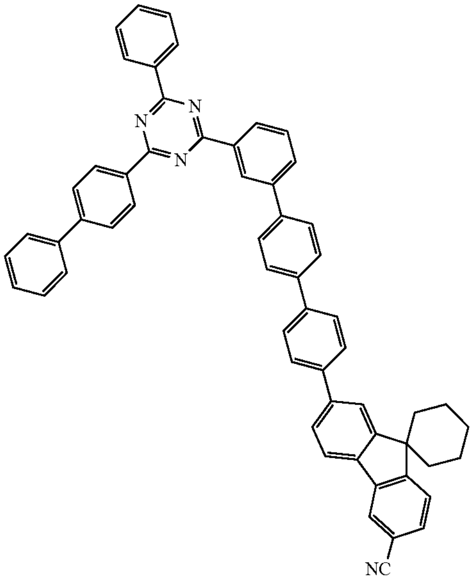
A-145
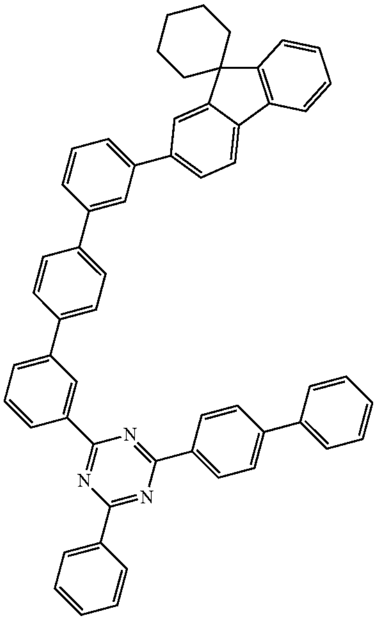

-continued
A-146
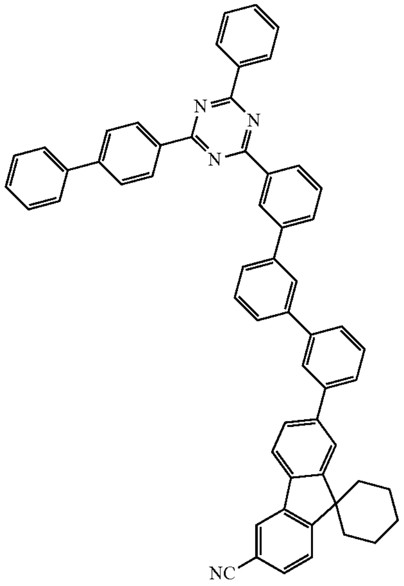
A-147
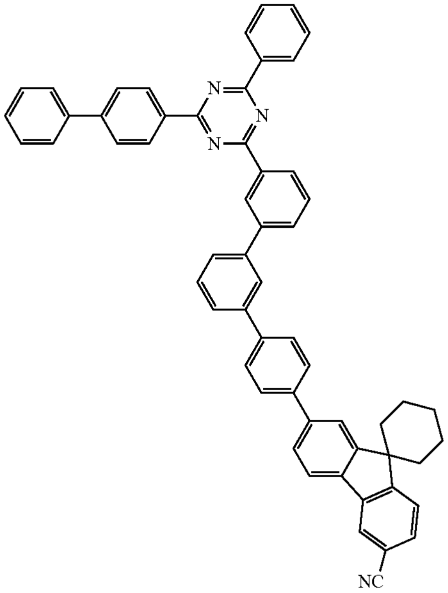
-continued
A-148
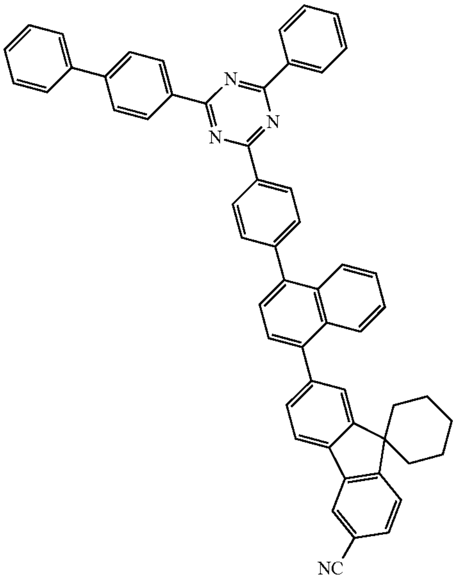
A-149
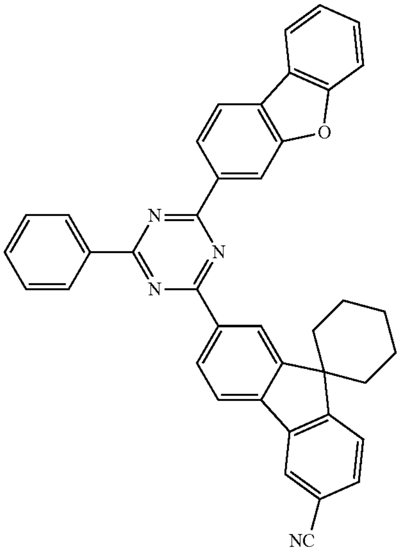

-continued
A-150
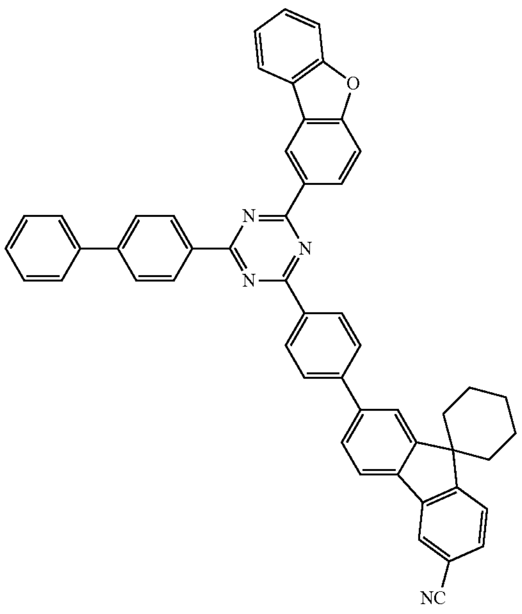
A-151
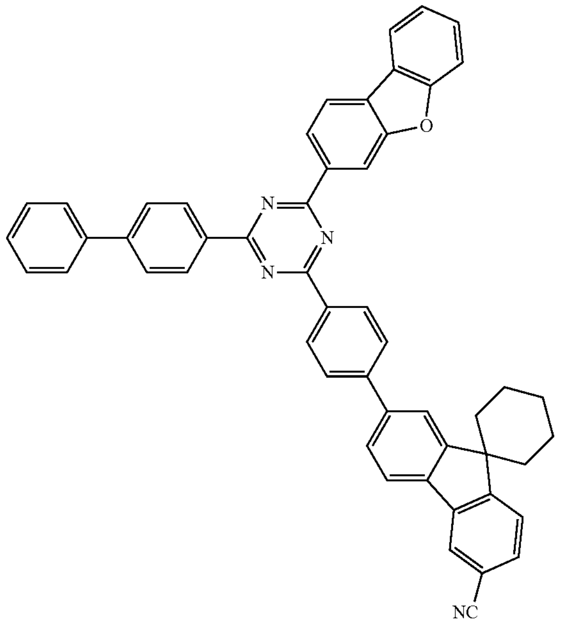
-continued
A-152
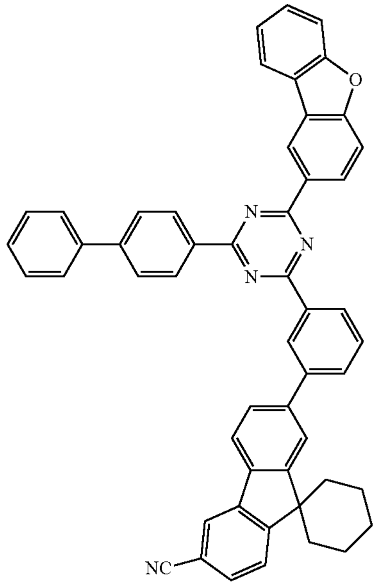
A-153
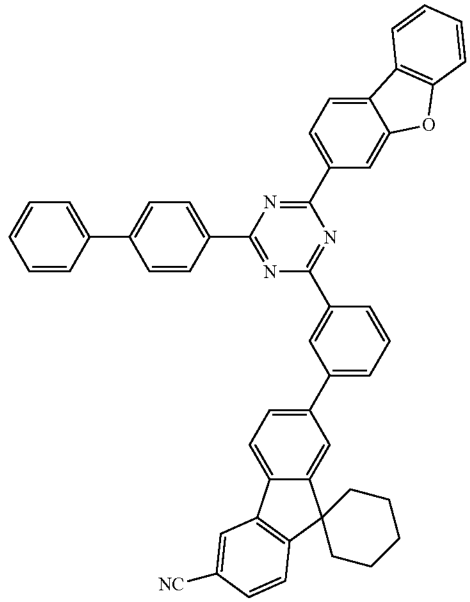

-continued
A-154
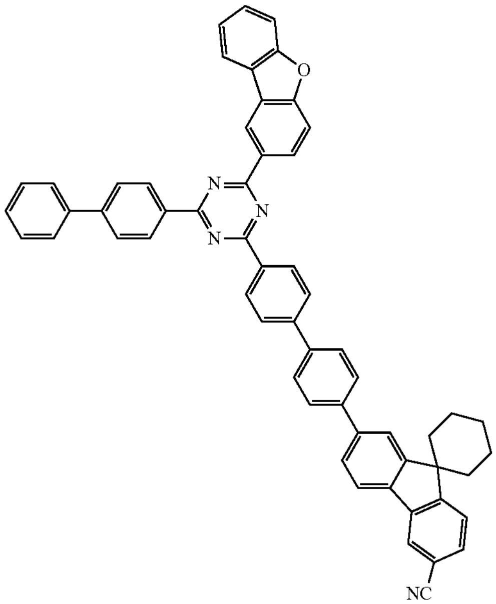
A-155
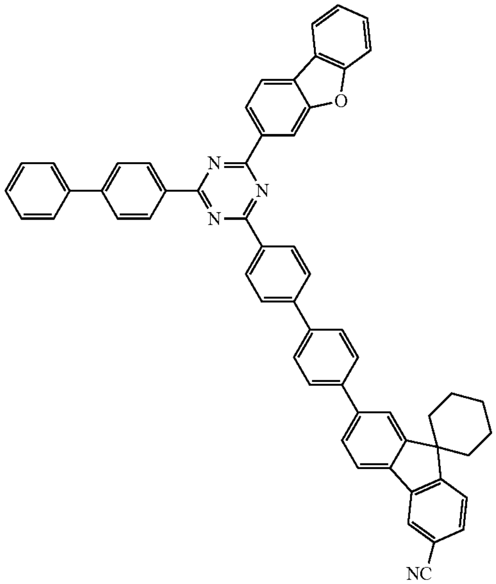
-continued
A-156
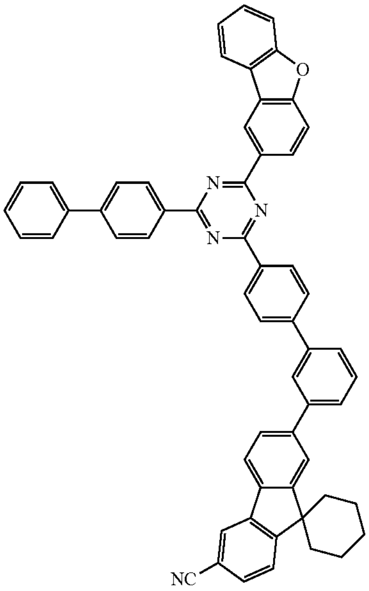
A-157
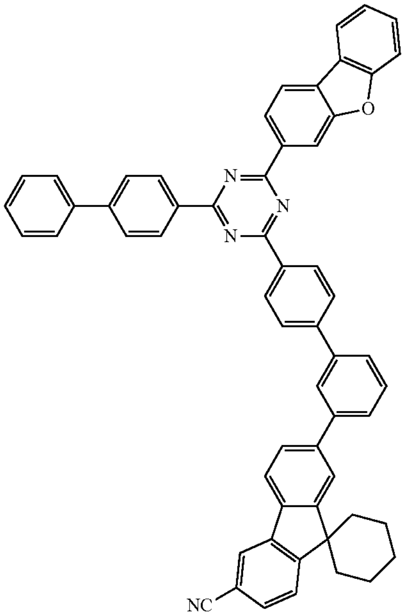

-continued
A-158
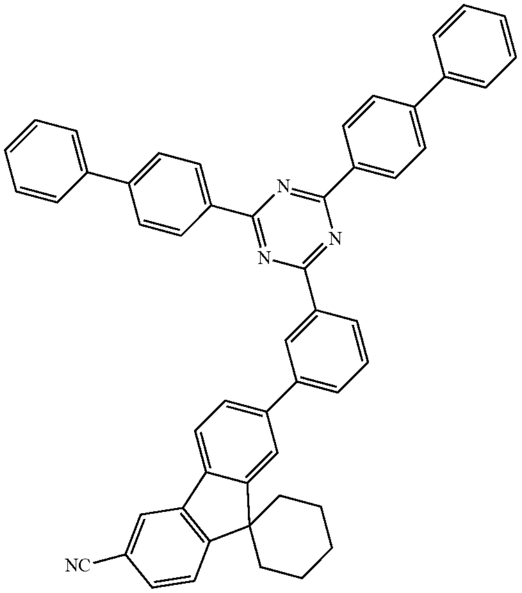
A-159
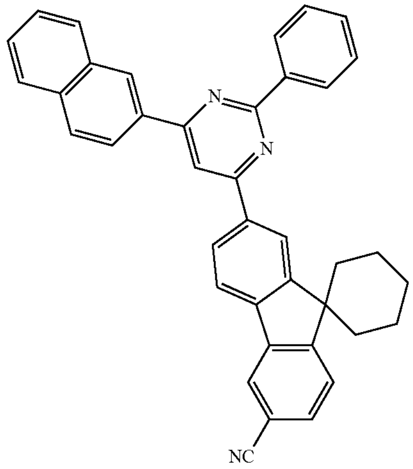
A-160
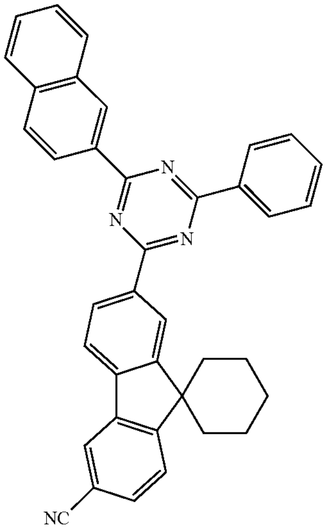
-continued
A-161
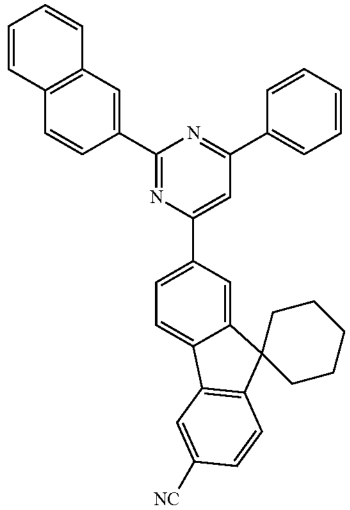
A-162
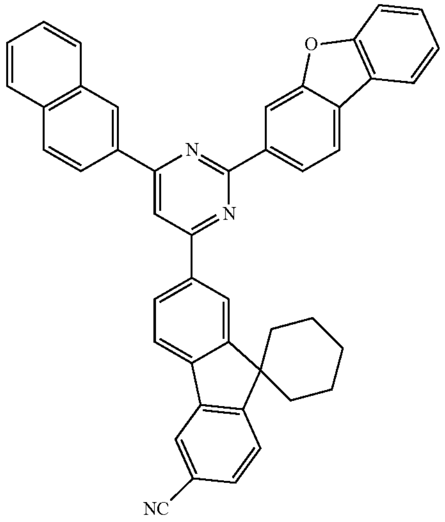
A-163
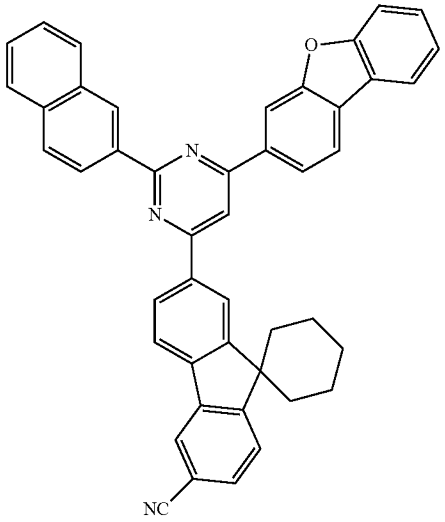

-continued
A-164
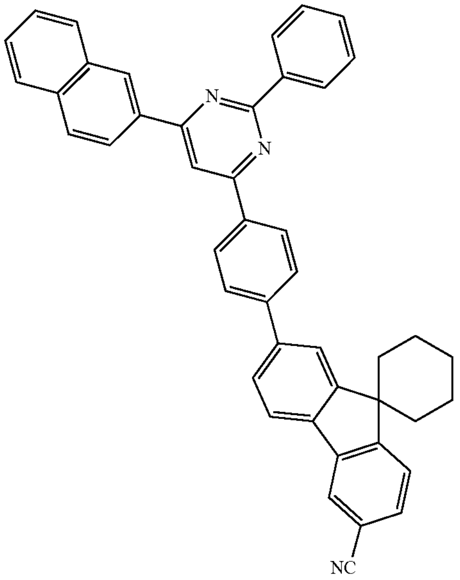
A-165
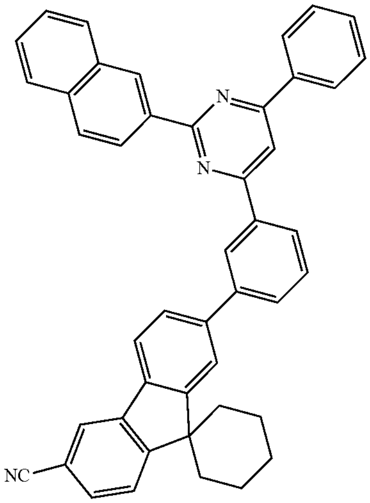
A-166
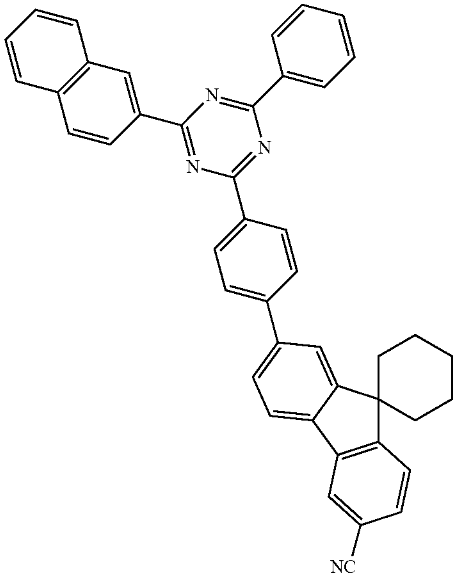
-continued
A-167
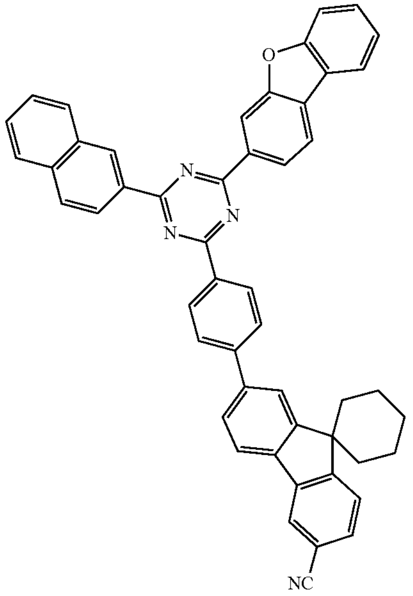
A-168
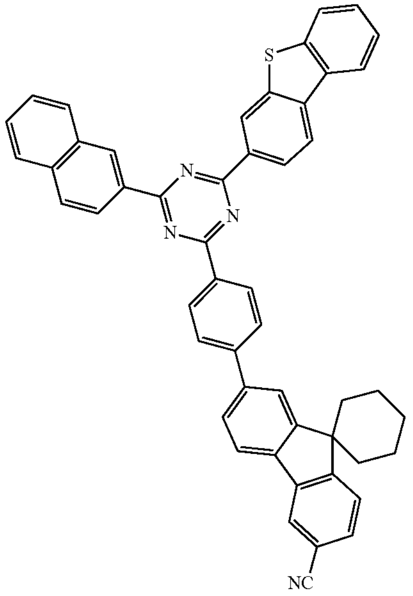

-continued
A-169
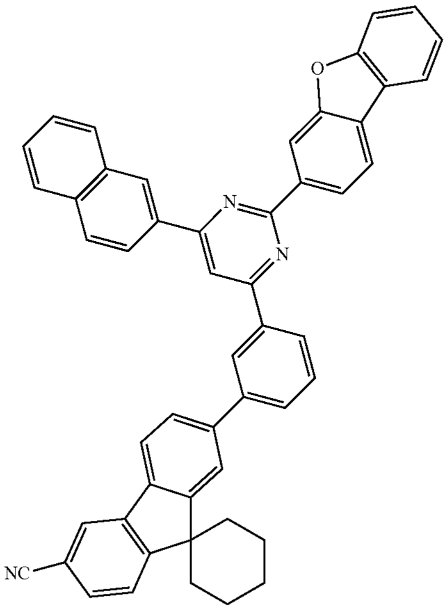
A-170
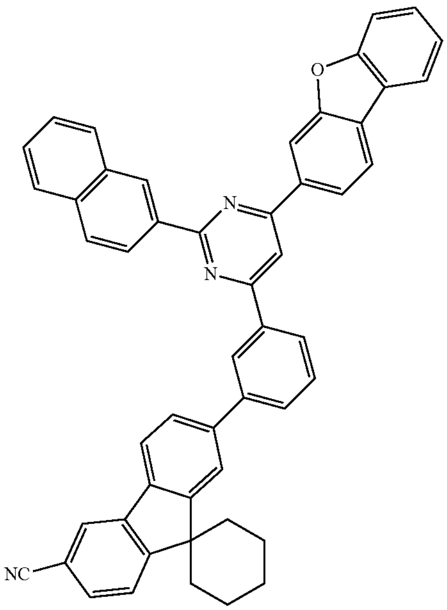
-continued
A-171
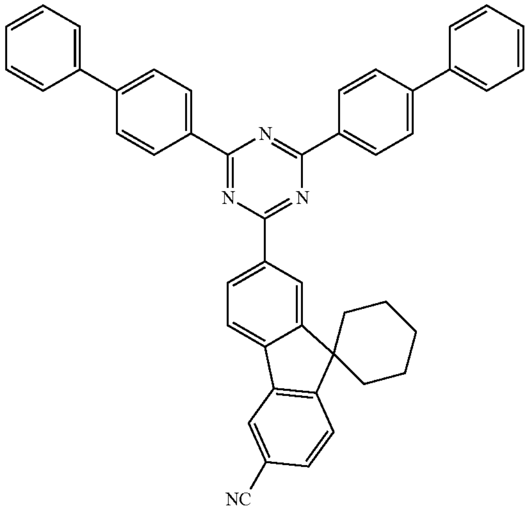
A-172
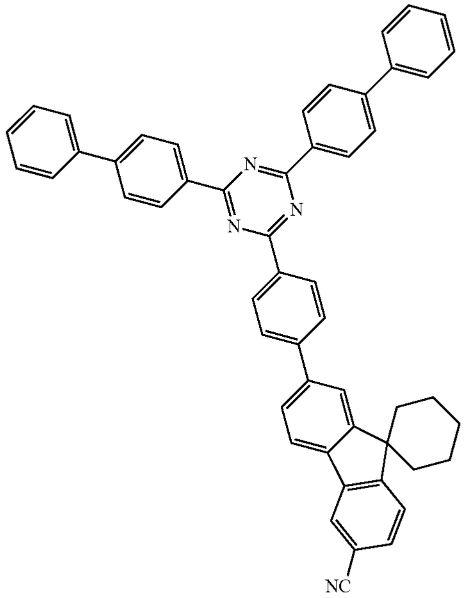

-continued
A-173
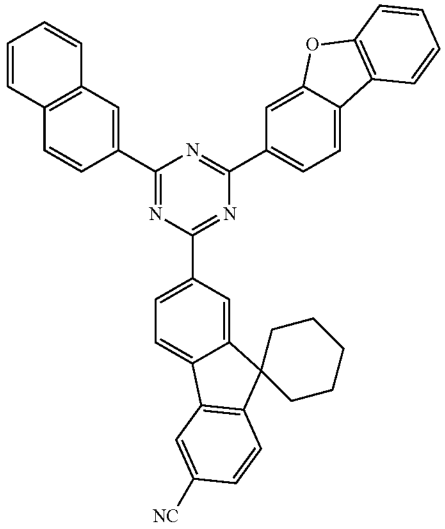
A-174
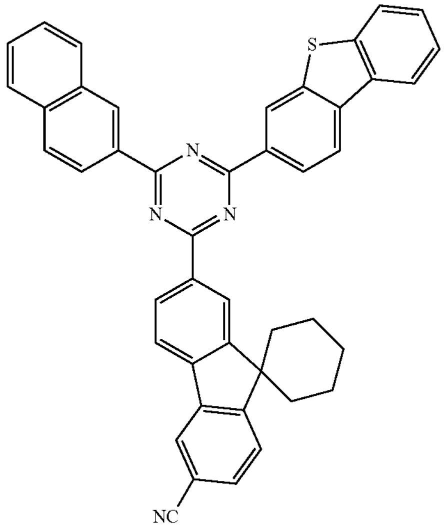
A-175
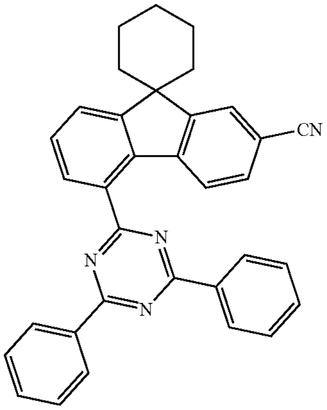
-continued
A-176
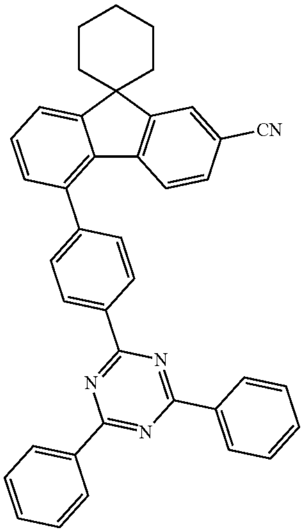
A-177
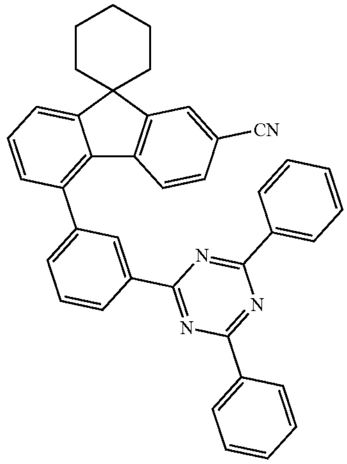
A-178
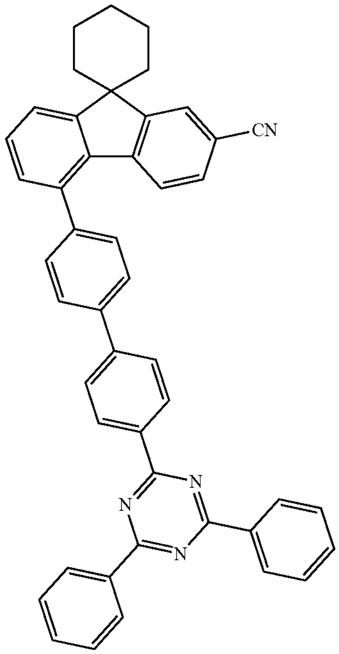

A-179
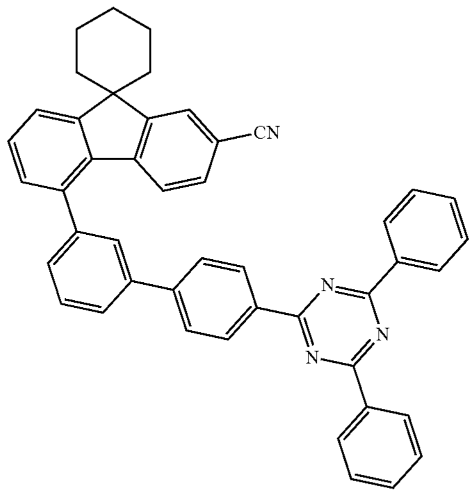
A-180
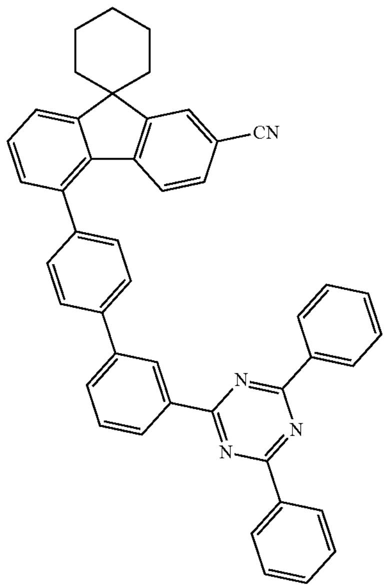
A-181
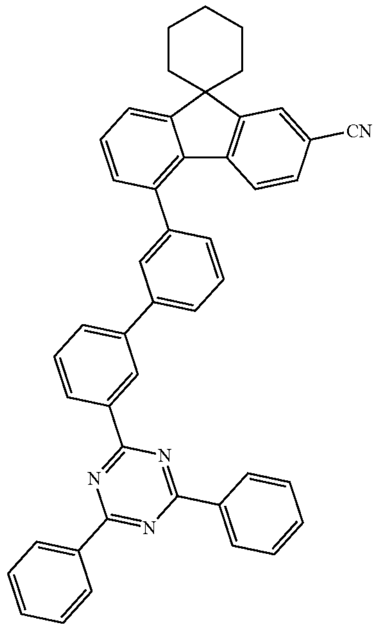
A-182
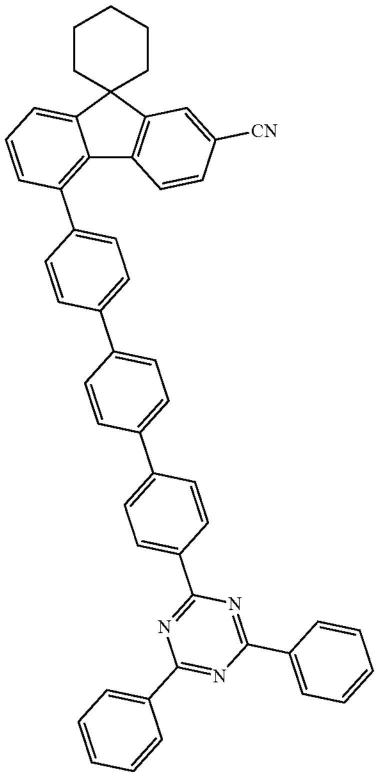

-continued
A-183
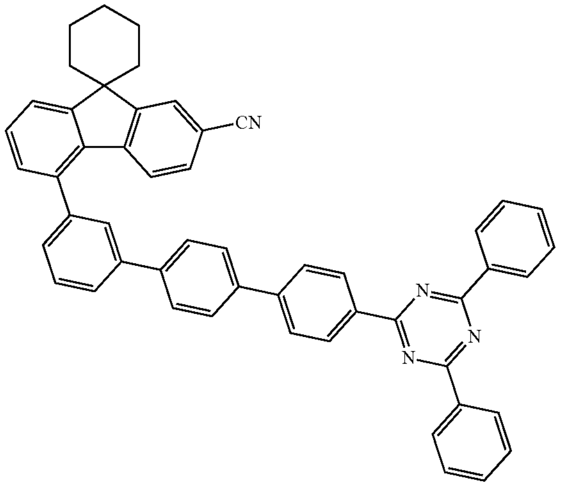
A-184
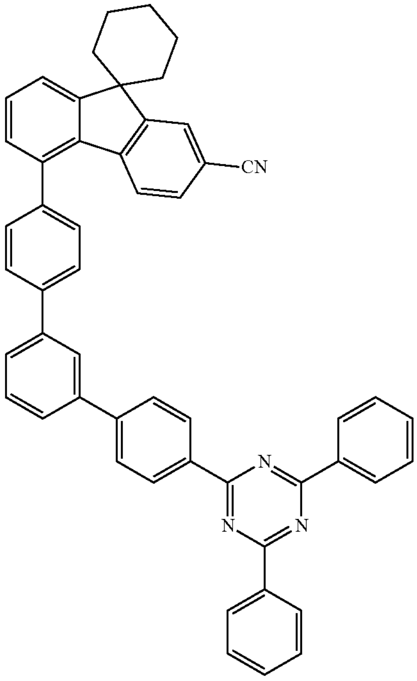
A-185
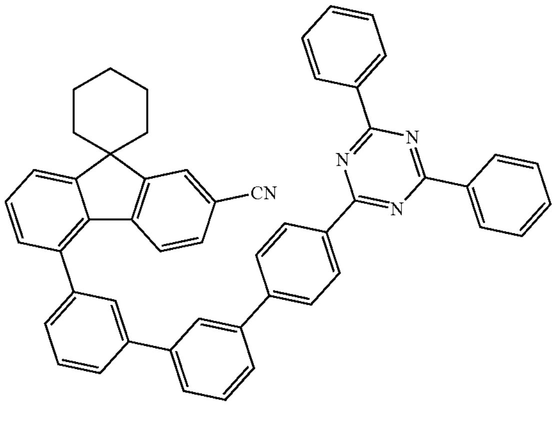
-continued
A-186
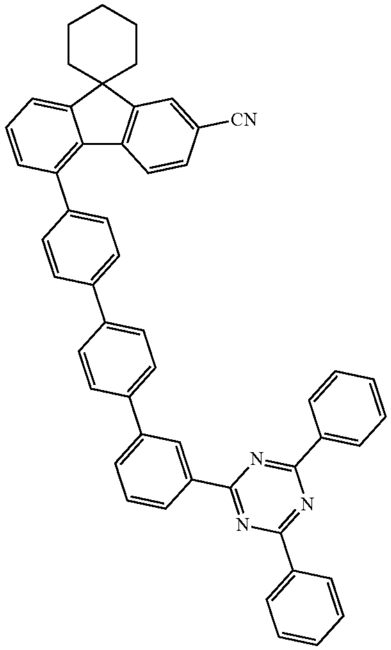
A-187
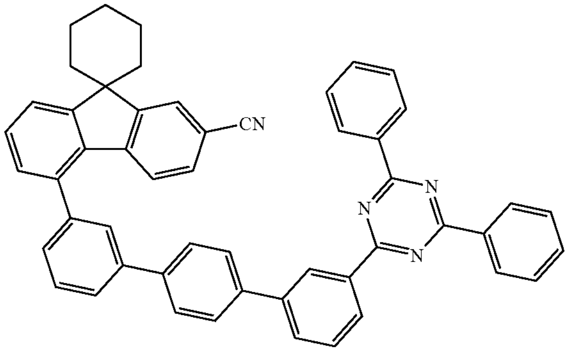
A-188
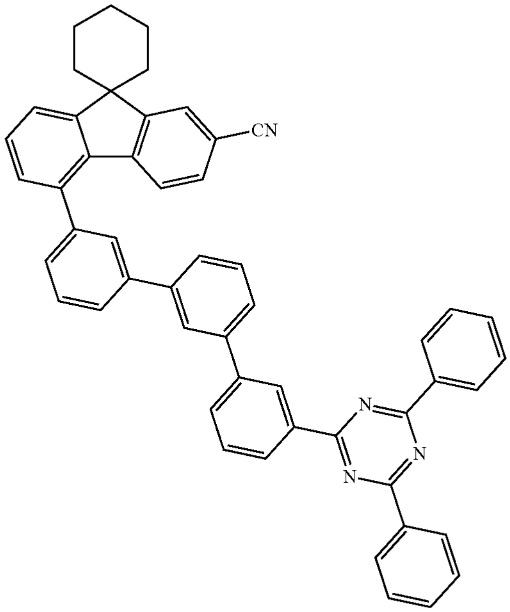

-continued
A-189
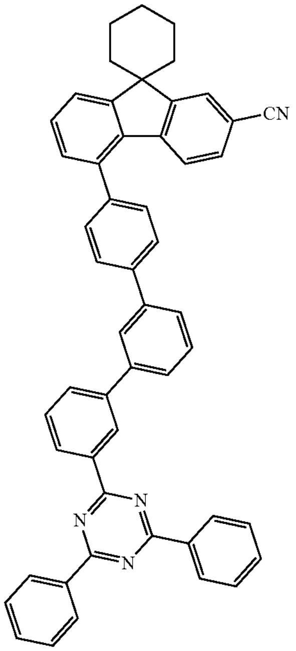
A-190
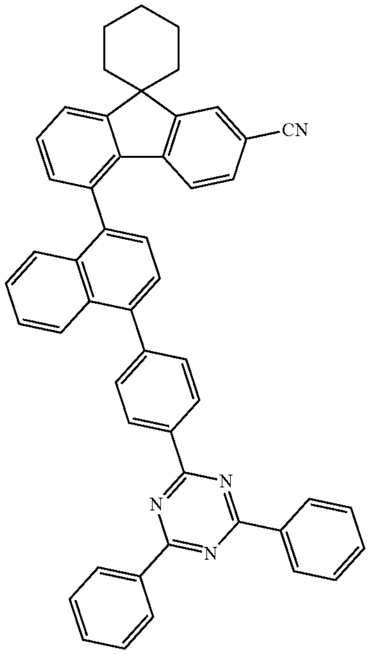
-continued
A-191
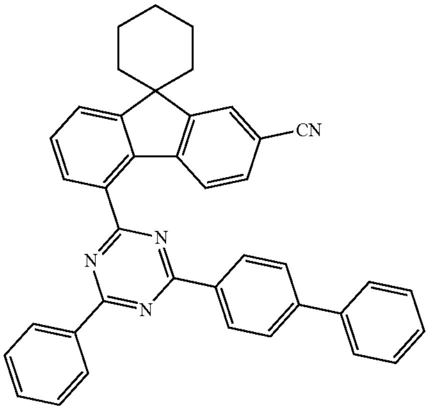
A-192
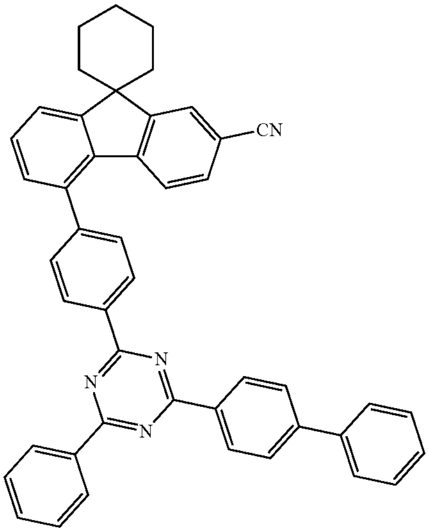
A-193
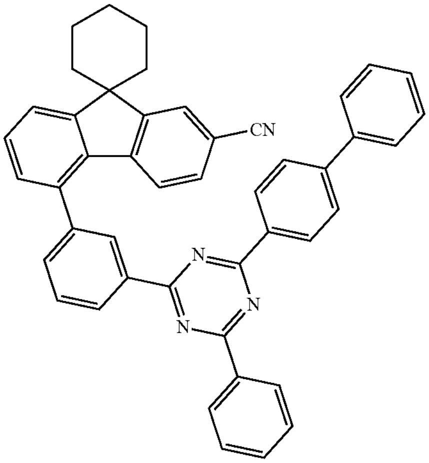

-continued
A-194
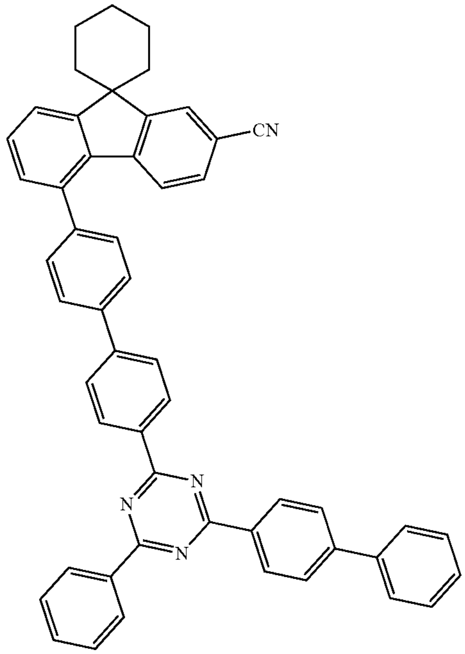
A-195
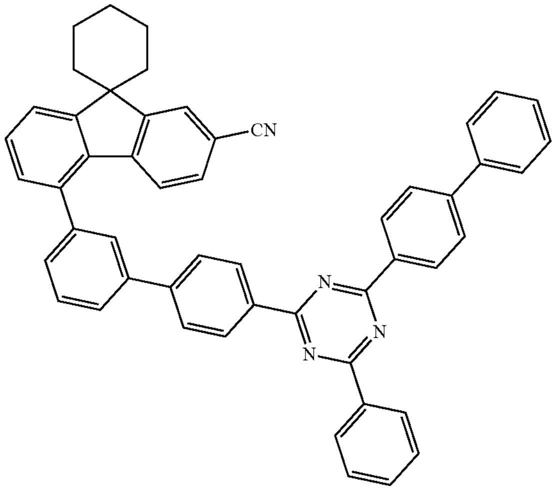
-continued
A-196
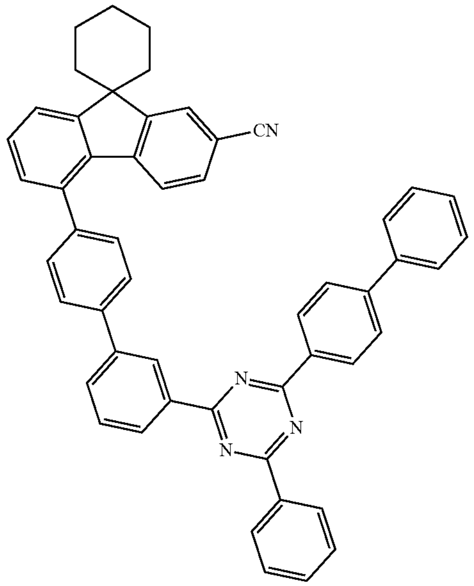
A-197
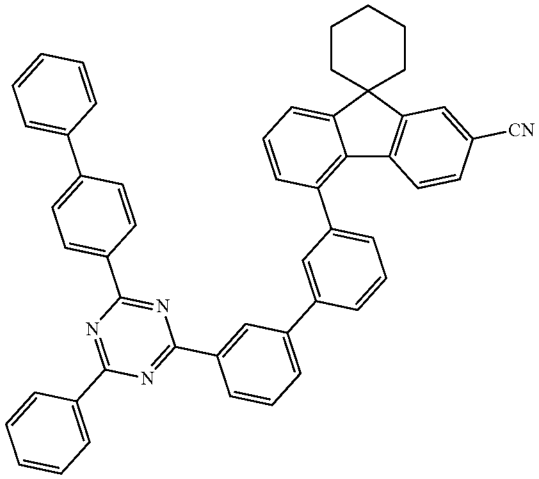

A-198
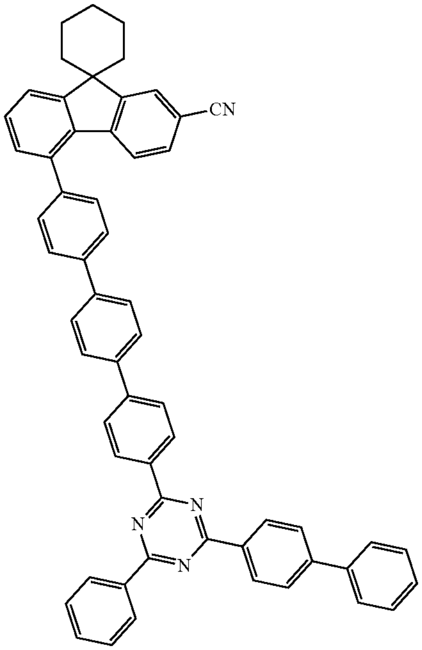
A-199
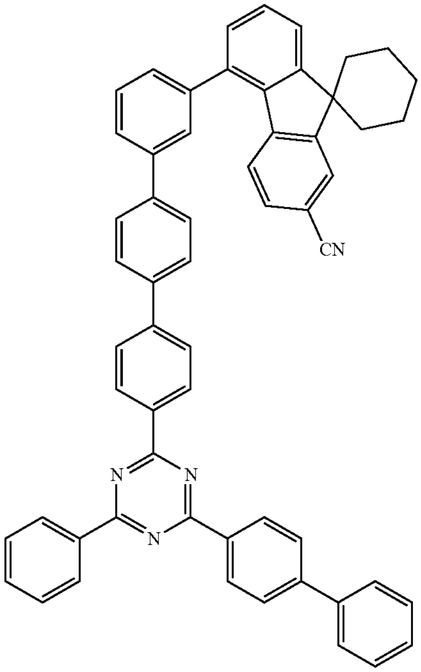
A-200
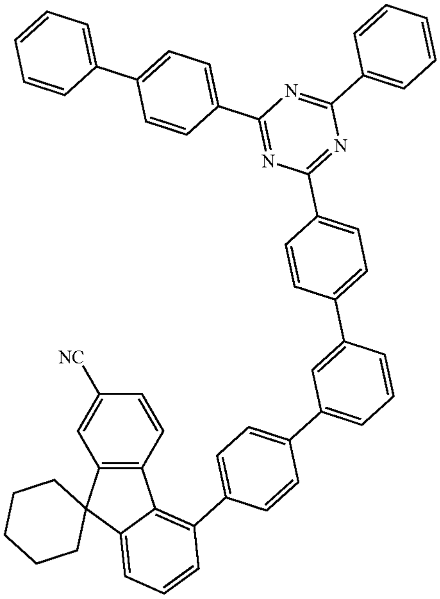
A-201
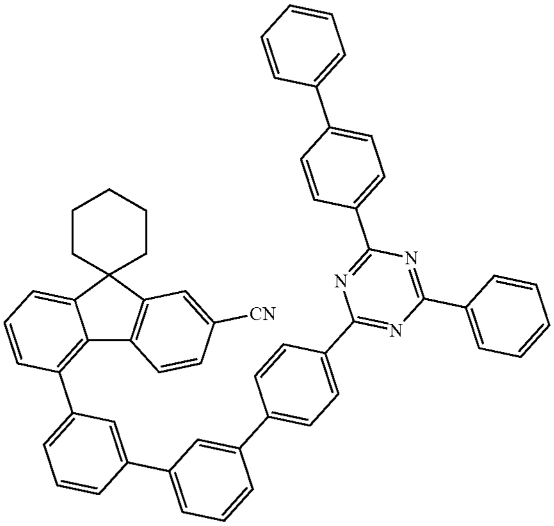

-continued
A-202
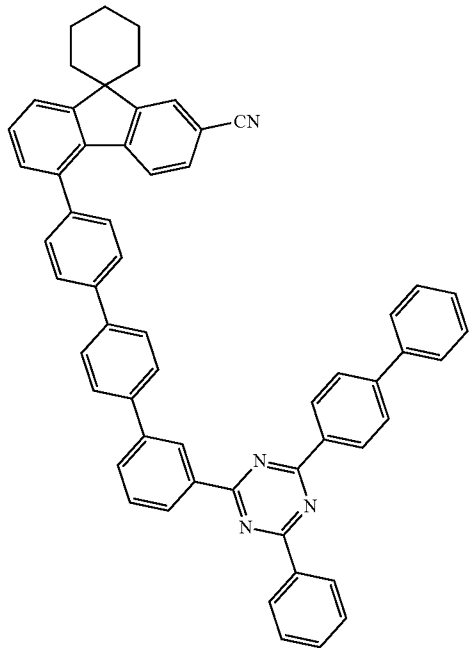
A-203
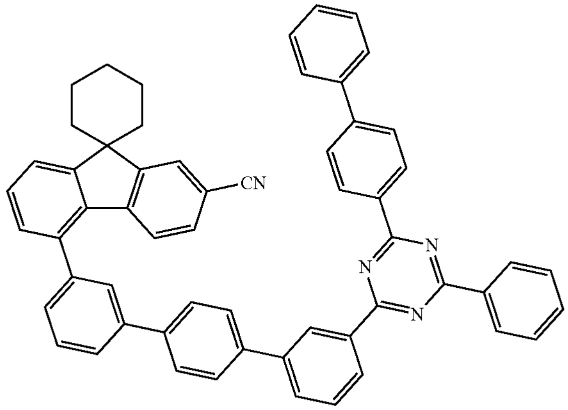
-continued
A-204
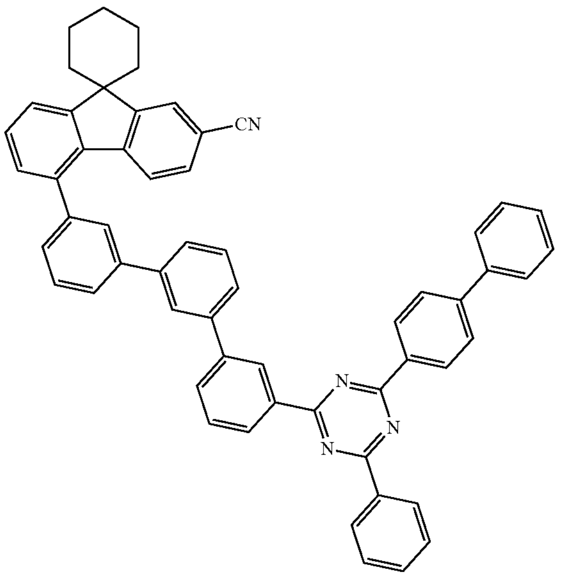
A-205
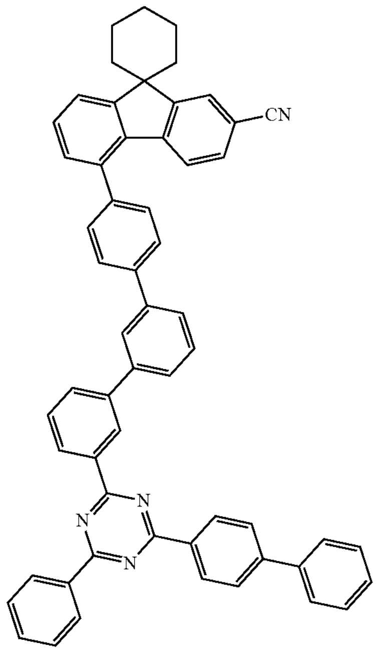

-continued
A-206
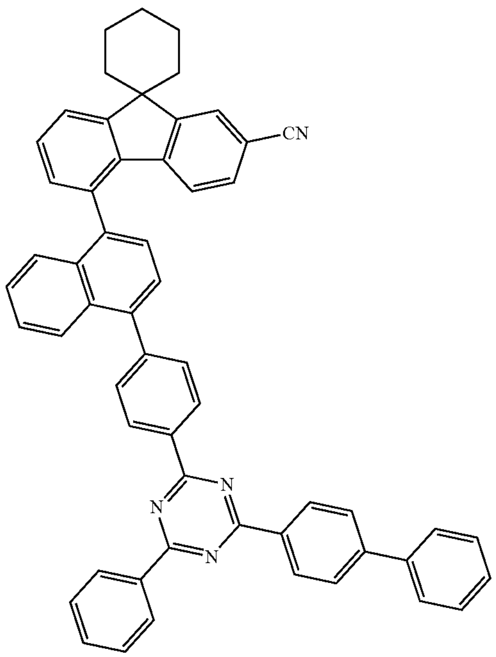
A-207
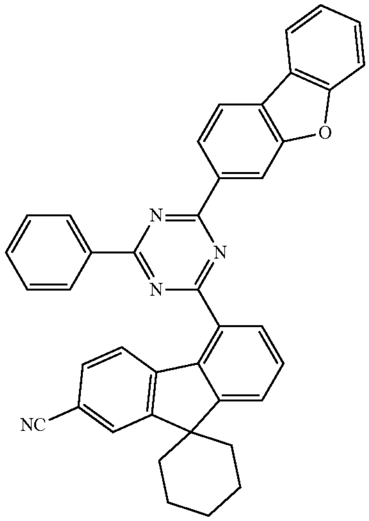
-continued
A-208
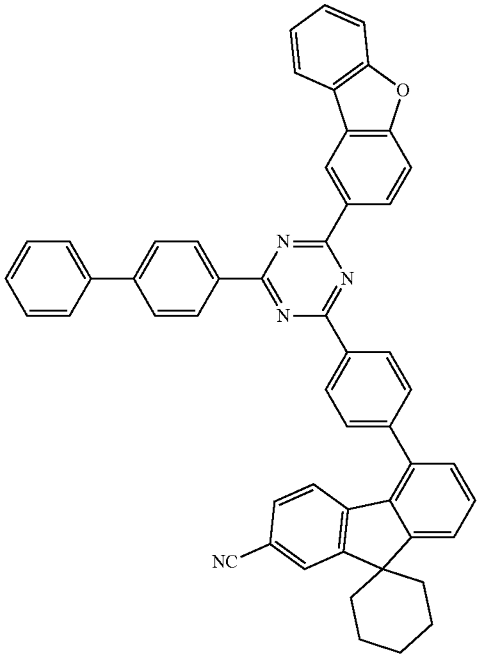
A-209
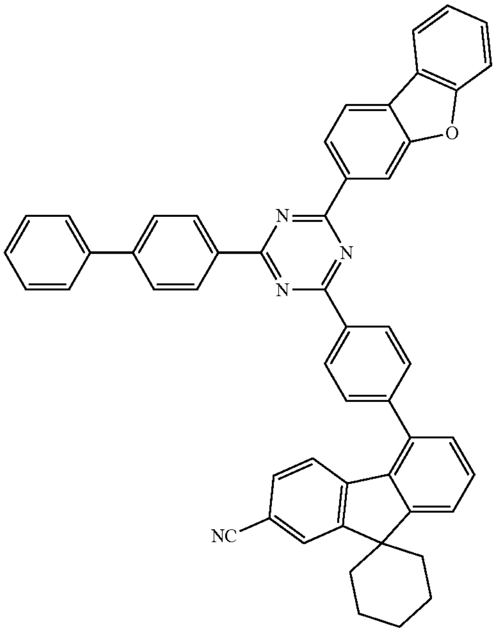

-continued
A-210
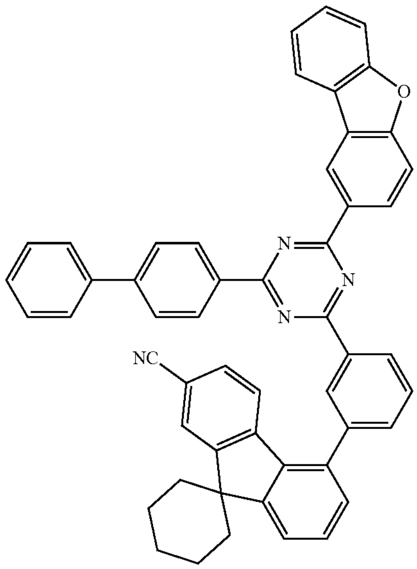
A-211
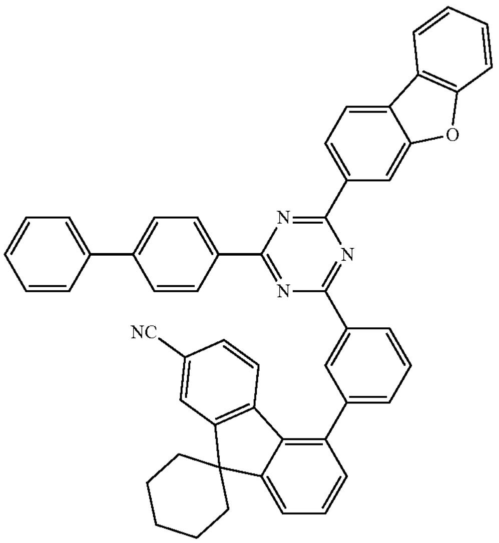
-continued
A-212
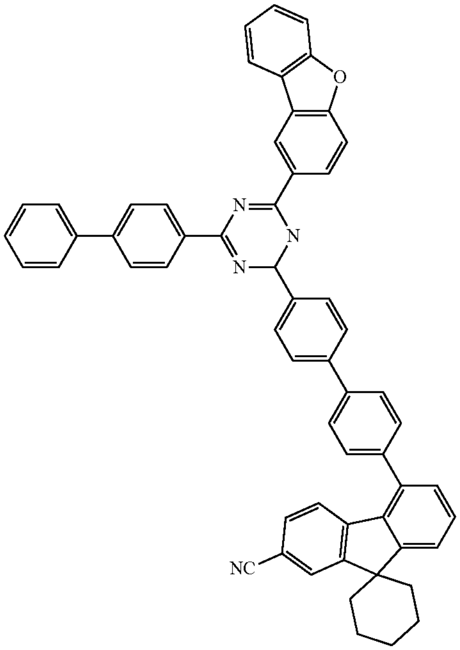
A-213
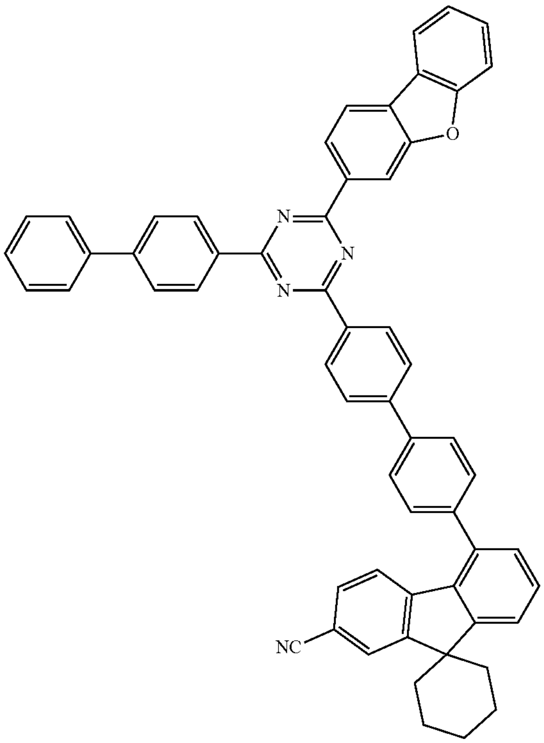

-continued
A-214
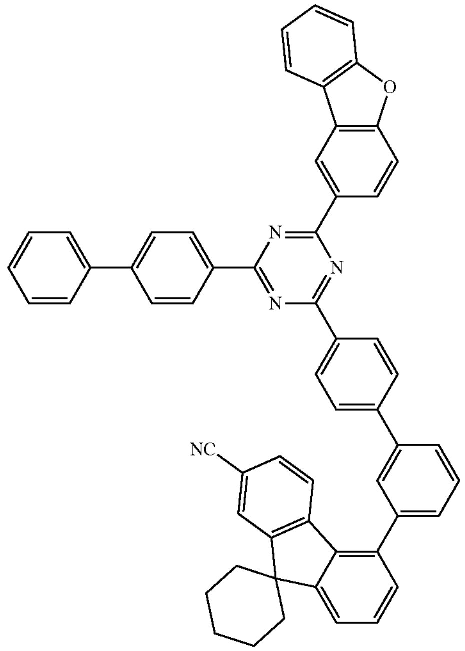
A-215
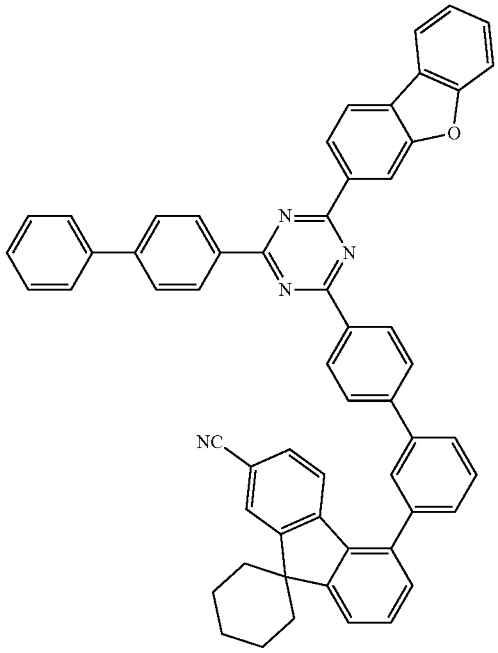
-continued
A-216
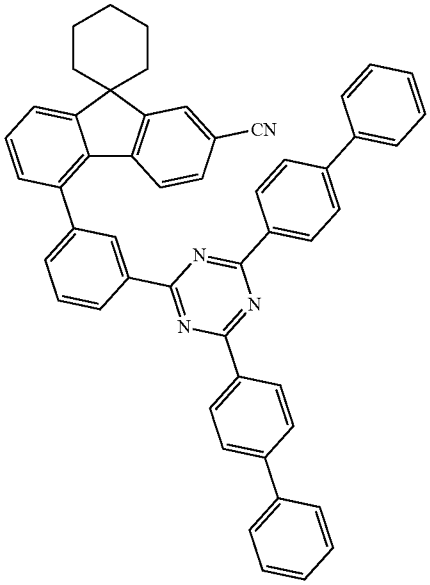
A-217
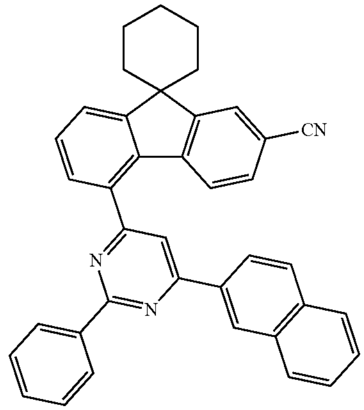
A-218
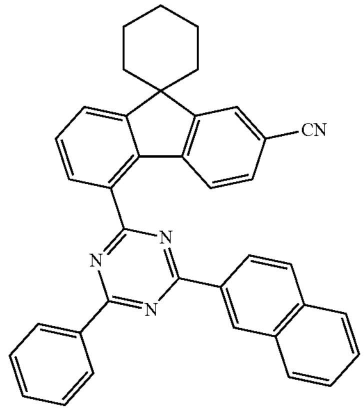

-continued
A-219
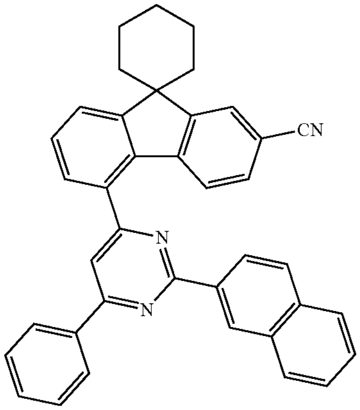
A-220
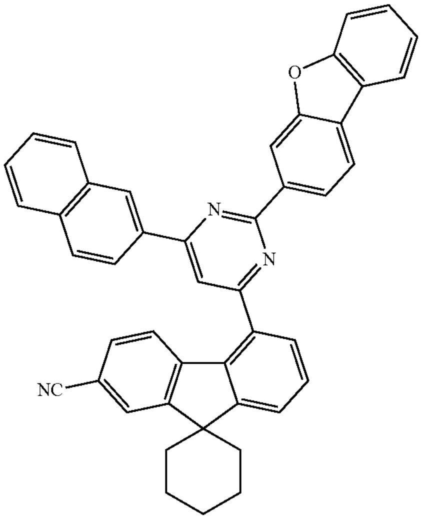
A-221
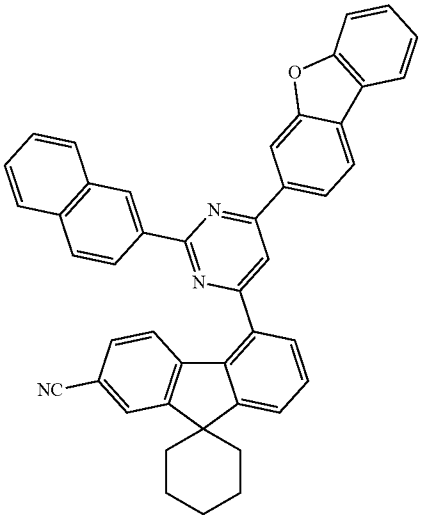
-continued
A-222
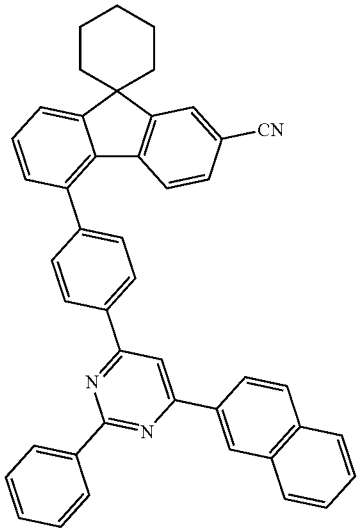
A-223
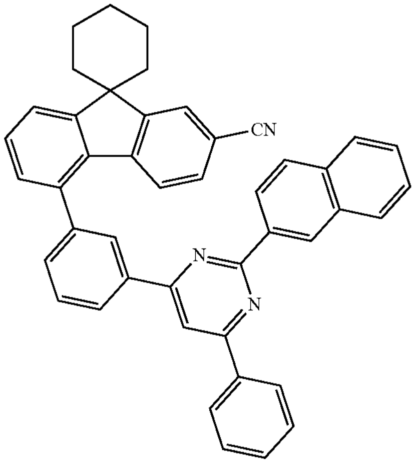
A-224
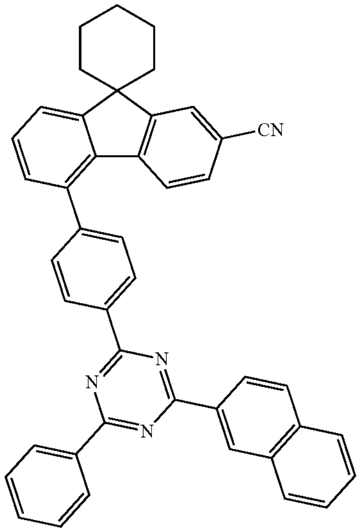

-continued
A-225
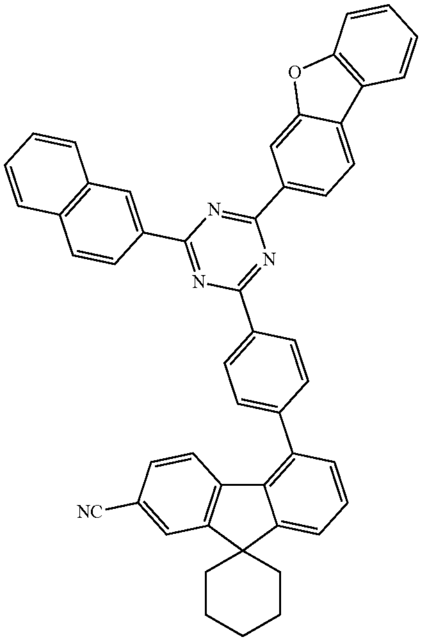
A-226
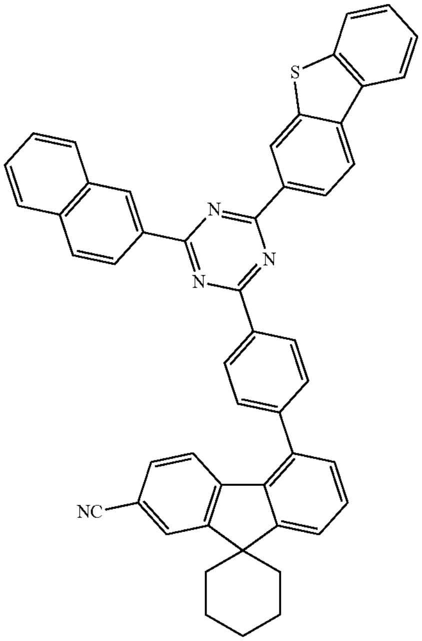
-continued
A-227
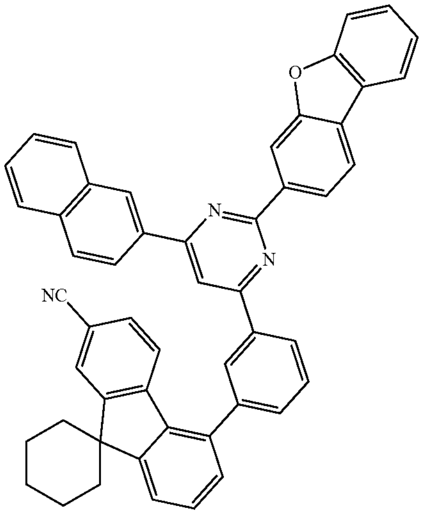
A-228
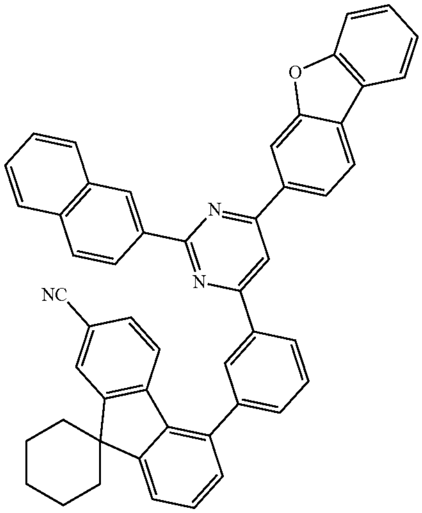
A-229
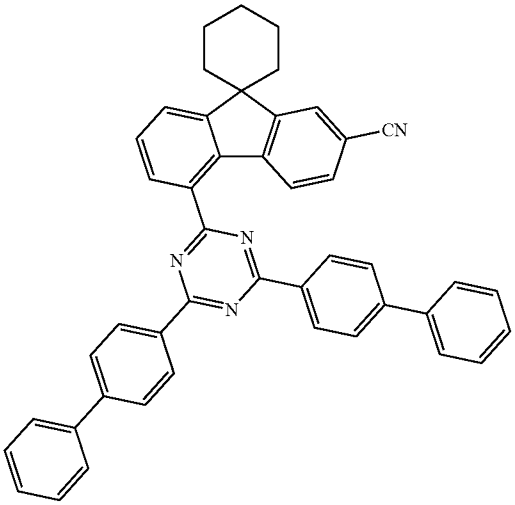

-continued
A-230
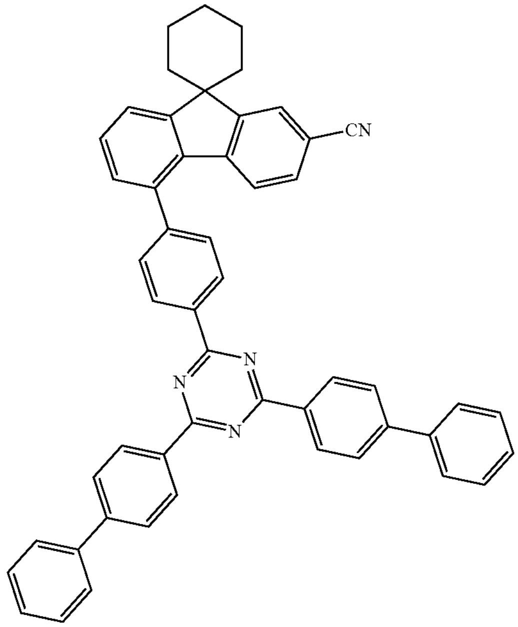
A-231
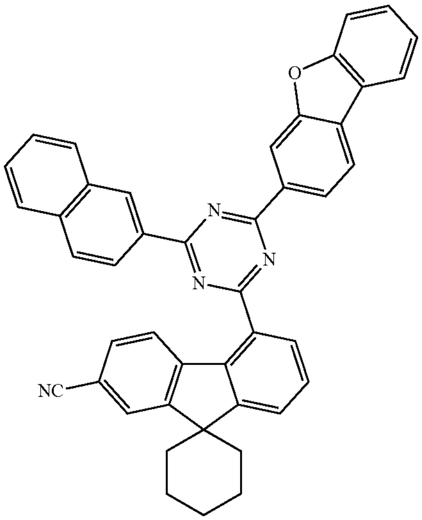
-continued
A-232
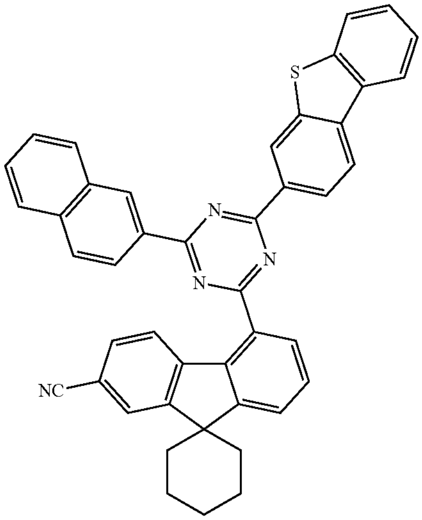
B-1
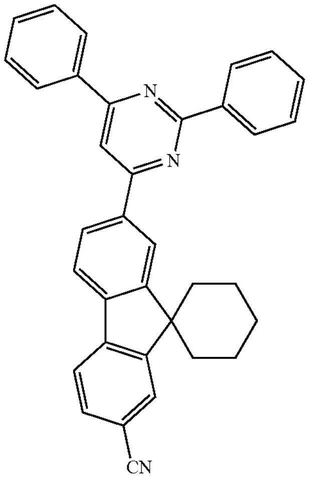
B-2
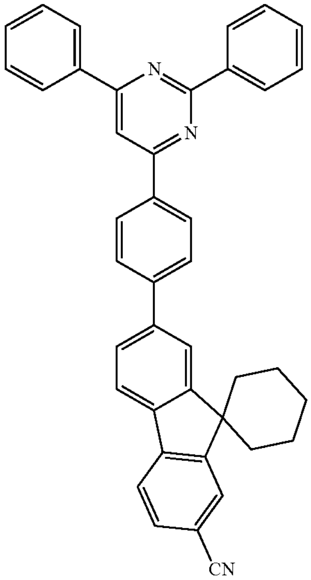

-continued
B-3
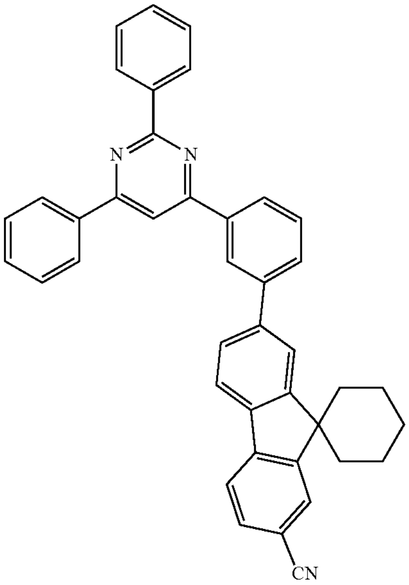
B-4
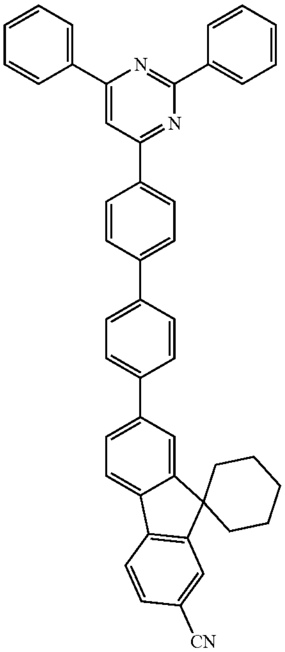
-continued
B-5
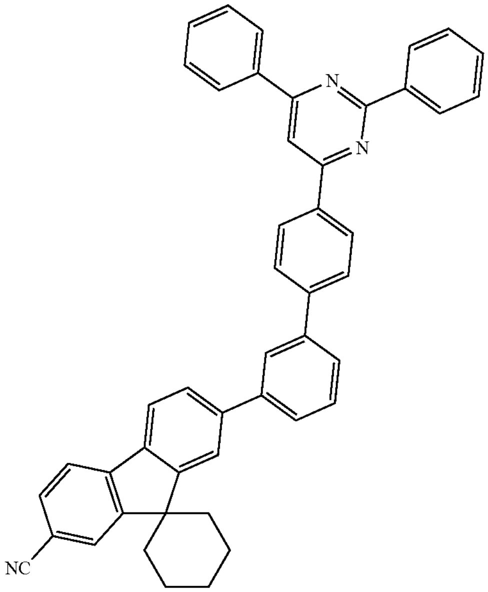
B-6
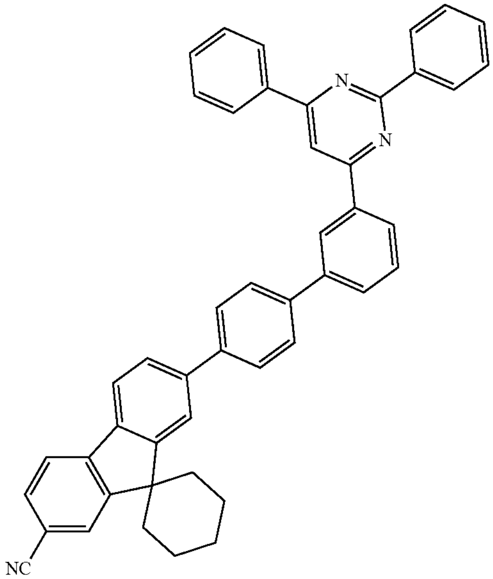

-continued
B-7
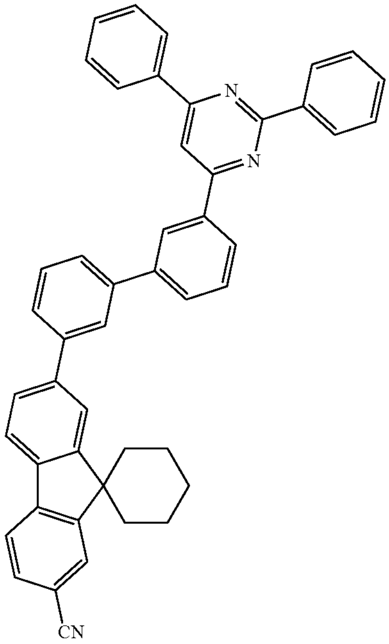
B-8
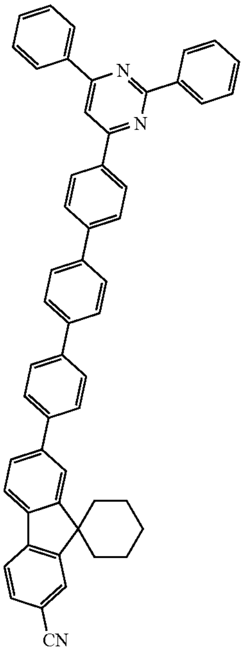
-continued
B-9
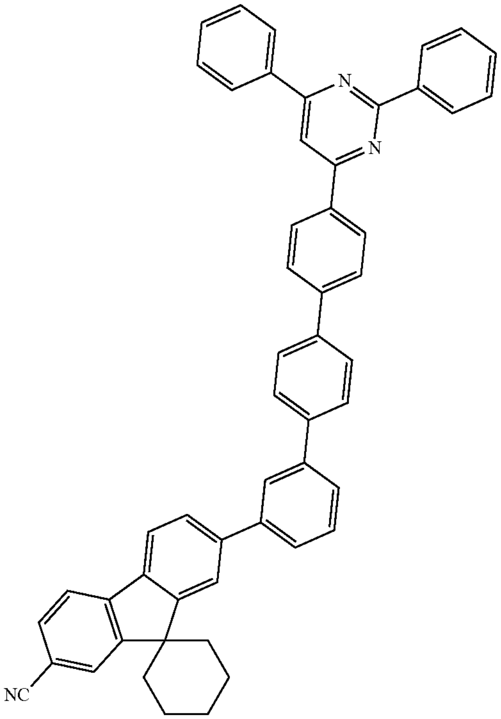
B-10
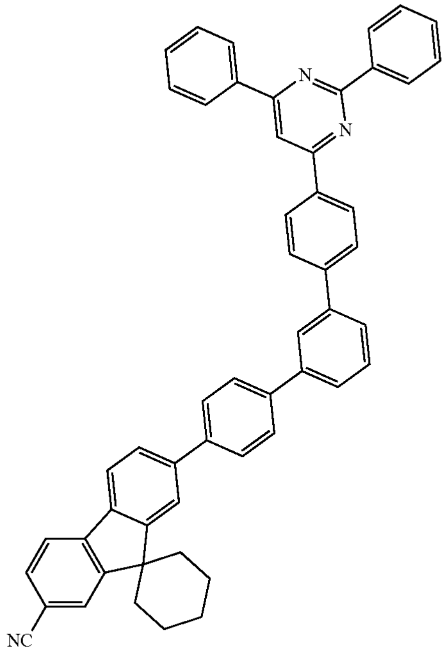

-continued
B-11
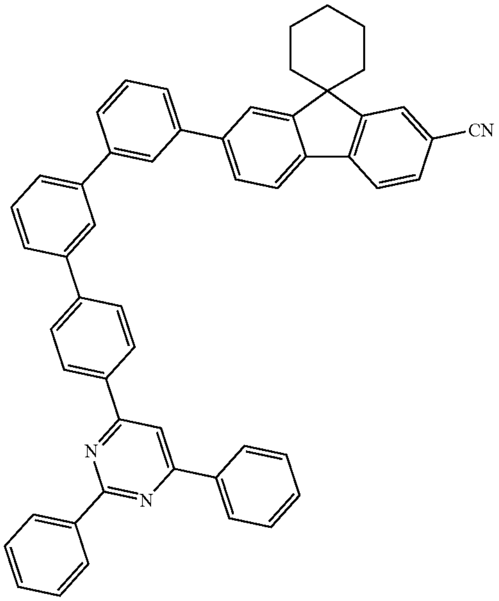
B-12
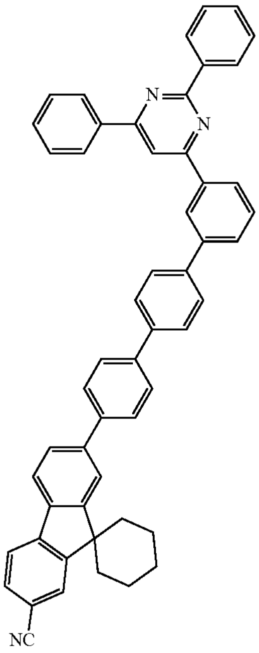
-continued
B-13
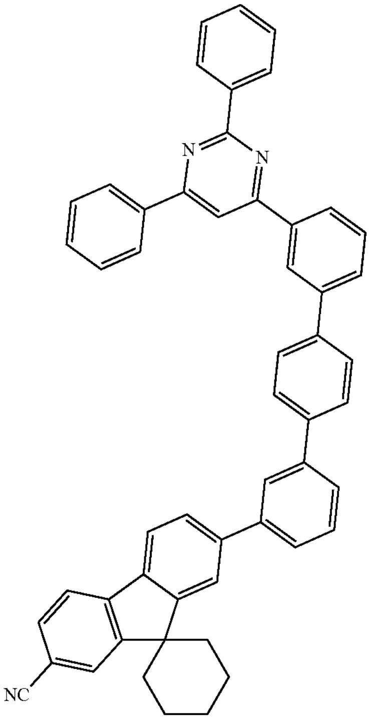
B-14
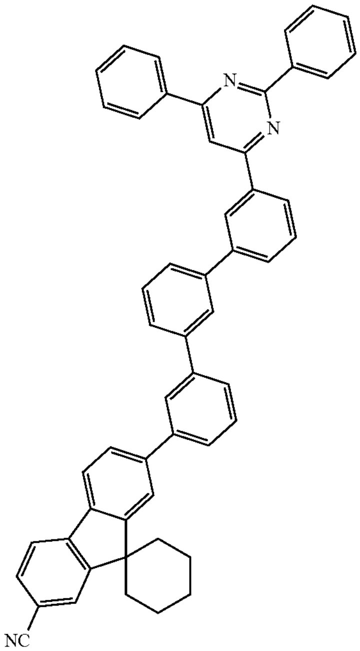

-continued
B-15
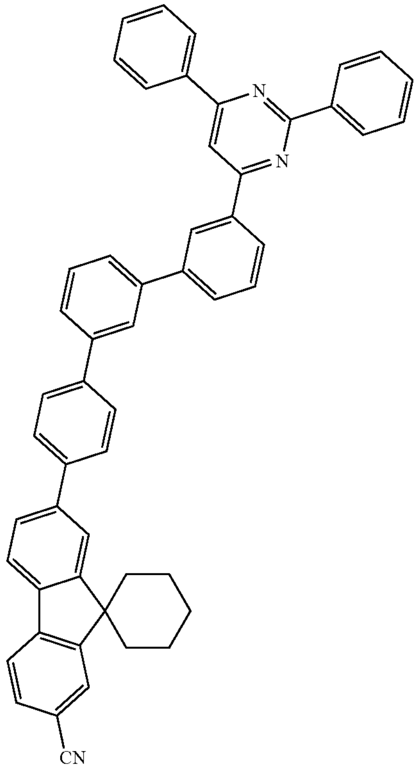
B-16
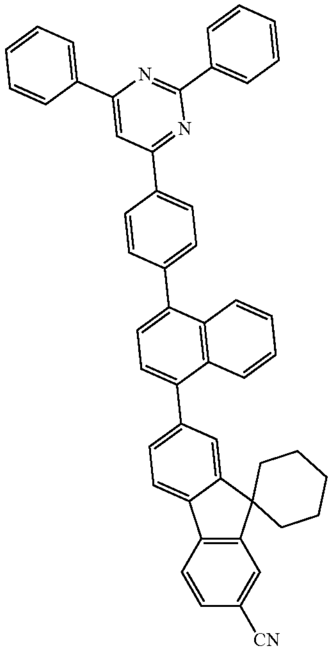
-continued
B-17
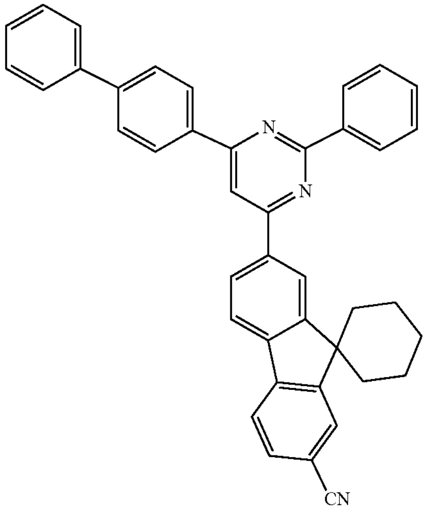
B-18
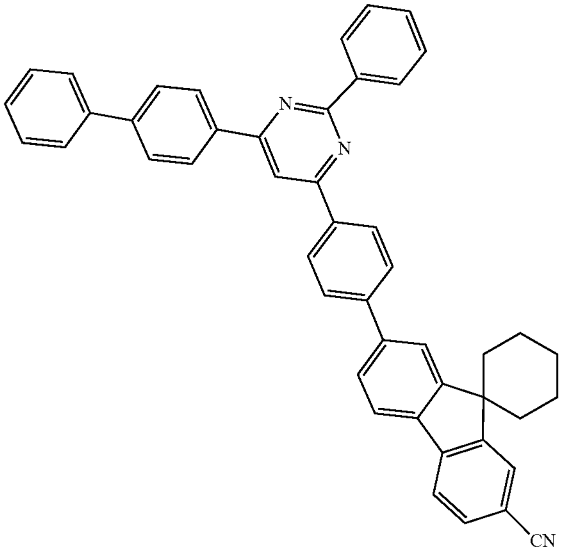
B-19
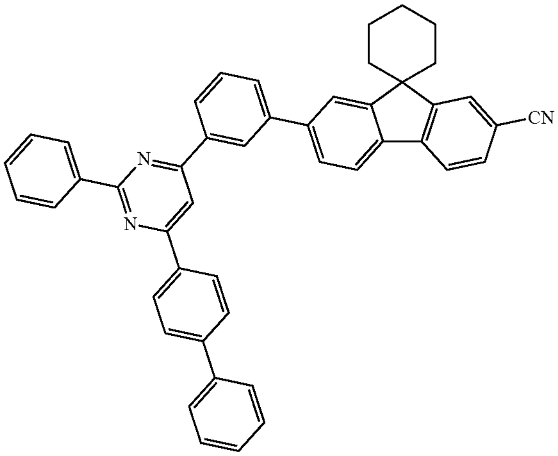

-continued
B-20
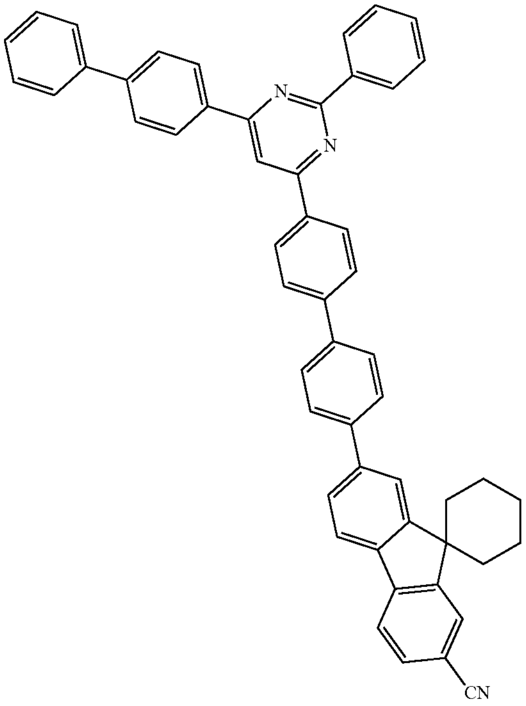
B-21
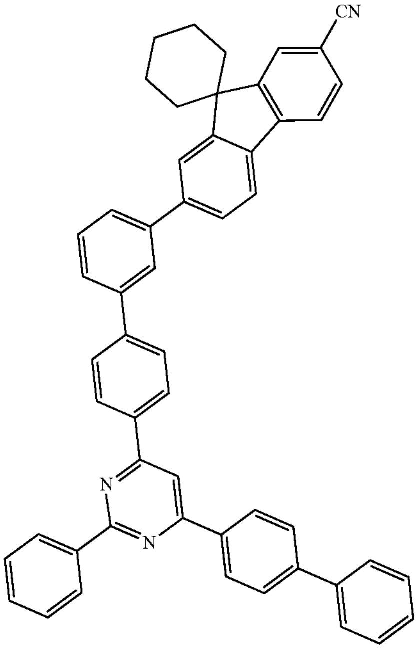
-continued
B-22
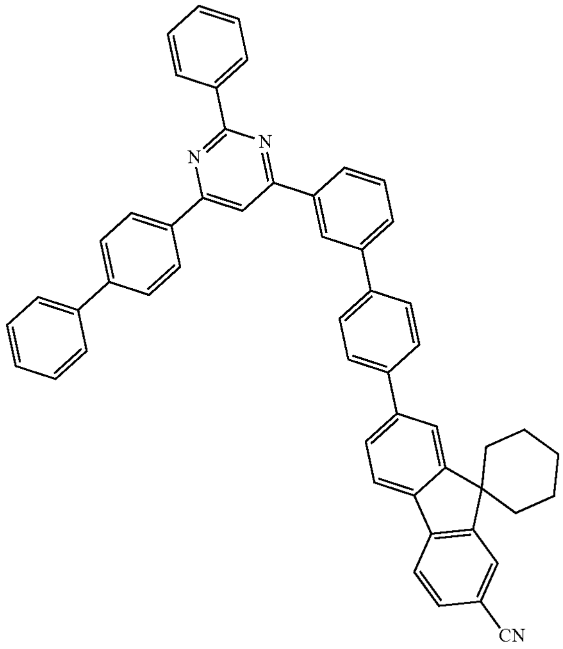
B-23
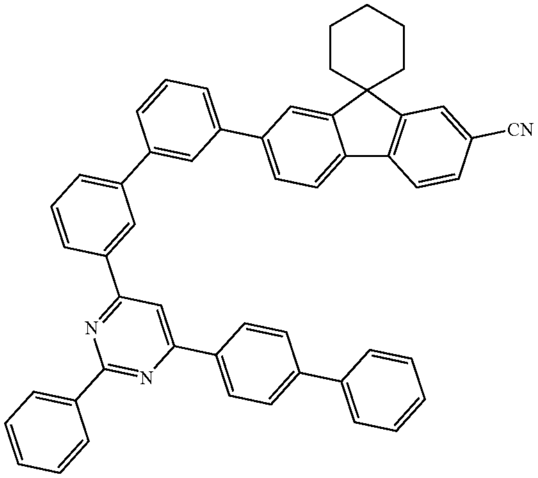

-continued
B-24
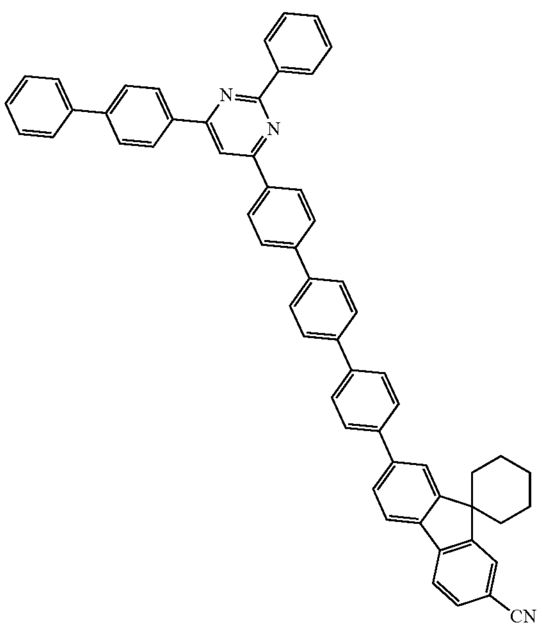
-continued
B-26
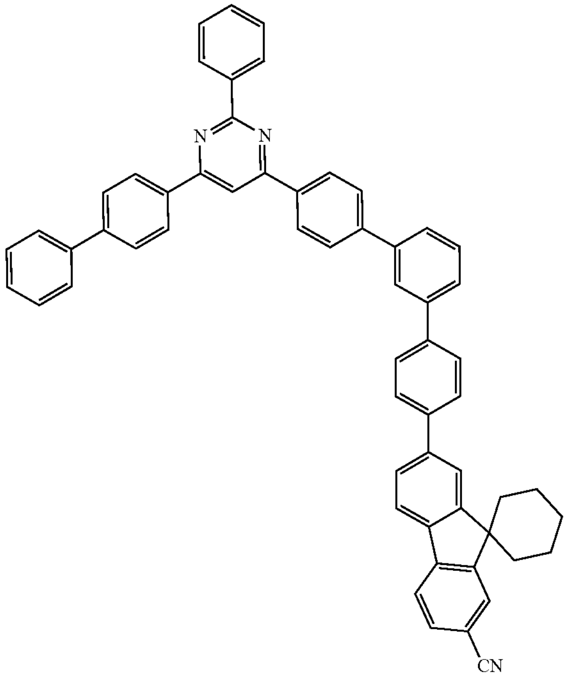
B-25
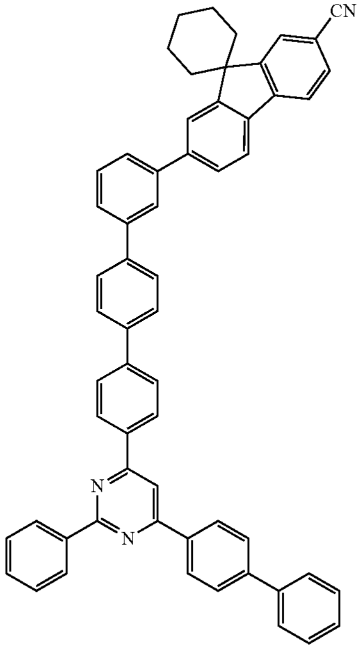
B-27
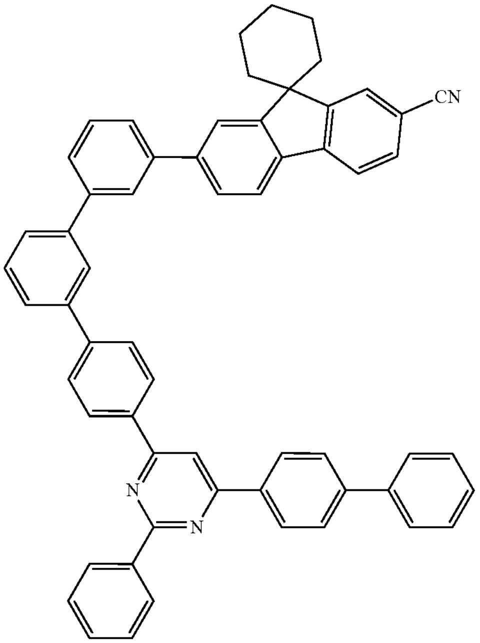

-continued
B-28
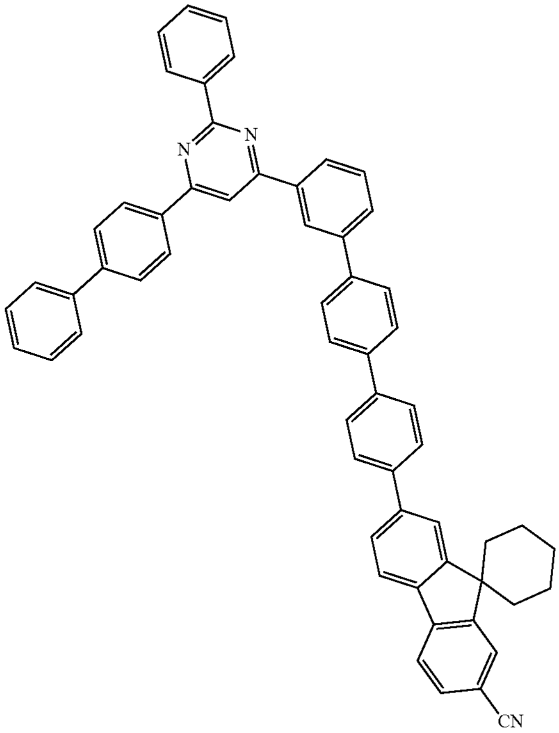
B-29
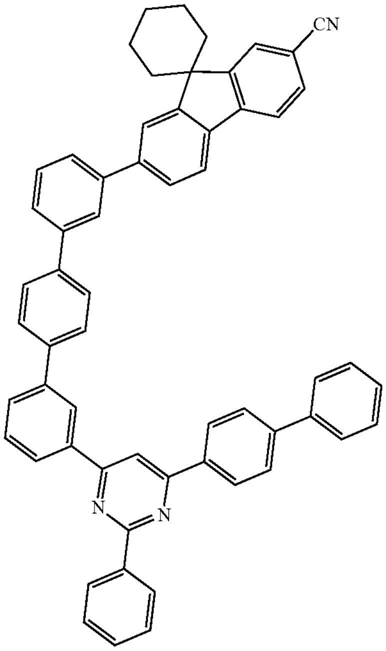
-continued
B-30
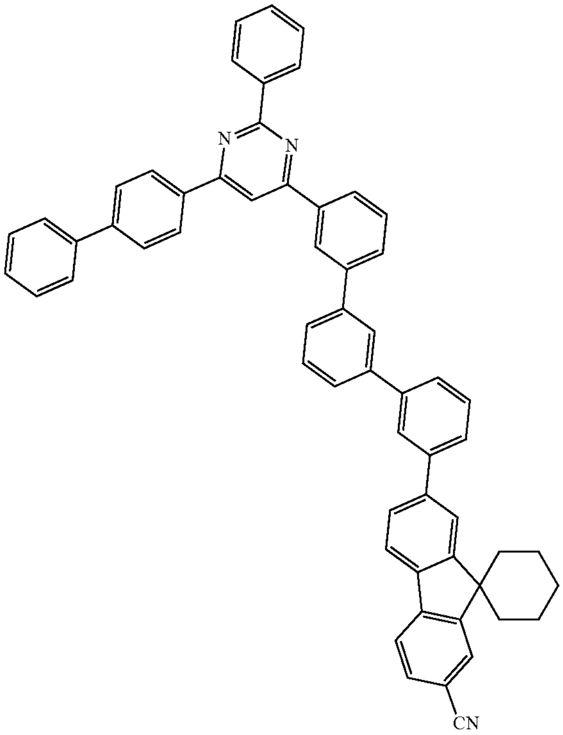
B-31
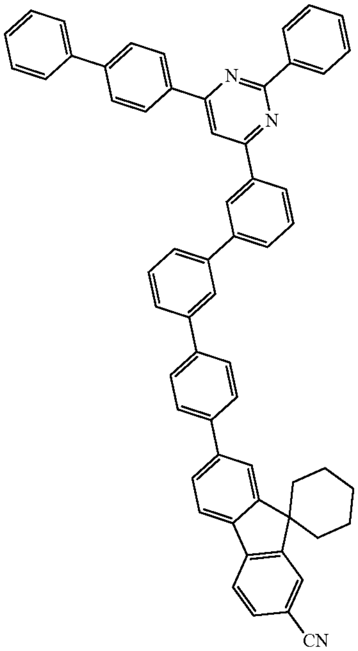

-continued
B-32
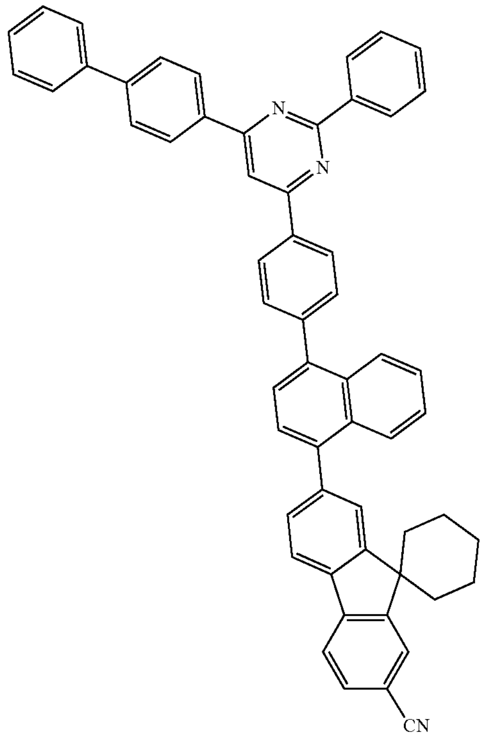
B-33
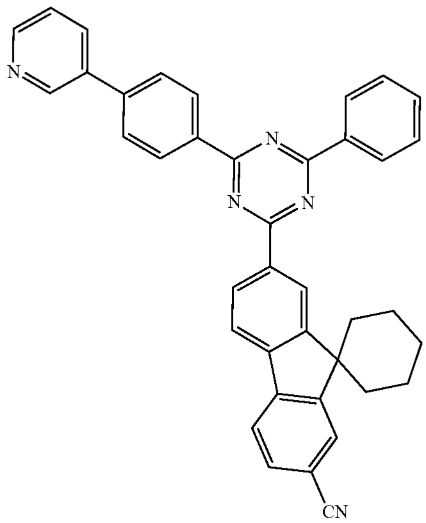
-continued
B-34
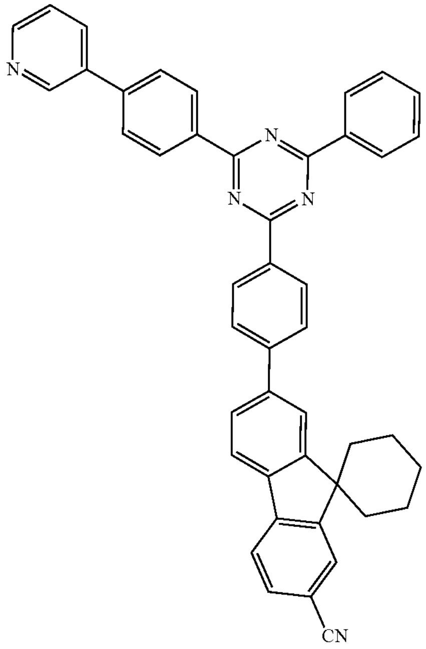
B-35
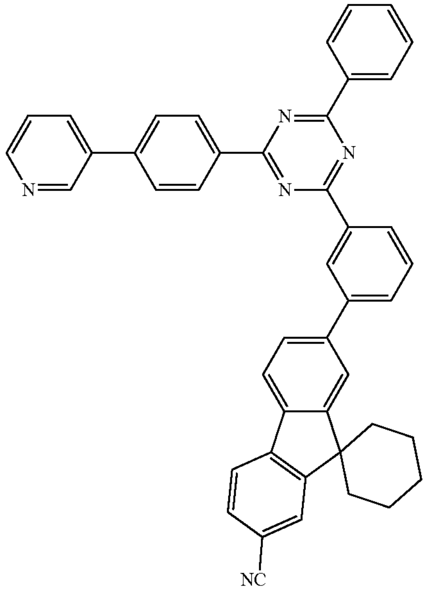

B-36
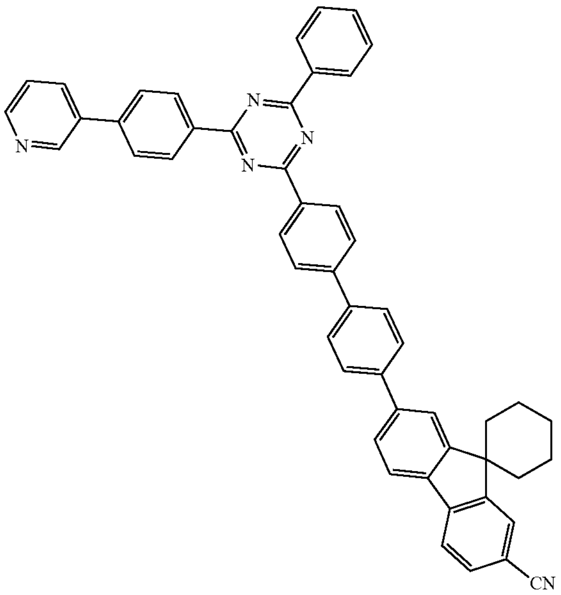
B-37
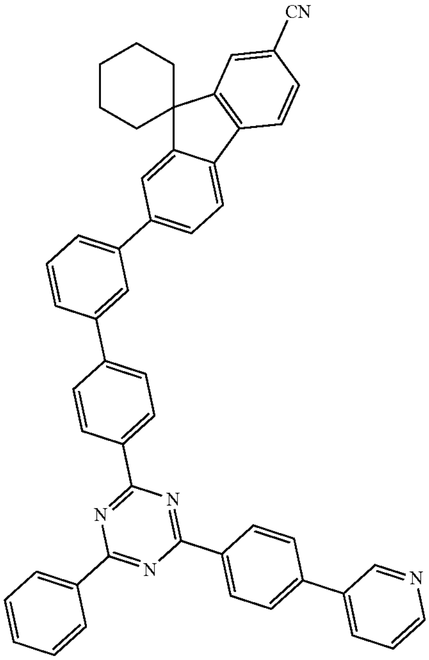
B-38
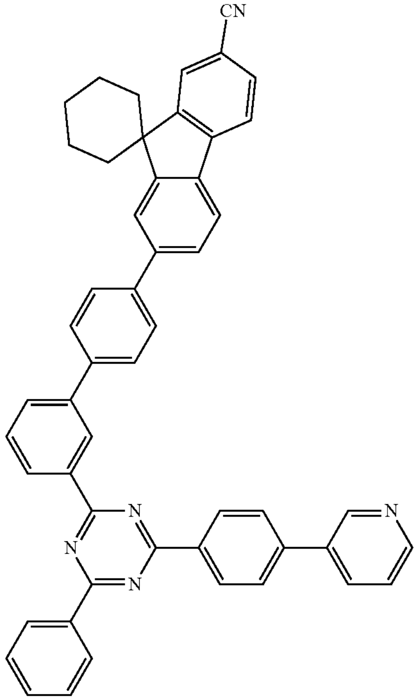
B-39
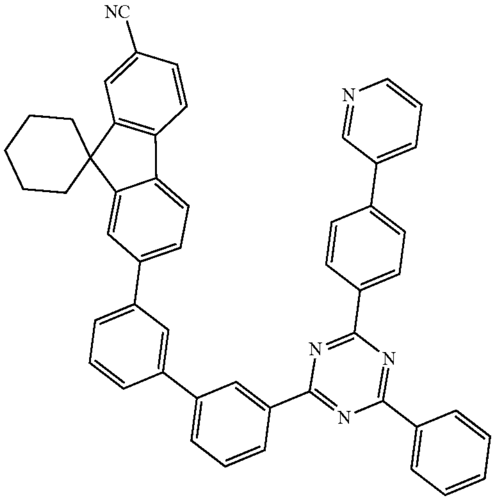

-continued
B-40
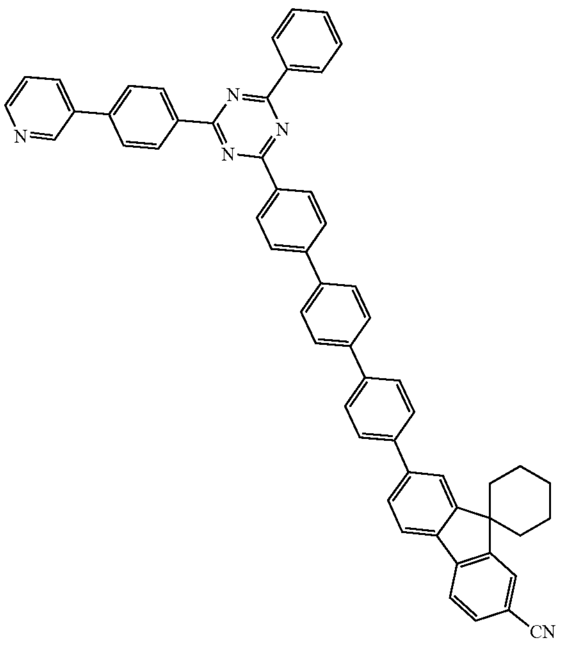
B-41
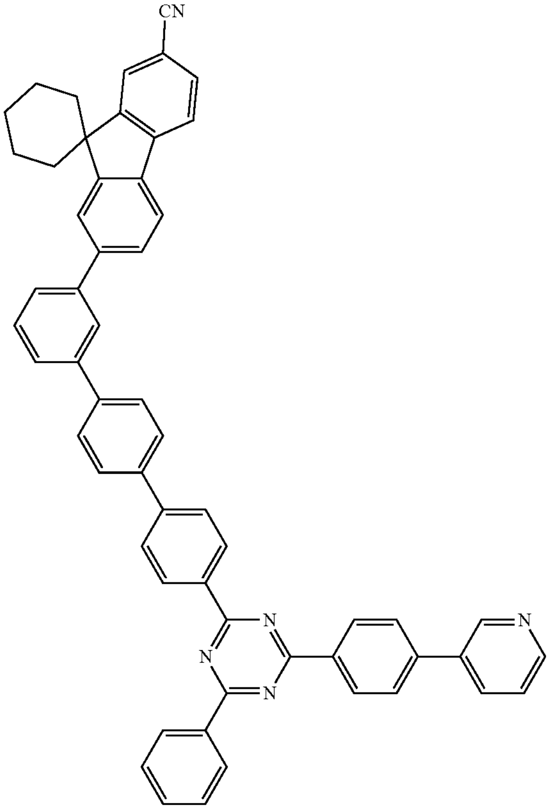
-continued
B-42
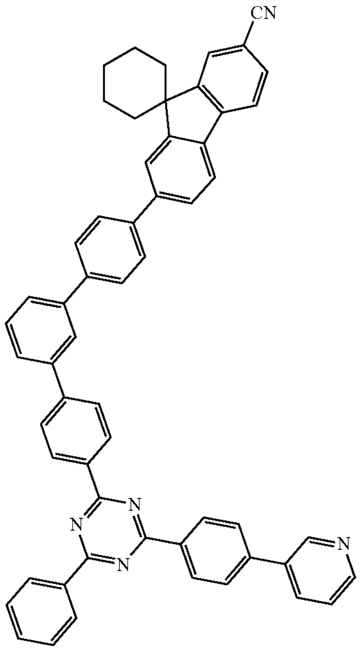
B-43
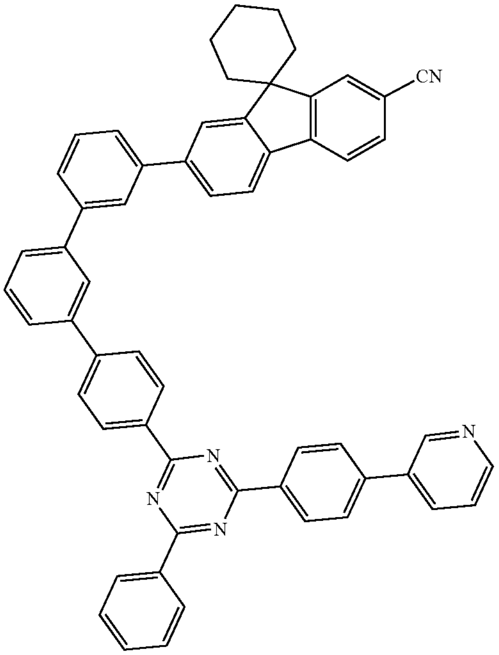

-continued
B-44
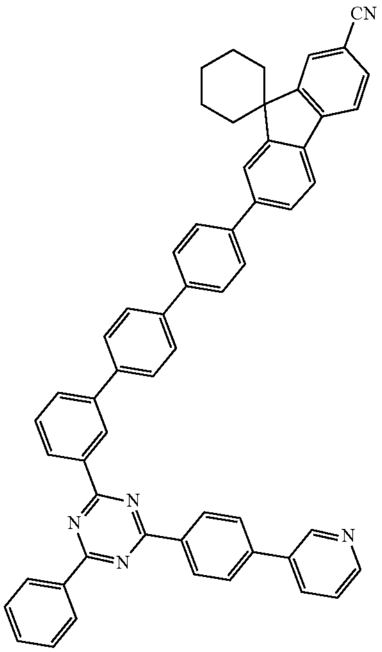
B-45
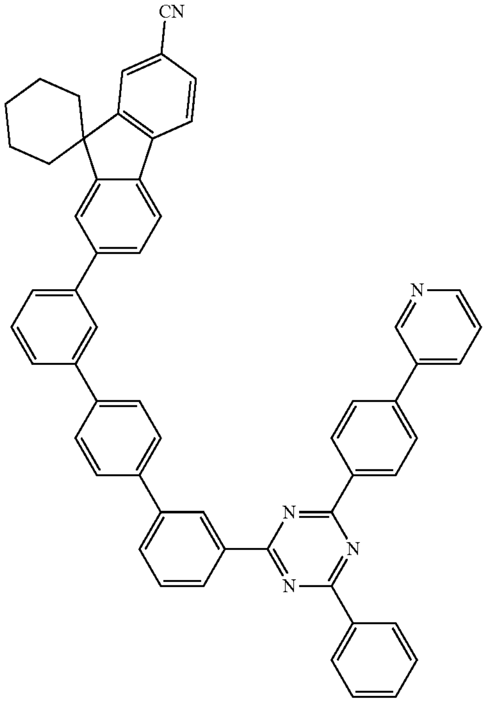
-continued
B-46
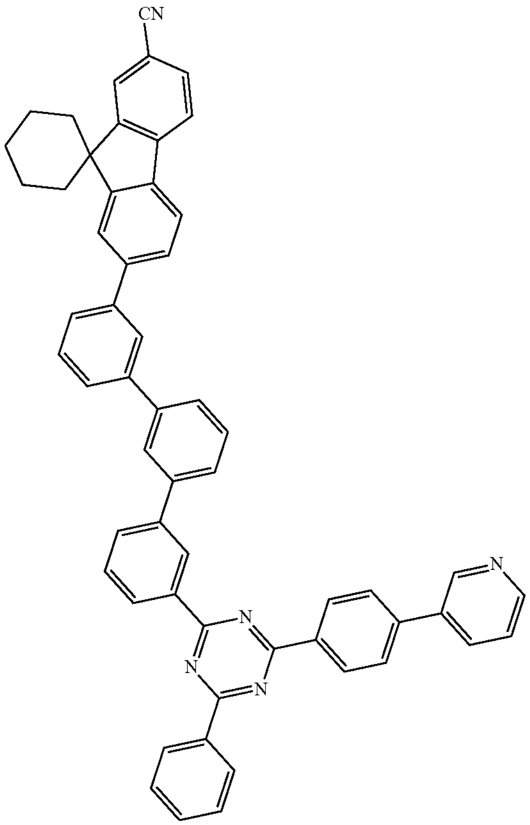
B-47
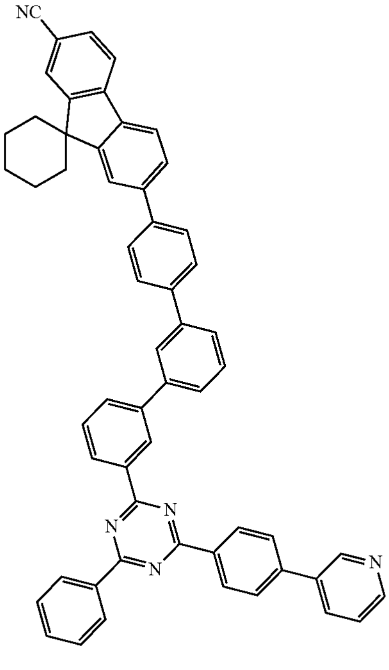

-continued
B-48
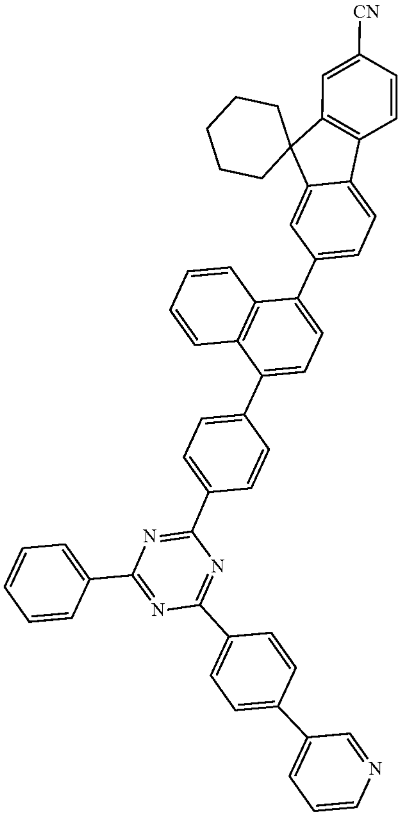
B-49
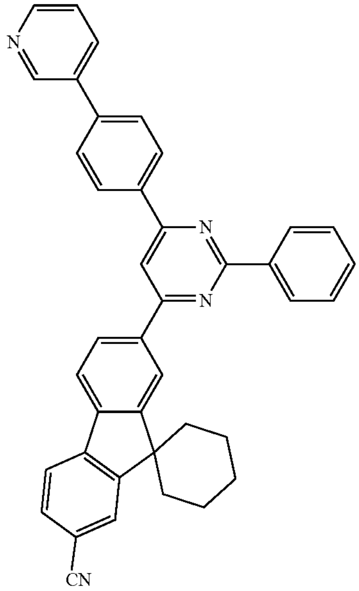
-continued
B-50
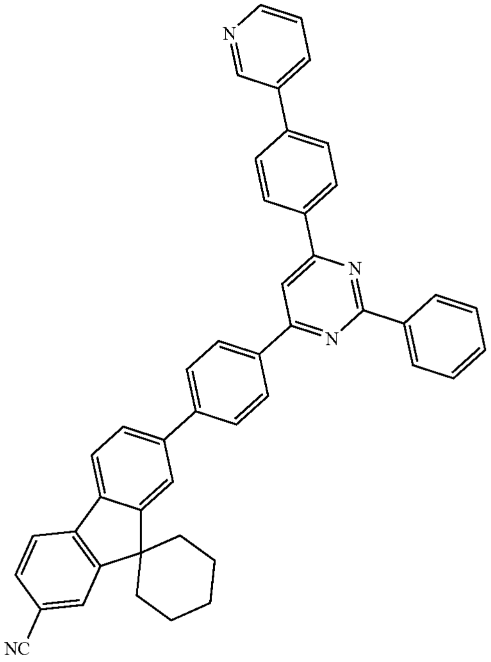
B-51
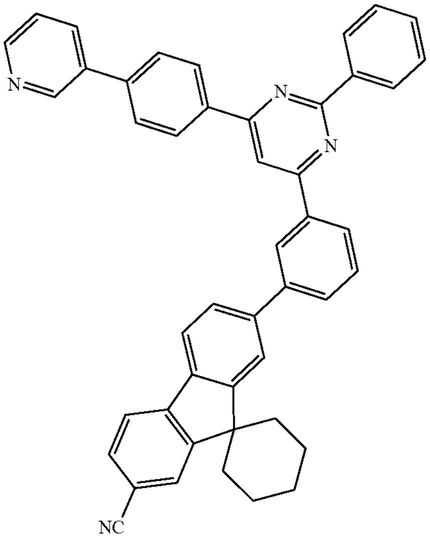

-continued
B-52
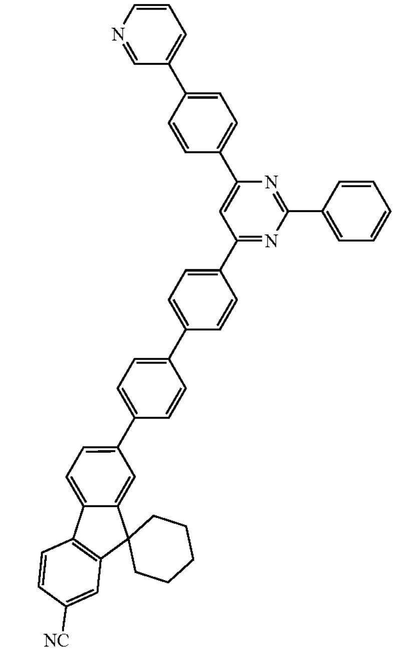
B-53
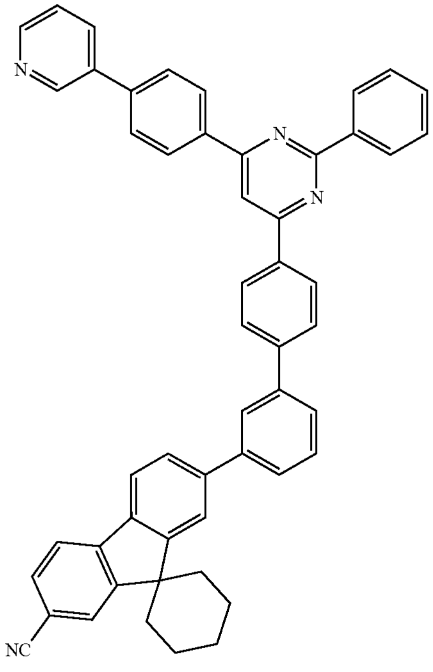
-continued
B-54
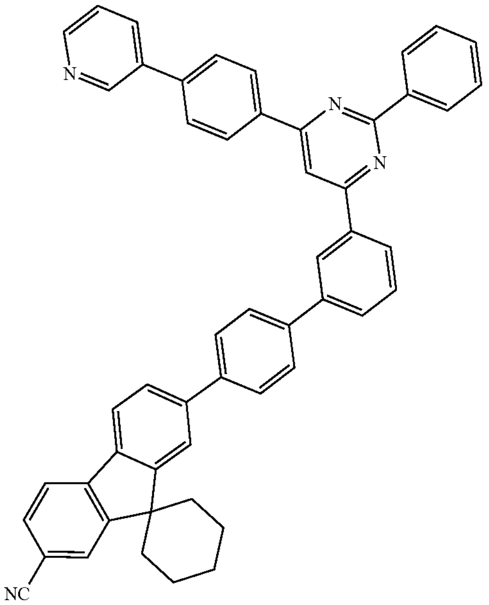
B-55
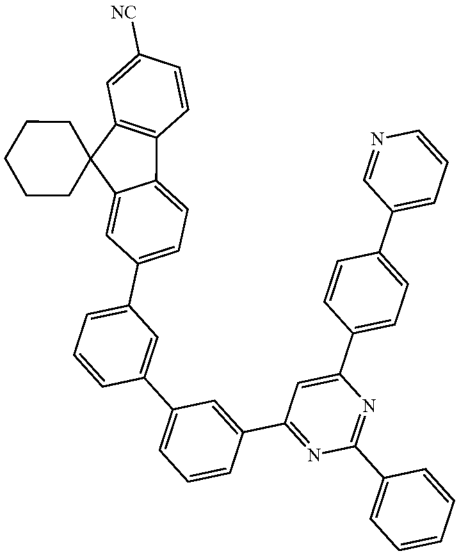

-continued
B-56
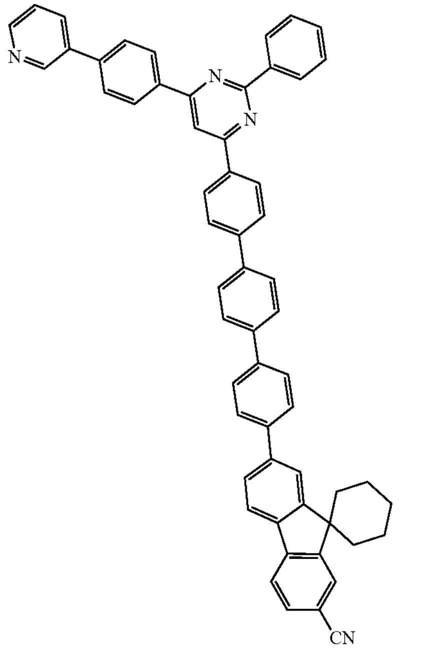
B-57
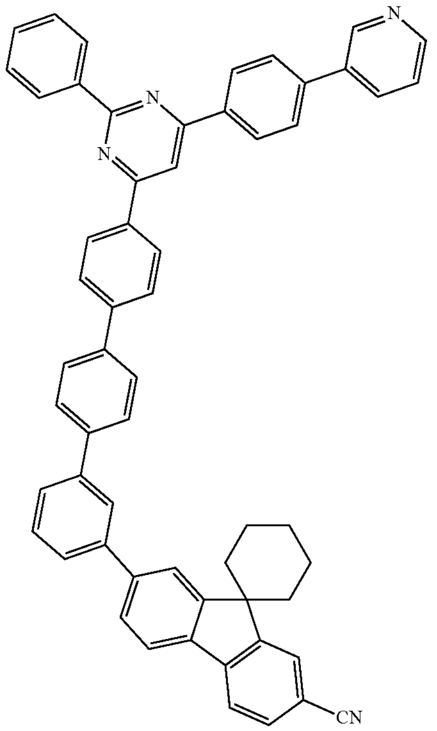
-continued
B-58
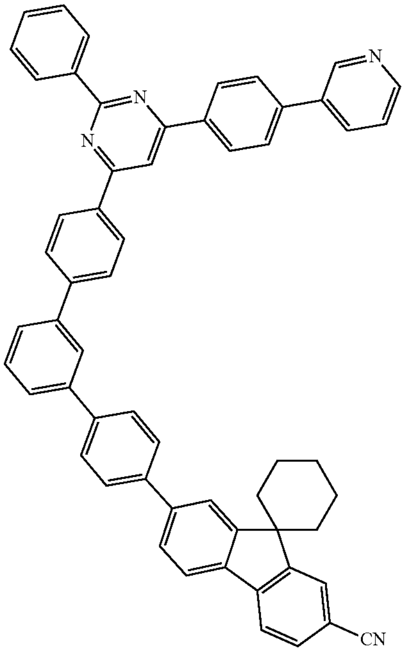
B-59
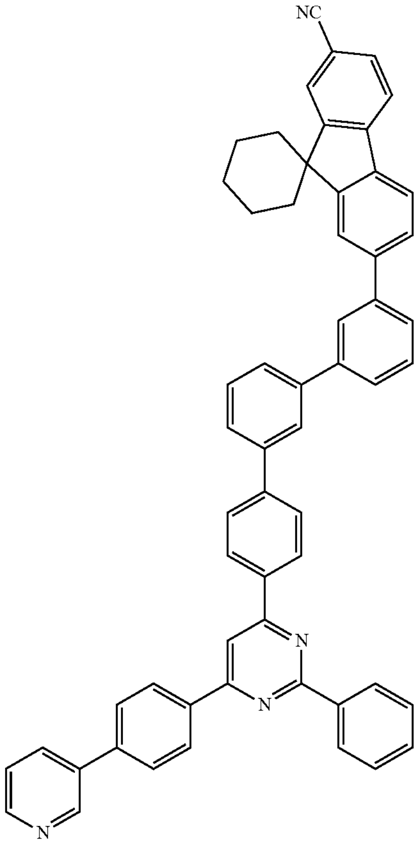

-continued
B-60
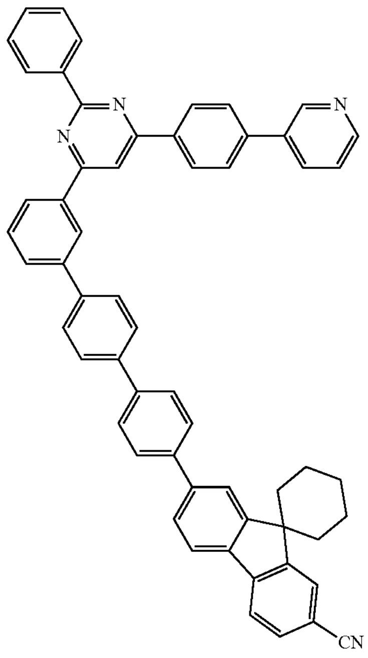
B-61
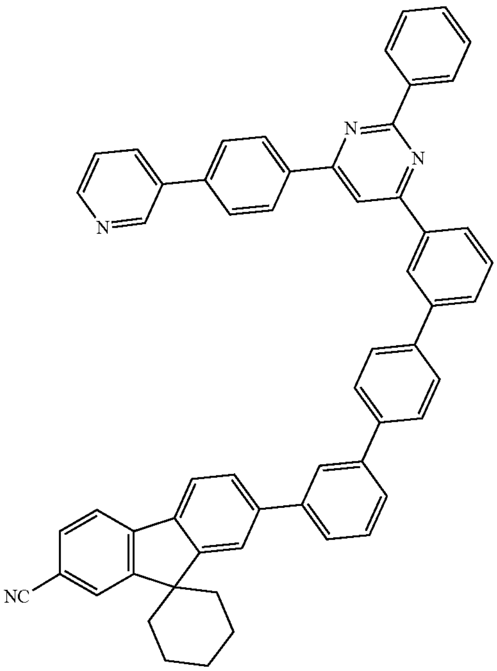
-continued
B-62
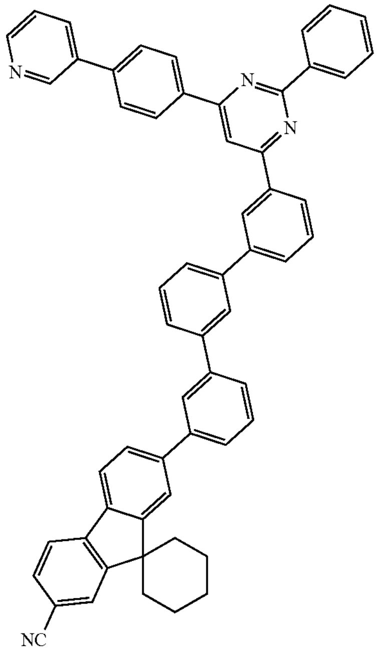
B-63
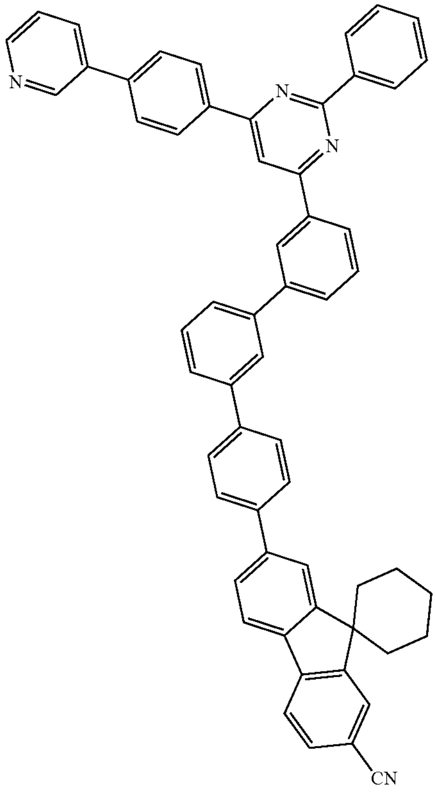

-continued
B-64
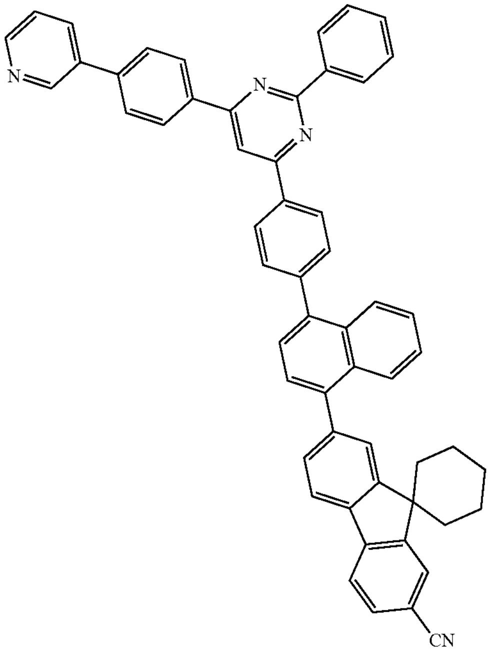
B-65
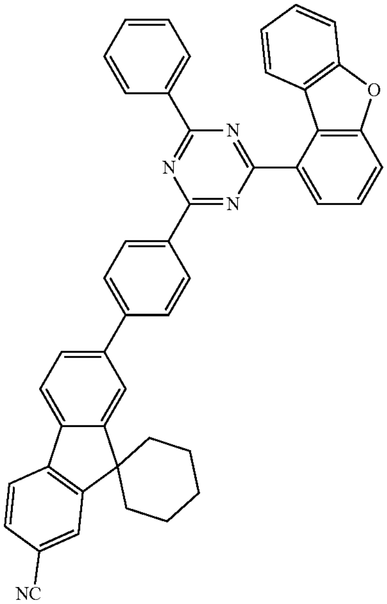
-continued
B-66
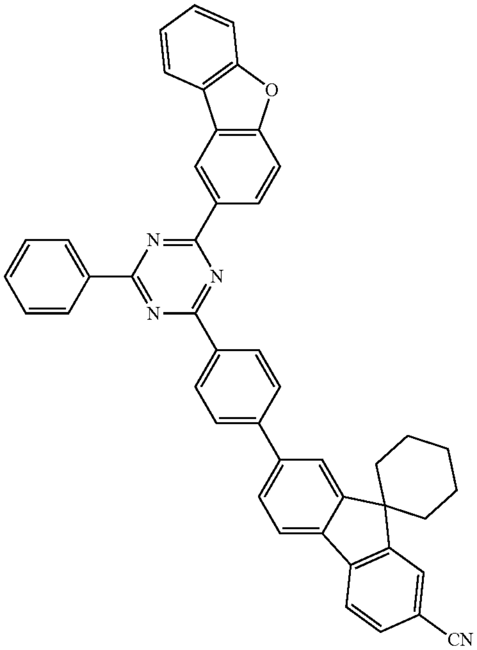
B-67
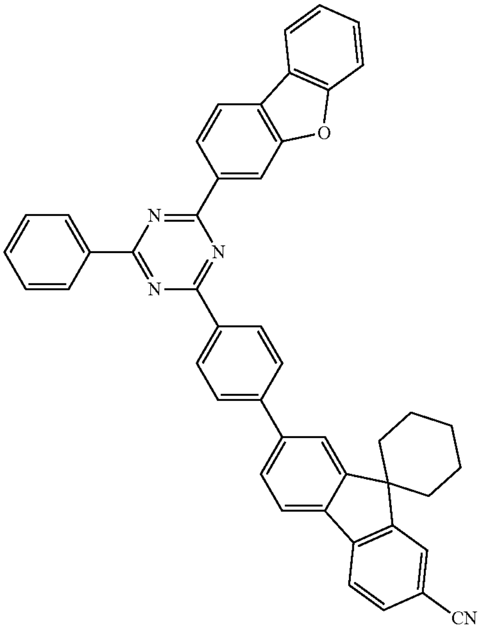

-continued
B-68
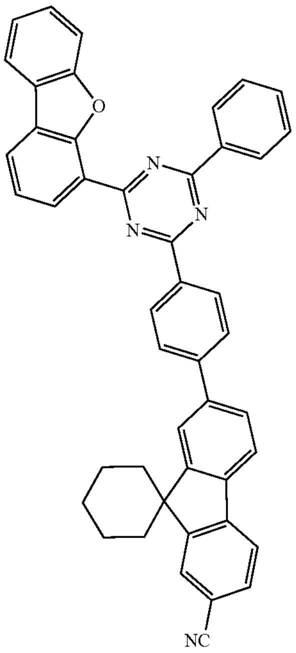
B-69
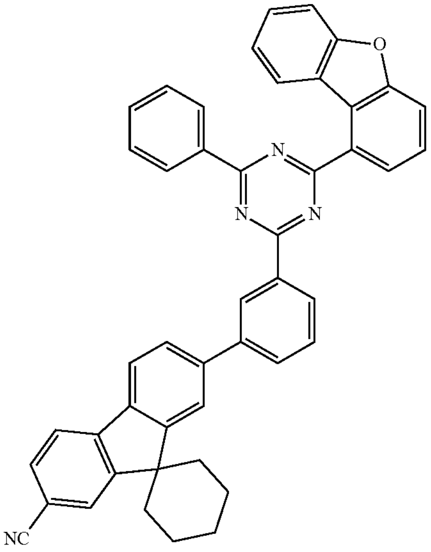
-continued
B-70
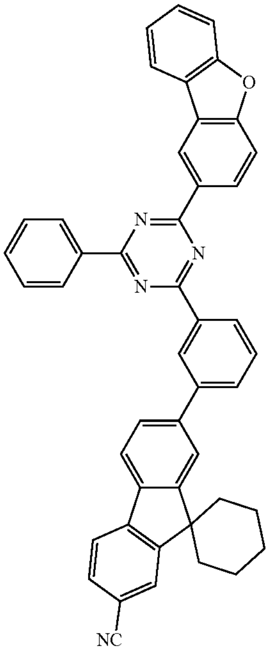
B-71
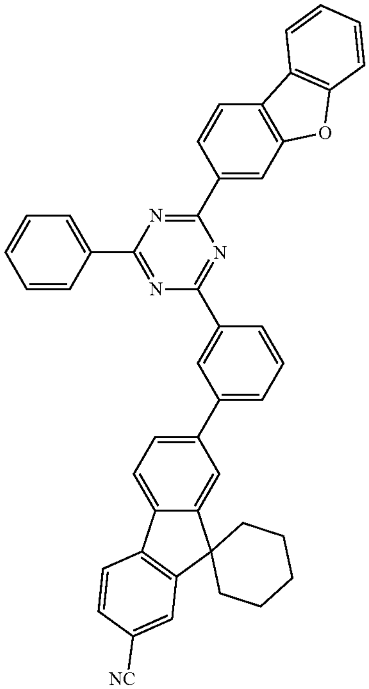

-continued
B-72
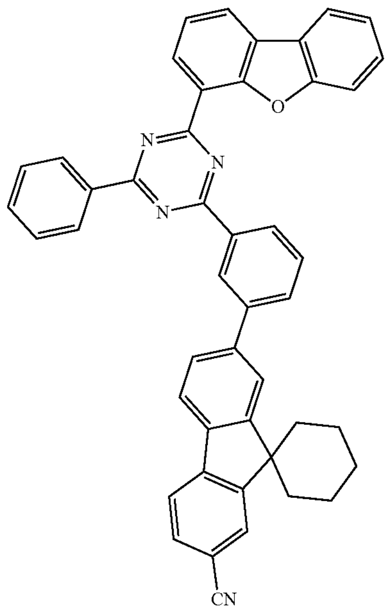
B-73
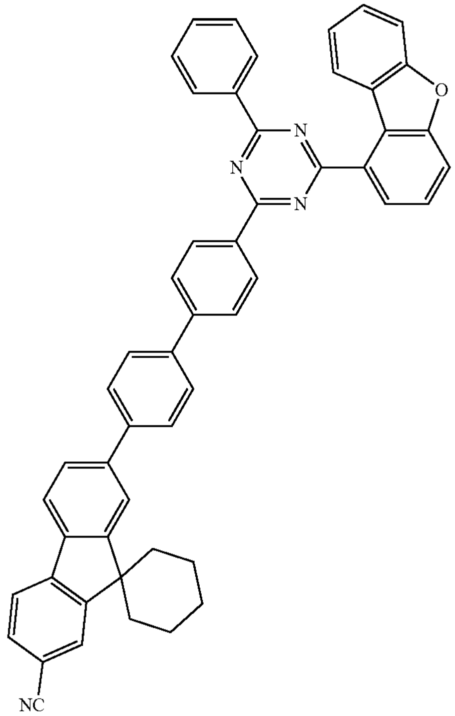
-continued
B-74
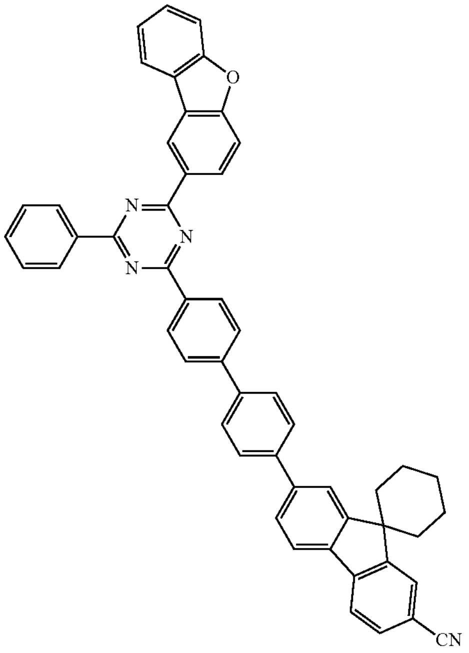
B-75
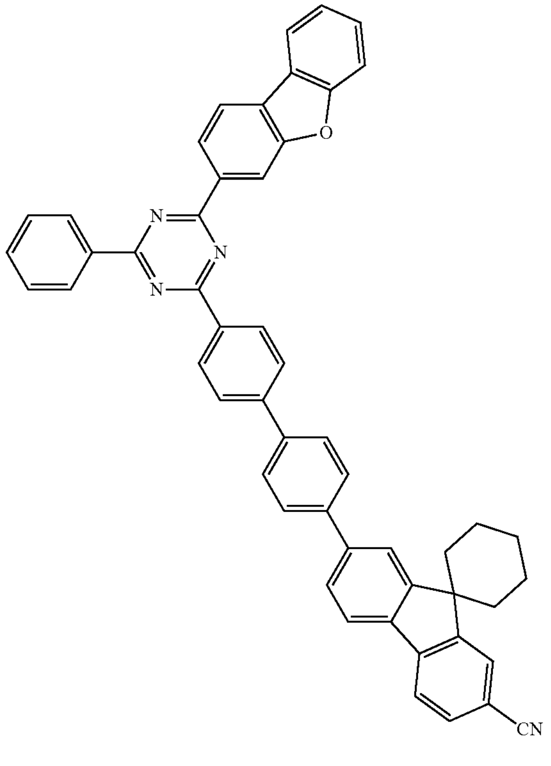

-continued
B-76
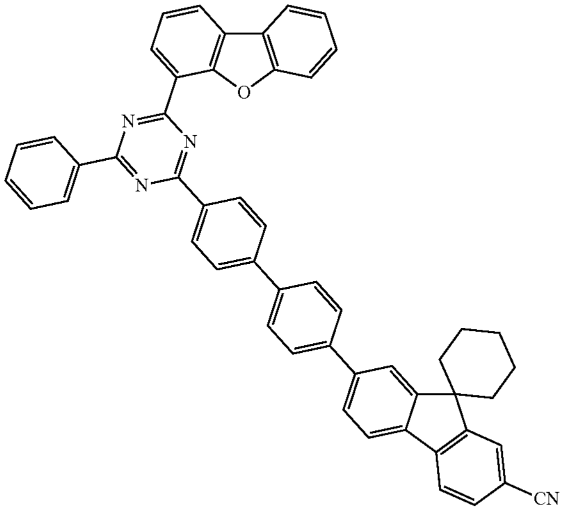
B-77
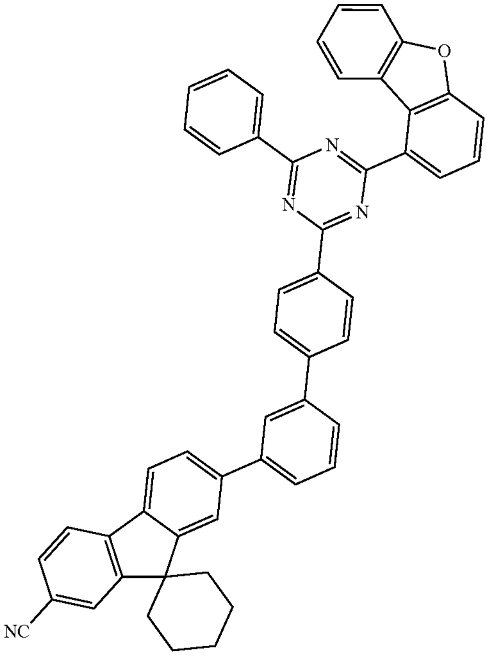
-continued
B-78
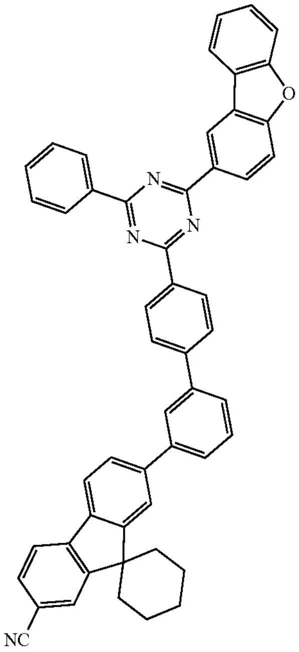
B-79
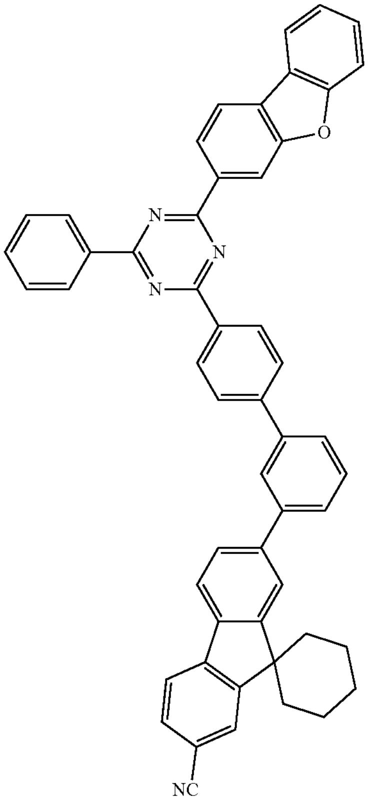

-continued
B-80
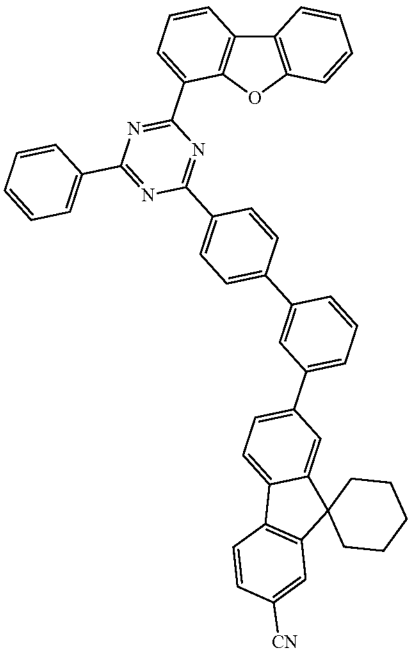
B-81
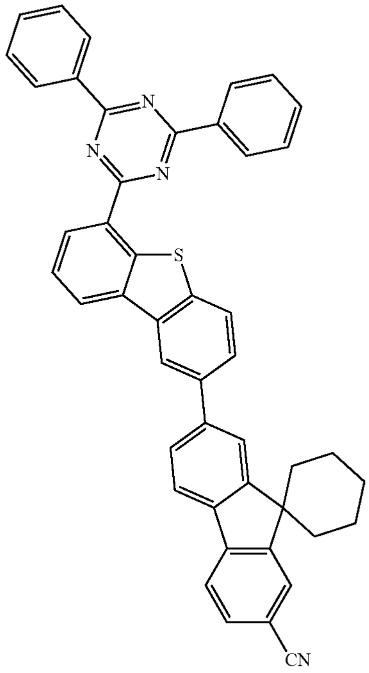
-continued
B-82
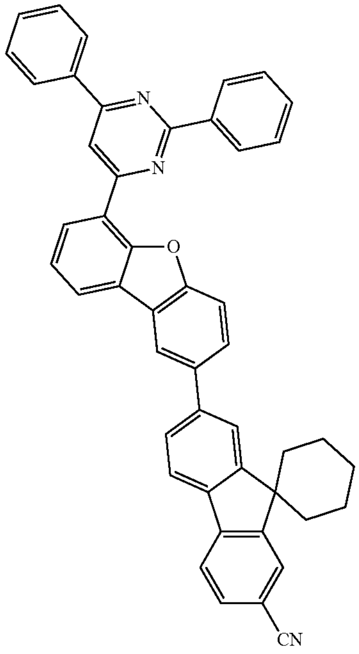
B-83
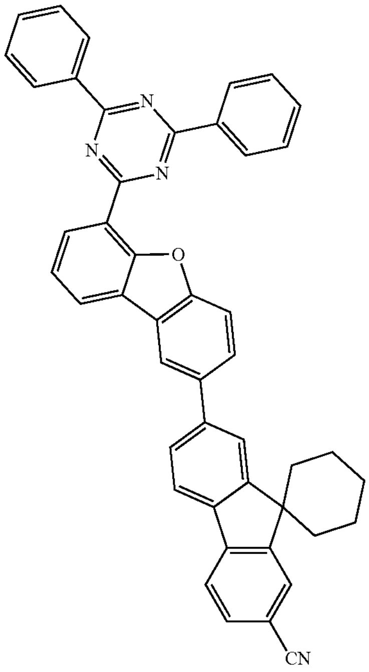

-continued
B-84
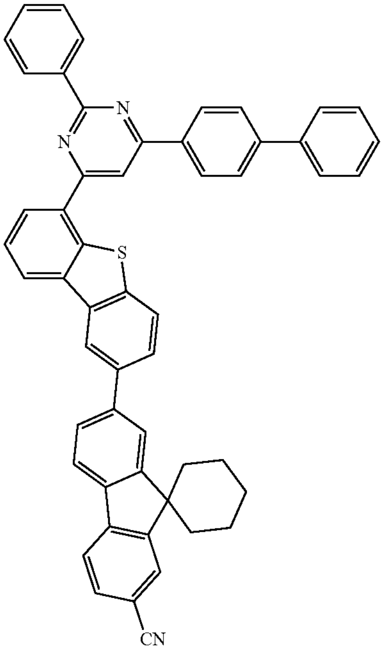
B-85
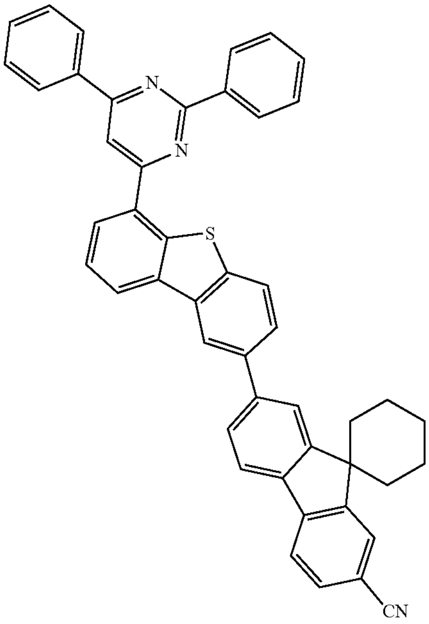
-continued
B-86
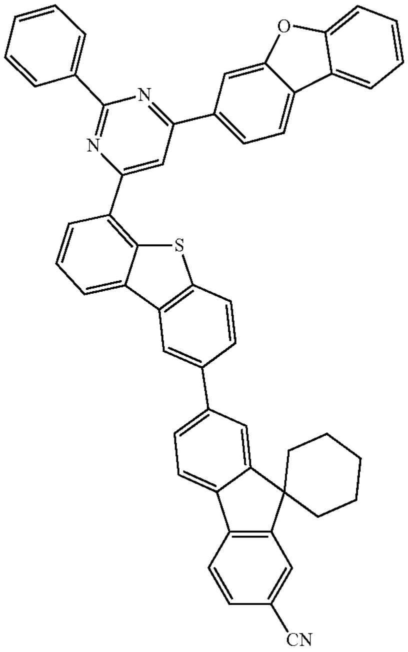
B-87
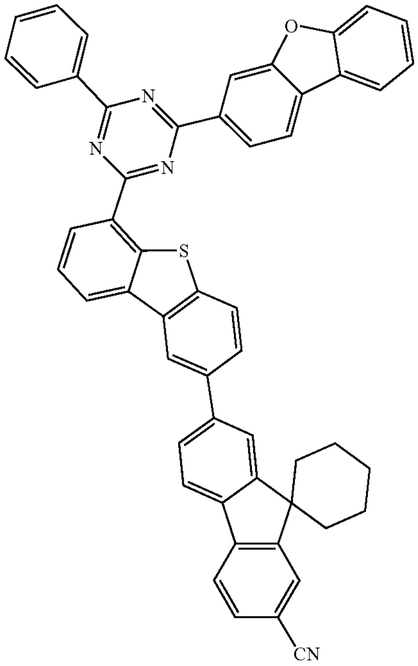

-continued
B-88
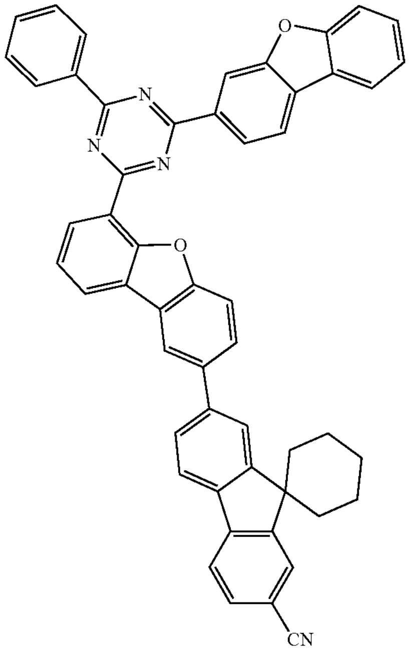
B-89
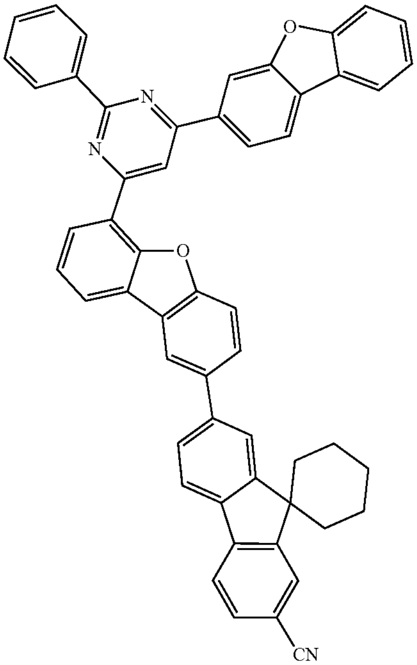
-continued
B-90
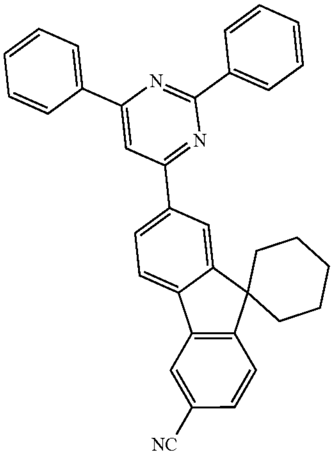
B-91
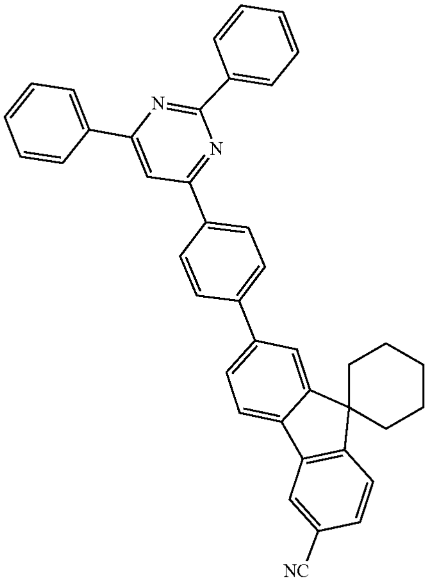
B-92
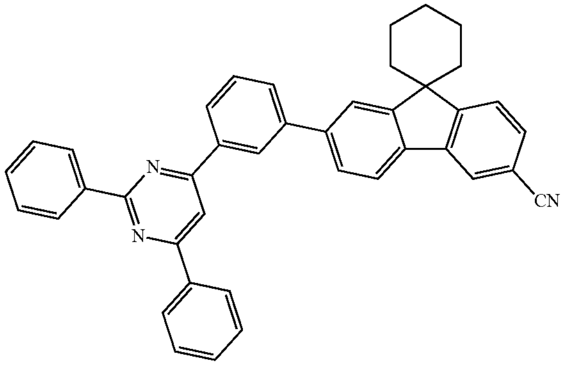

-continued
B-93
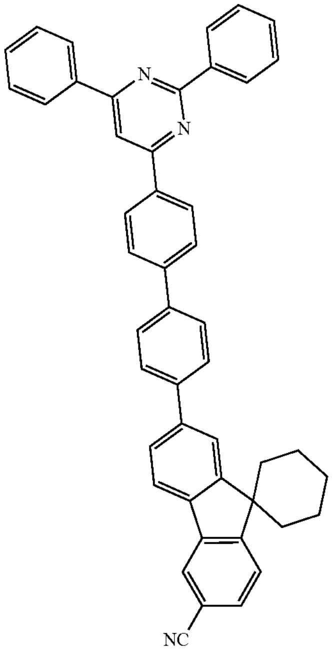
B-94
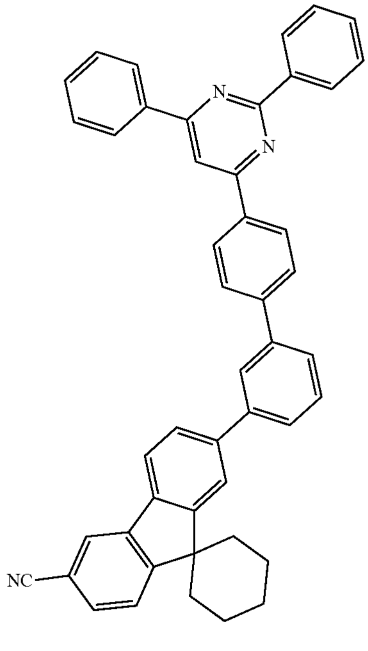
-continued
B-95
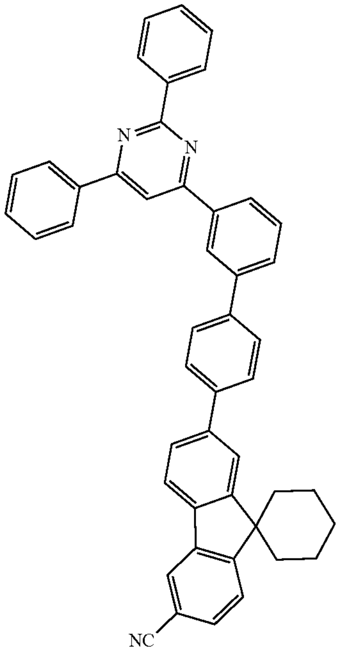
B-96
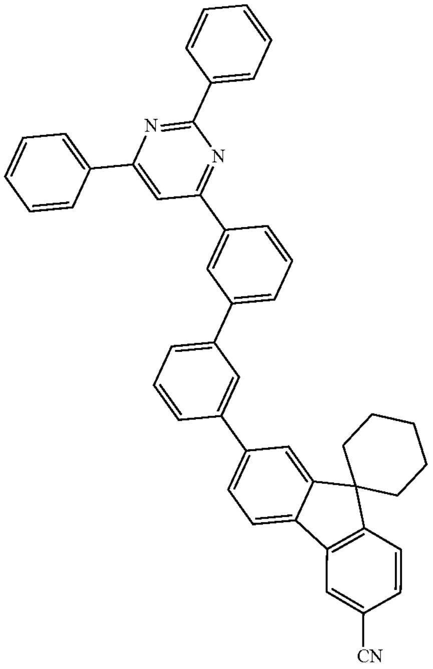

B-97
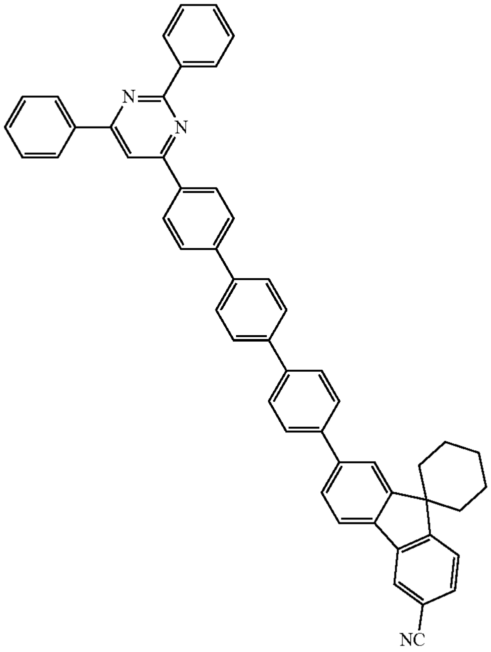
B-98
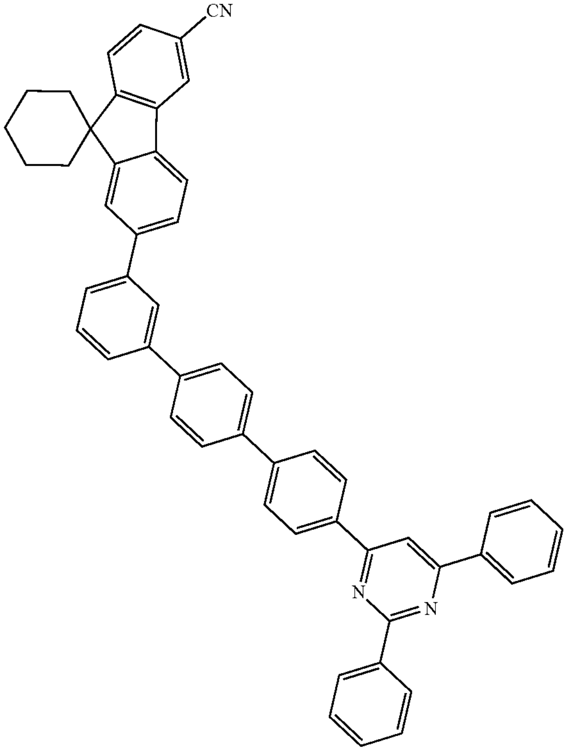
B-99
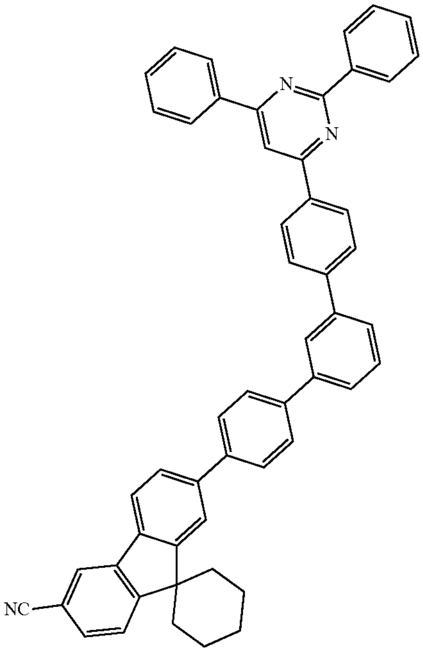
B-100
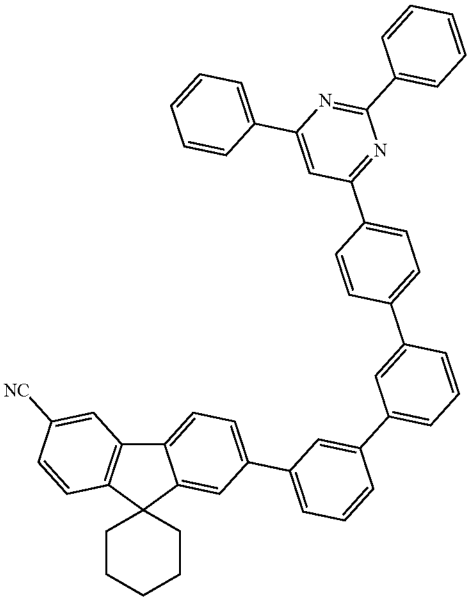

-continued
B-101
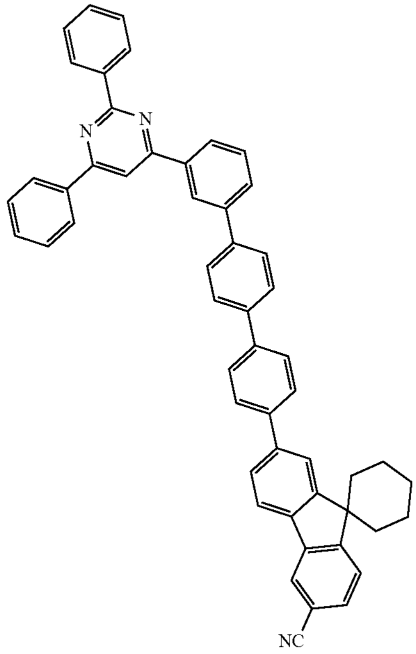
B-102
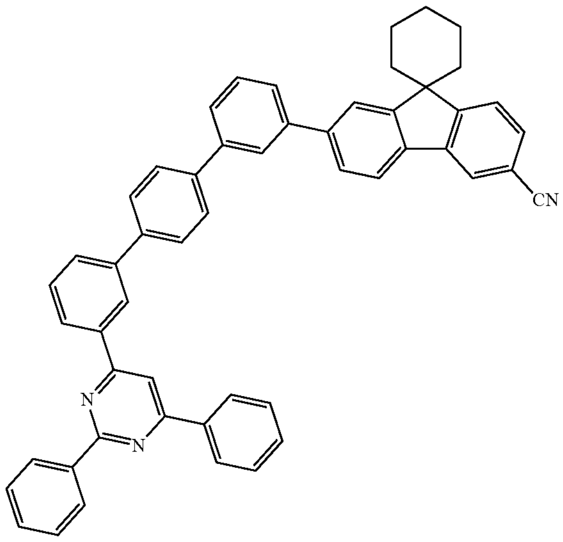
-continued
B-103
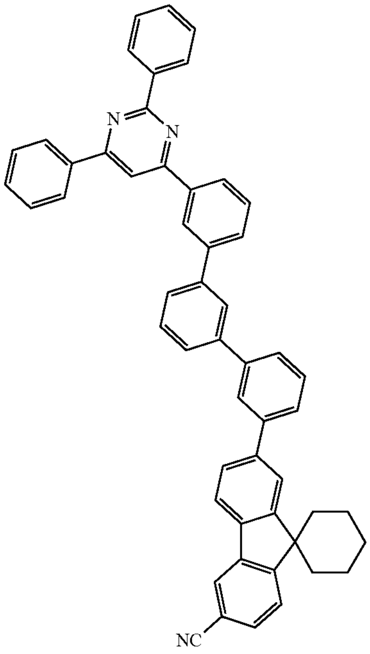
B-104
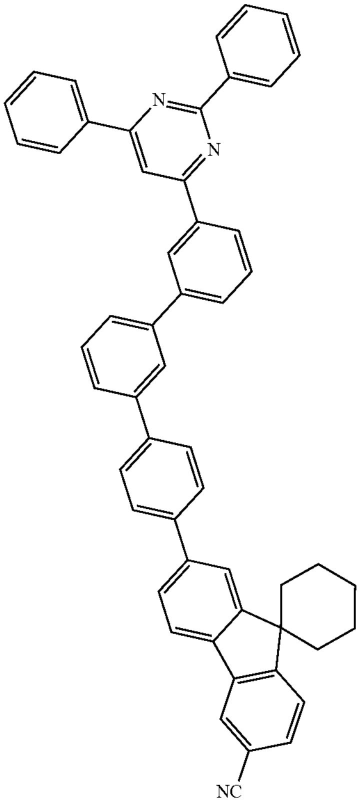

-continued
B-105
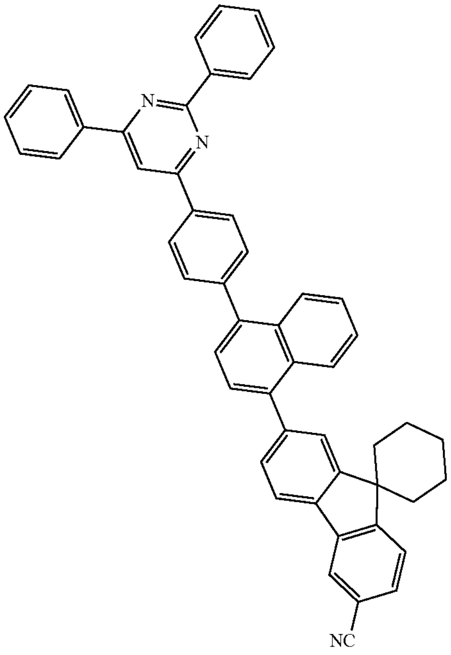
-continued
B-107
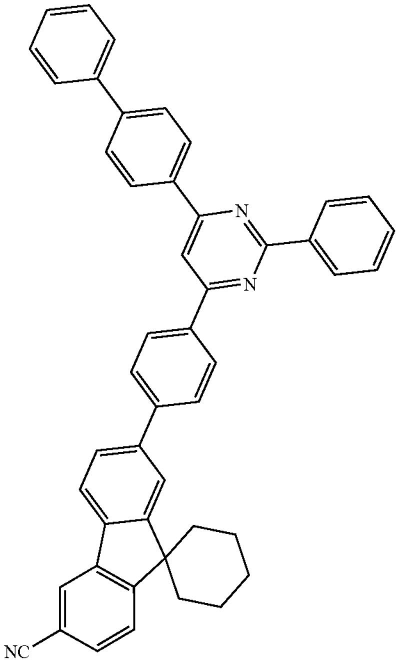
B-106
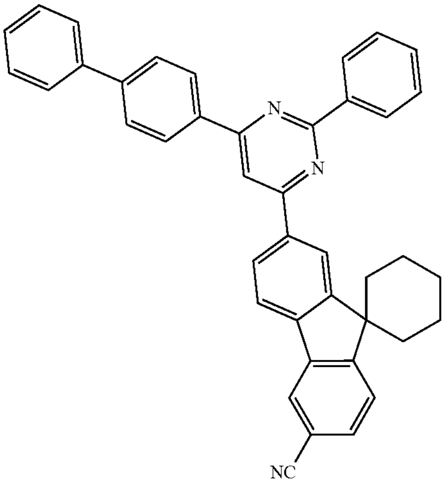
B-108
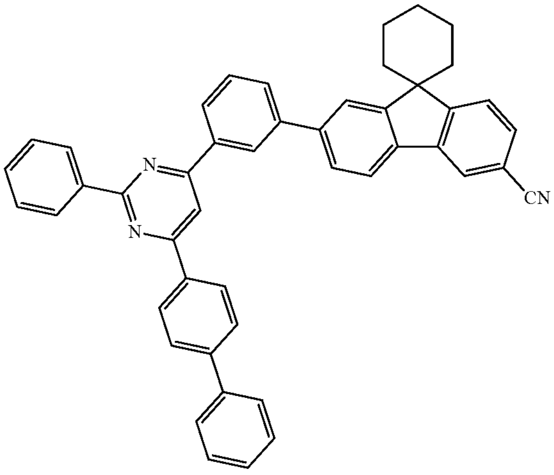

-continued
B-109
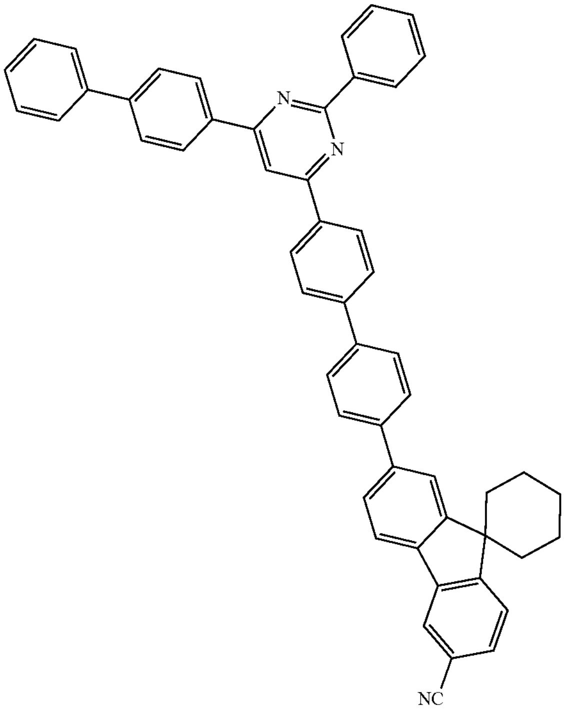
B-111
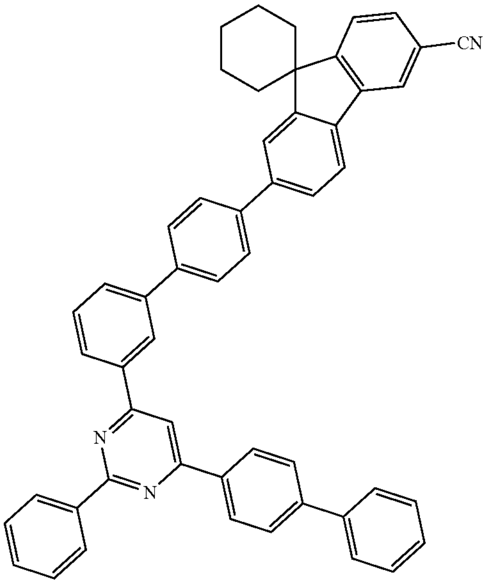
B-110
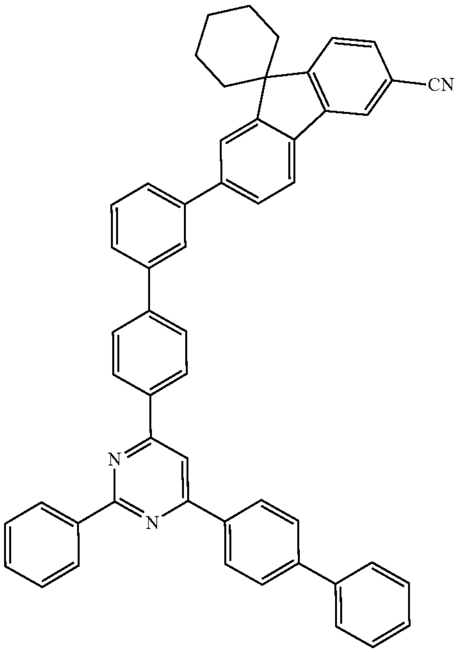
B-112
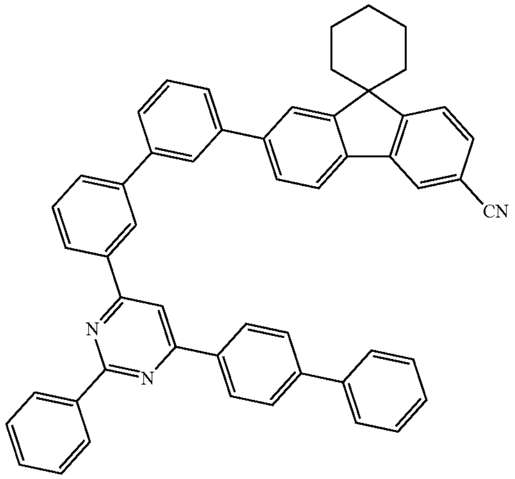

-continued
B-113
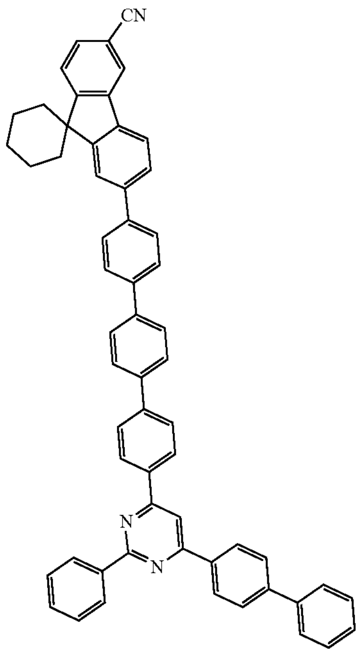
B-114
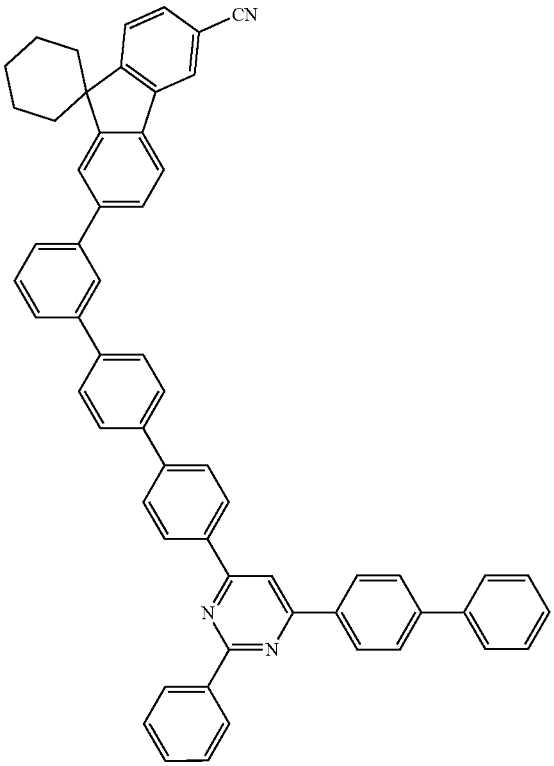
-continued
B-115
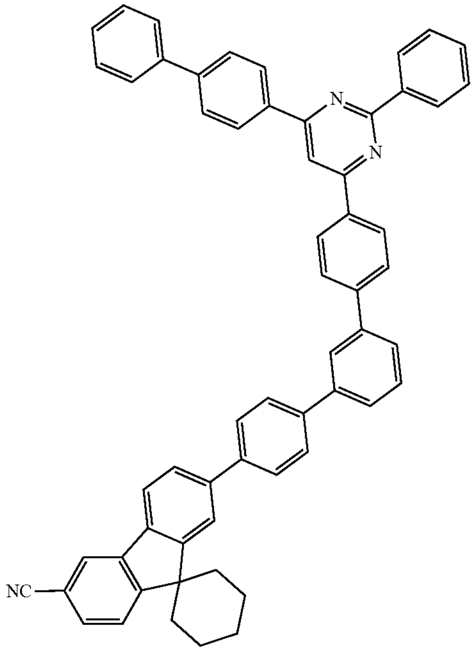
B-116
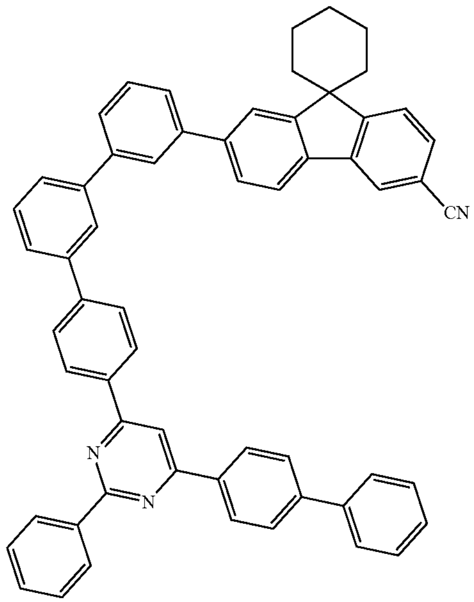

-continued
B-117
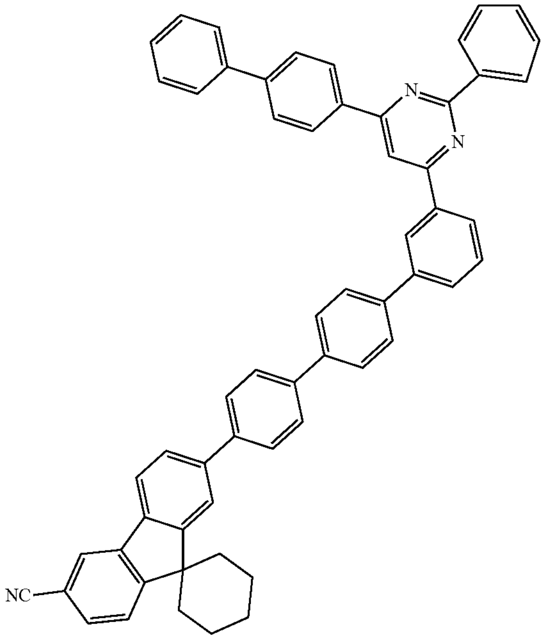
B-118
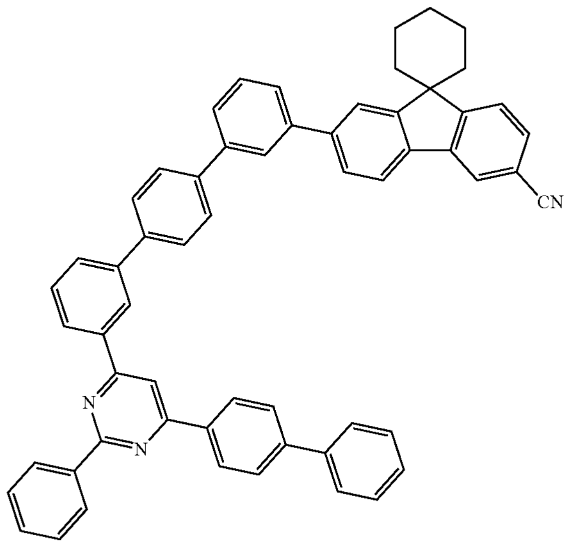
-continued
B-119
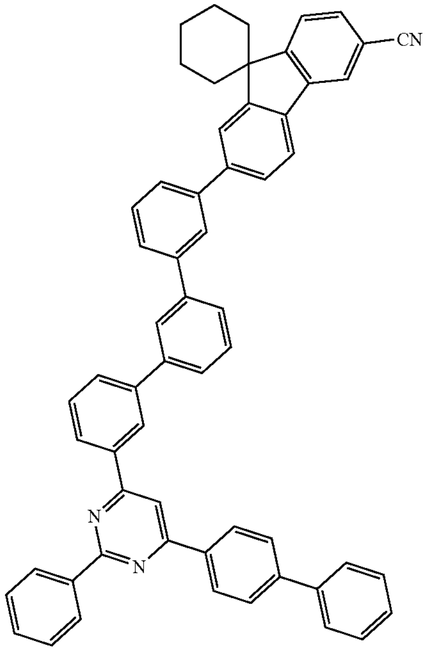
B-120
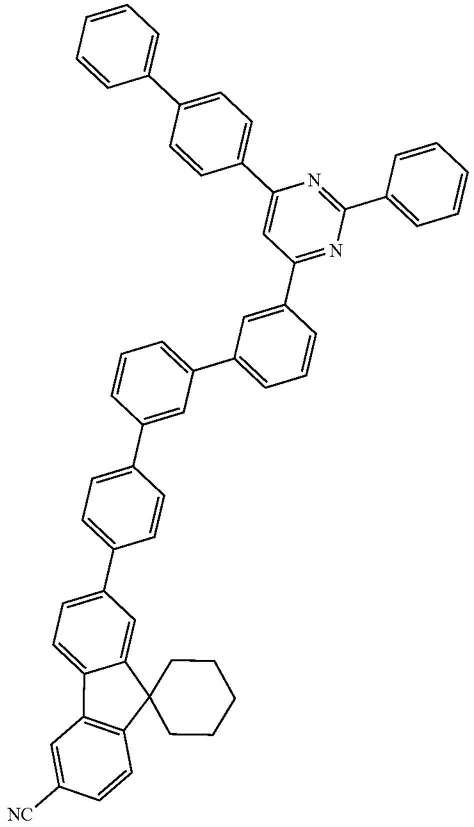

-continued
B-121
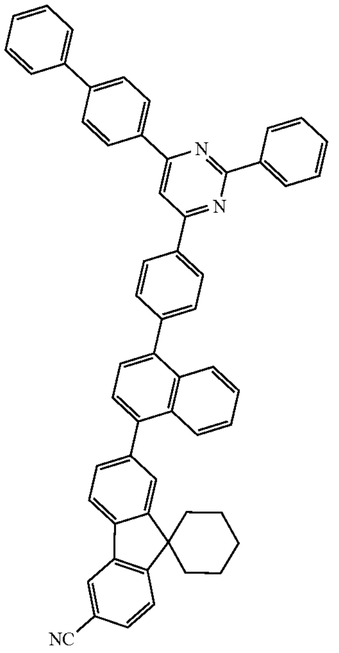
B-122
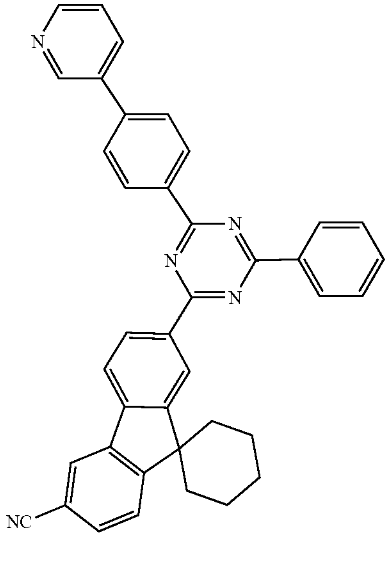
-continued
B-123
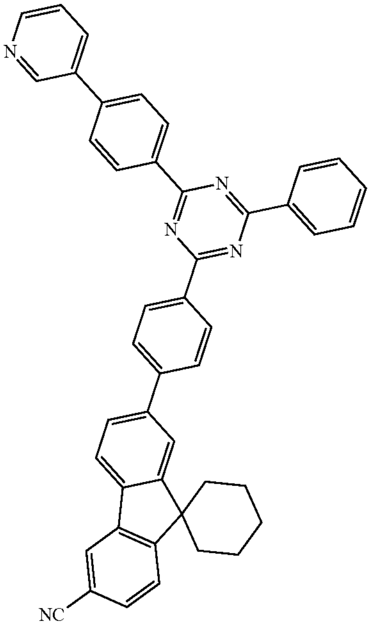
B-124
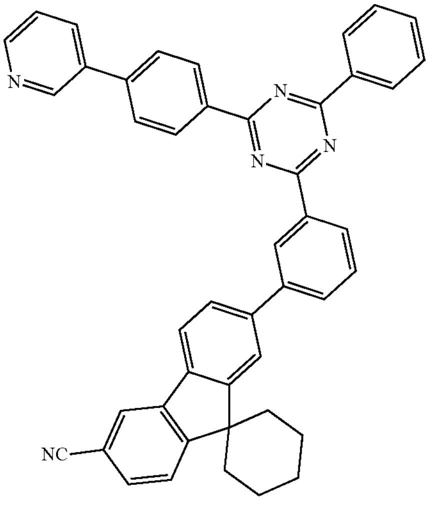

-continued
B-125
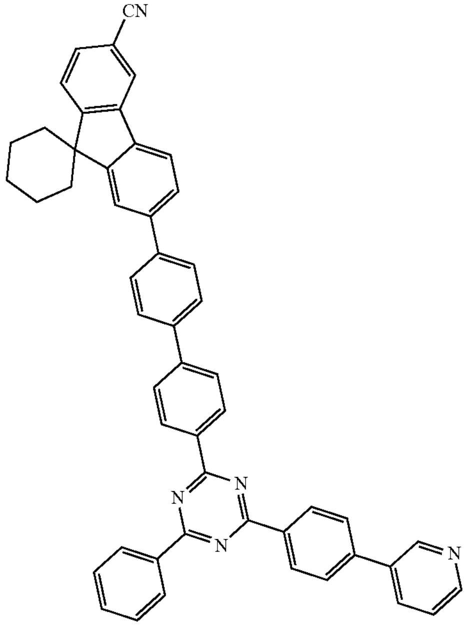
B-126
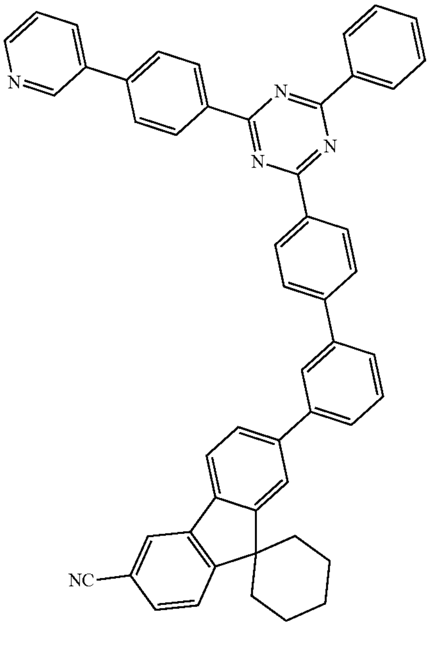
-continued
B-127
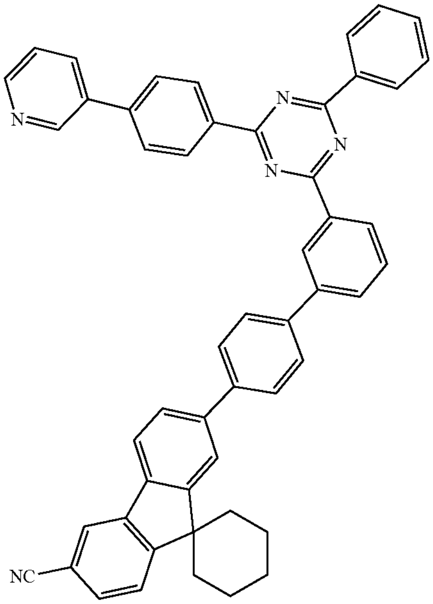
B-128
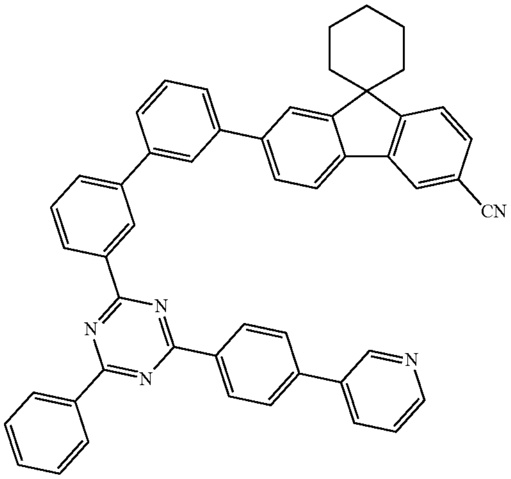

B-129
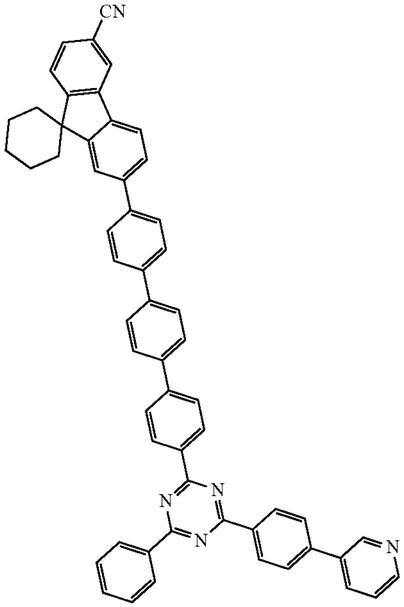
B-130
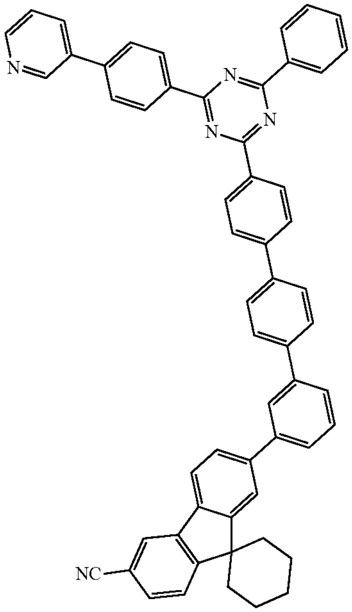
B-131
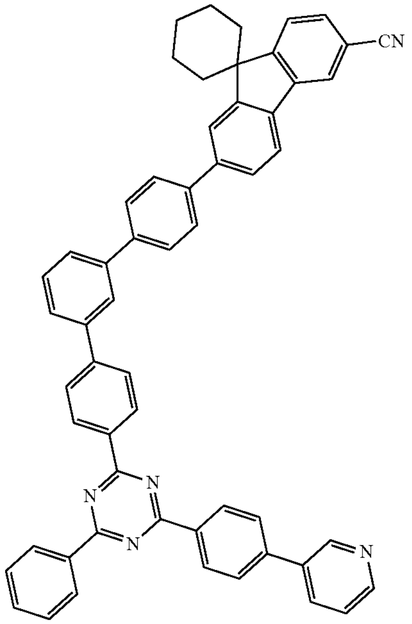
B-132
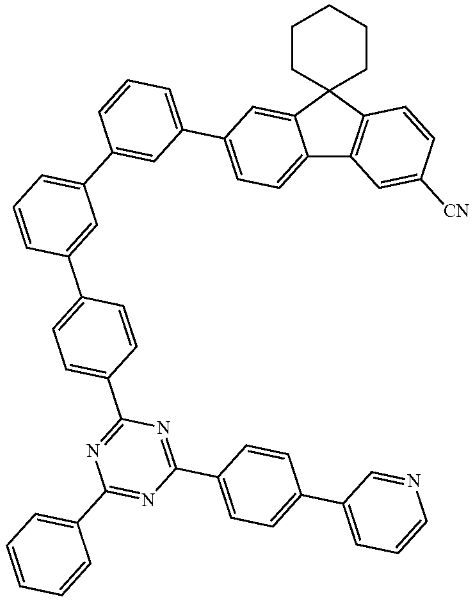

-continued
B-133
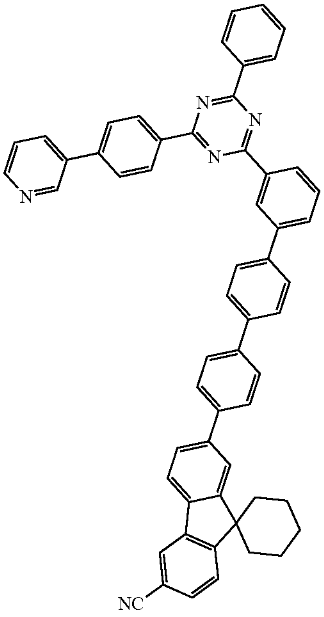
B-134
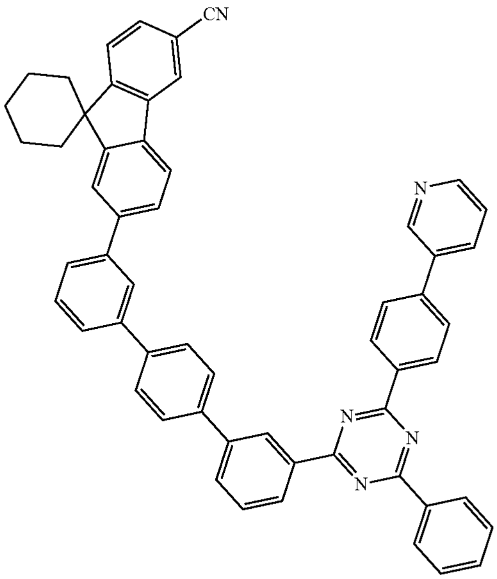
-continued
B-135
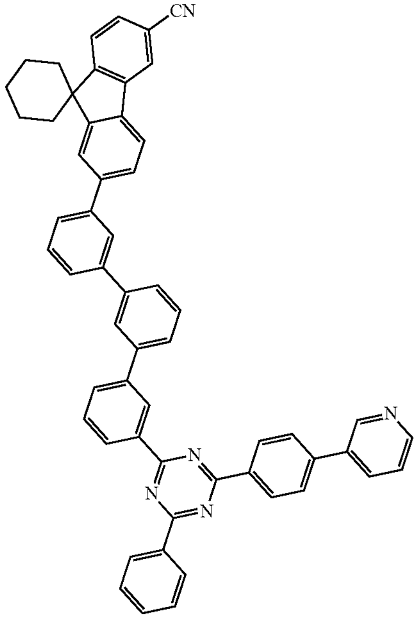
B-136
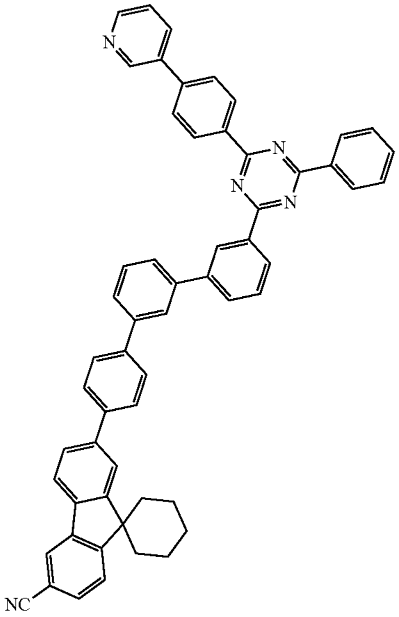

-continued
B-137
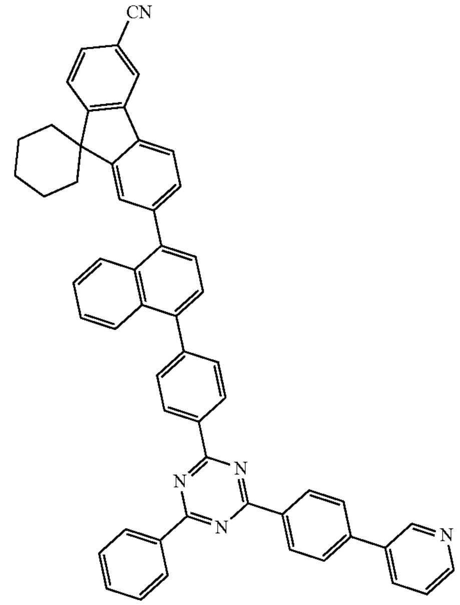
B-138
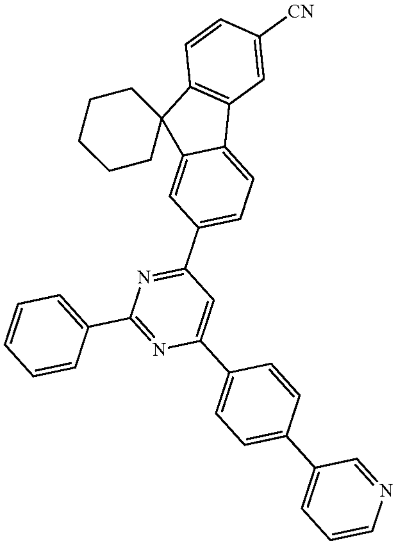
-continued
B-139
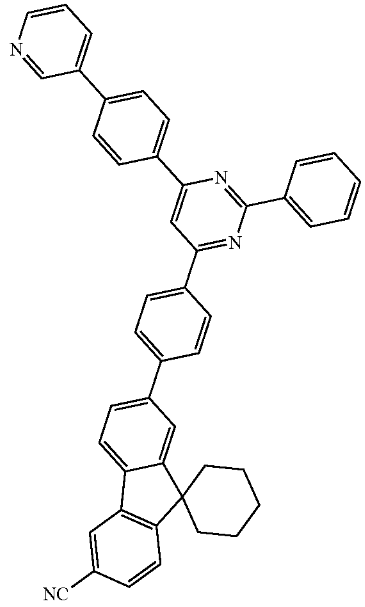
B-140
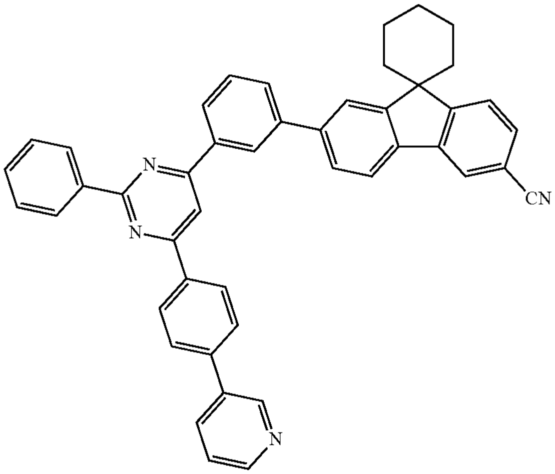

-continued
B-141
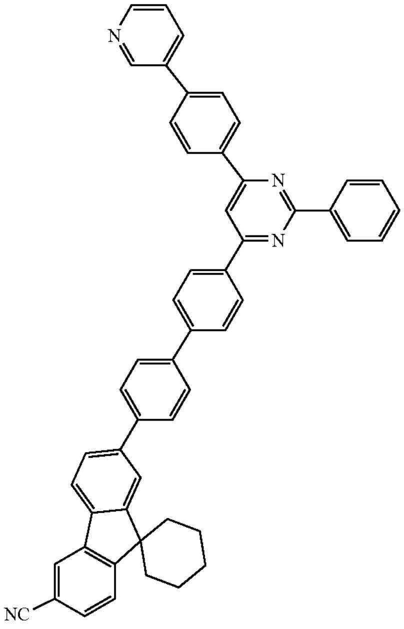
B-142
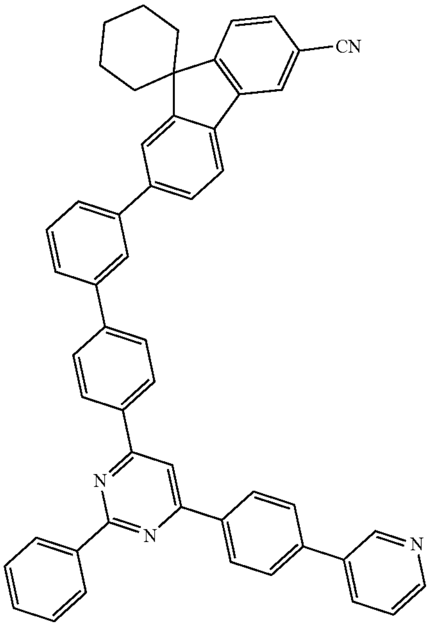
-continued
B-143
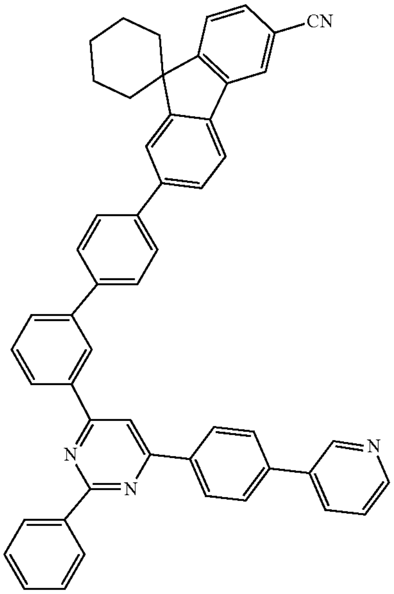
B-144
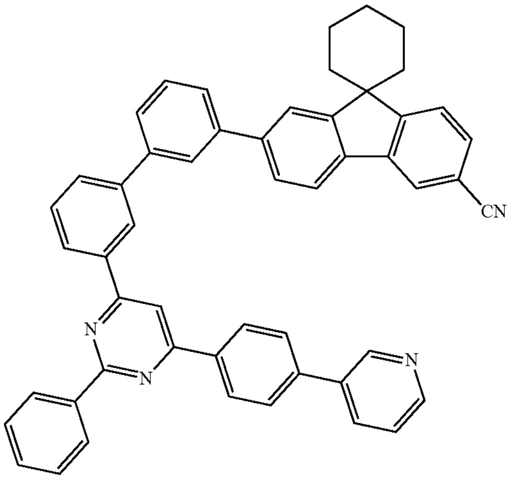

-continued
B-145
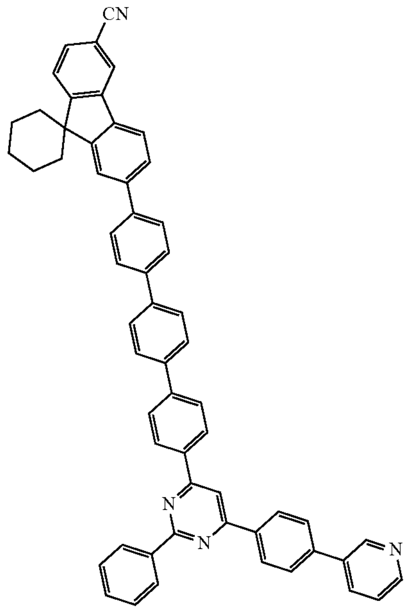
B-146
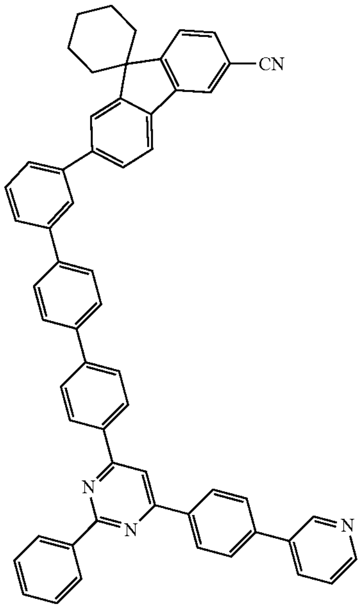
-continued
B-147
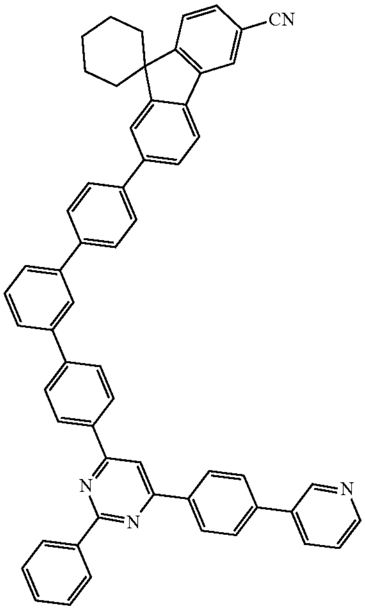
B-148
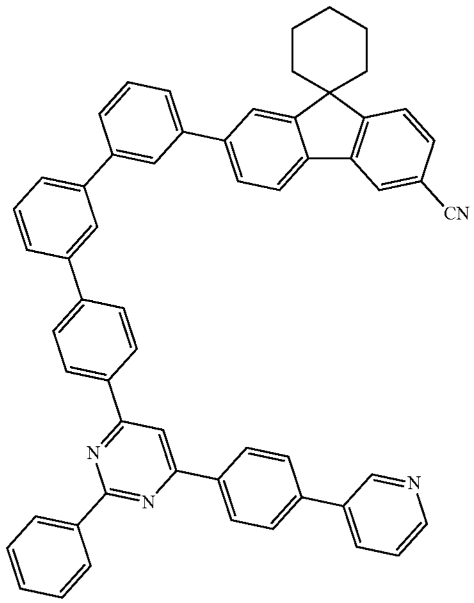

-continued
B-149
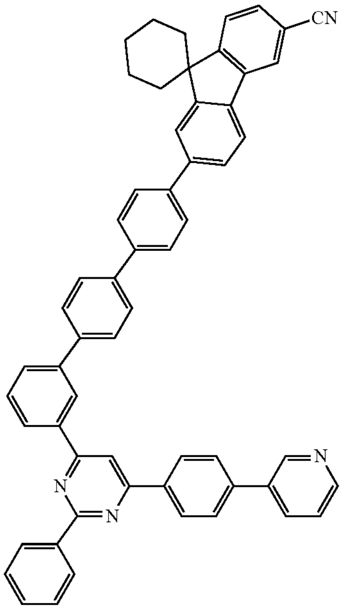
B-150
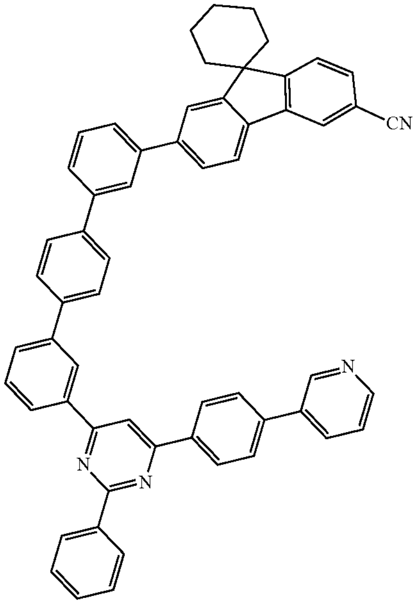
-continued
B-151
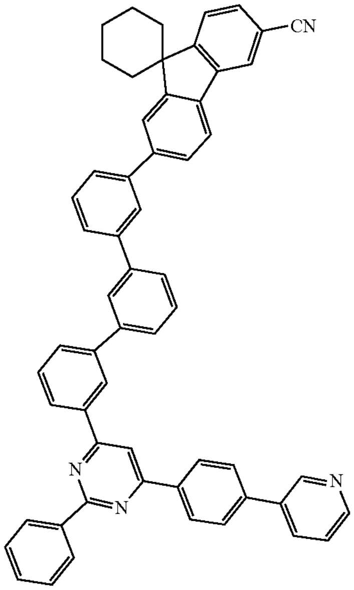
B-152
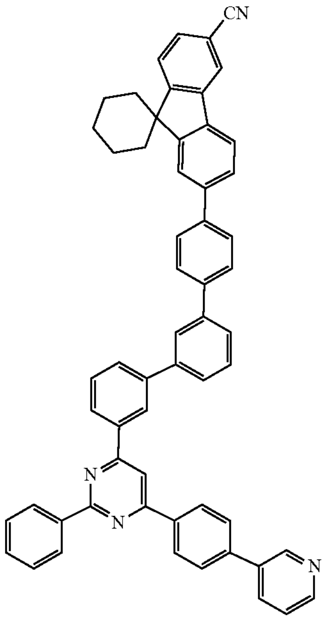

-continued
B-153
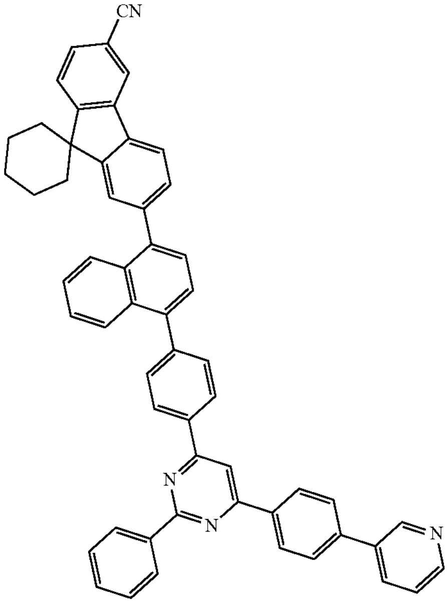
B-154
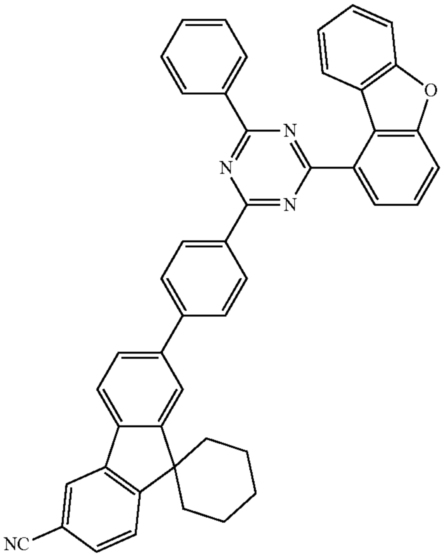
-continued
B-155
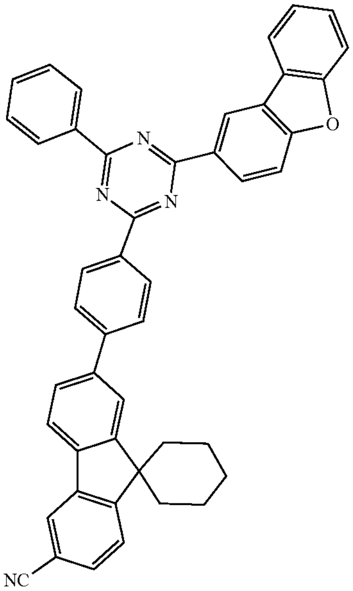
B-156
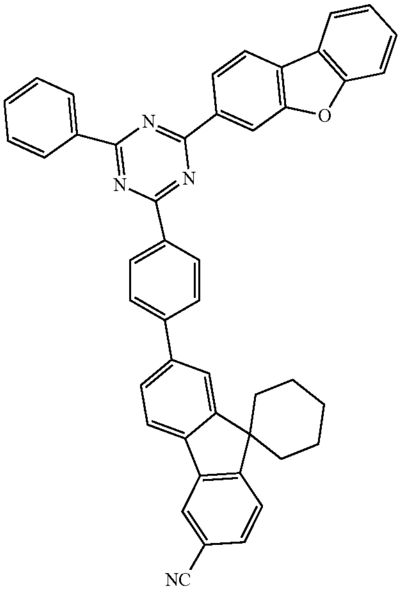

-continued
B-157
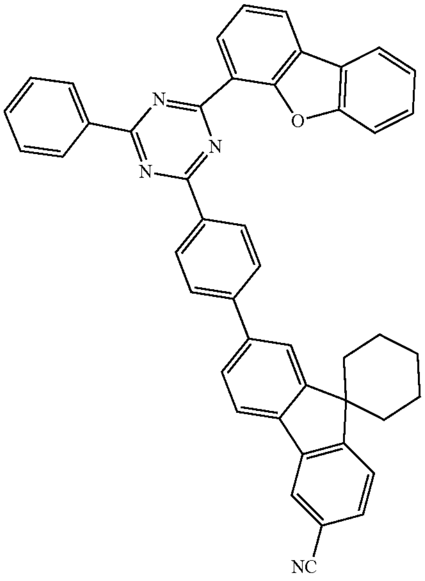
-continued
B-159
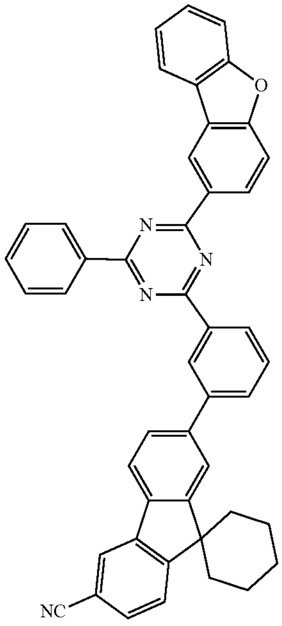
B-158
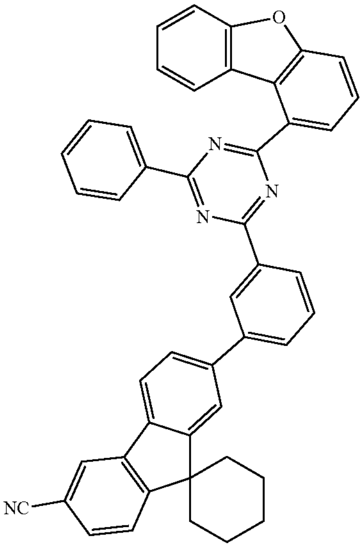
B-160
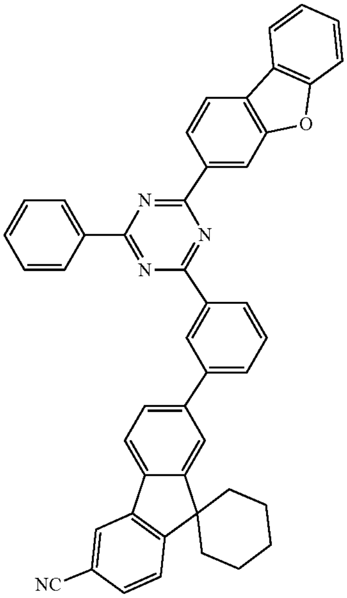

-continued
B-161
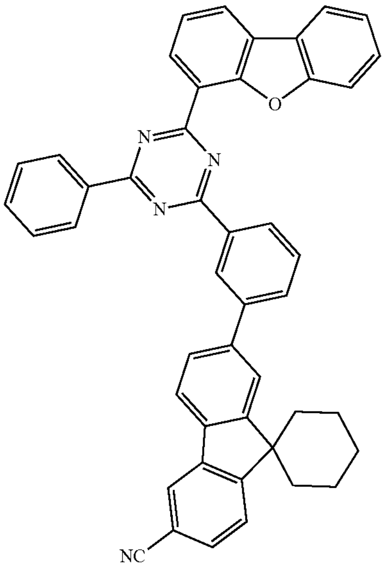
B-162
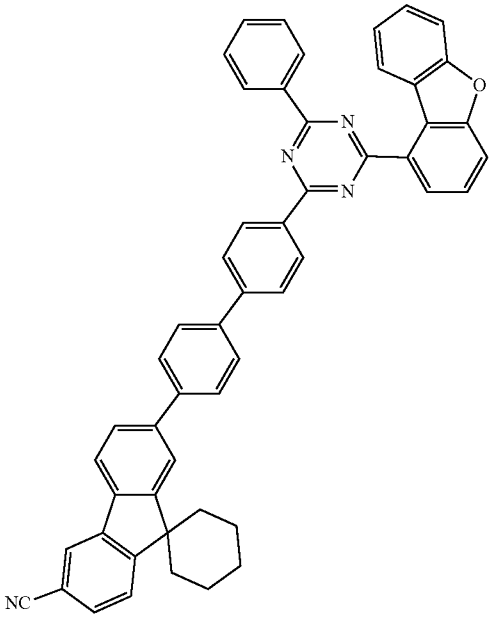
-continued
B-163
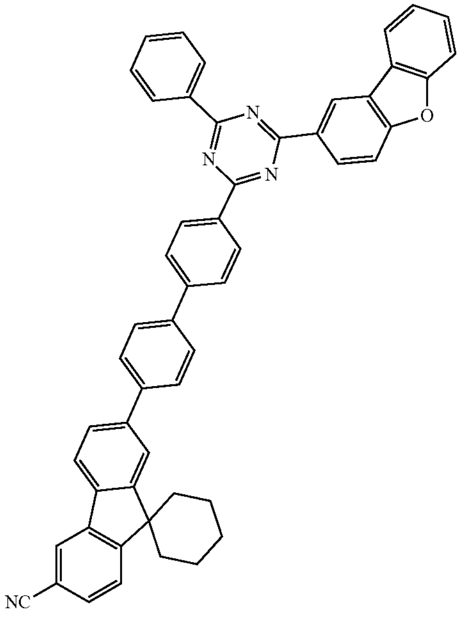
B-164
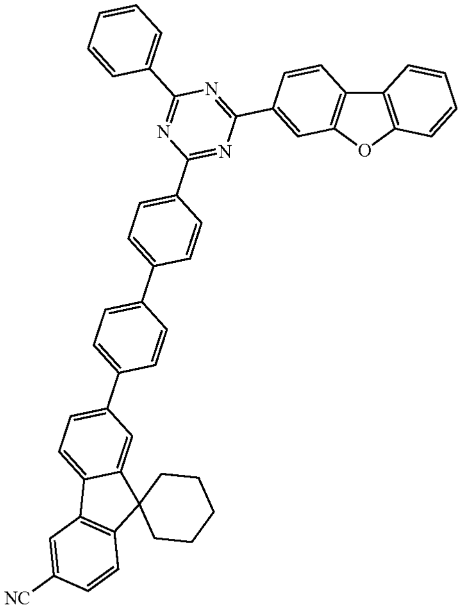

-continued
B-165
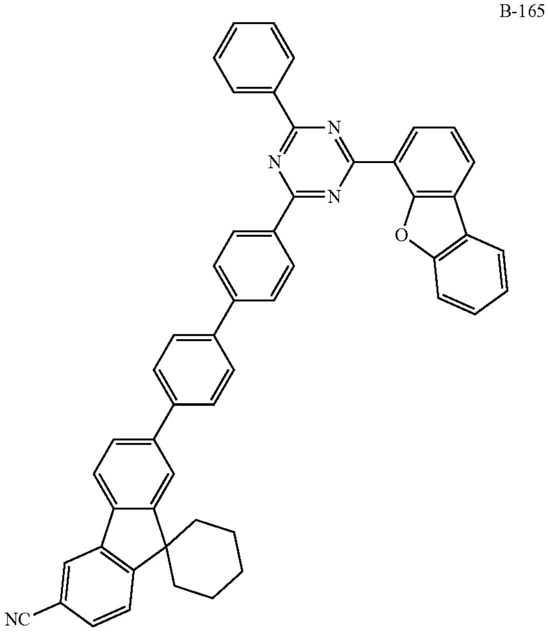
B-166
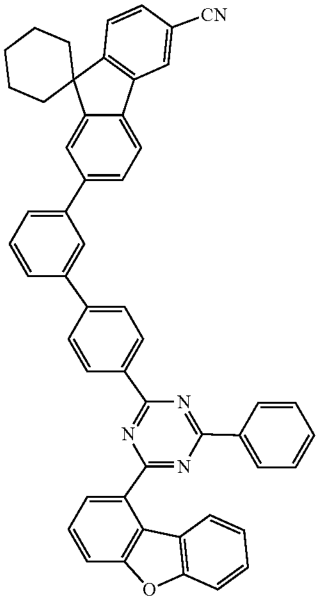
-continued
B-167
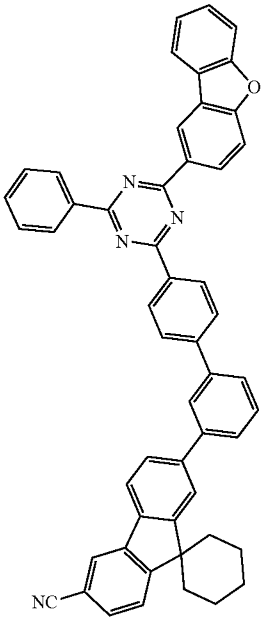
B-168
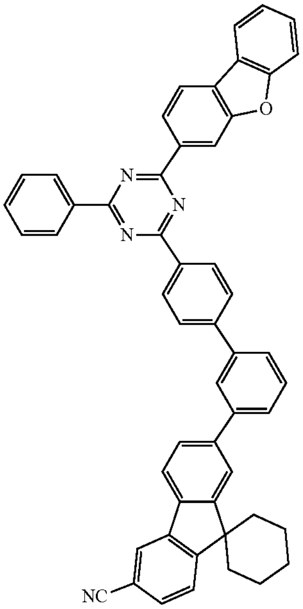

-continued
B-169
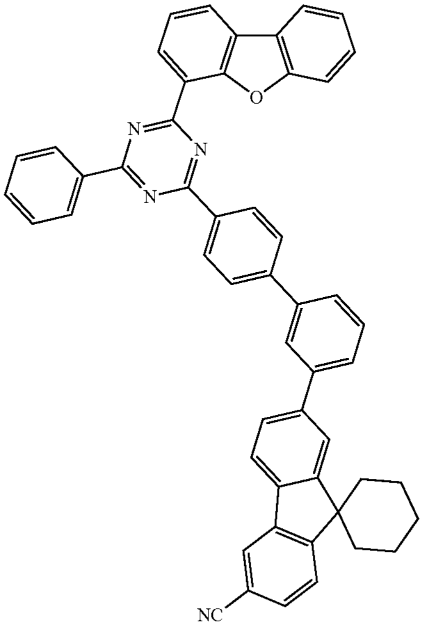
B-170
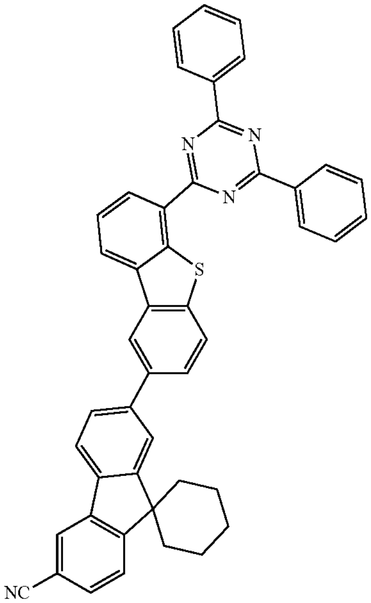
-continued
B-171
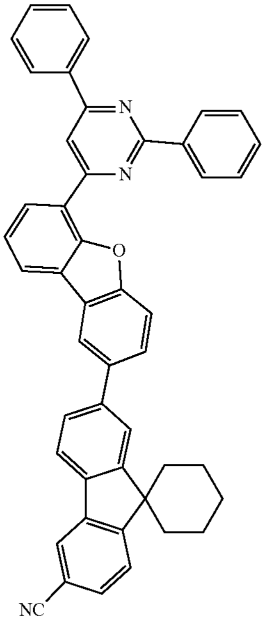
B-172
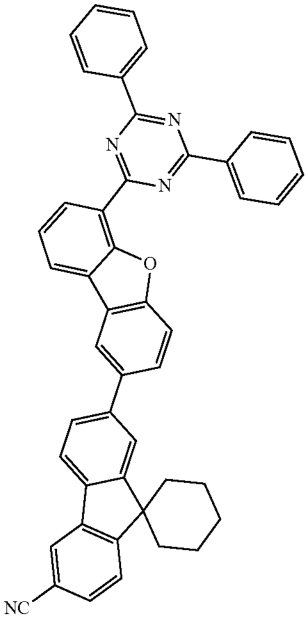

-continued
B-173
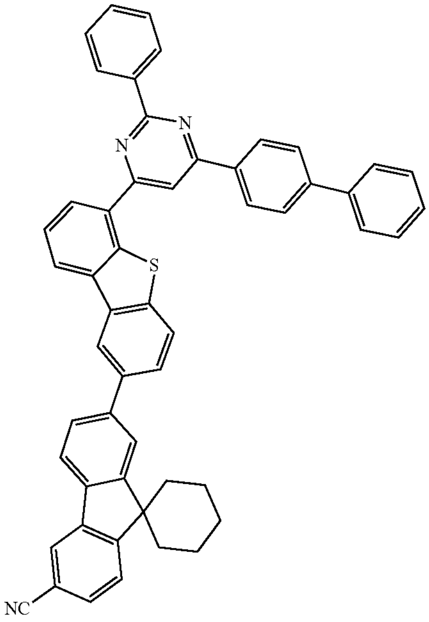
B-174
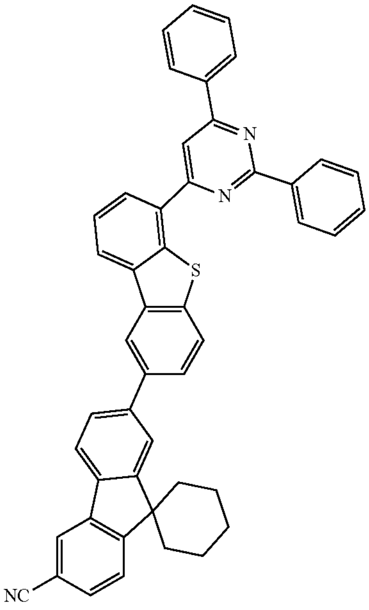
-continued
B-175
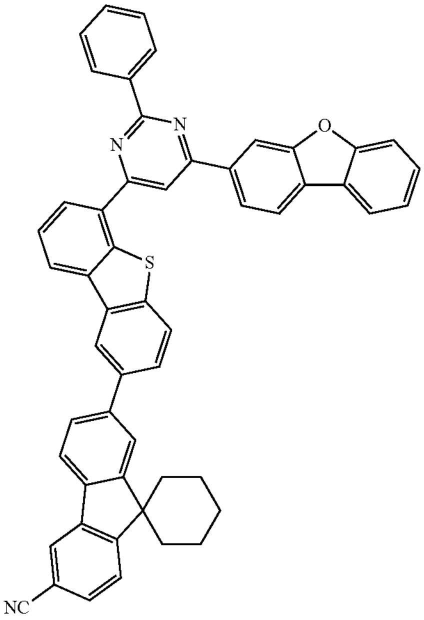
B-176
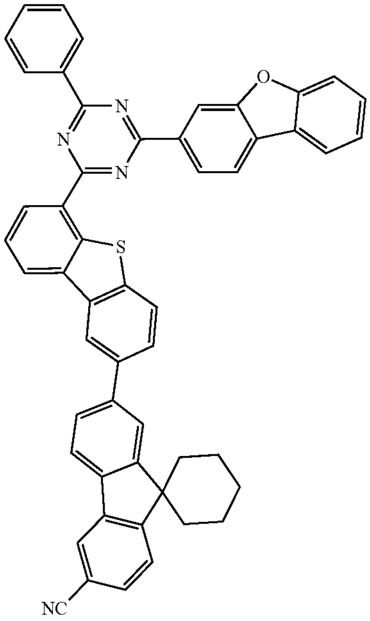

-continued
B-177
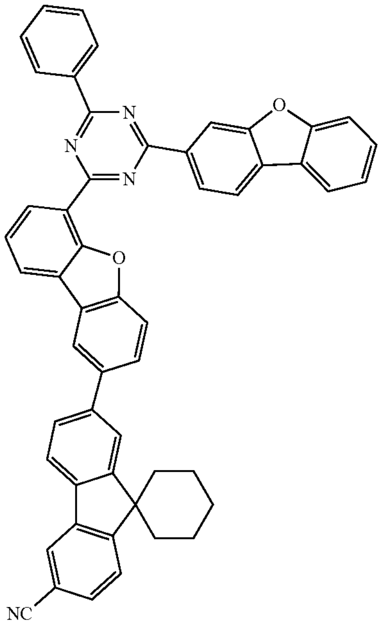
B-178
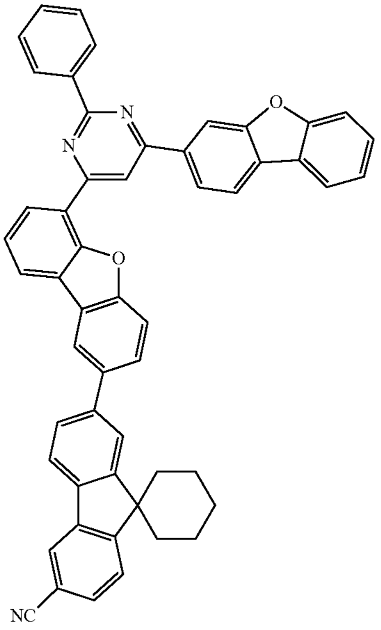
-continued
B-179
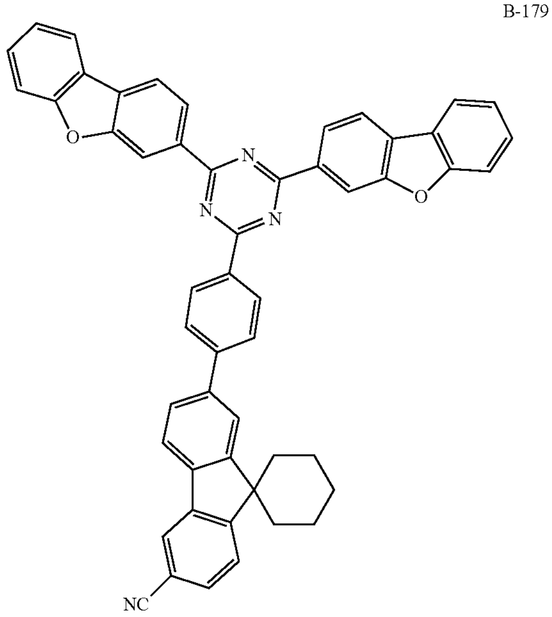
B-180
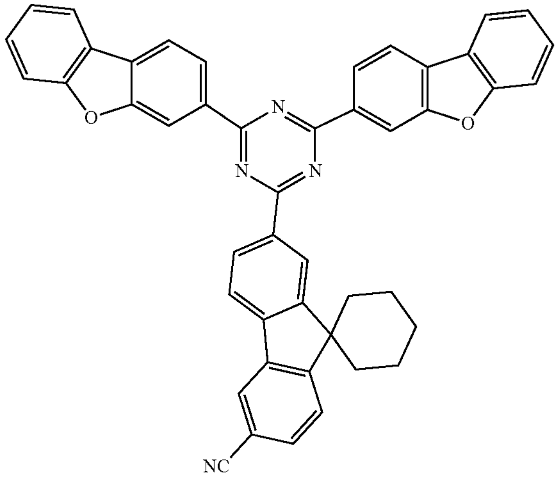
B-181
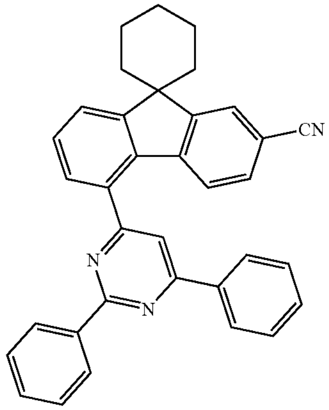

-continued
B-182
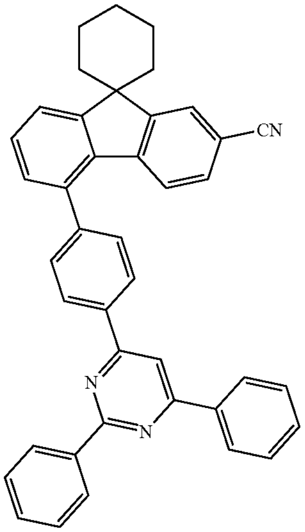
B-183
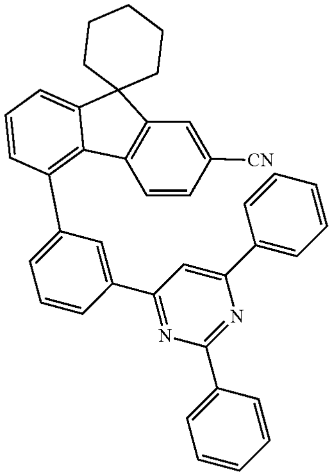
B-184
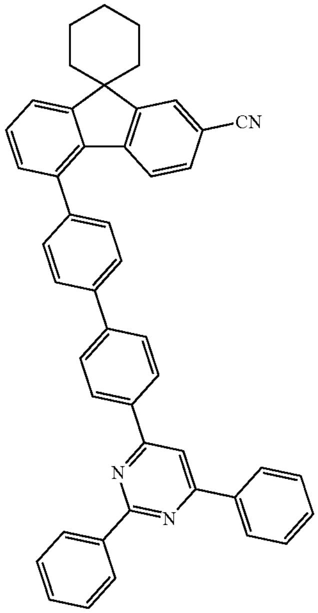
-continued
B-185
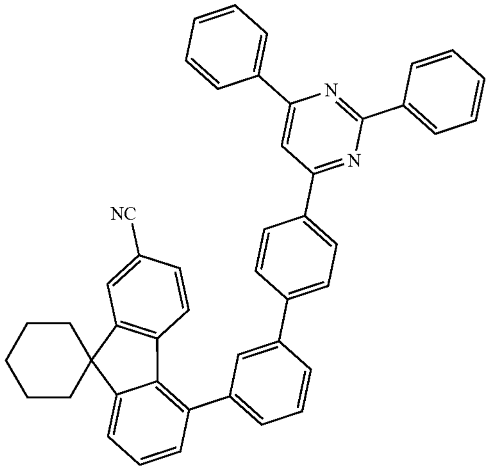
B-186
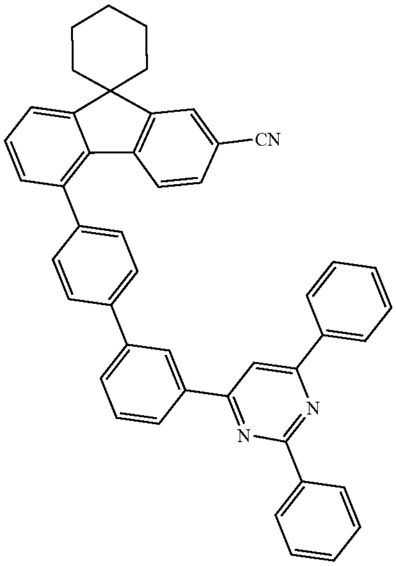
B-187
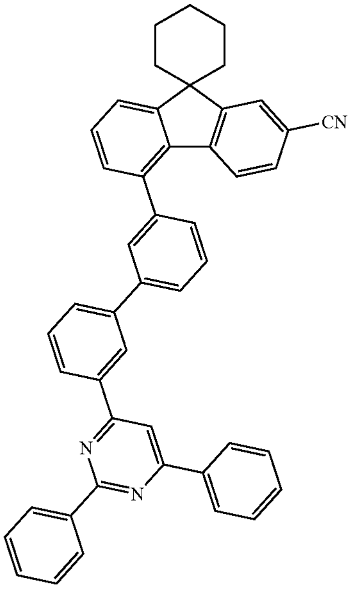

-continued
B-188
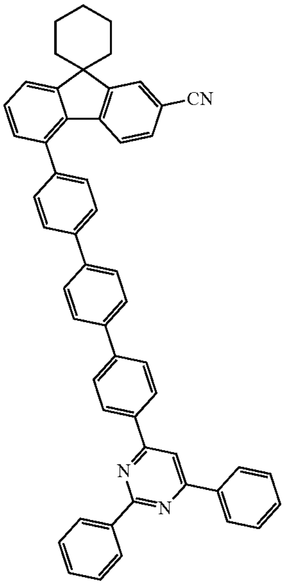
B-189
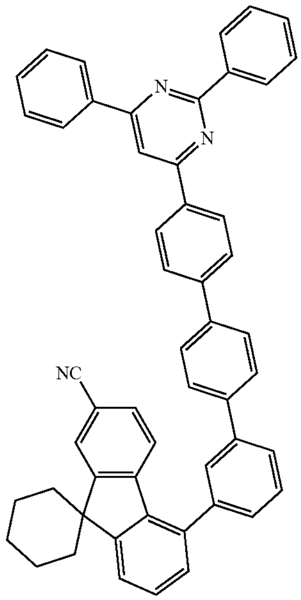
-continued
B-190
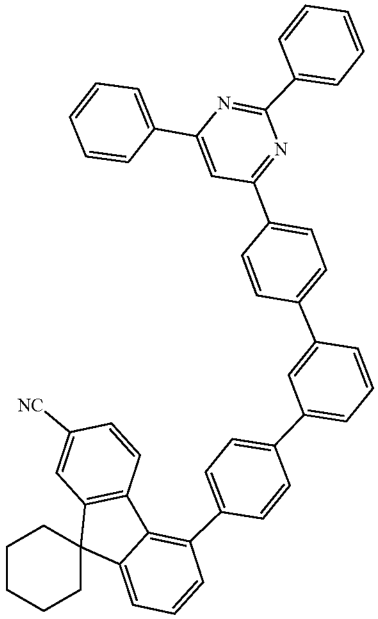
B-191
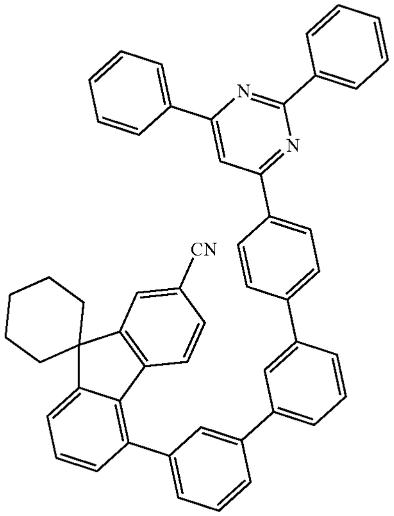

B-192
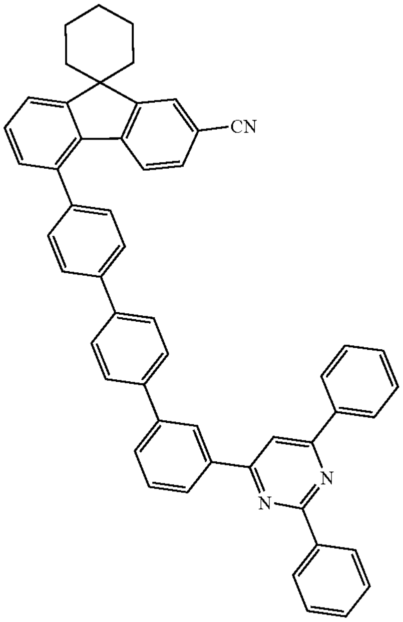
B-193
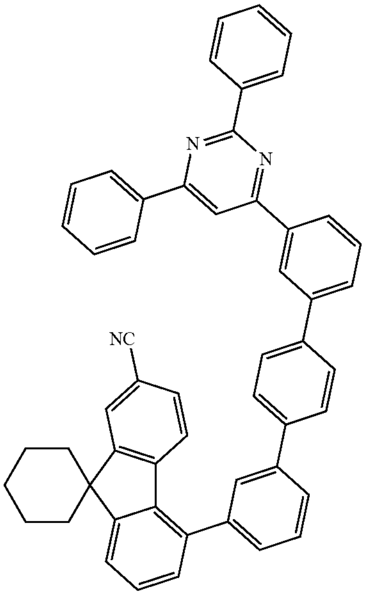
B-194
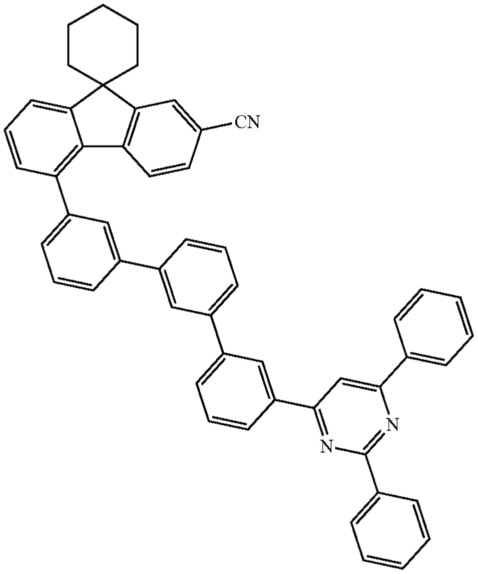
B-195
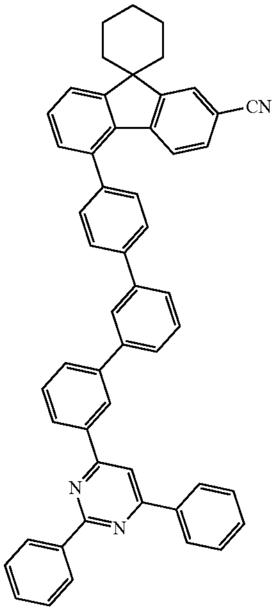

-continued
B-196
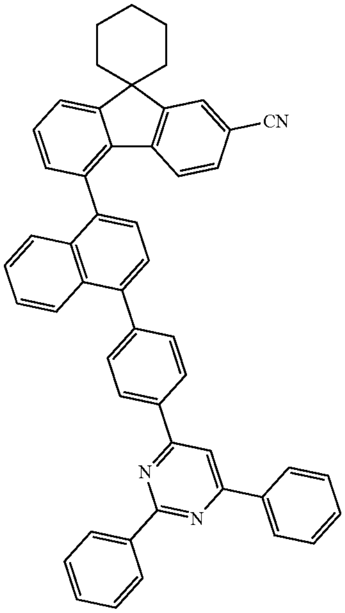
B-197
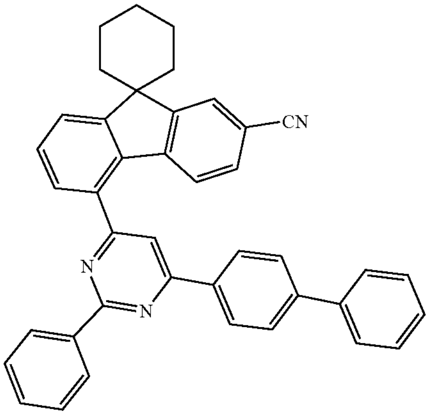
B-198
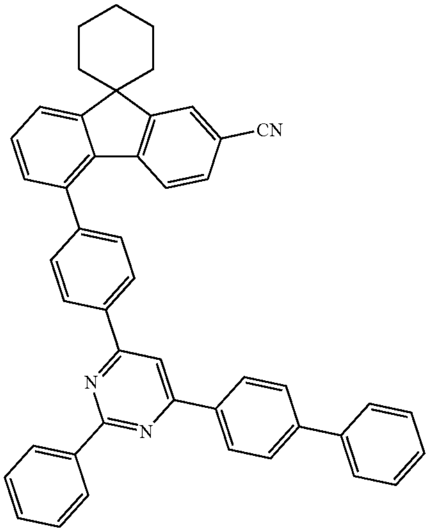
-continued
B-199
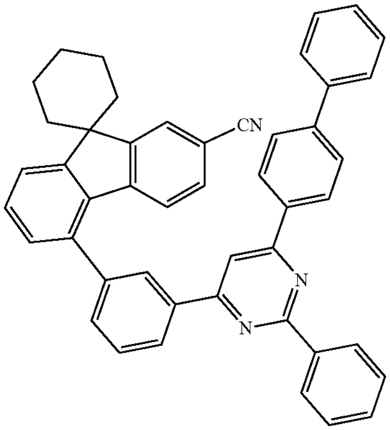
B-200
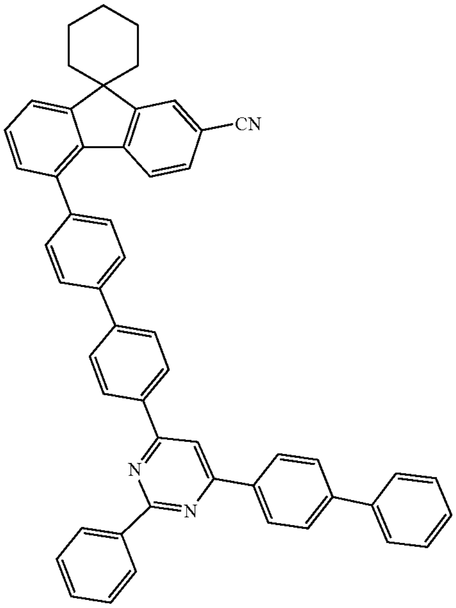
B-201
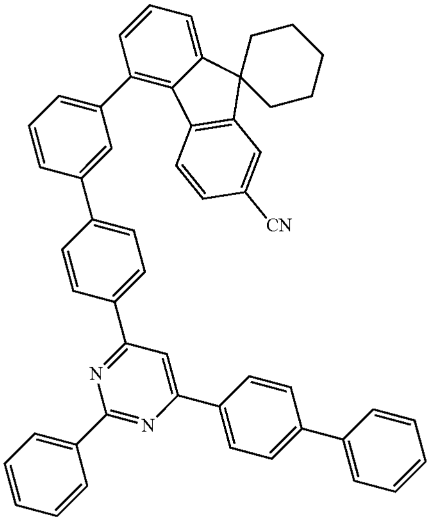

-continued
B-202
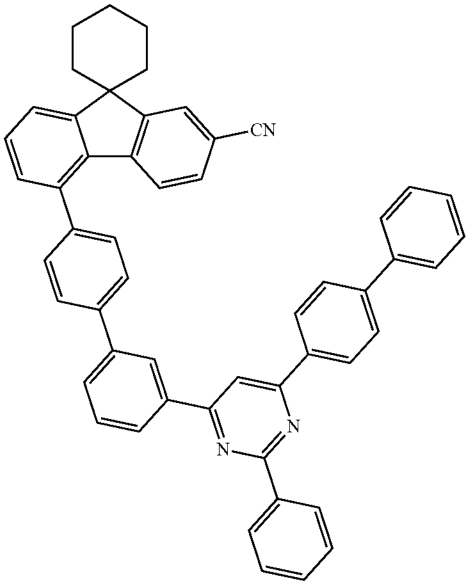
B-203
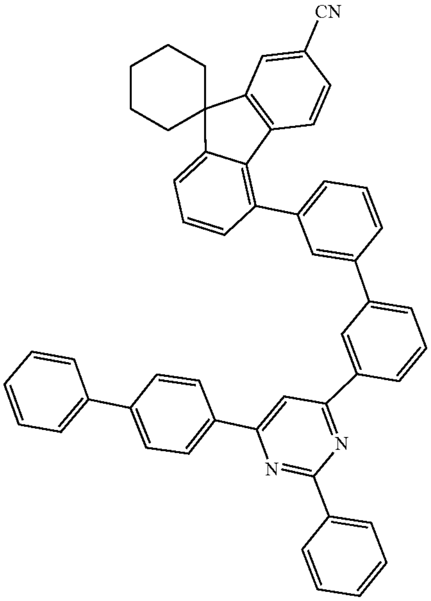
-continued
B-204
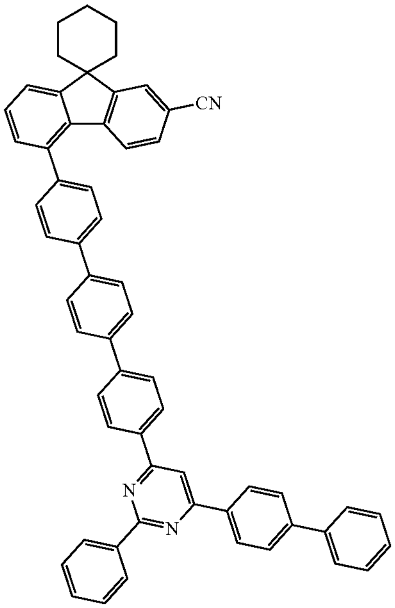
B-205
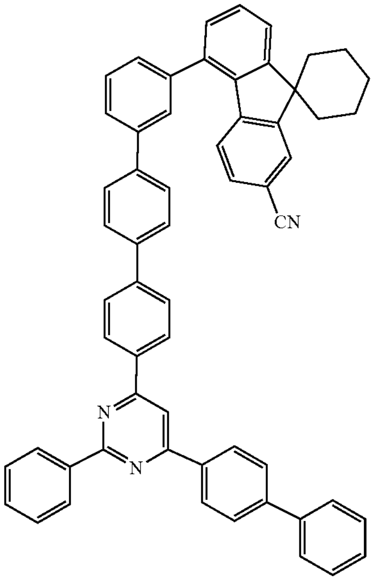

-continued
B-206
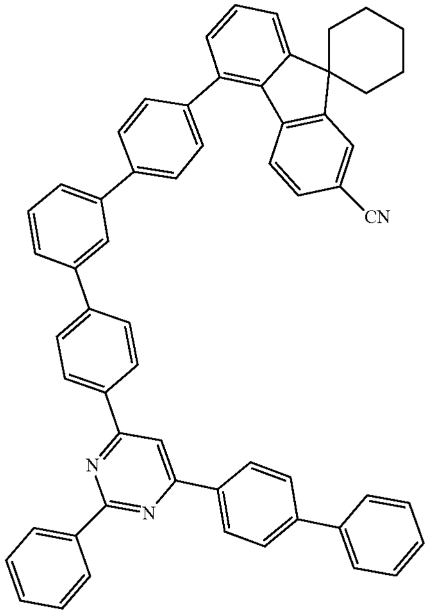
B-207
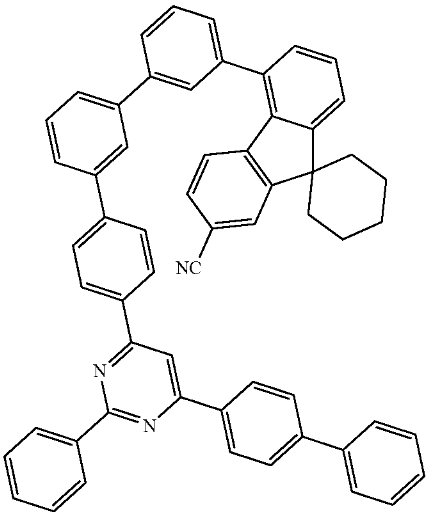
-continued
B-208
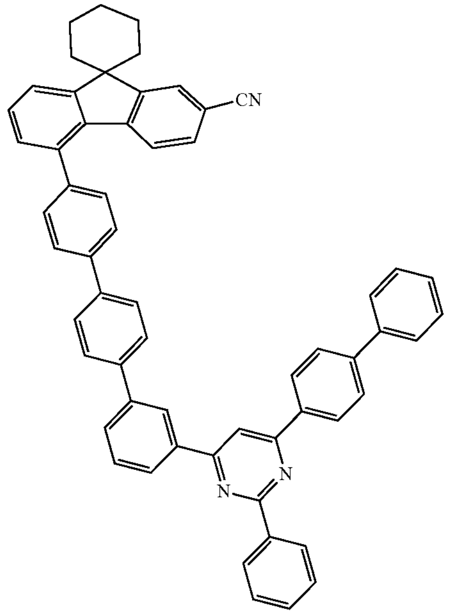
B-209
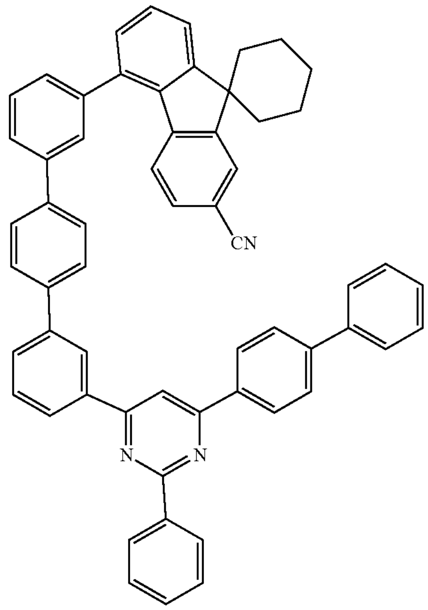

-continued
B-210
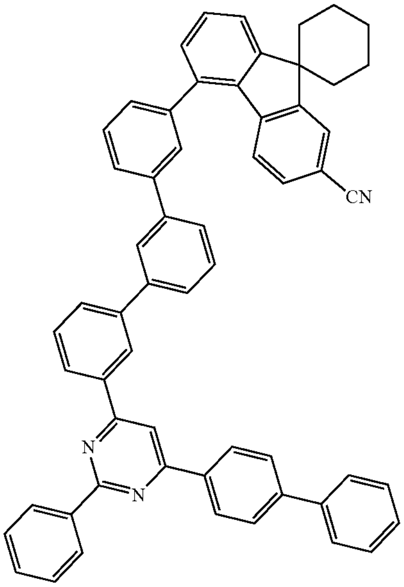
B-211
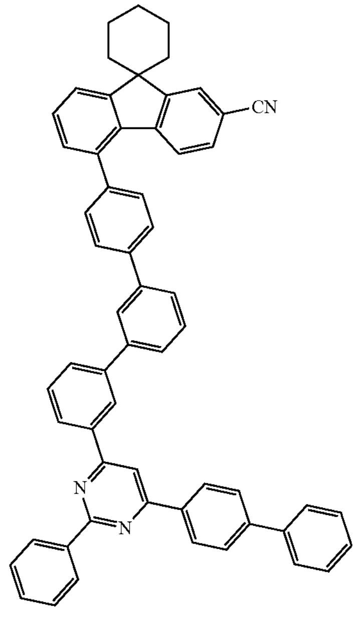
-continued
B-212
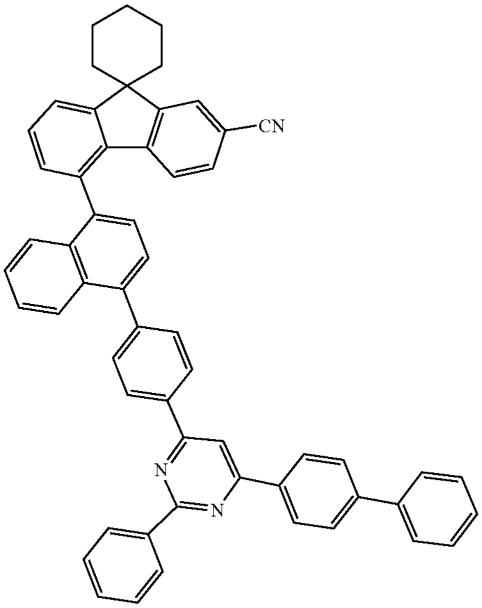
B-213
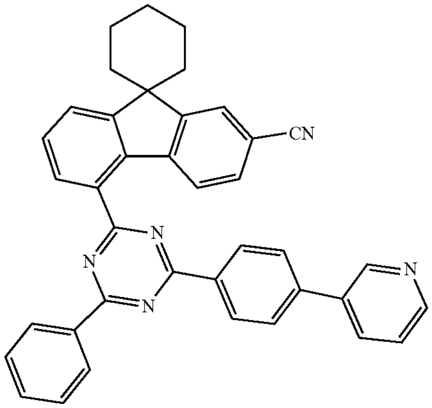
B-214
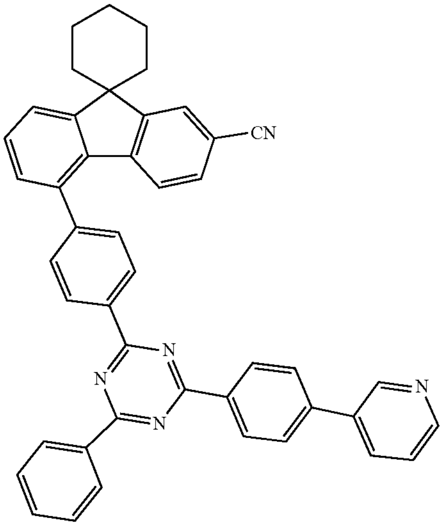

-continued
B-215
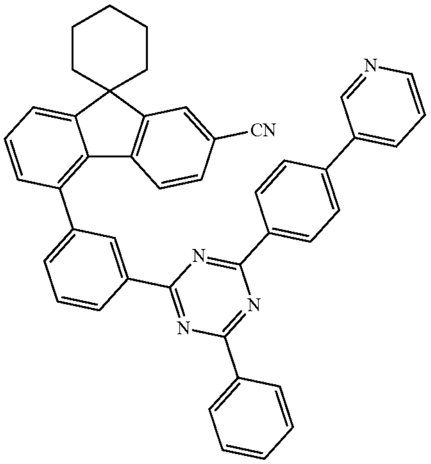
B-216
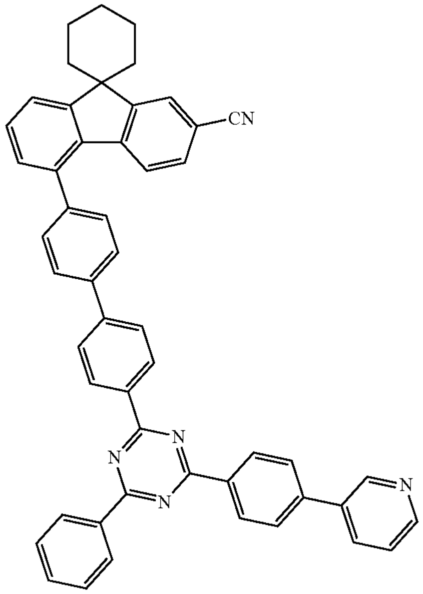
B-217
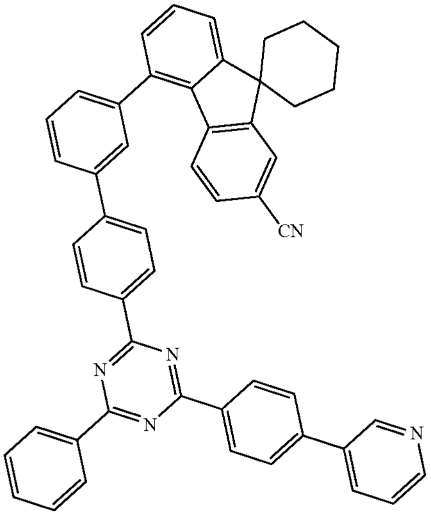
-continued
B-218
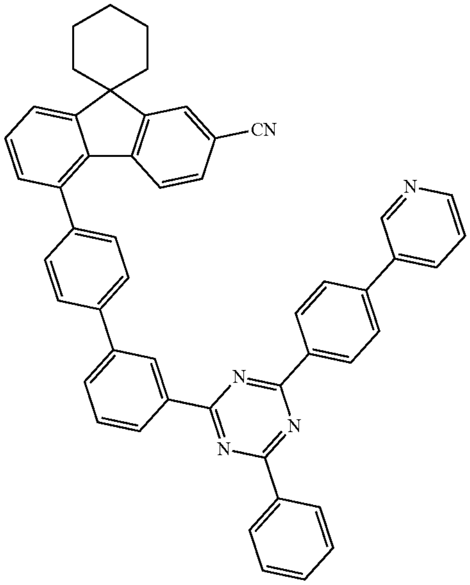
B-219
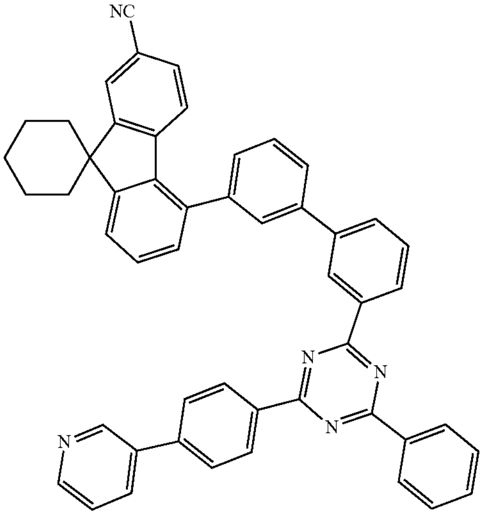

-continued
B-220
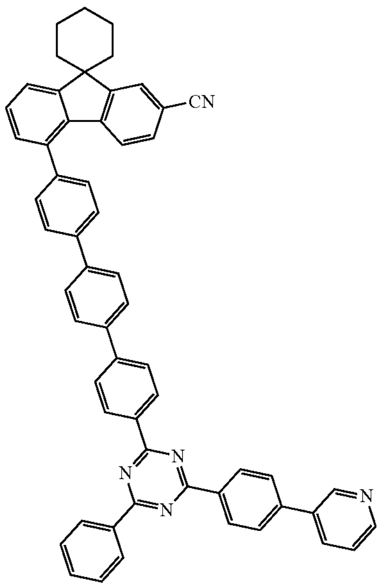
B-221
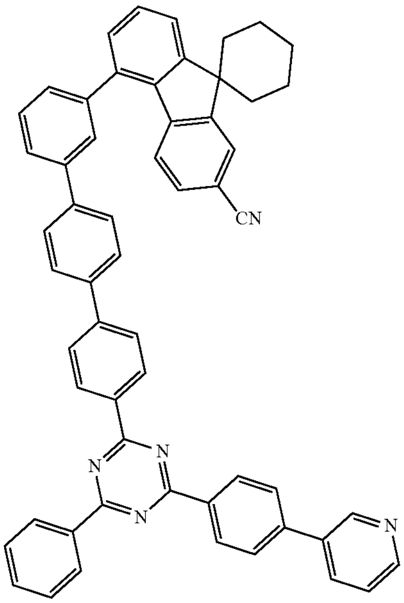
-continued
B-222
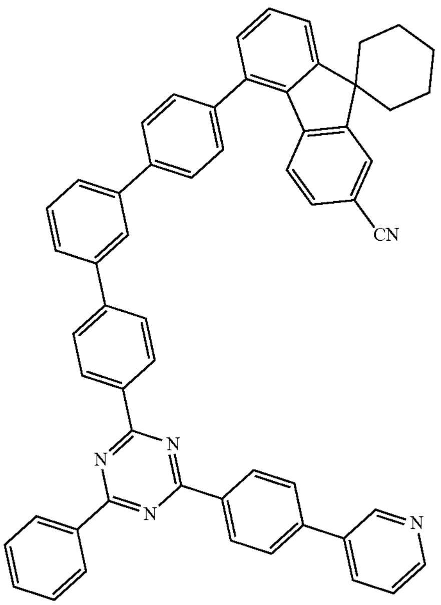
B-223
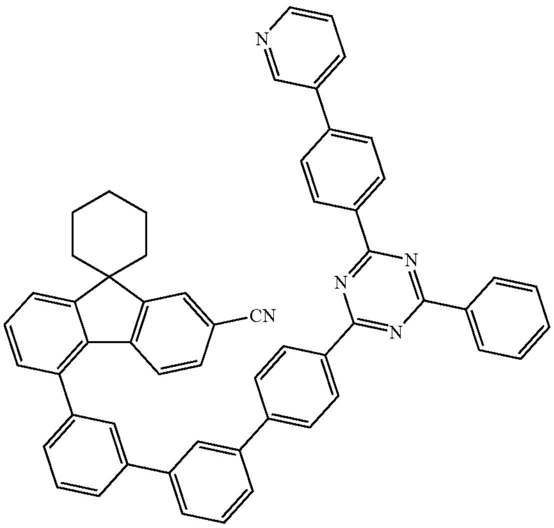

-continued
B-224
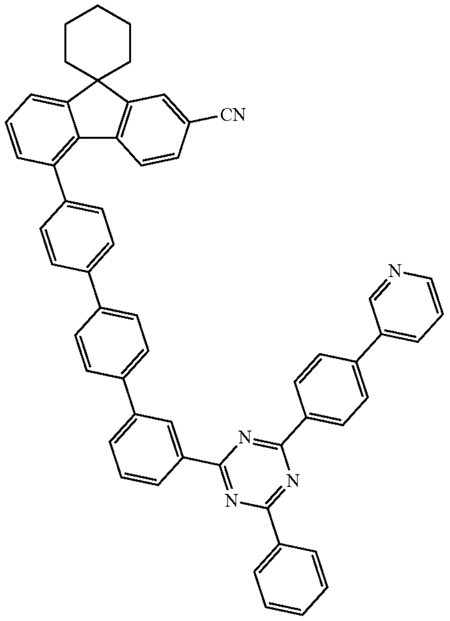
B-226
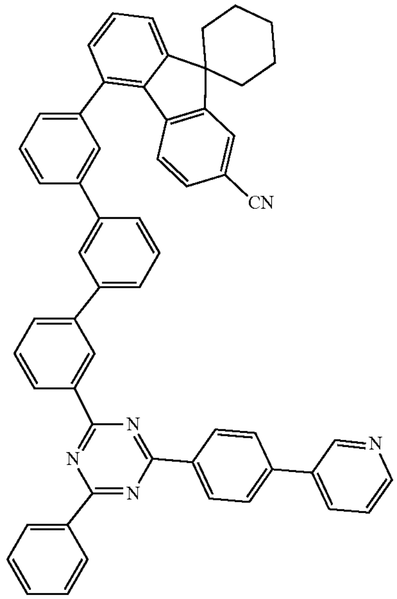
B-225
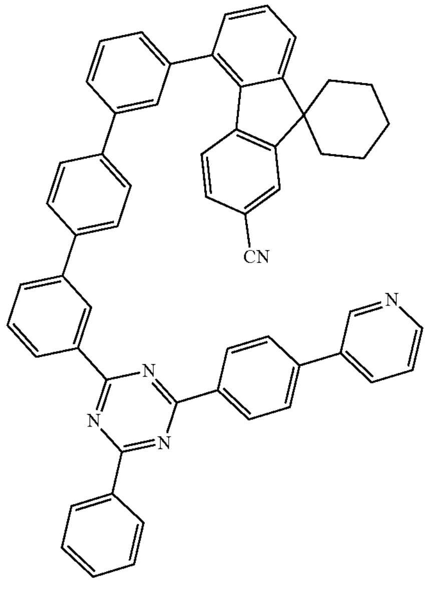
B-227
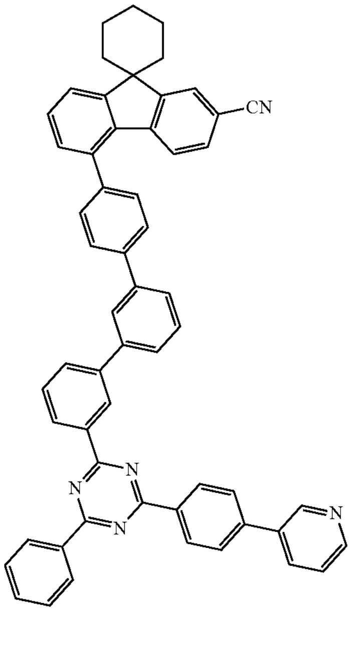

-continued
B-228
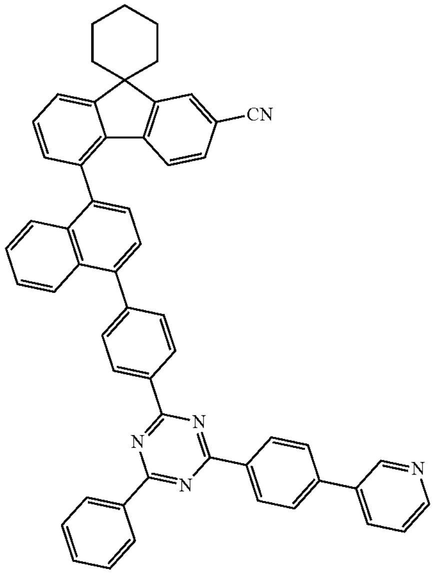
B-229
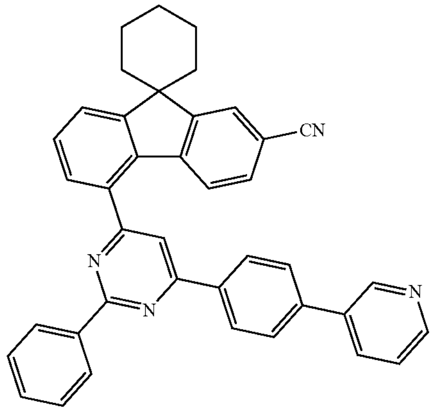
B-230
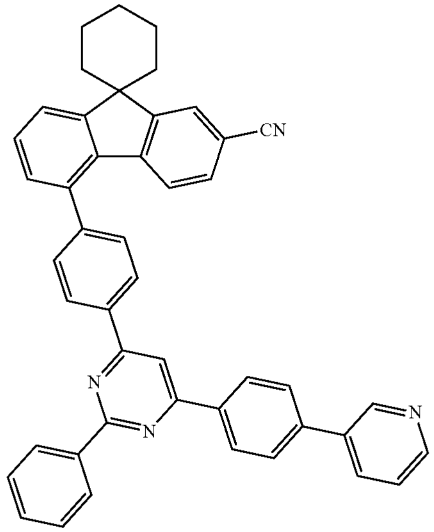
-continued
B-231
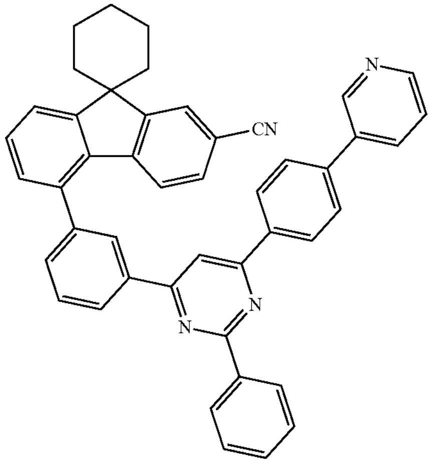
B-232
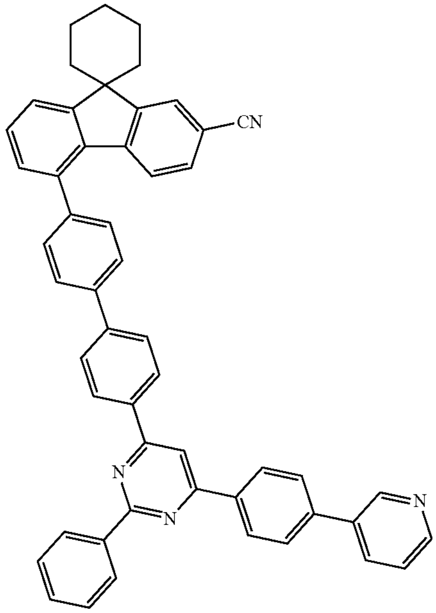
B-233
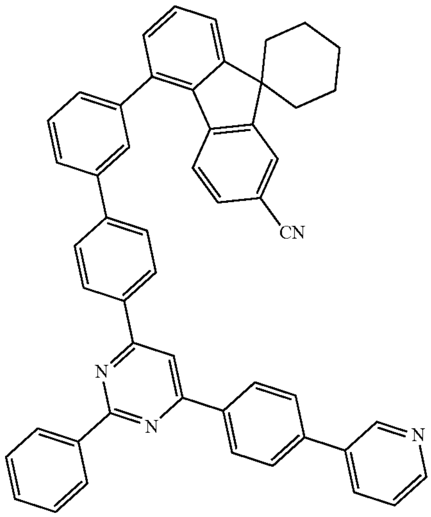

B-234
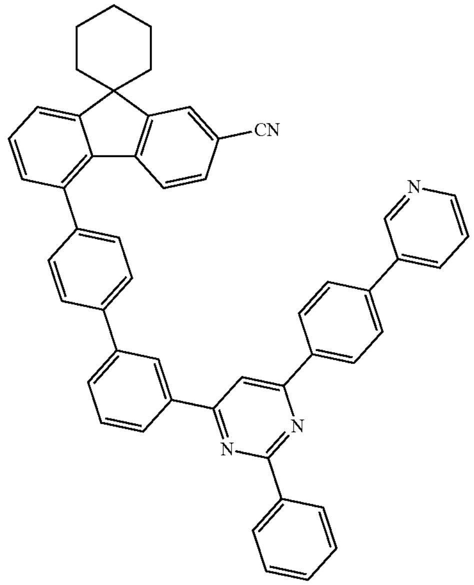
B-236
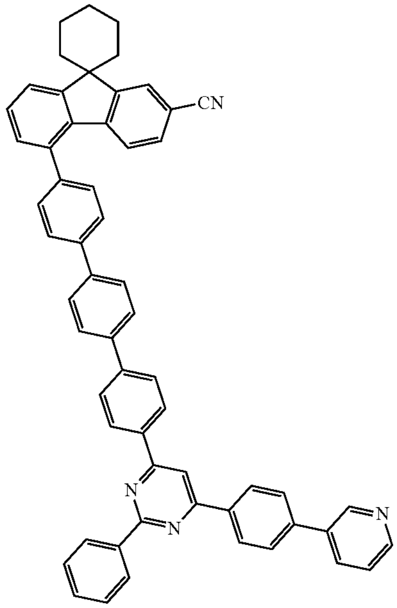
B-235
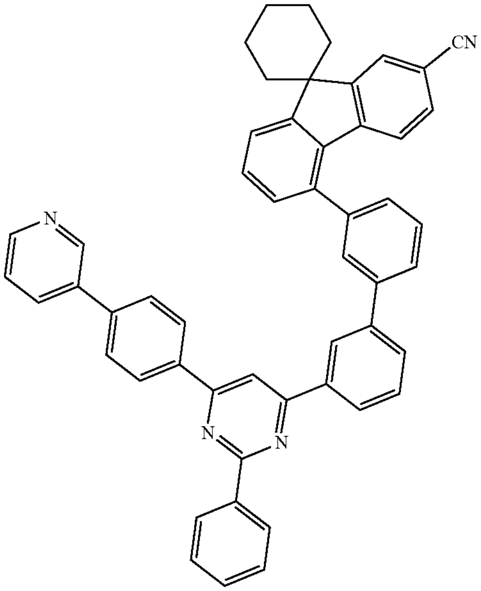
B-237
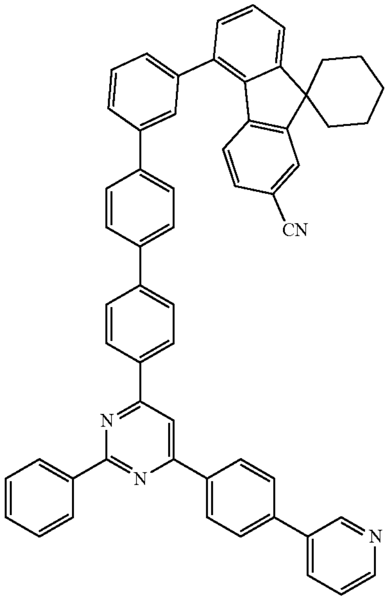

-continued
B-238
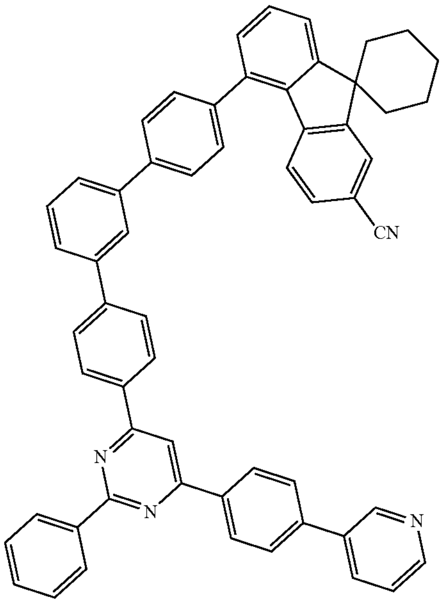
B-239
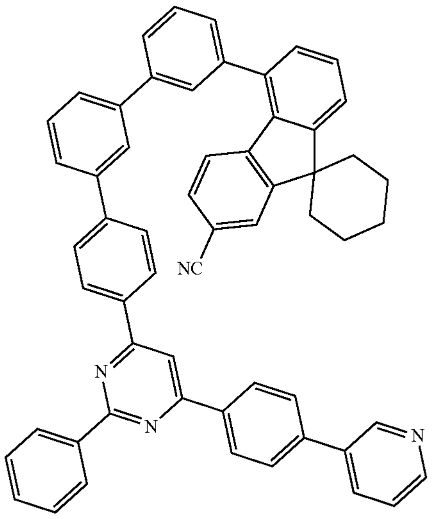
-continued
B-240
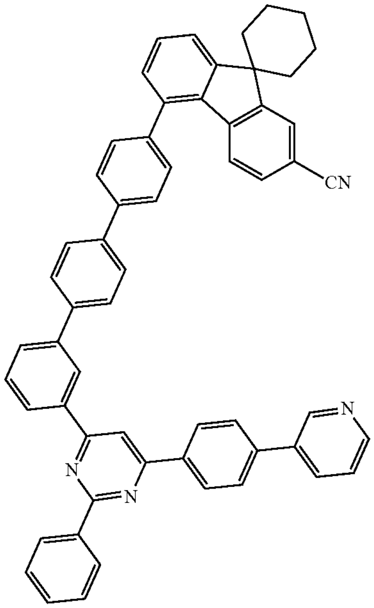
B-241
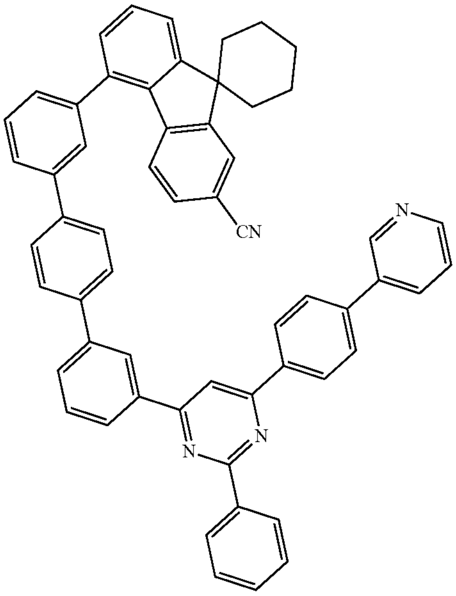

-continued
B-242
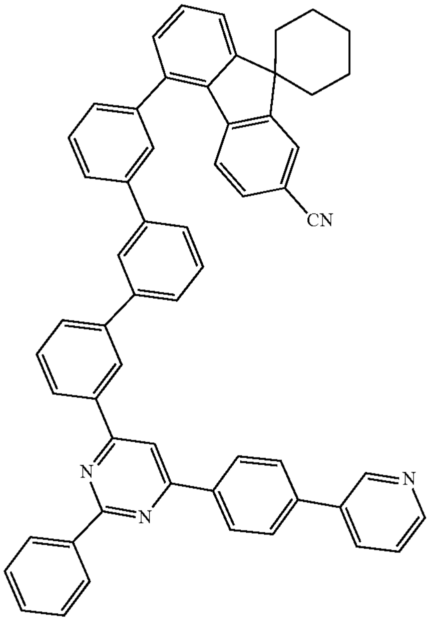
B-243
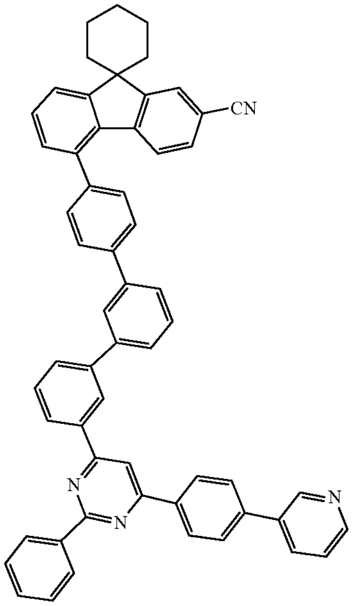
-continued
B-244
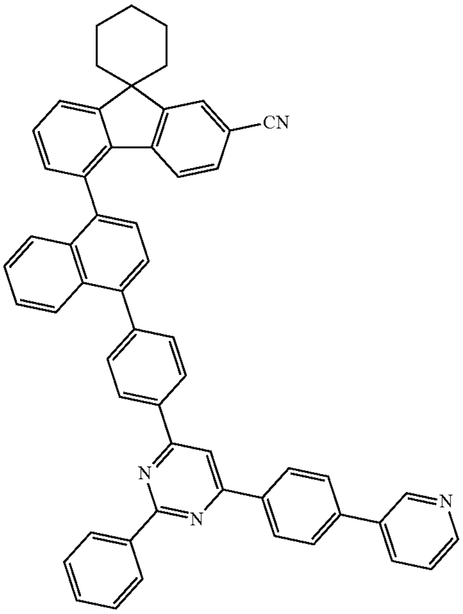
B-245
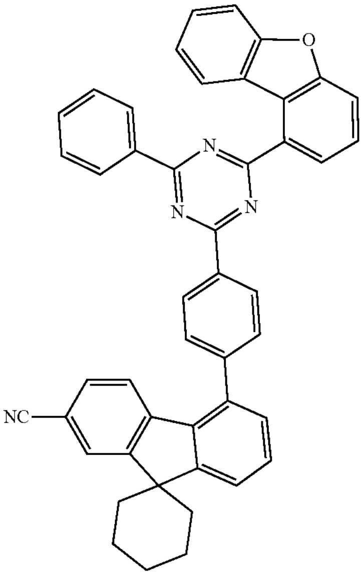

-continued
B-246
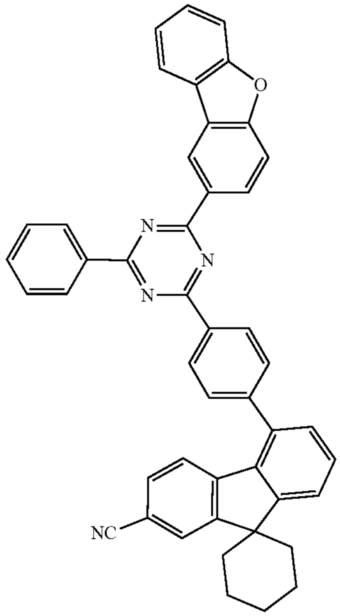
B-247
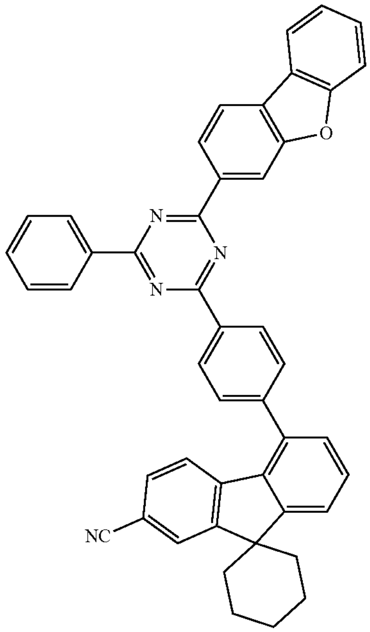
-continued
B-248
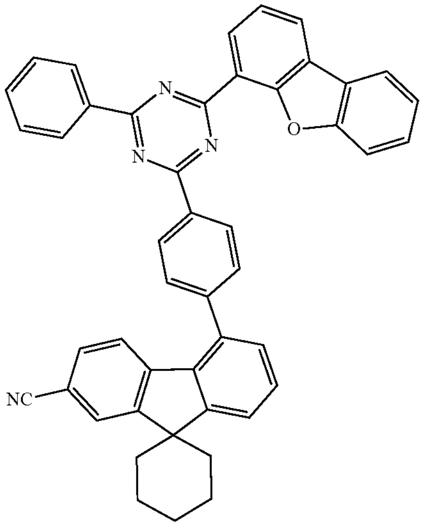
B-249
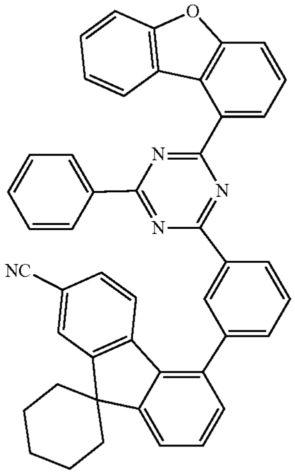
B-250
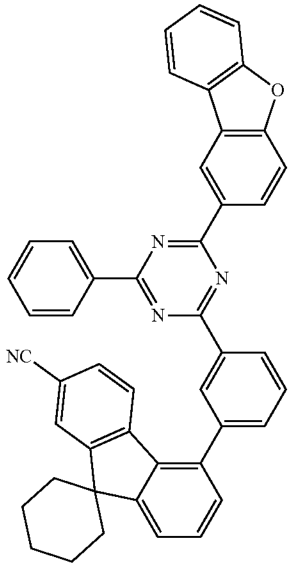

-continued
B-251
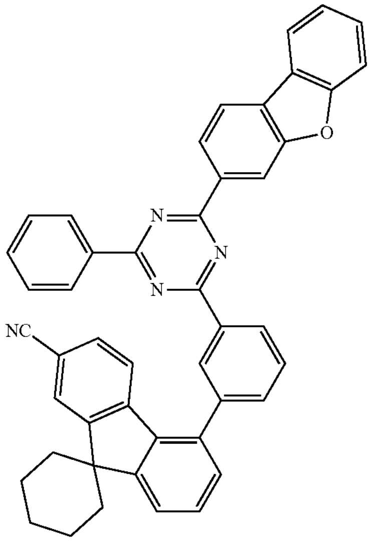
B-252
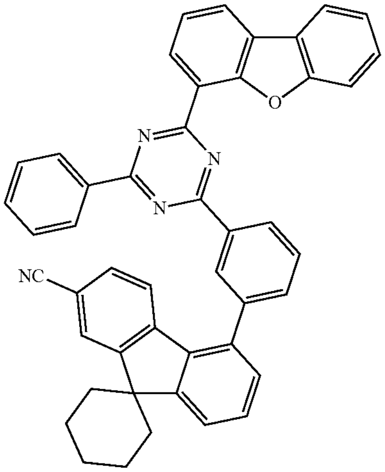
B-253
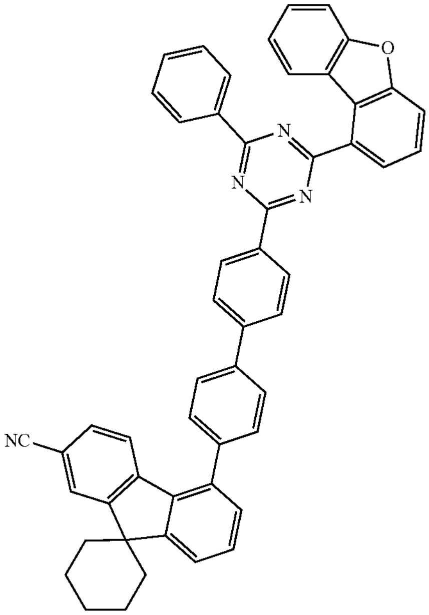
-continued
B-254
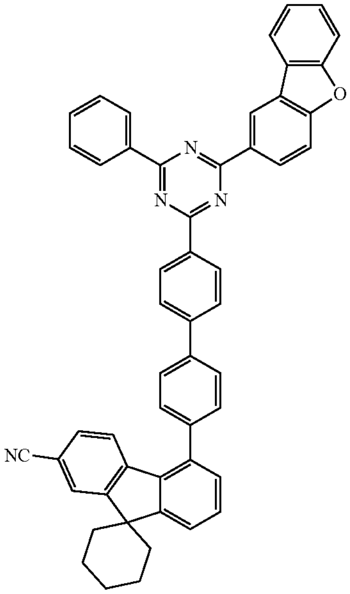
B-255
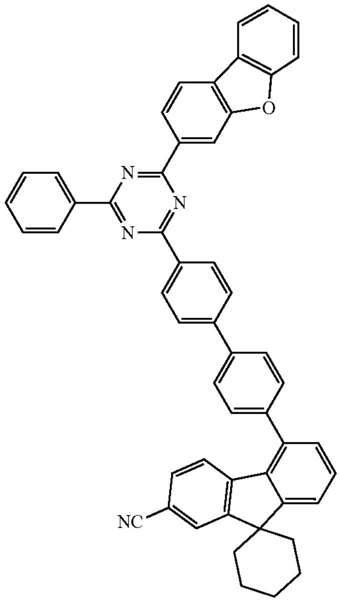

B-256
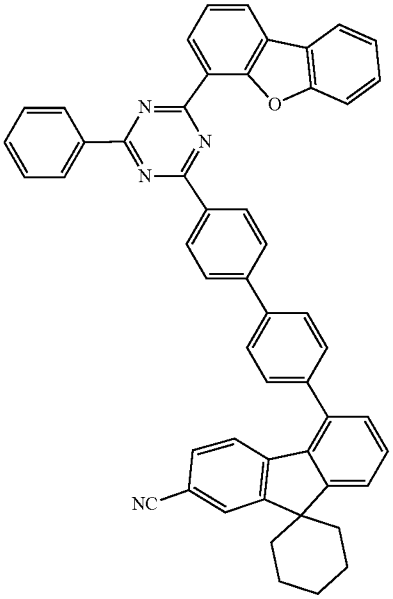
B-257
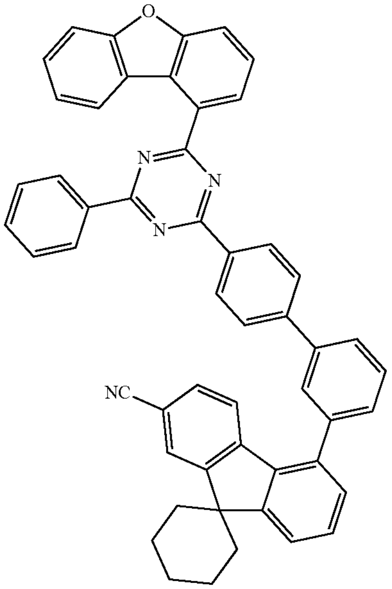
B-258
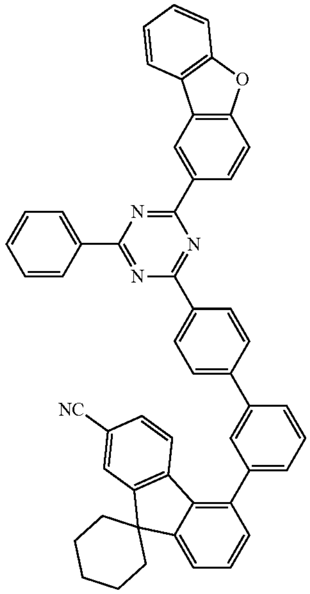
B-259
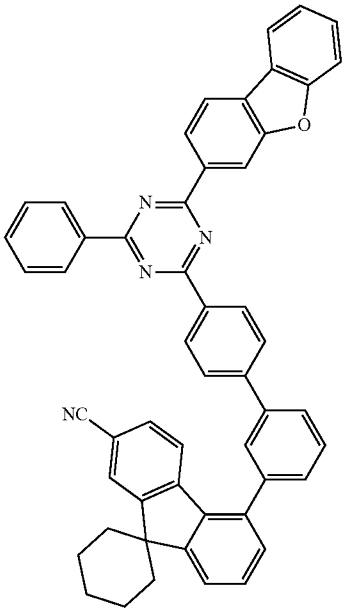

-continued
B-260
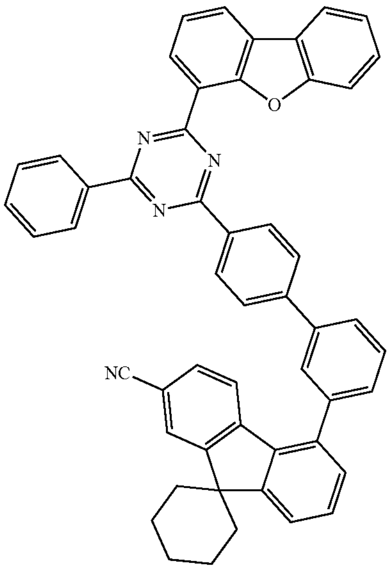
B-261
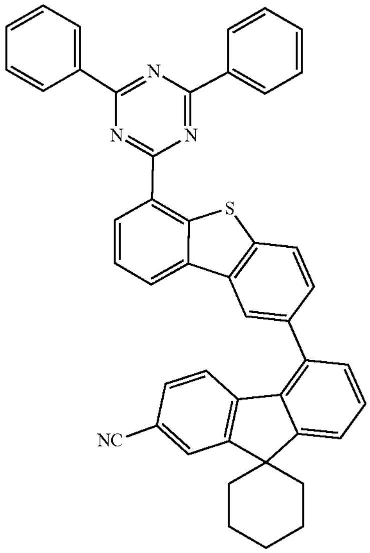
-continued
B-262
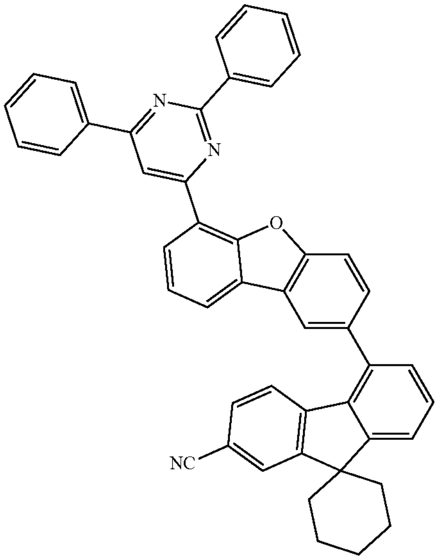
B-263
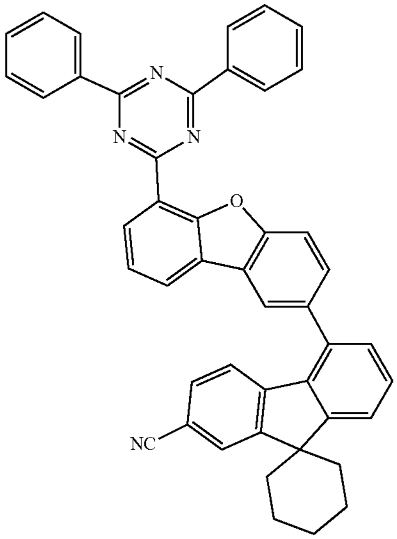

-continued
B-264
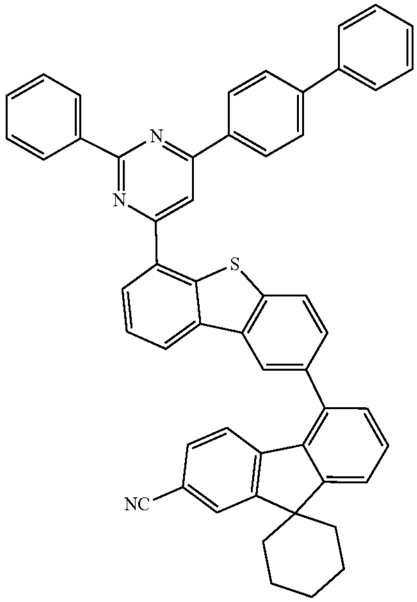
B-265
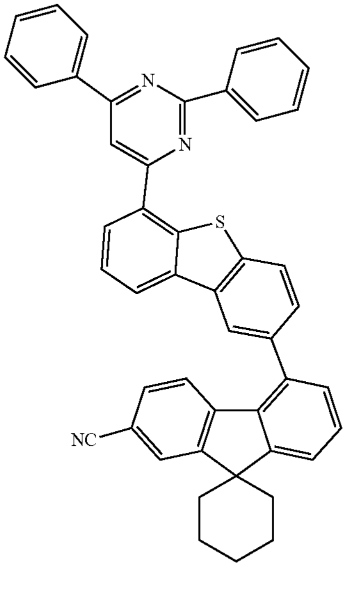
-continued
B-266
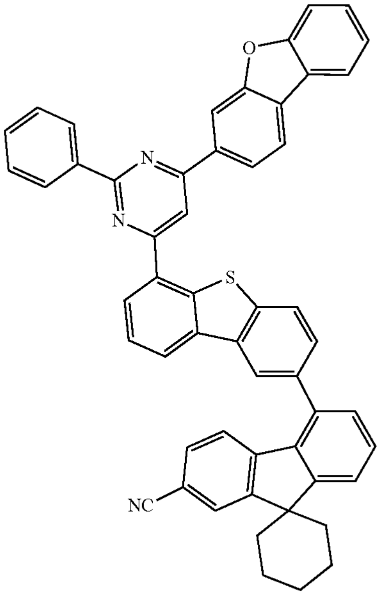
B-267
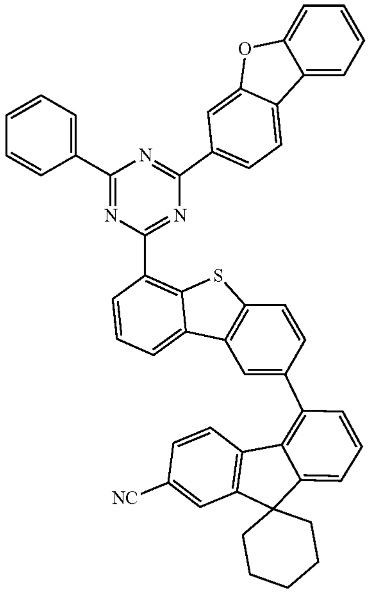

-continued
B-268
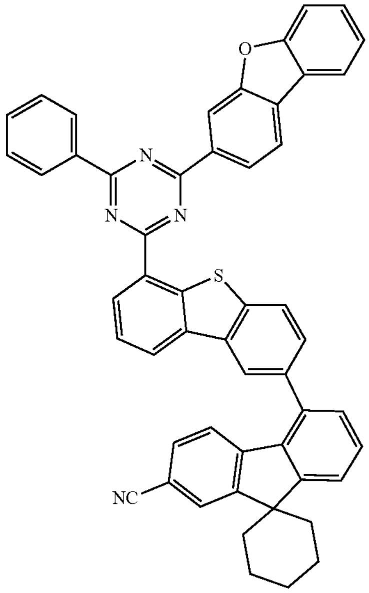
B-269
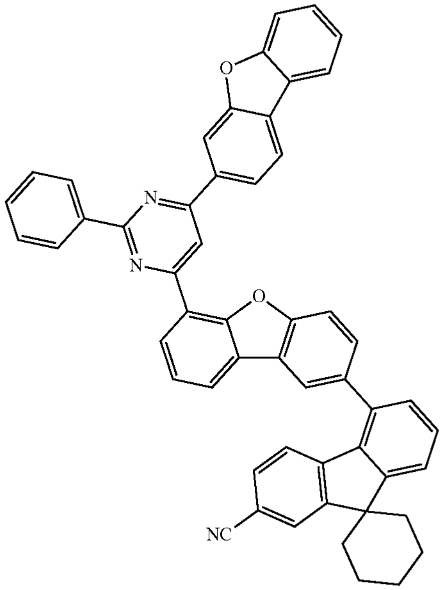
B-270
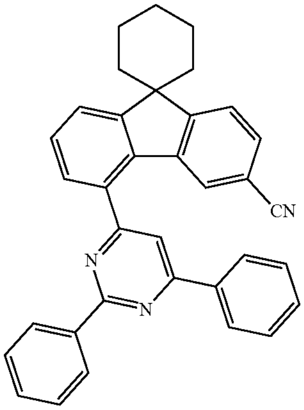
-continued
B-271
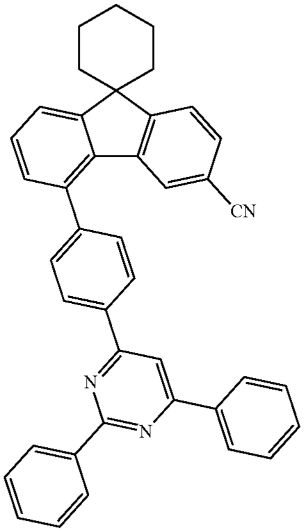
B-272
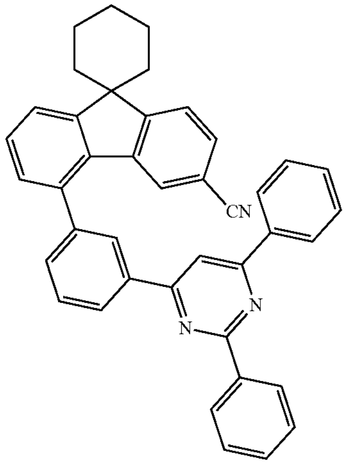
B-273
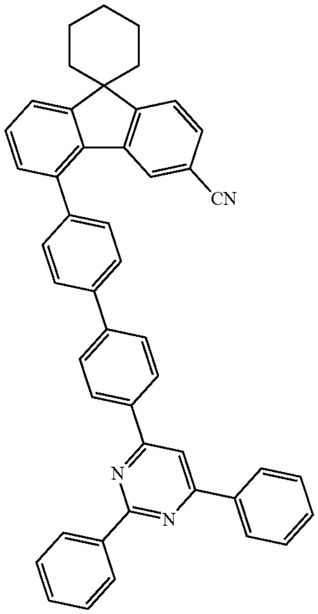

-continued
B-274
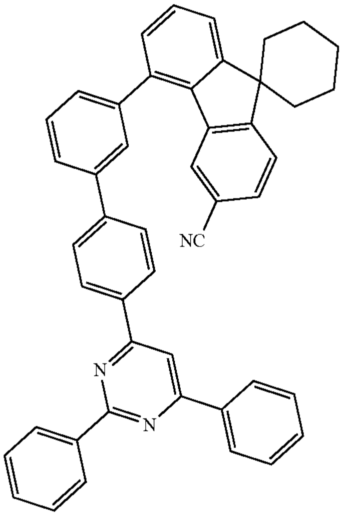
B-275
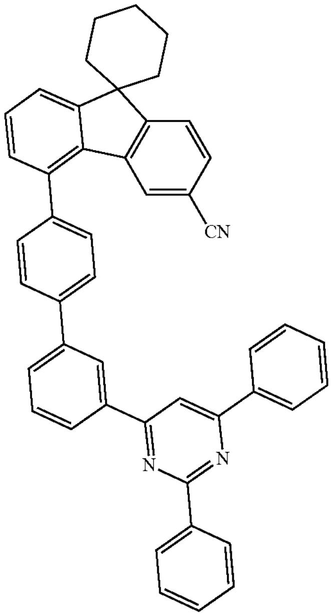
-continued
B-276
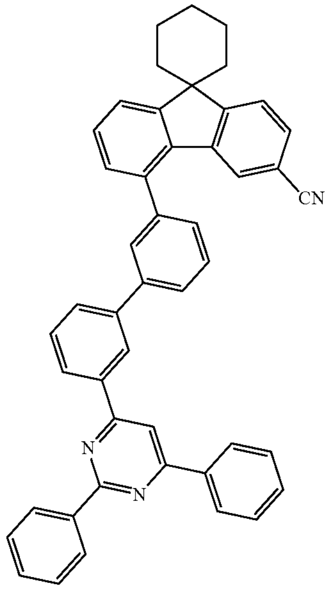
B-277
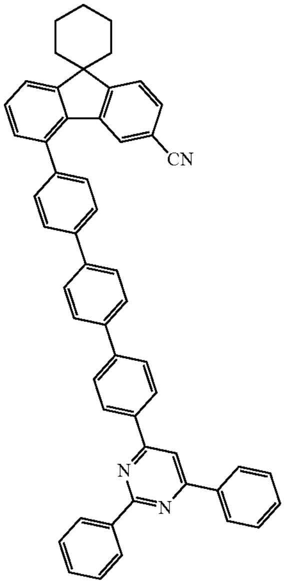

B-278
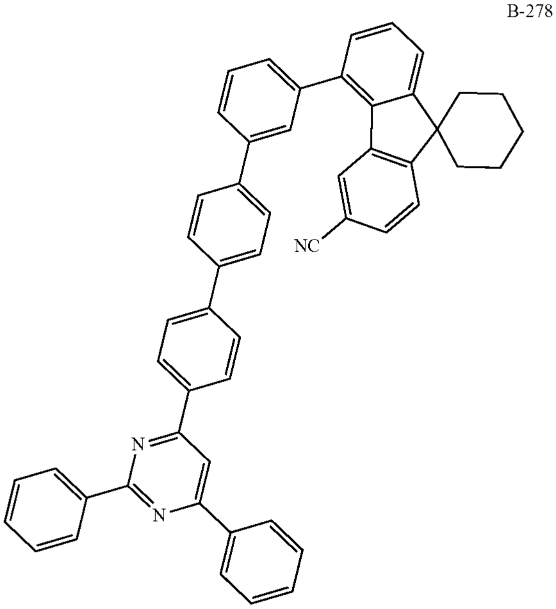
B-279
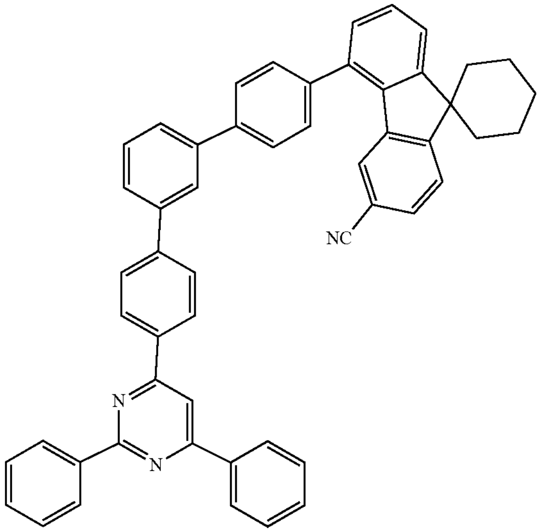
B-280
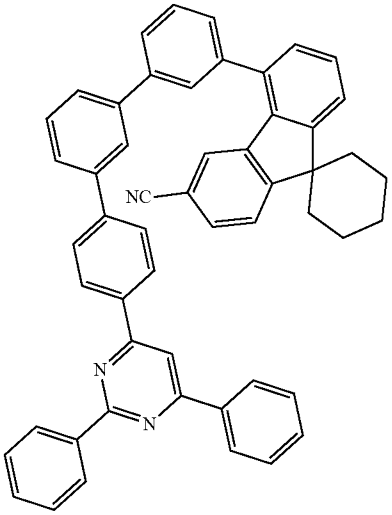
B-281
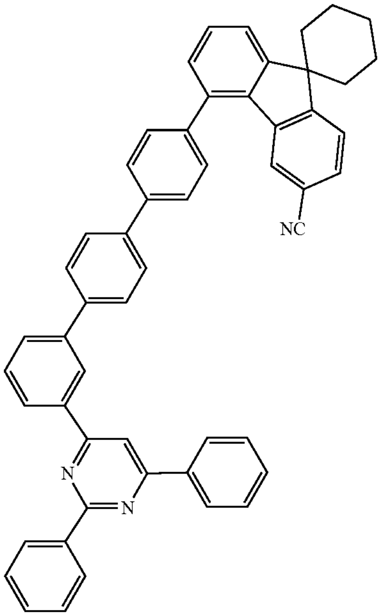
B-282
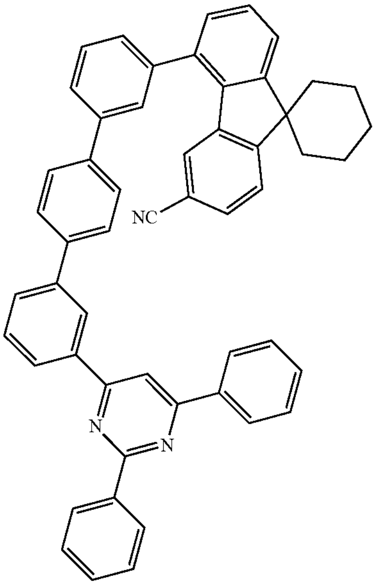

-continued
B-283
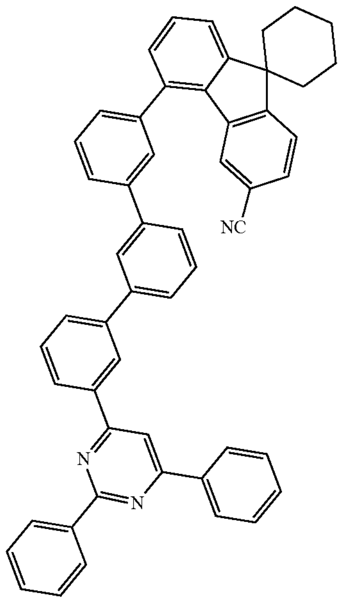
B-284
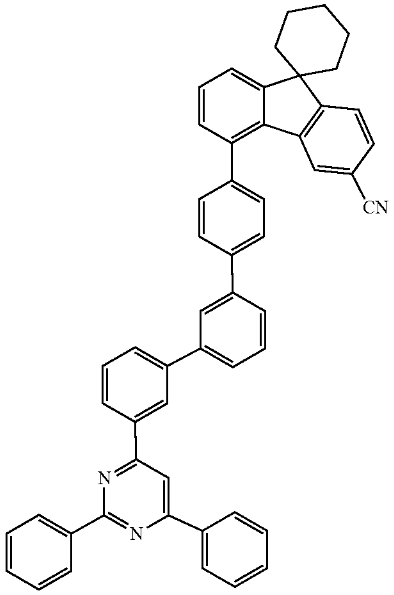
-continued
B-285
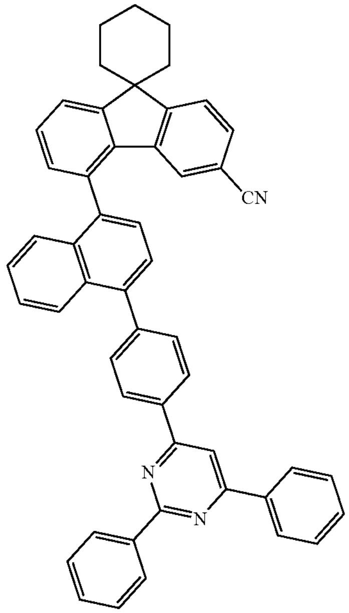
B-286
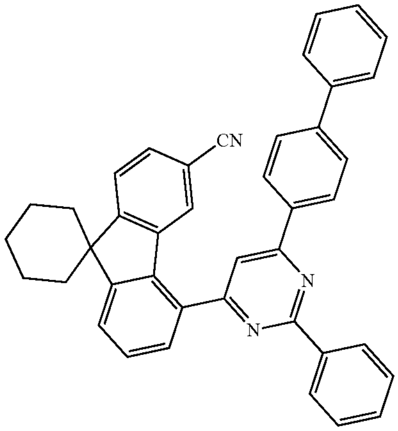
B-287
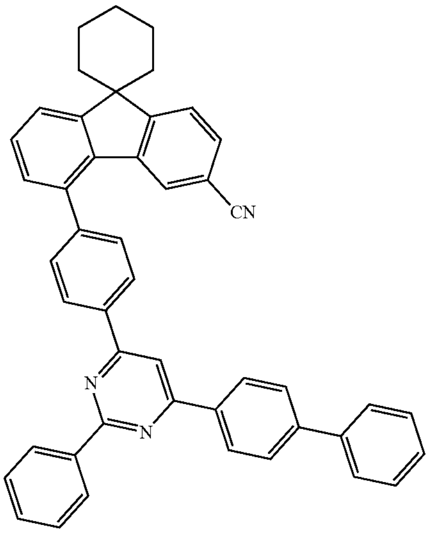

-continued
B-288
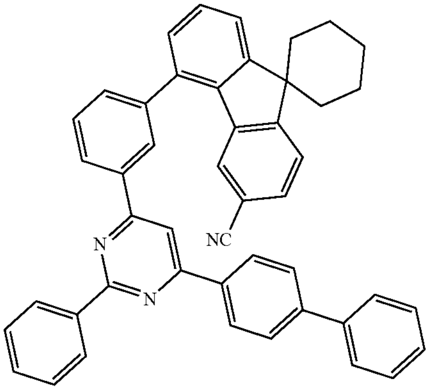
B-289
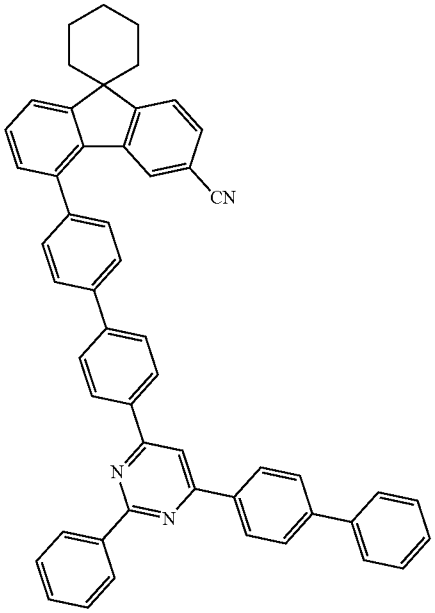
B-290
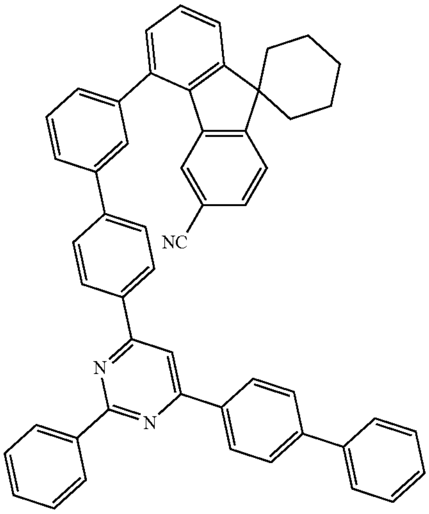
-continued
B-291
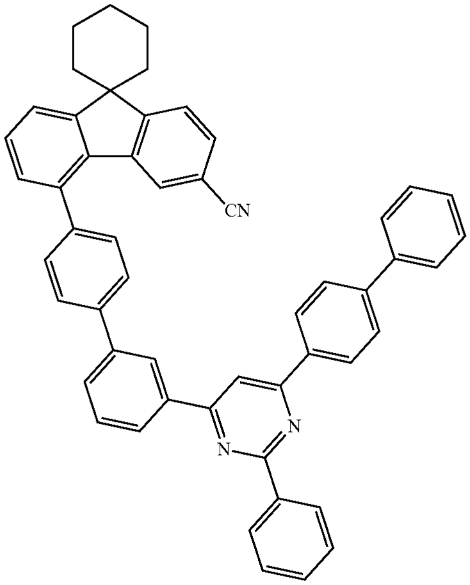
B-292
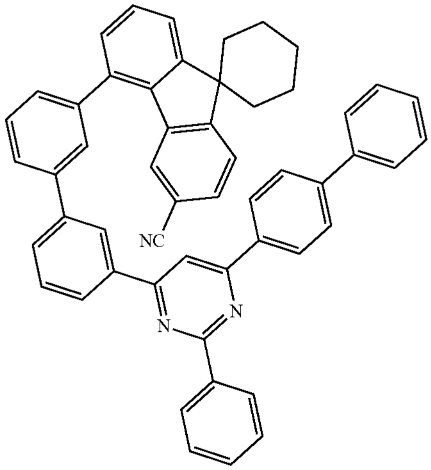
B-293
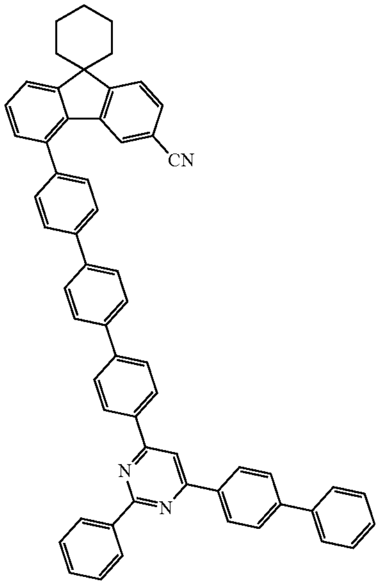

-continued
B-294
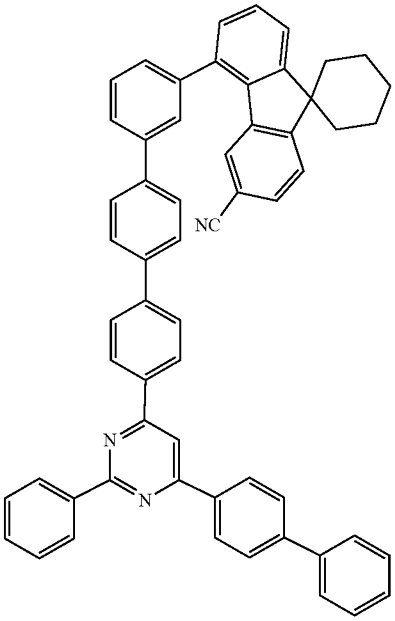
B-295
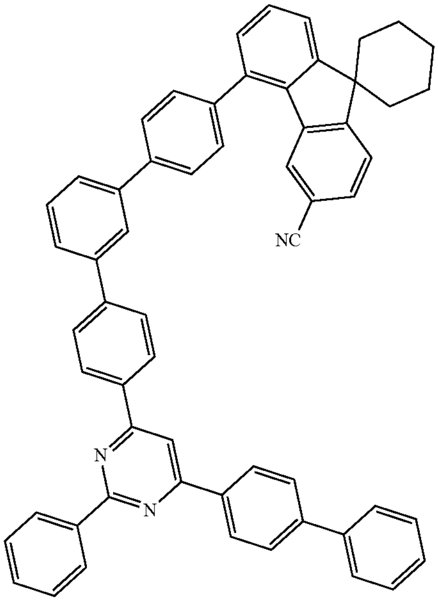
-continued
B-296
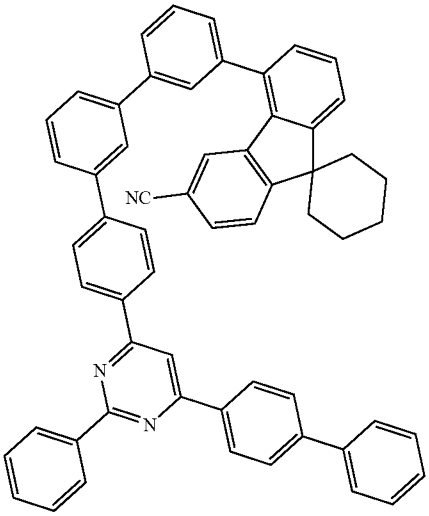
B-297
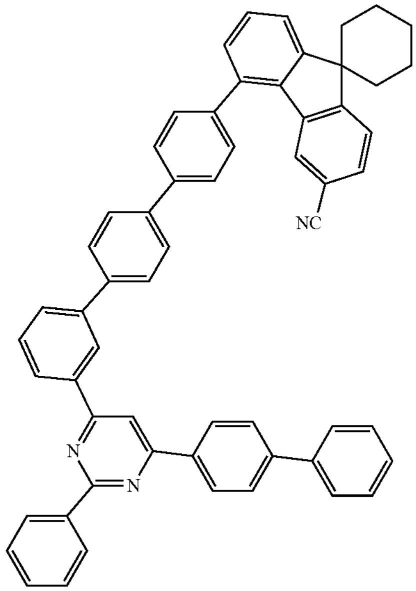

-continued
B-298
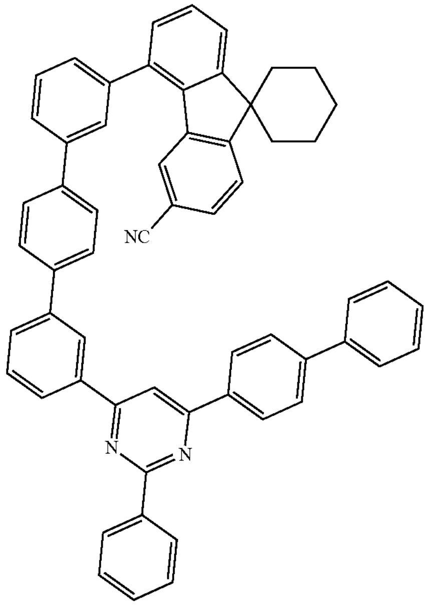
-continued
B-300
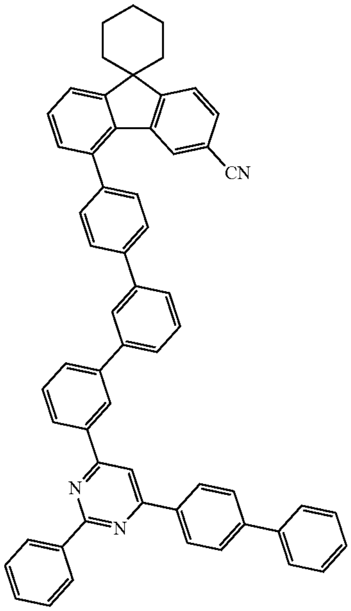
B-299
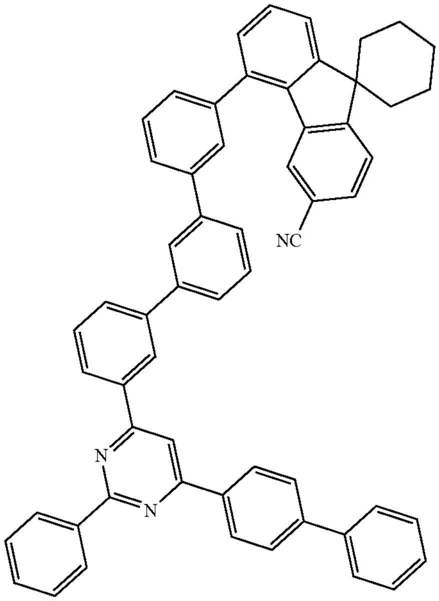
B-301
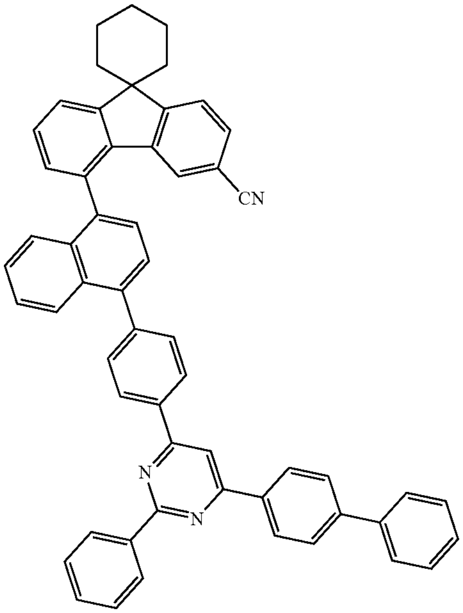

-continued
B-302
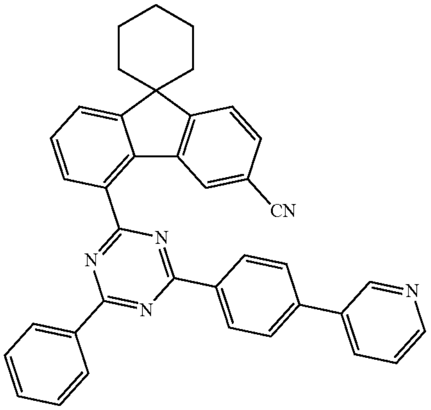
B-303
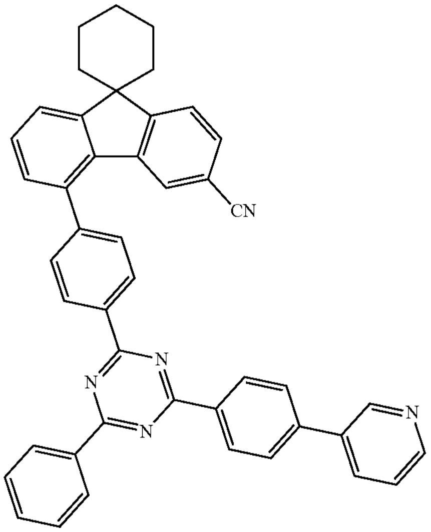
B-304
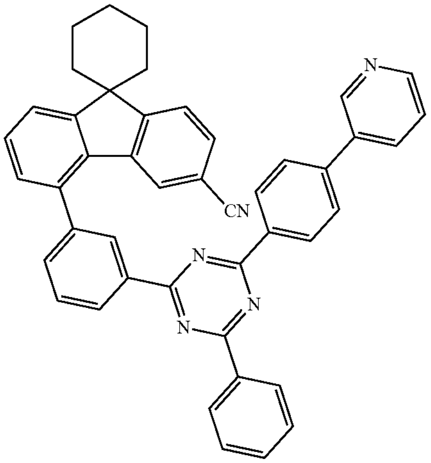
B-305
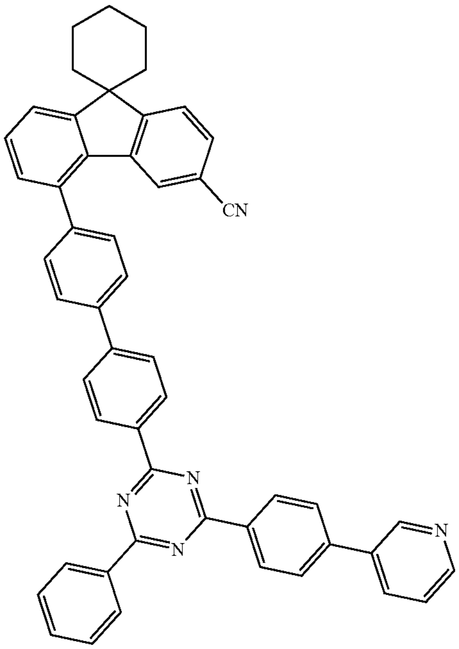
B-306
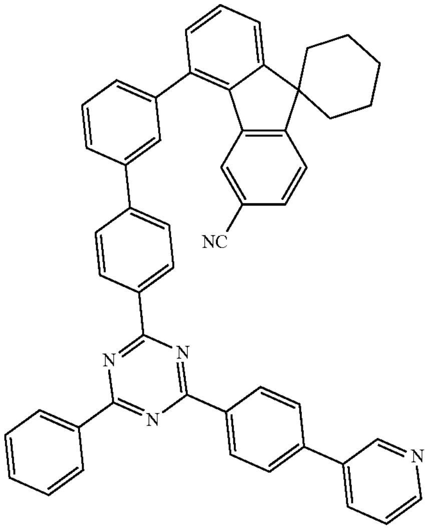

-continued
B-307
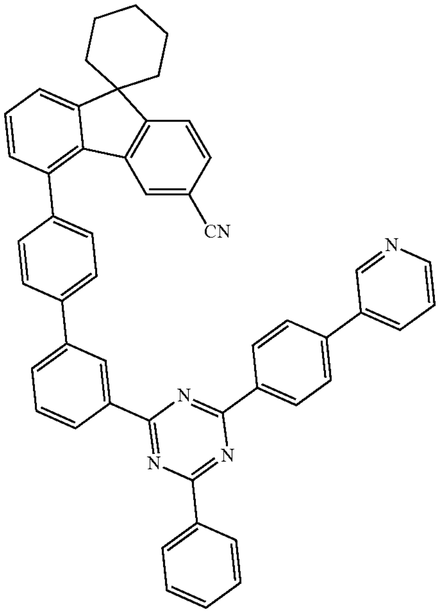
B-308
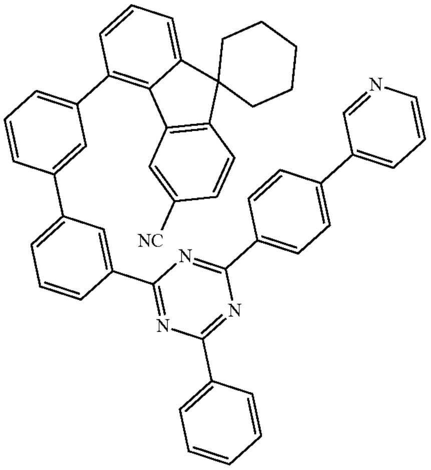
-continued
B-309
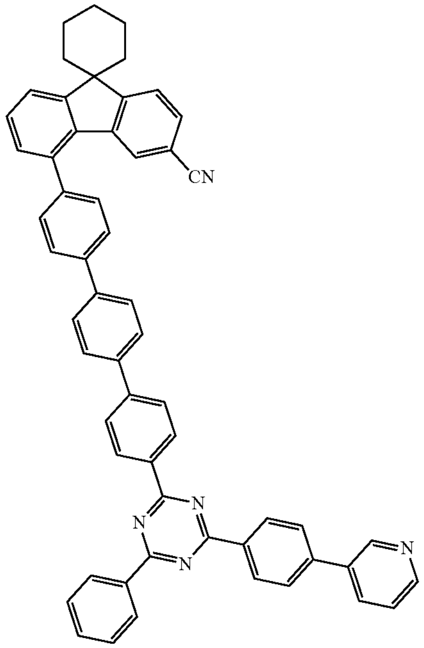
B-310
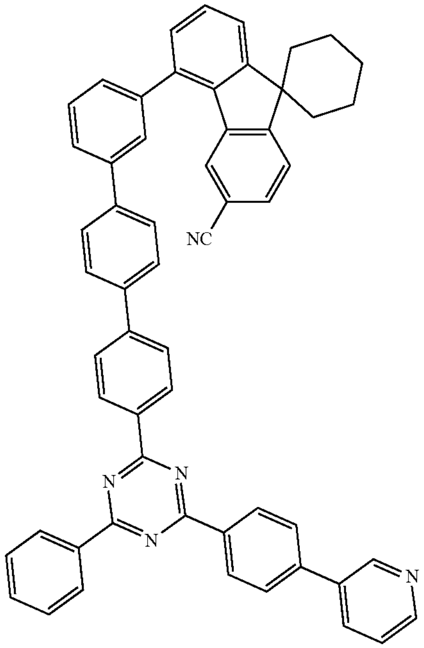

-continued
B-311
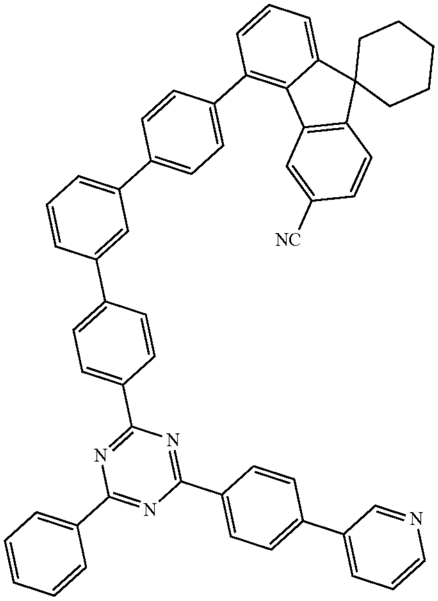
B-312
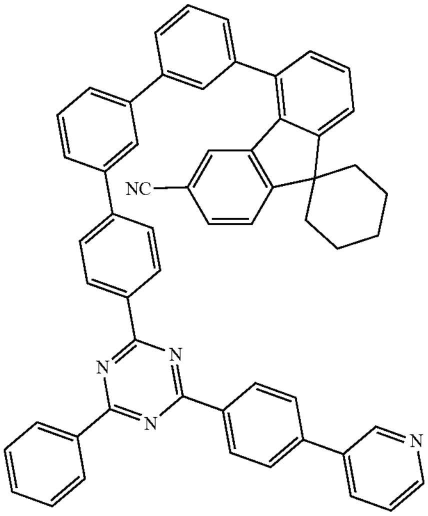
-continued
B-313
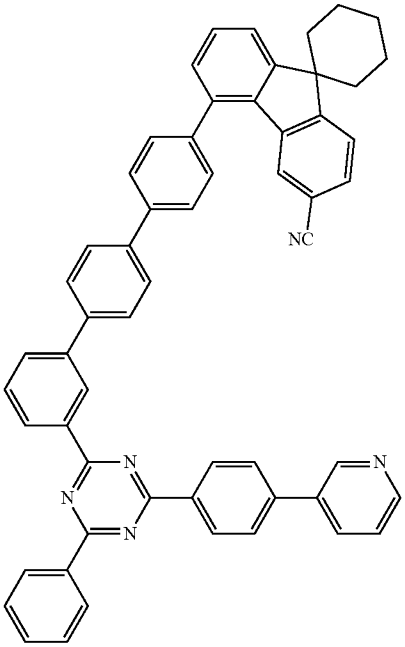
B-314
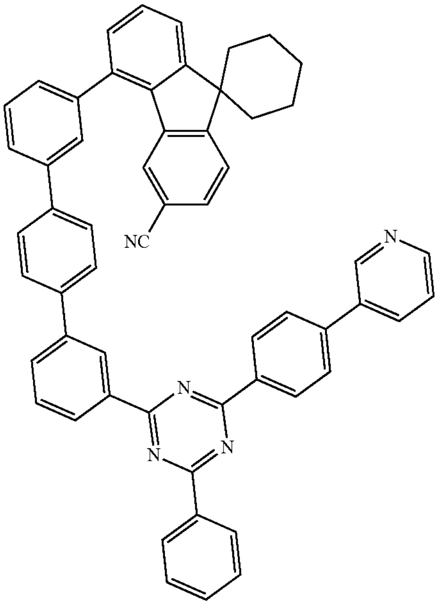

-continued
B-315
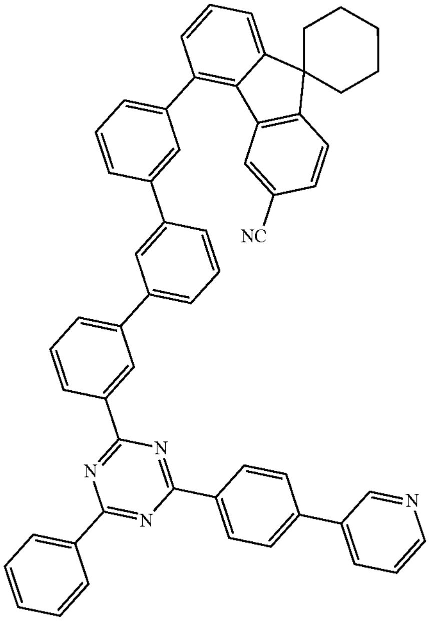
B-316
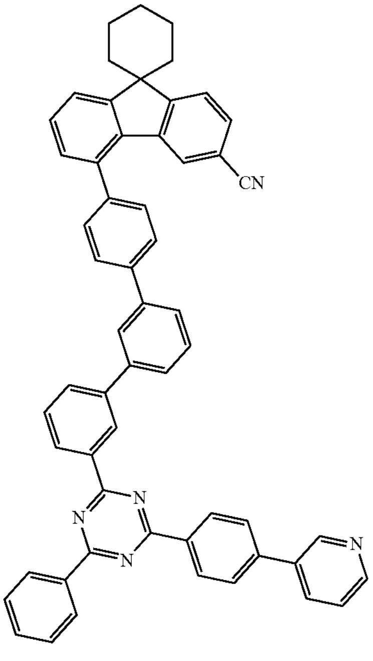
-continued
B-317
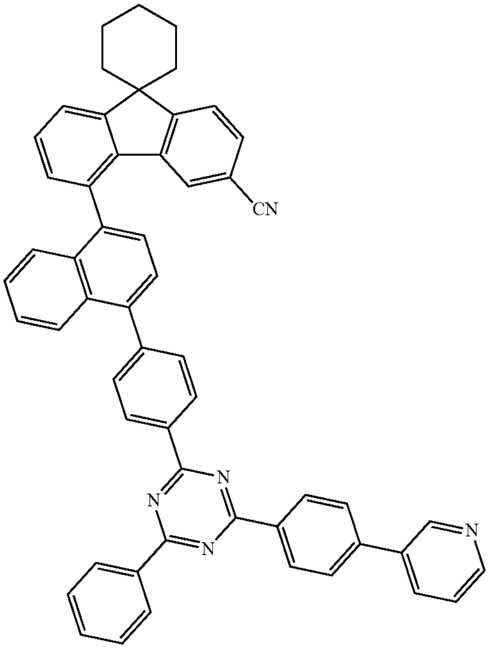
B-318
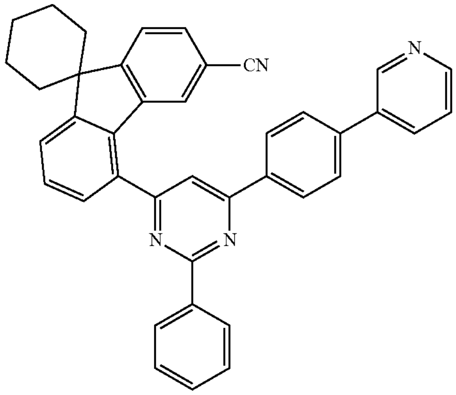
B-319
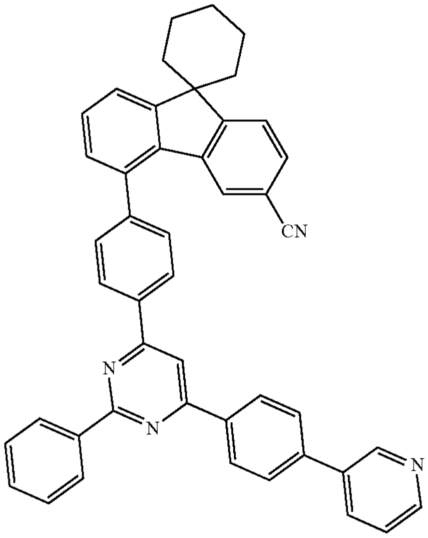

-continued
B-320
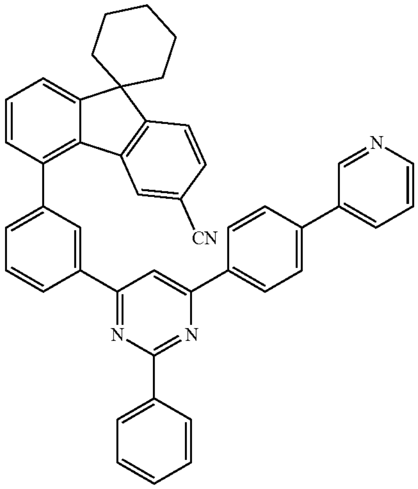
B-321
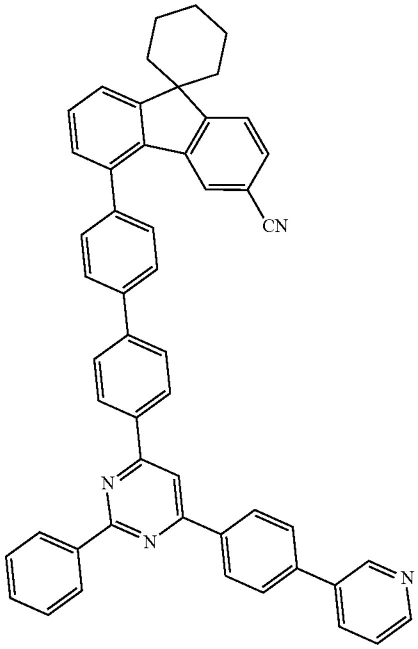
-continued
B-322
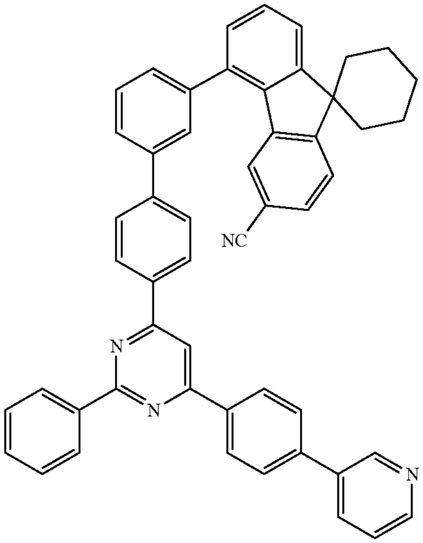
B-223
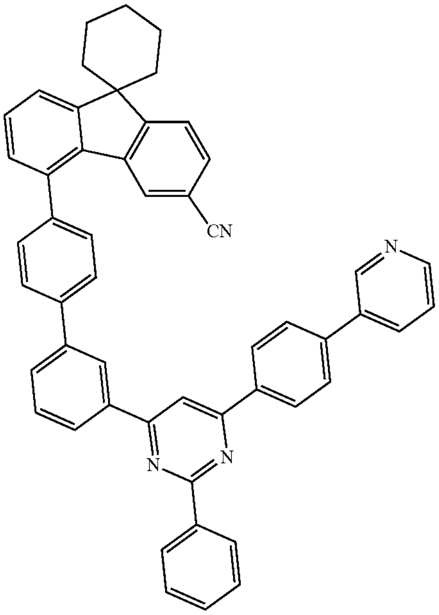
B-324
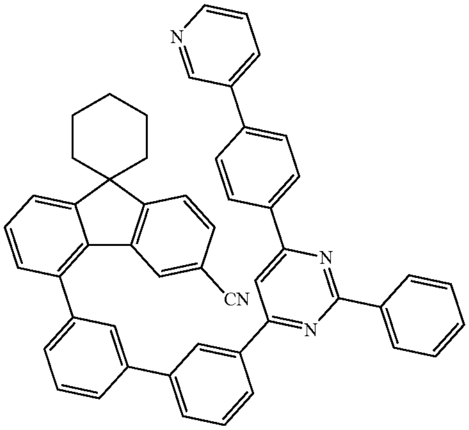

-continued
B-325
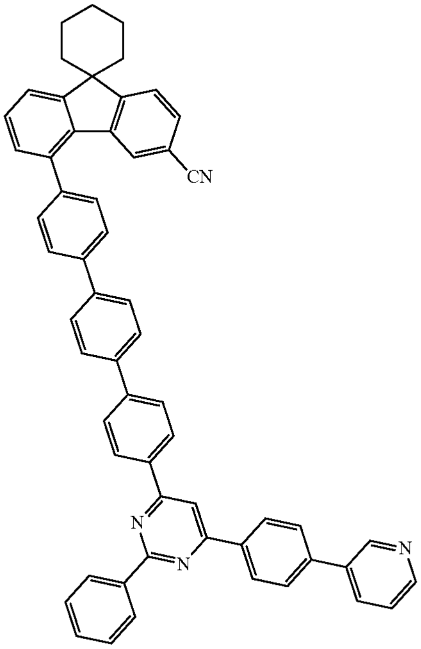
B-326
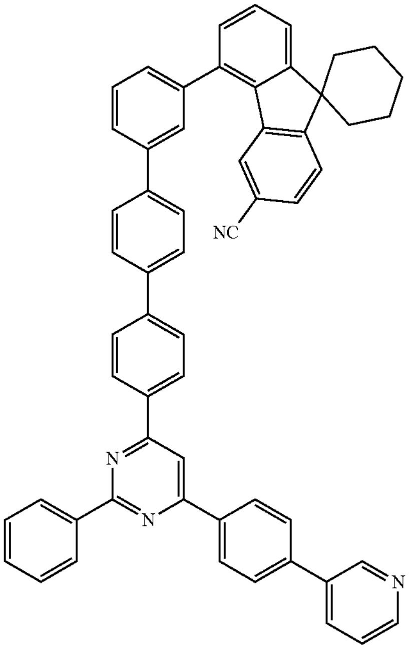
-continued
B-327
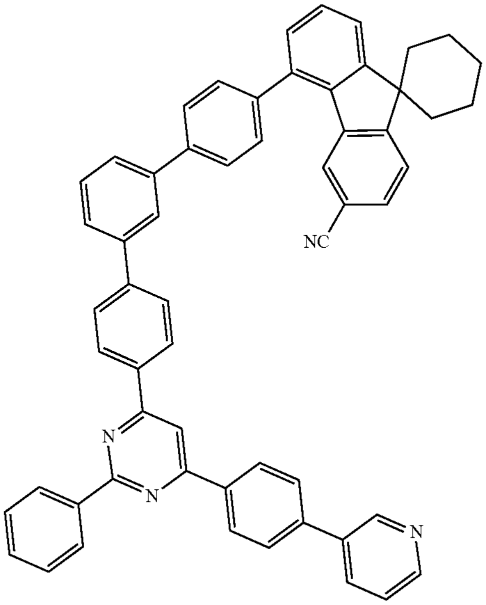
B-328
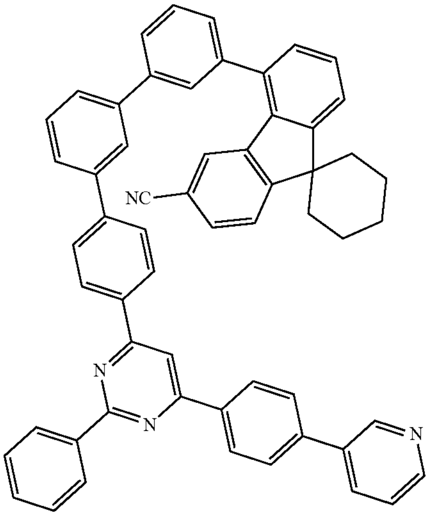

-continued
B-329
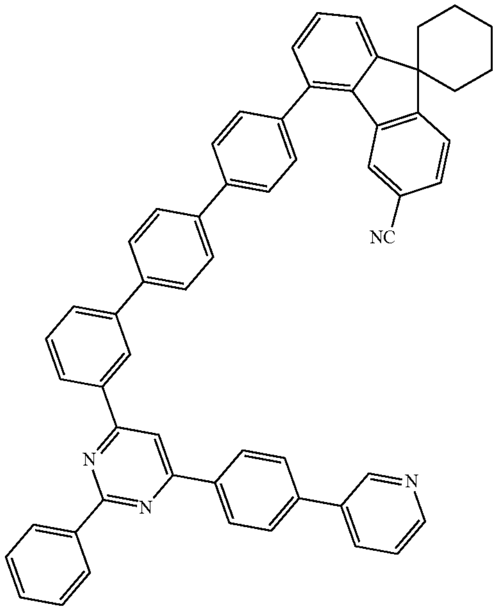
B-330
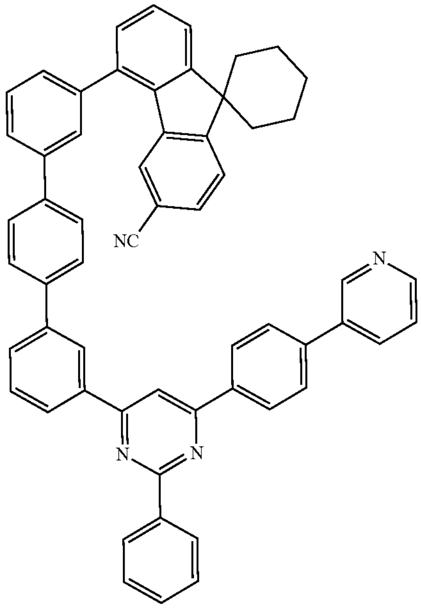
-continued
B-331
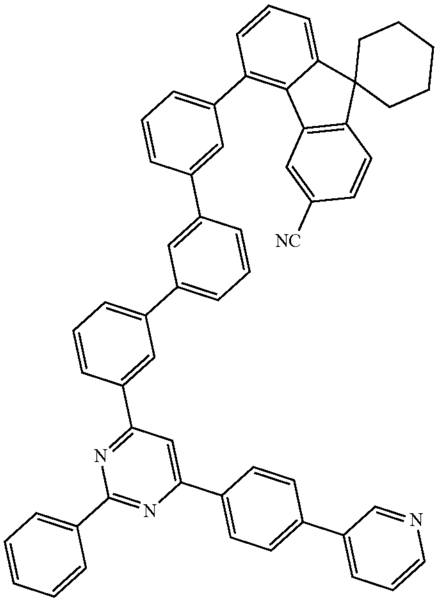
B-332
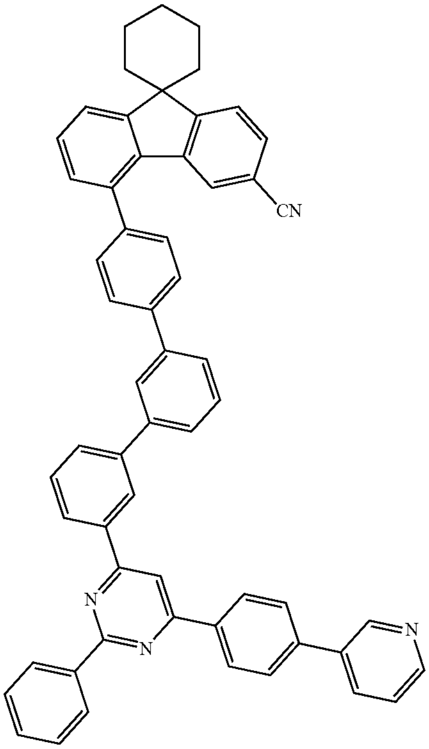

-continued
B-333
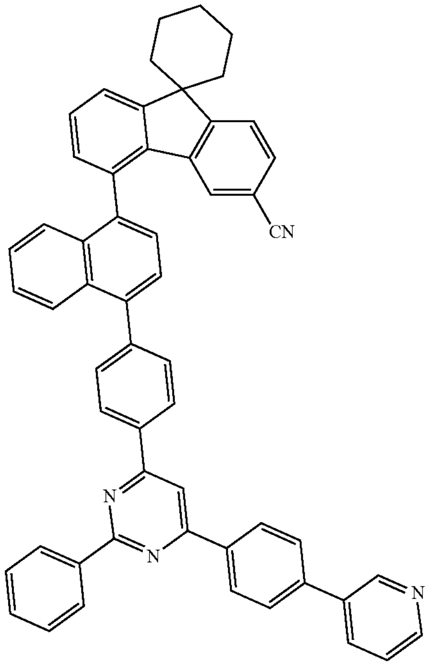
B-334
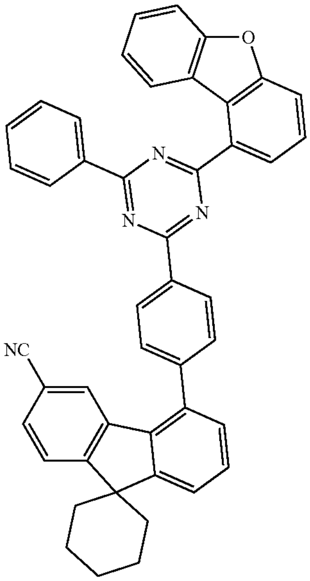
-continued
B-335
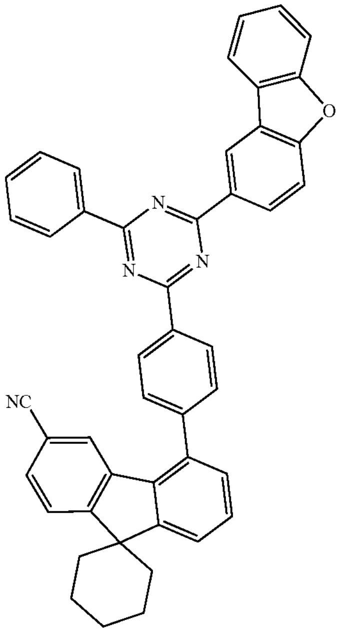
B-336
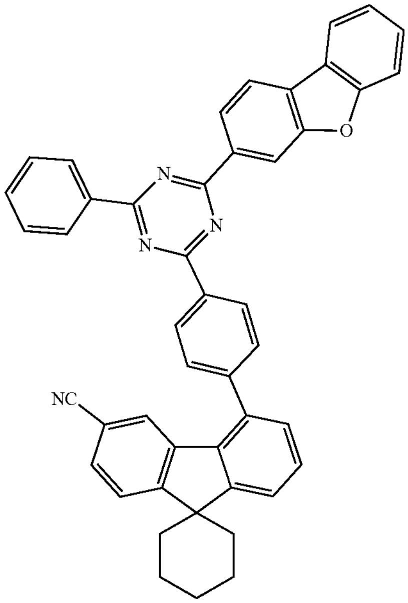

B-337
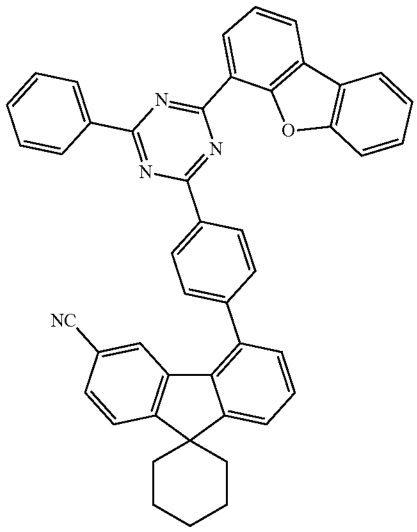
B-338
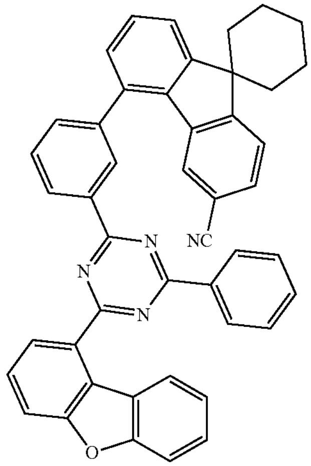
B-339
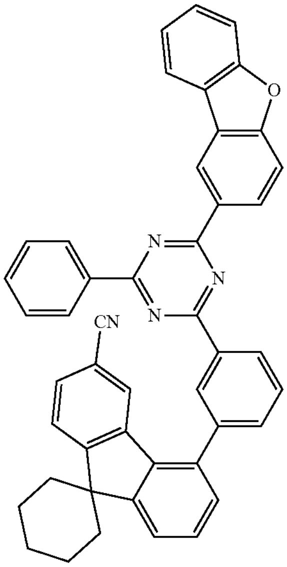
B-340
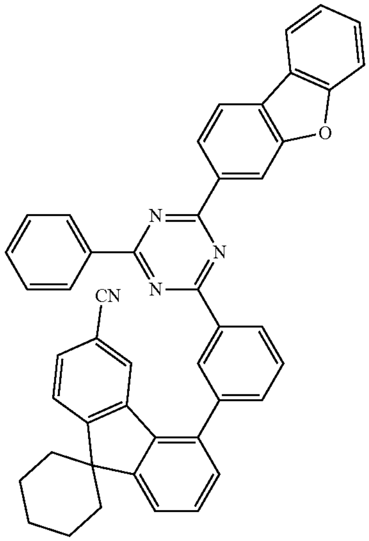
B-341
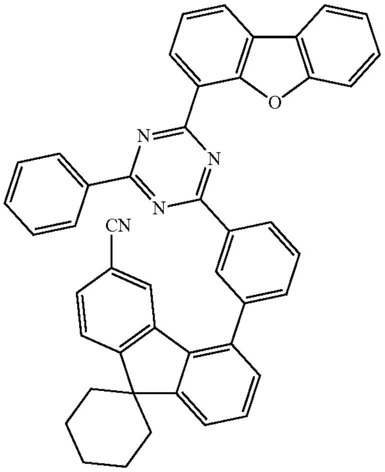
B-342
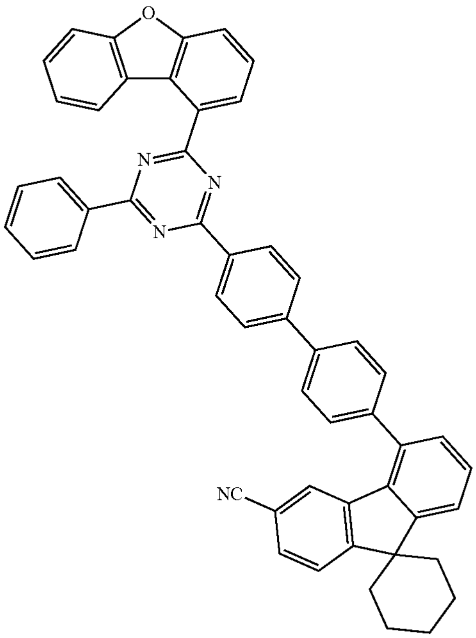

-continued
B-343
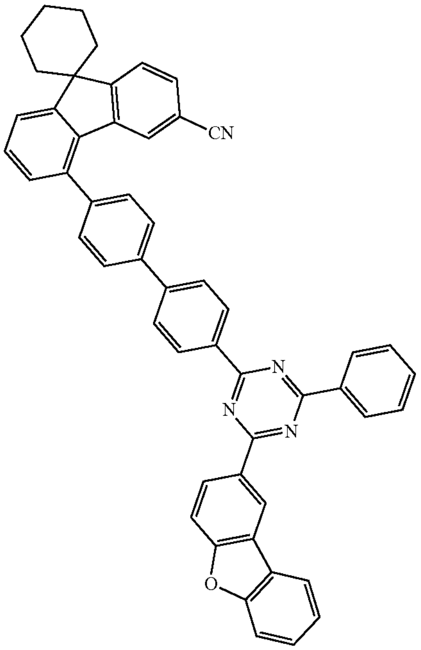
B-344
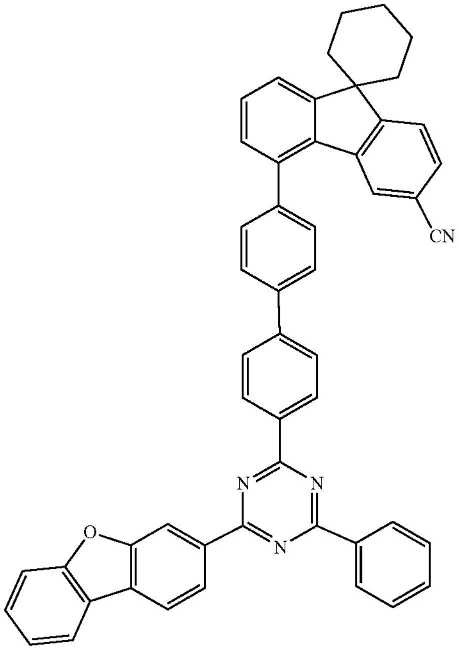
-continued
B-345
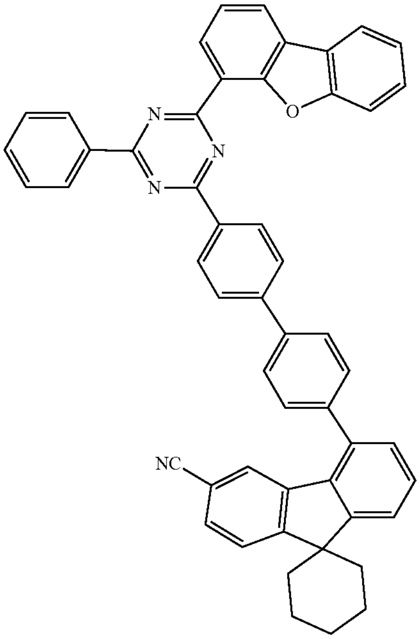
B-346
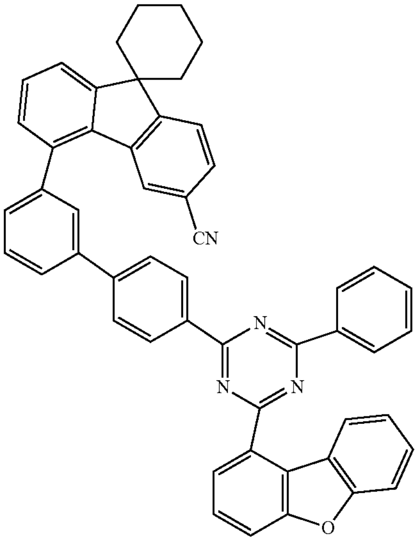

-continued
B-347
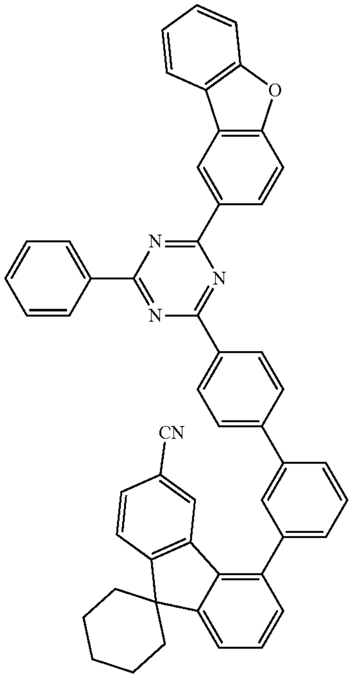
B-348
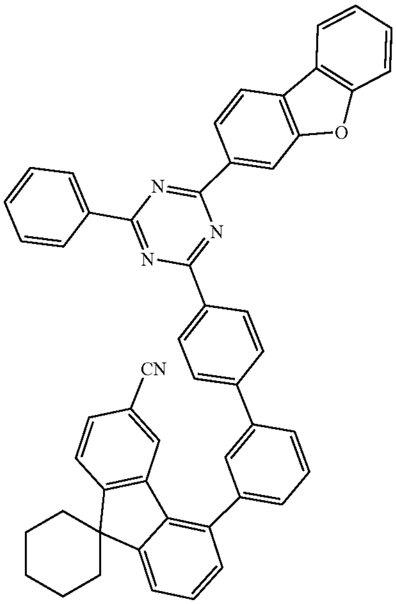
-continued
B-349
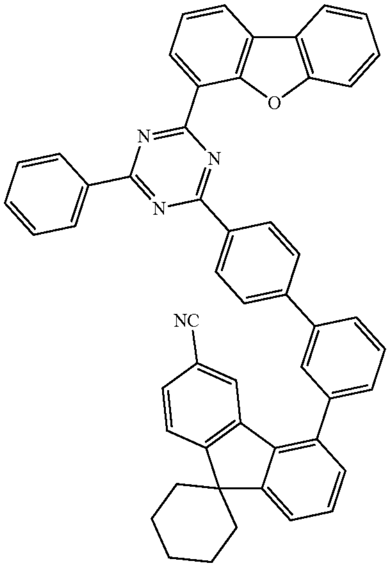
B-350
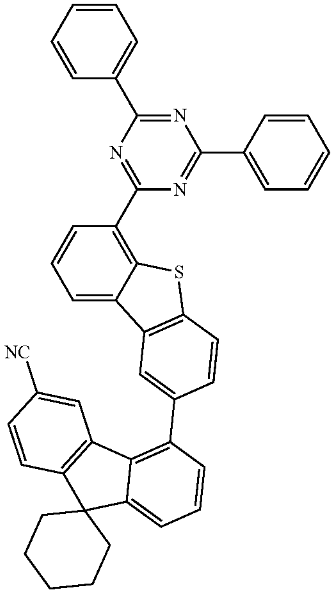

-continued
B-351
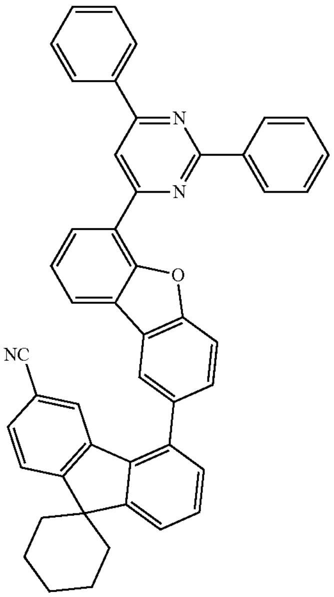
B-352
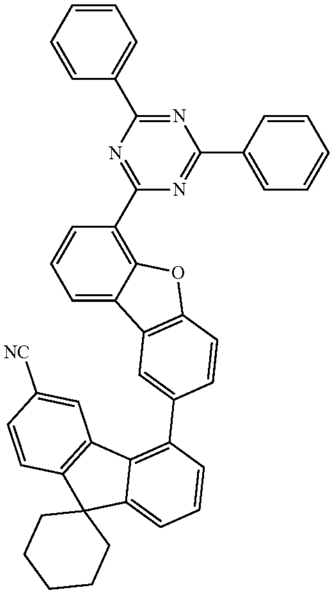
-continued
B-353
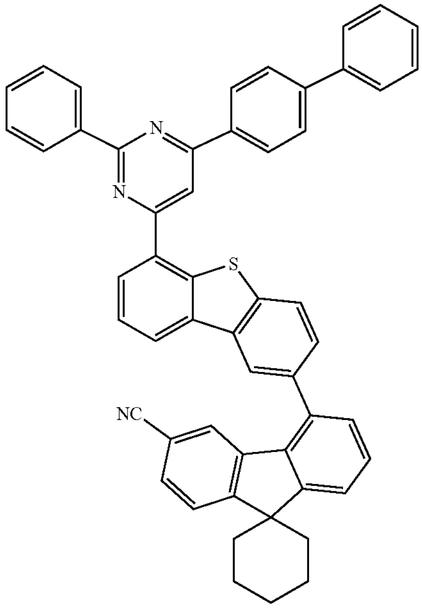
B-354
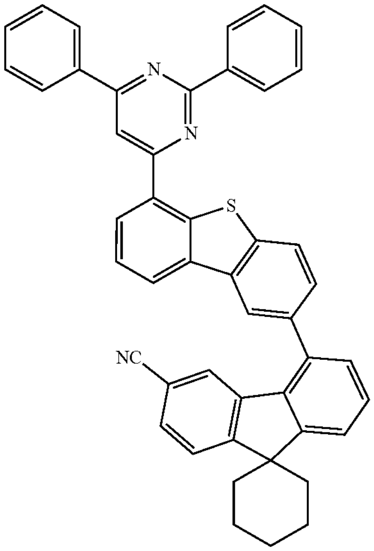

-continued
B-355
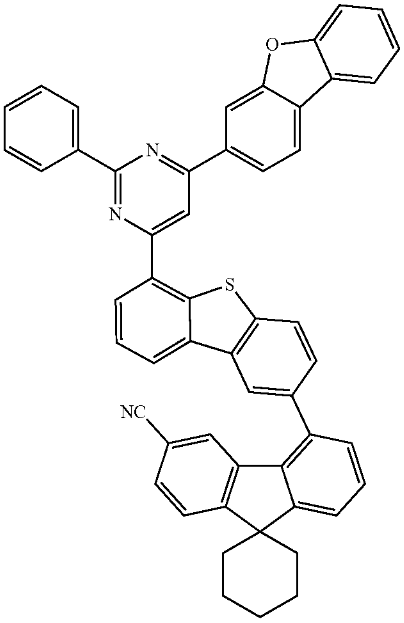
B-357
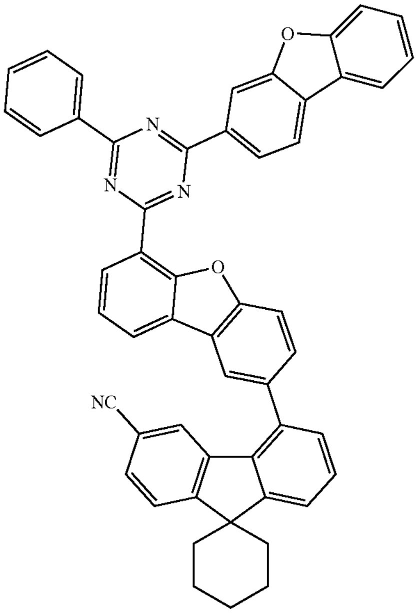
B-356
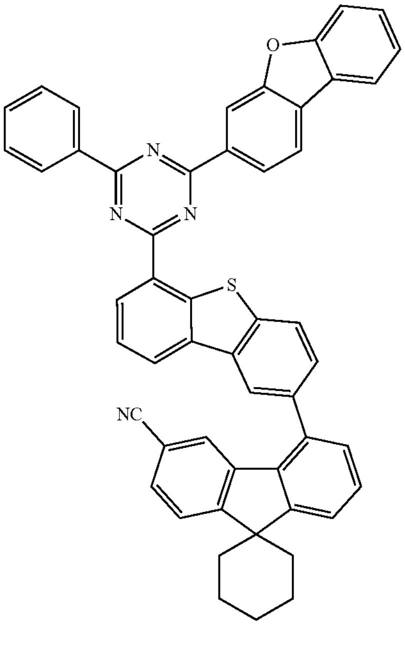
B-358
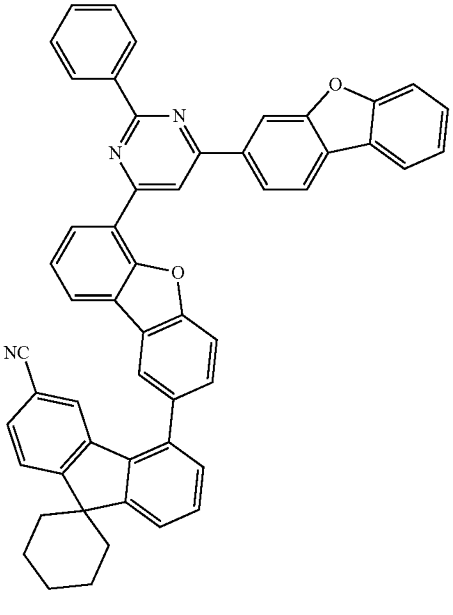

-continued
B-359
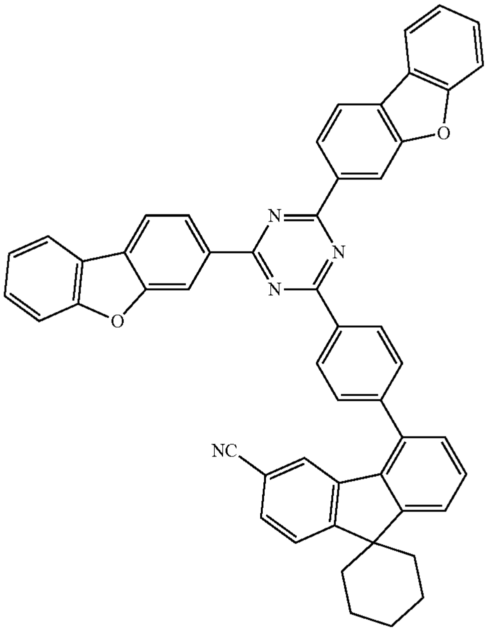
B-360
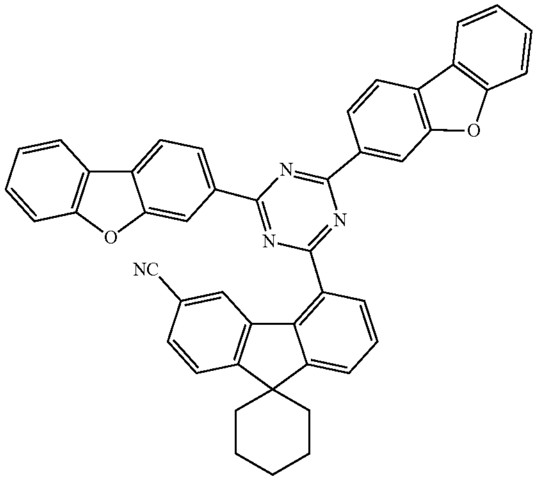
-continued
B-361
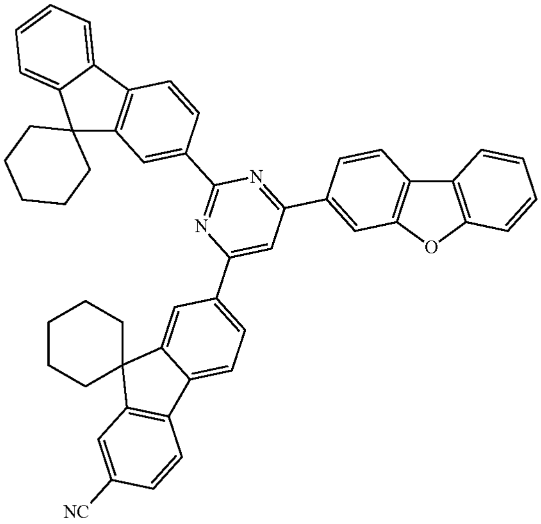
B-362
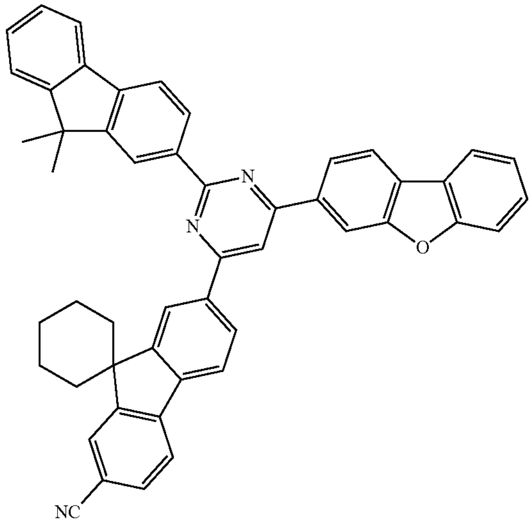
B-363
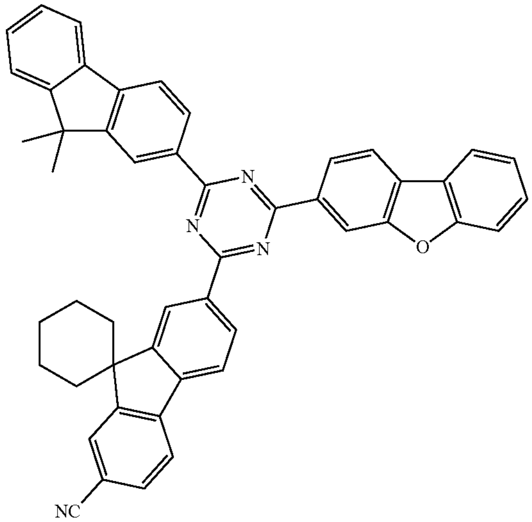

B-364
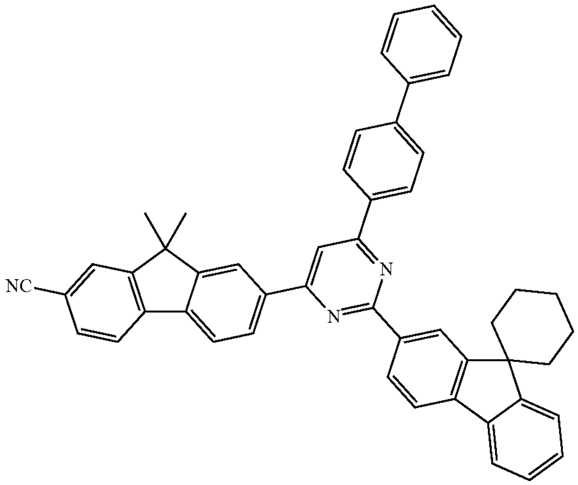
B-365
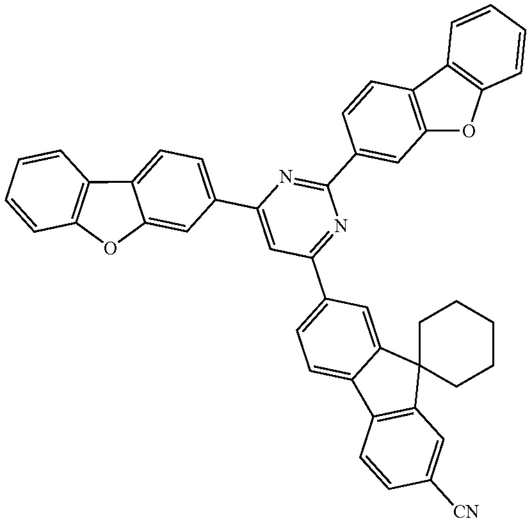
B-366
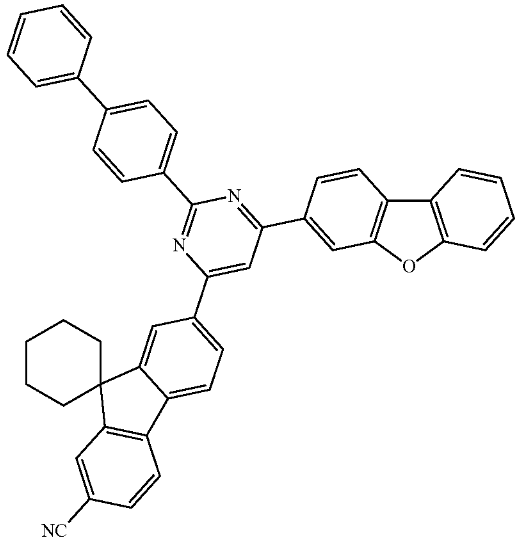
B-367
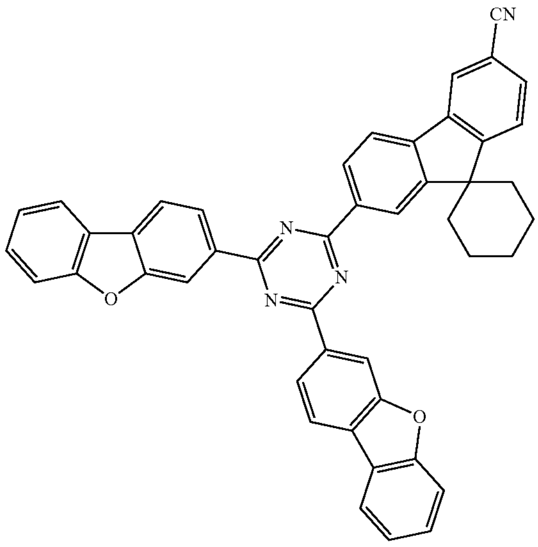
B-368
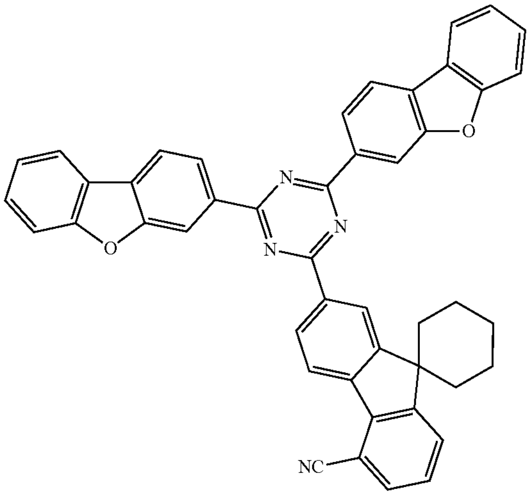
B-369
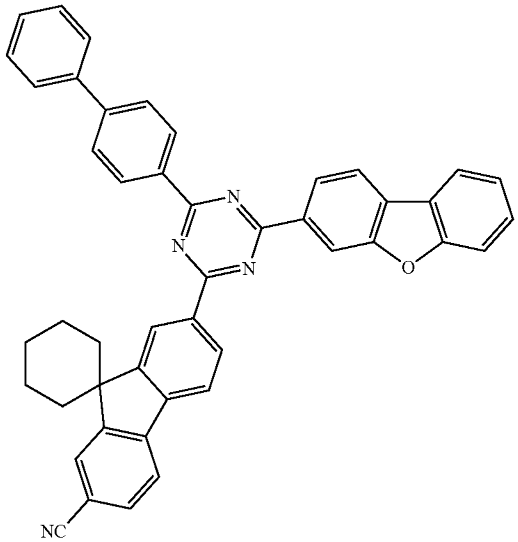

-continued
B-370
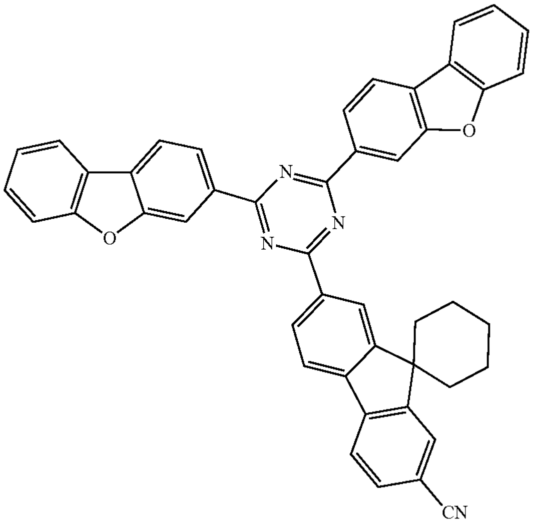
B-378
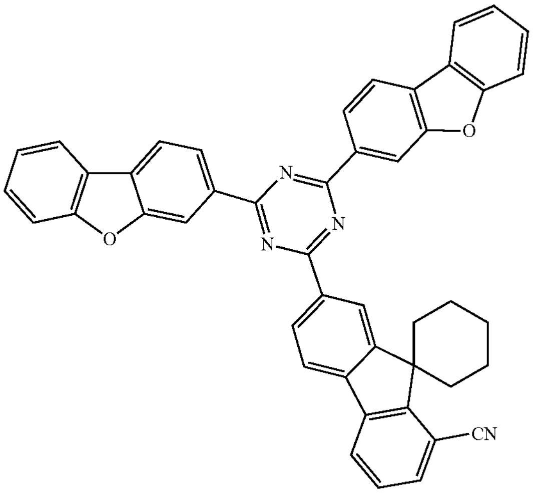
B-379
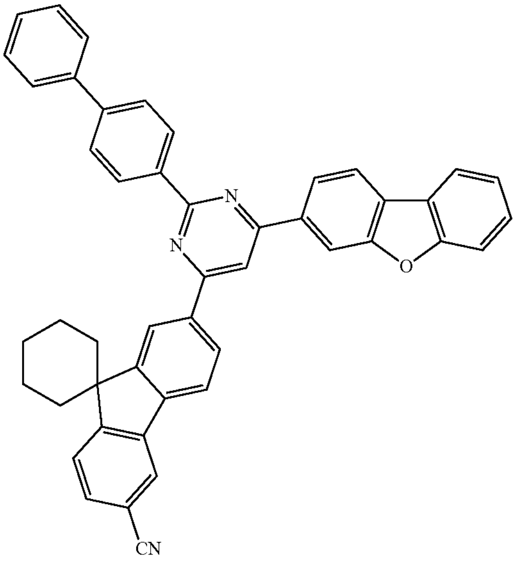
-continued
B-380
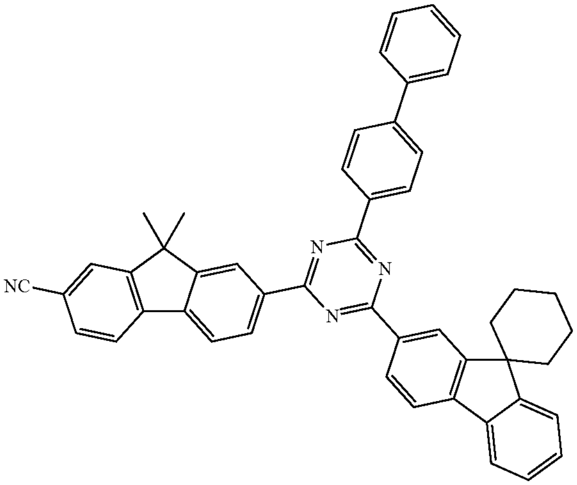
B-381
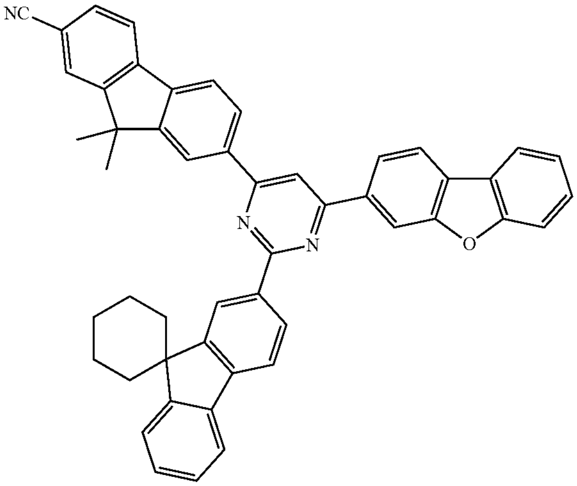
B-382
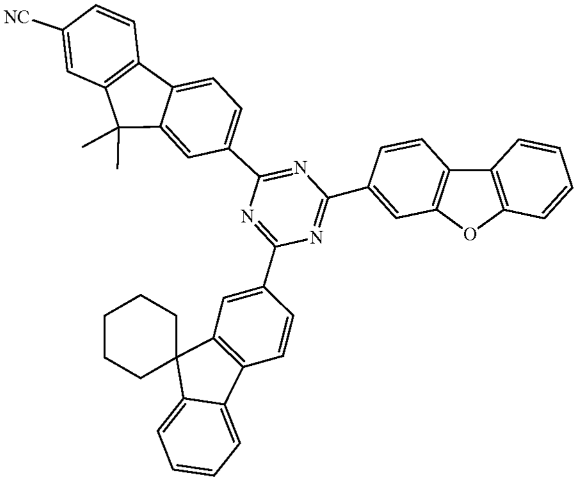

-continued
B-383
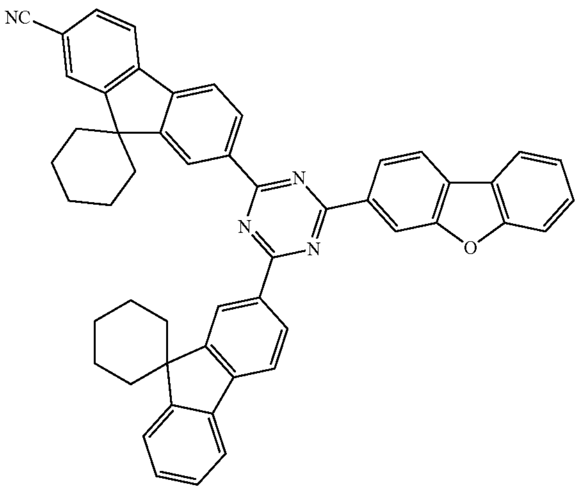
C-1
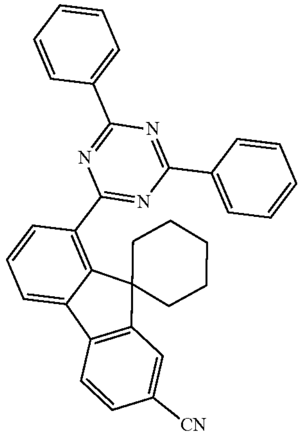
C-2
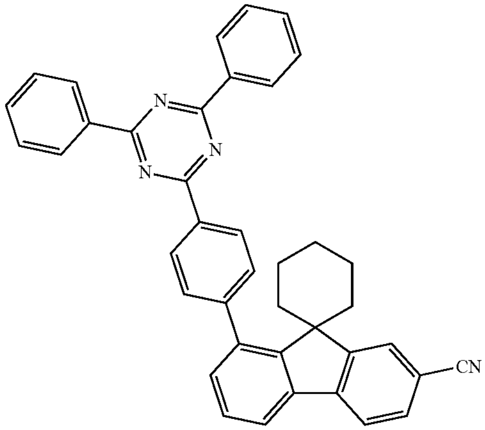
-continued
C-3
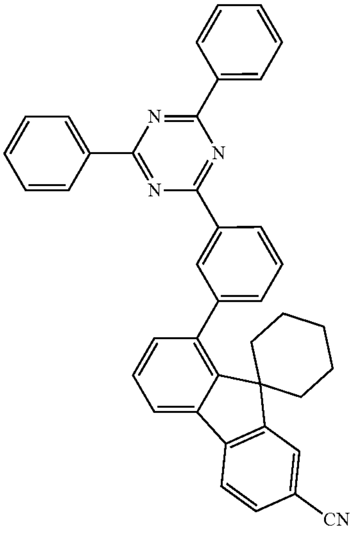
C-4
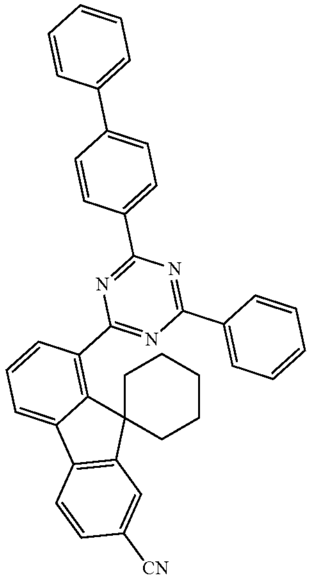

-continued
C-5
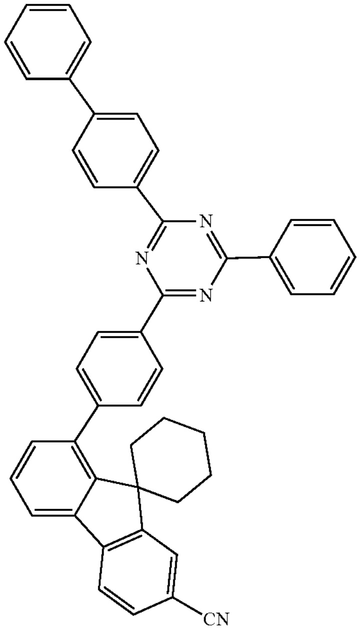
C-6
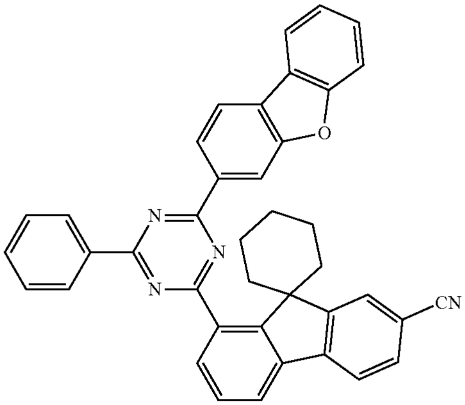
C-7
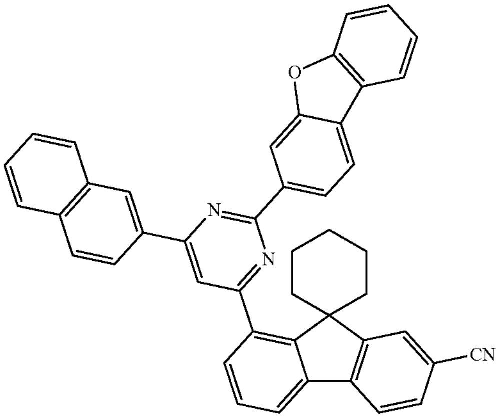
-continued
C-8
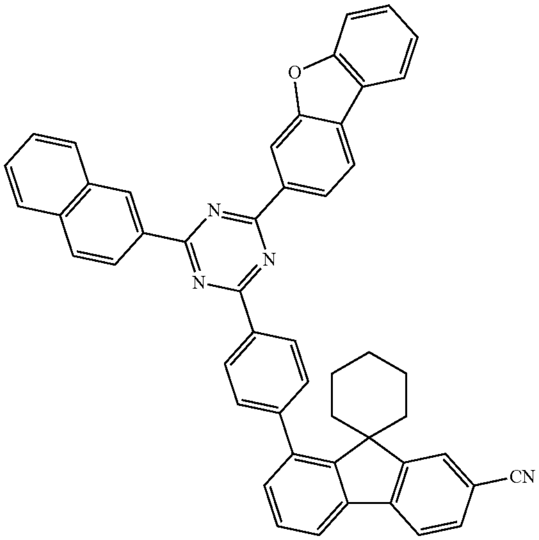
C-9
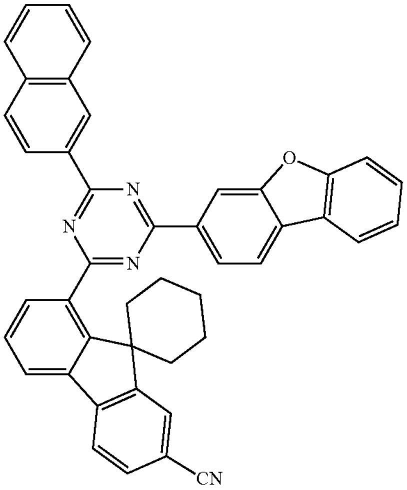
C-10
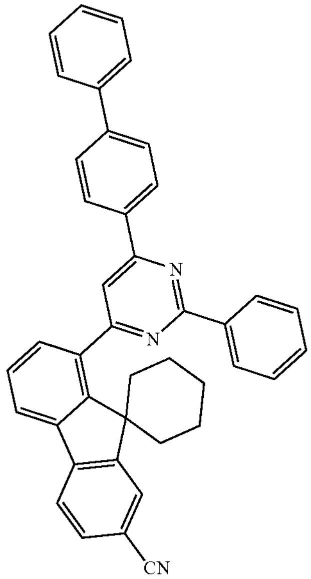

C-11
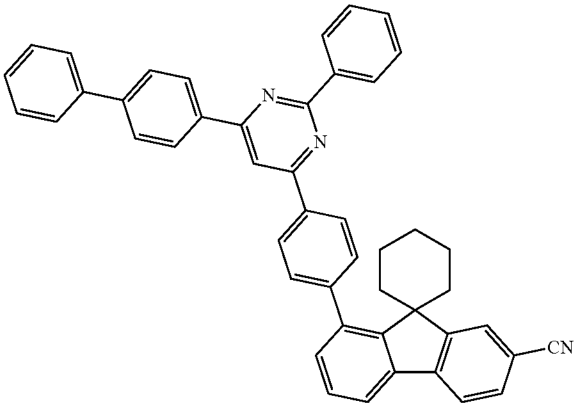
C-12
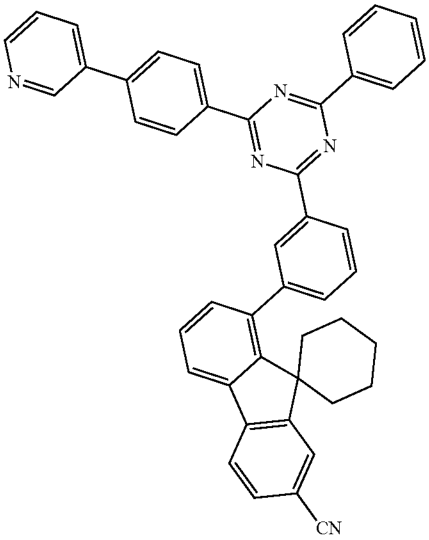
C-13
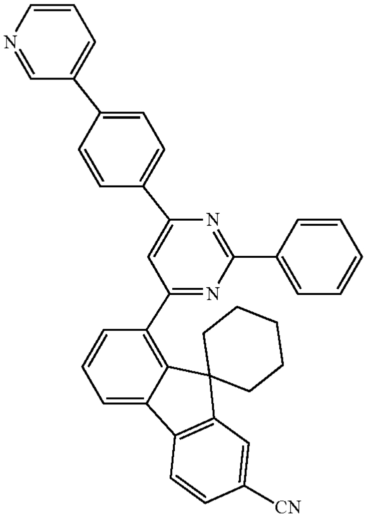
C-14
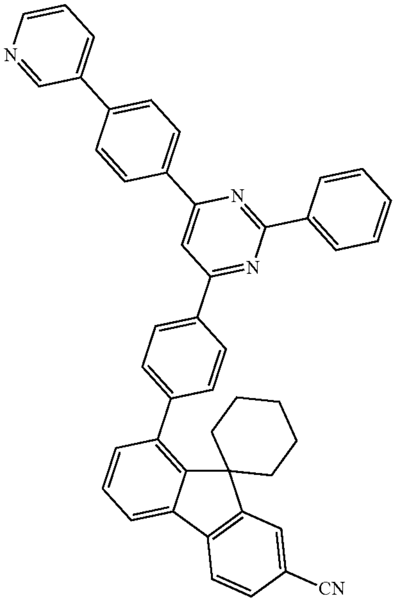
C-15
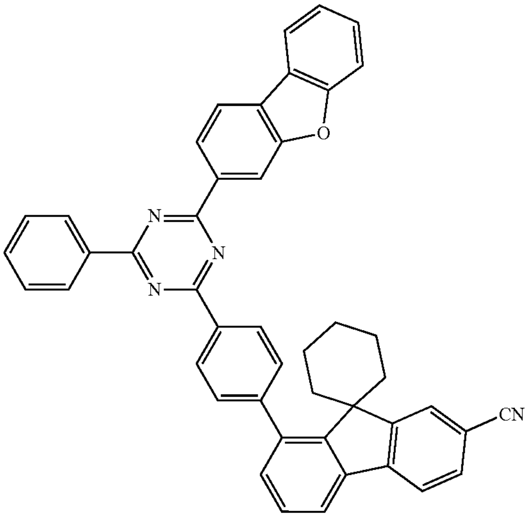

-continued
C-16
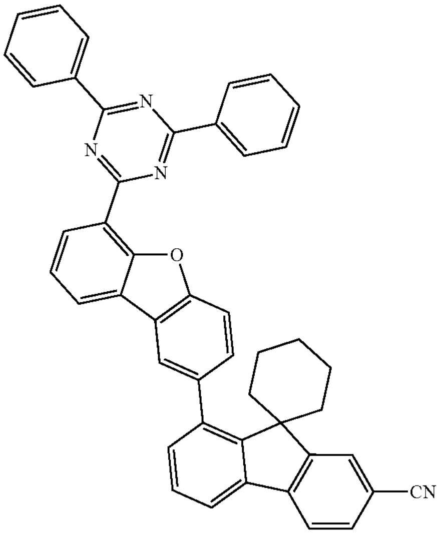
C-17
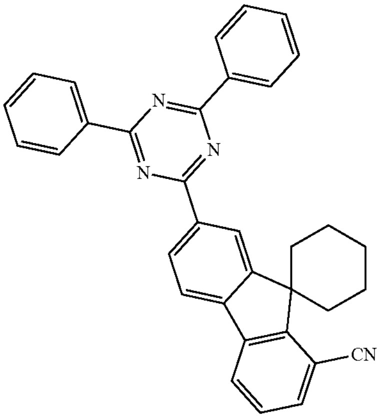
C-18
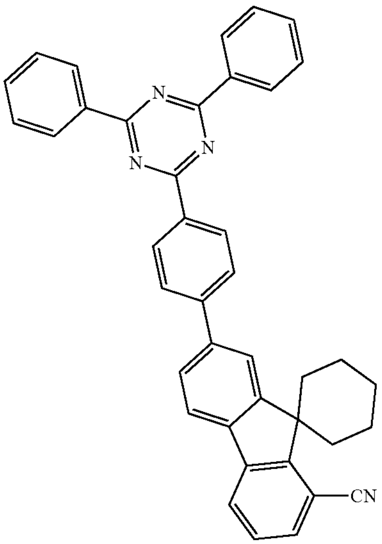
-continued
C-19
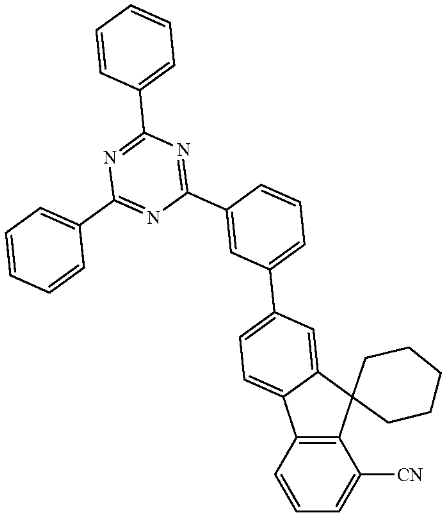
C-20
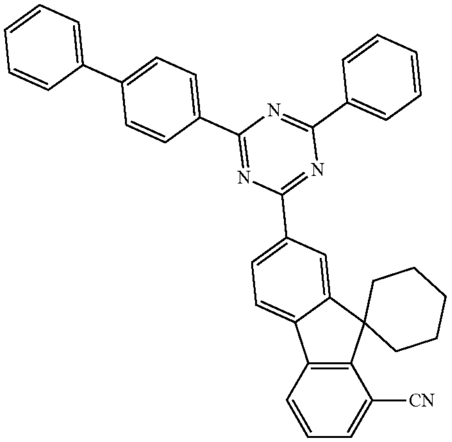
C-21
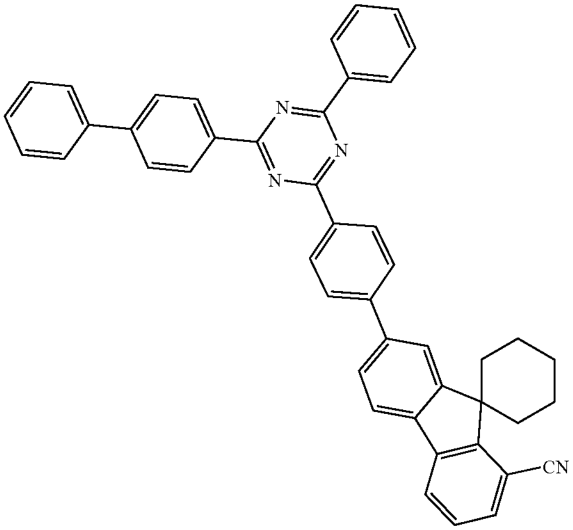

-continued
C-22
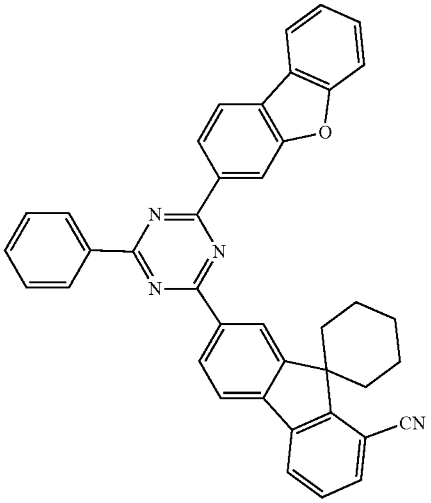
C-23
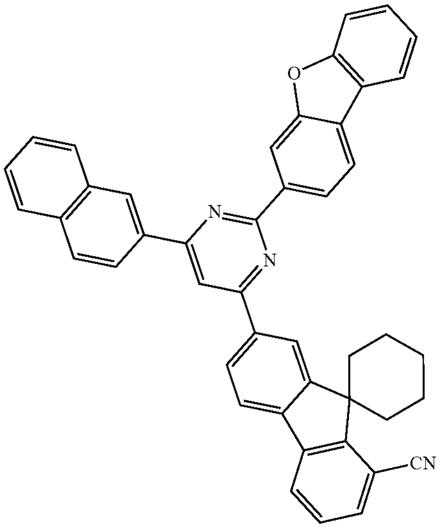
-continued
C-24
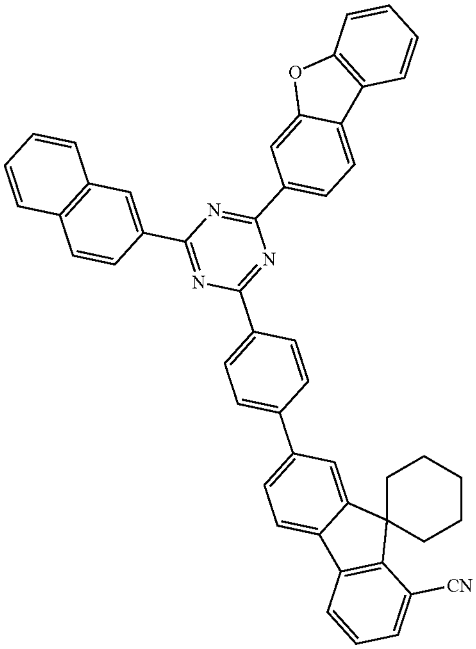
C-25
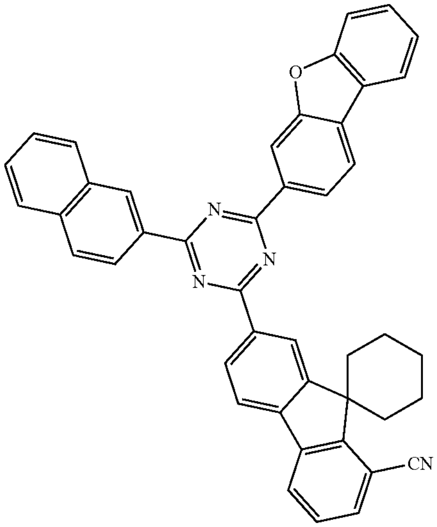
C-26
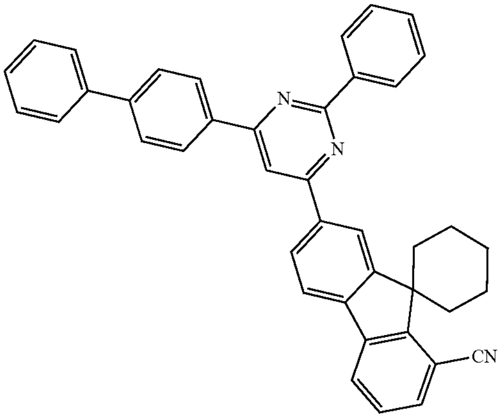

C-27
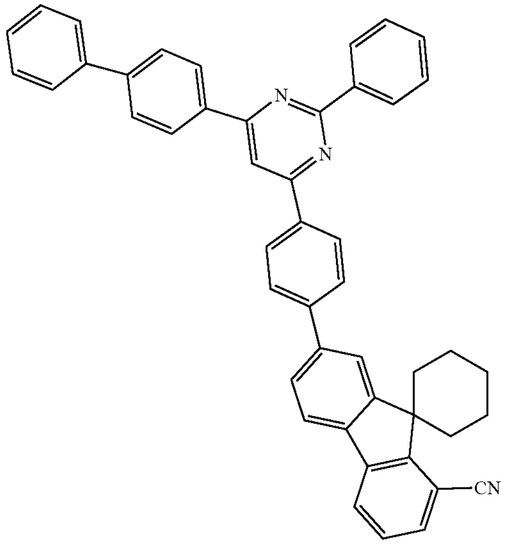
C-28
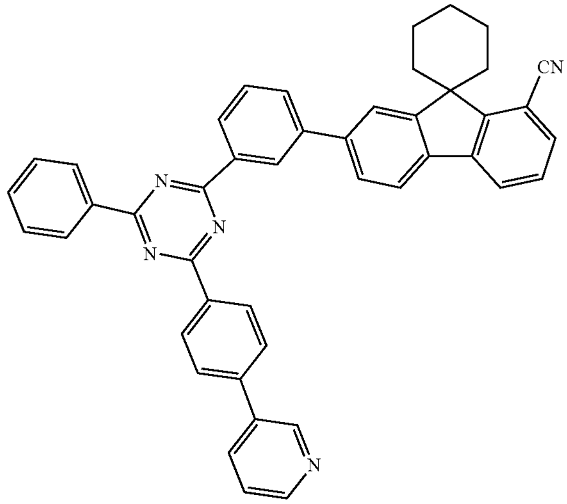
C-29
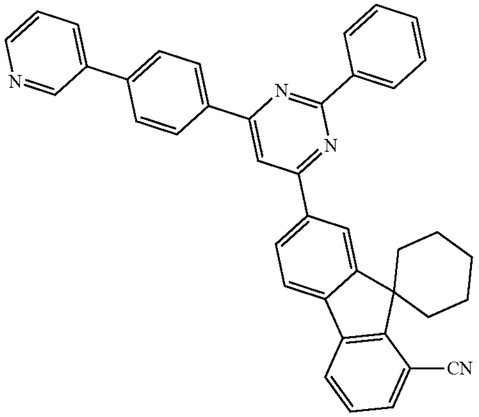
C-30
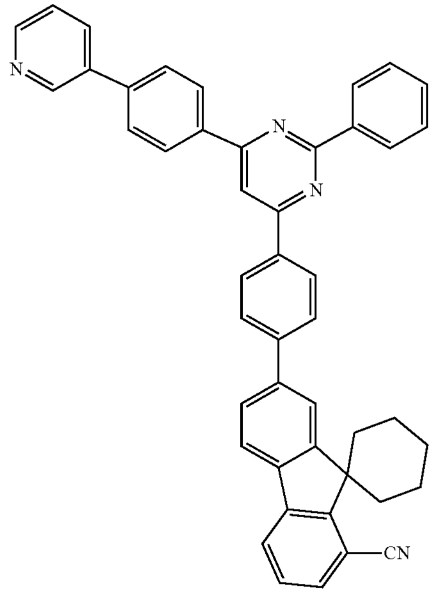
C-31
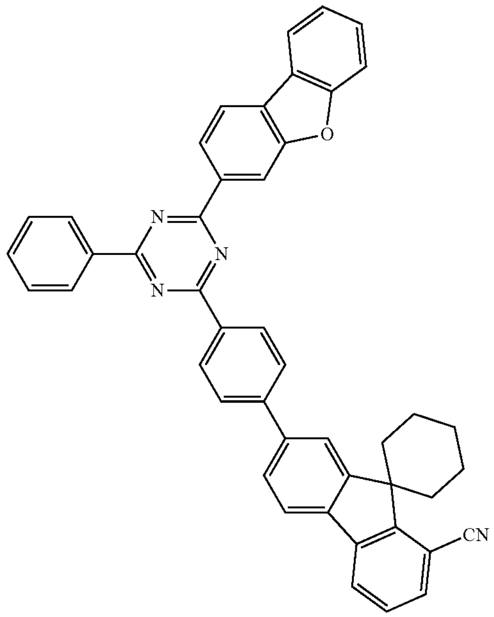

-continued
C-32
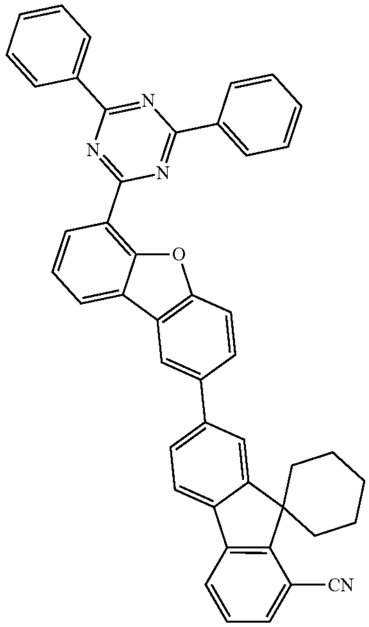
C-33
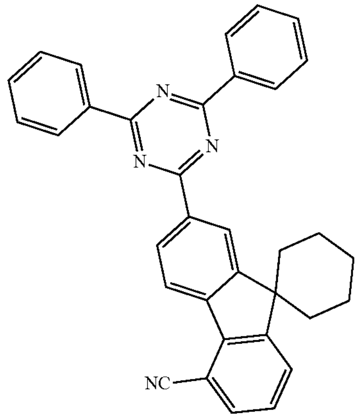
C-34
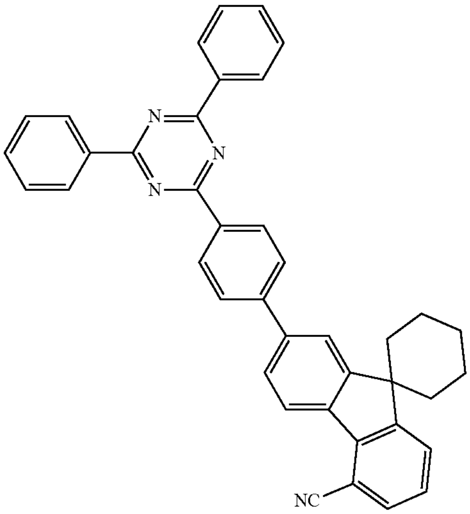
-continued
C-35
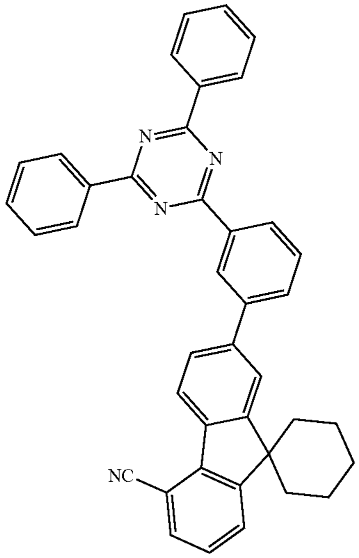
C-36
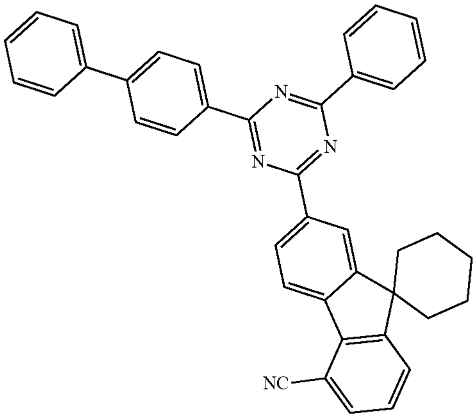
C-37
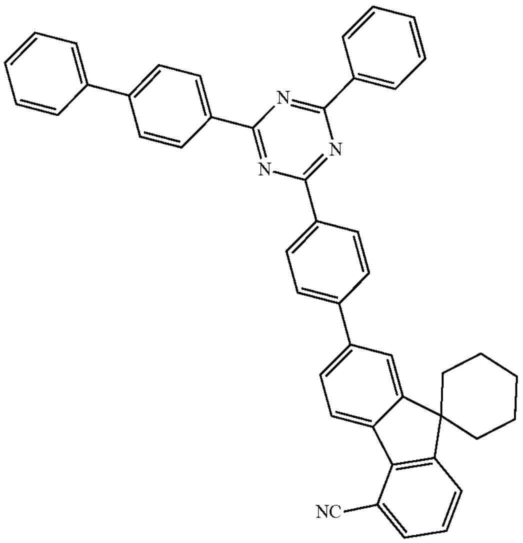

-continued
C-38
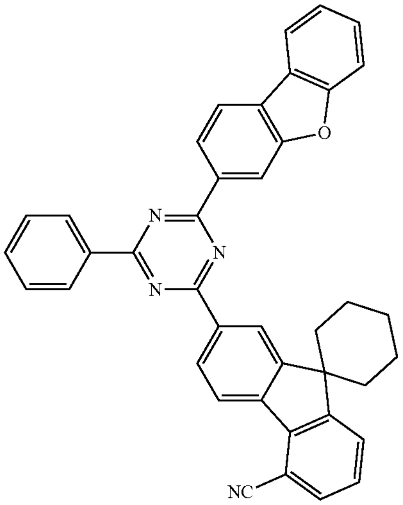
C-39
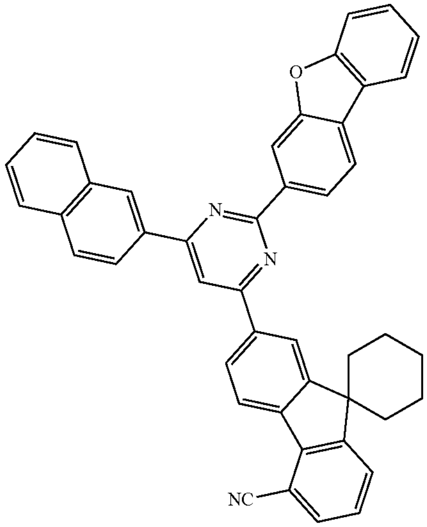
-continued
C-40
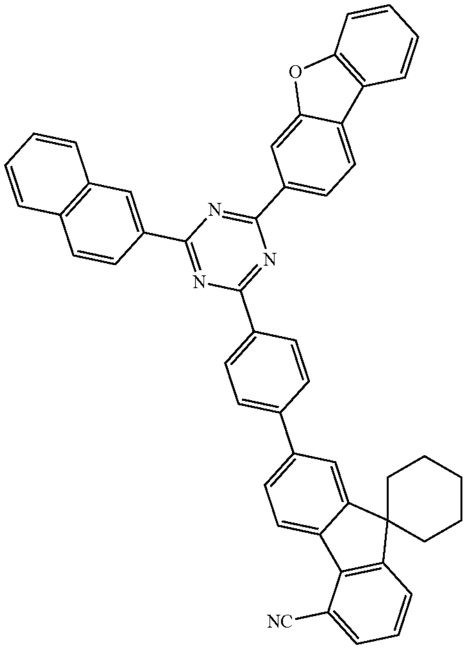
C-41
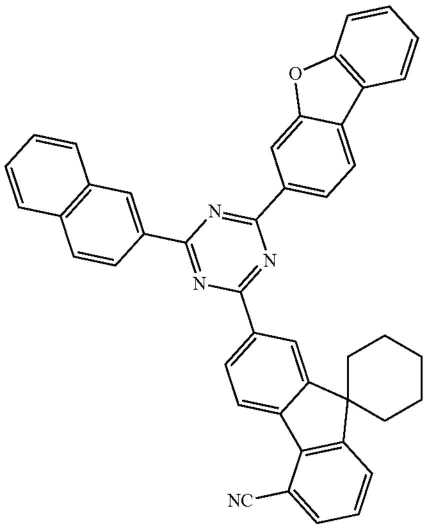
C-42
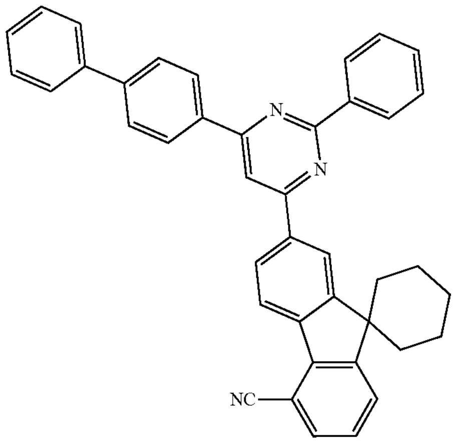

-continued
C-43
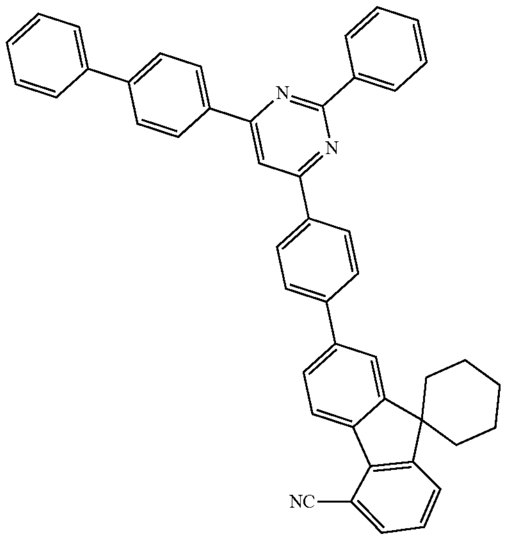
C-44
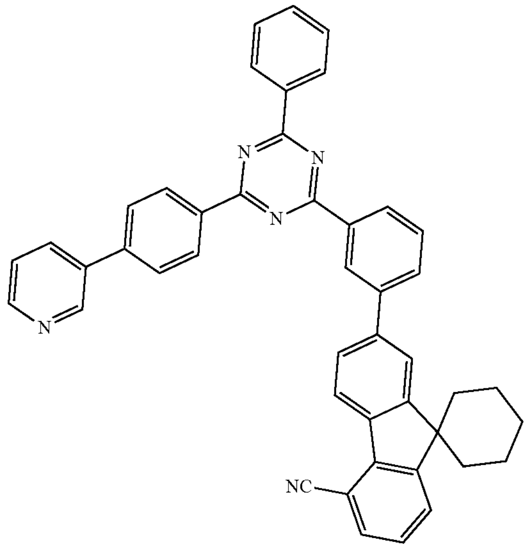
C-45
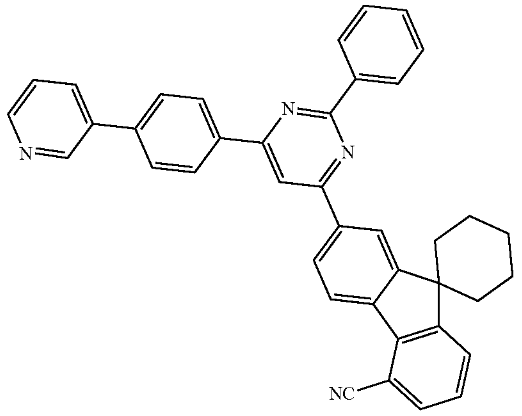
-continued
C-46
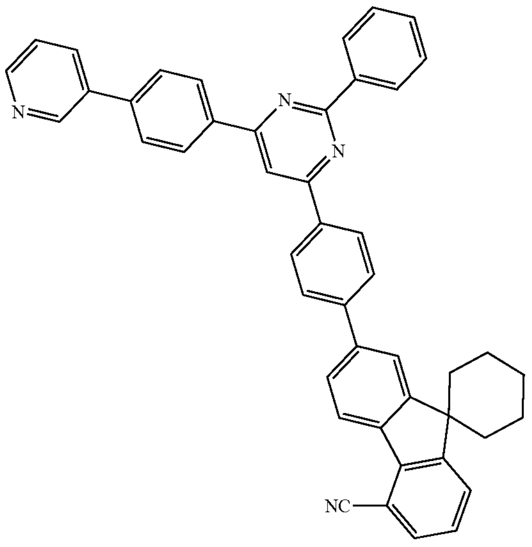
C-47
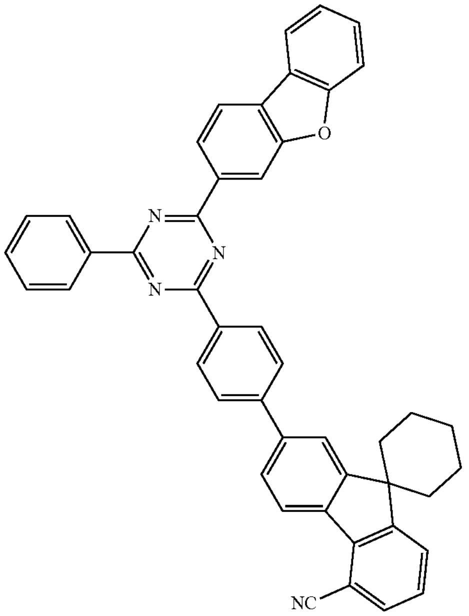

C-48
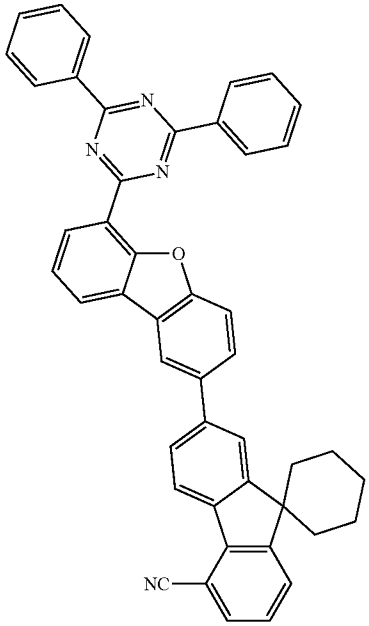
C-49
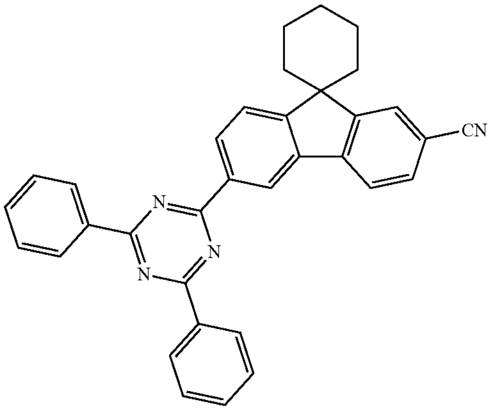
C-50
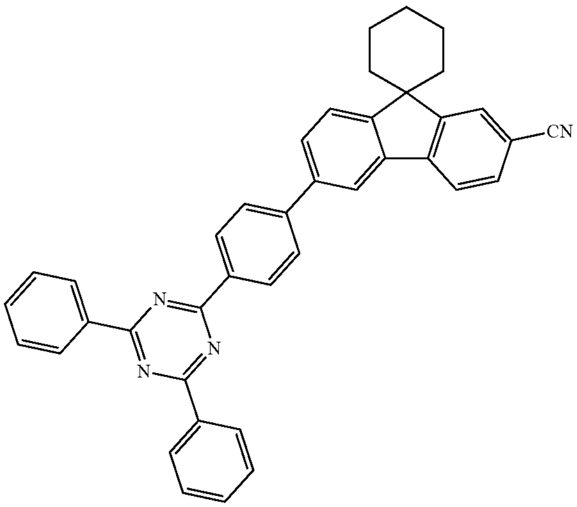
C-51
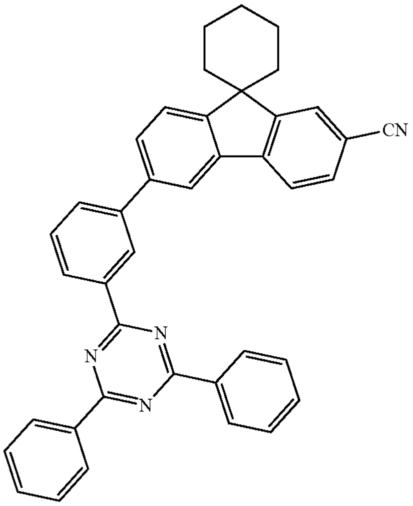
C-52
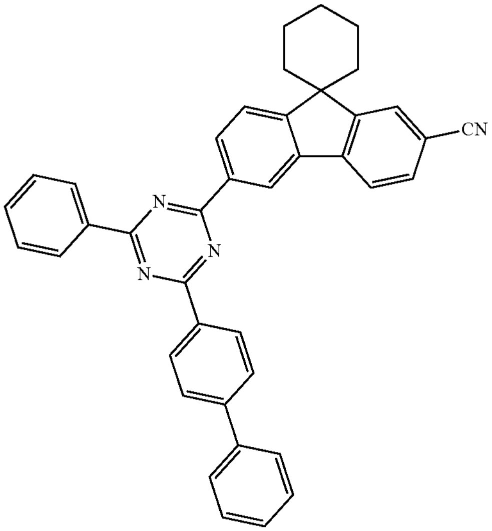

-continued
C-53
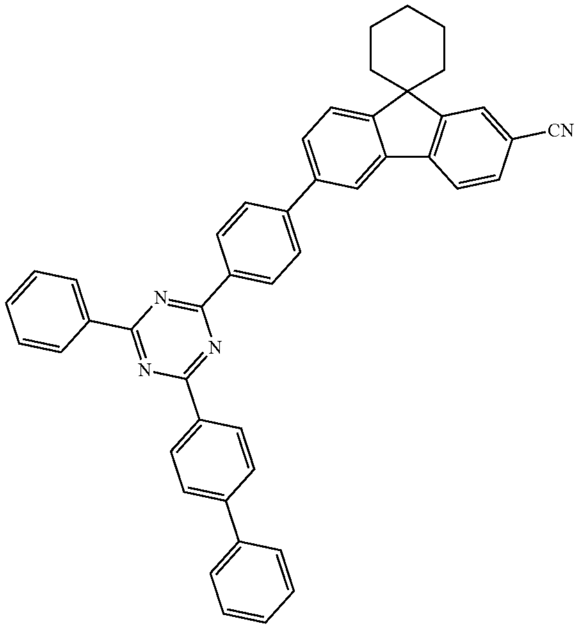
C-54
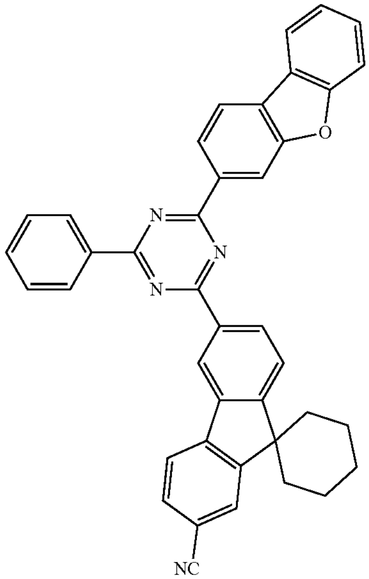
-continued
C-55
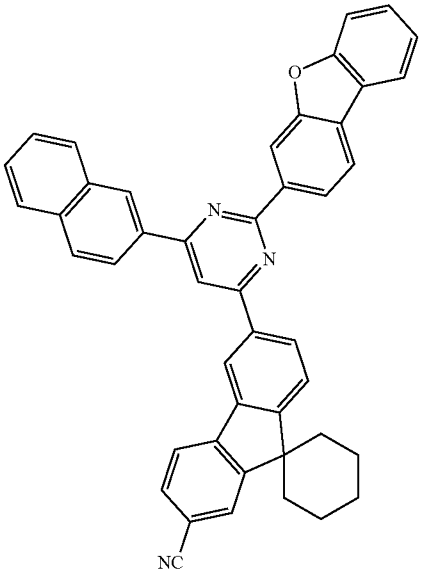
C-56
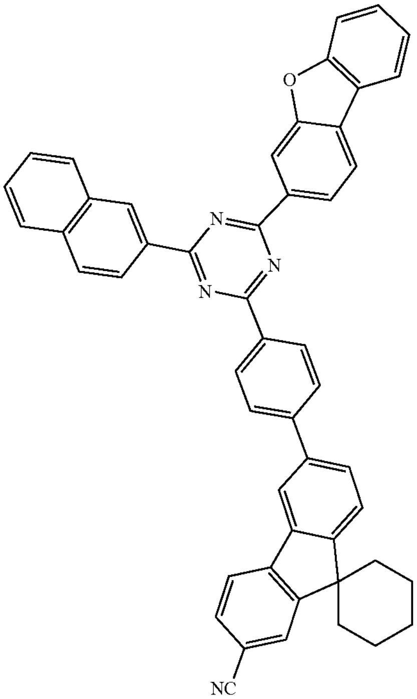

-continued
C-57
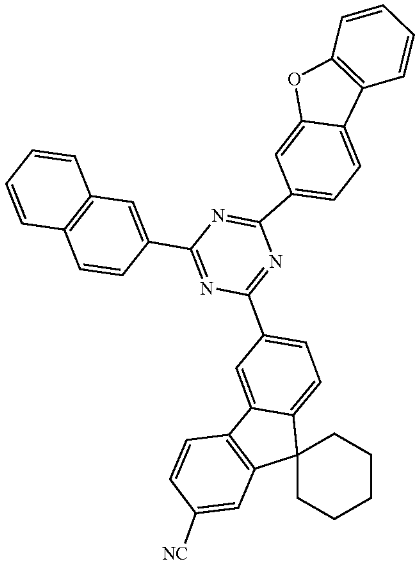
C-58
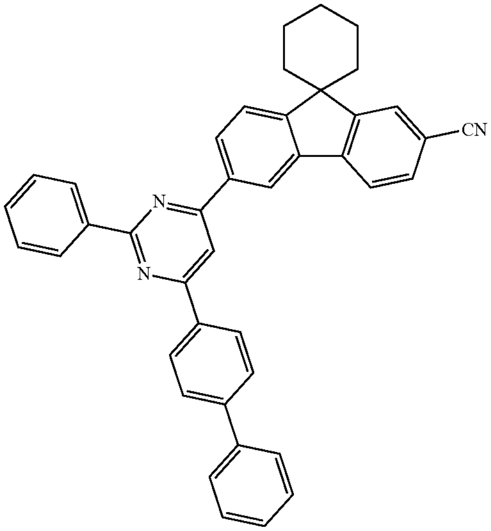
-continued
C-59
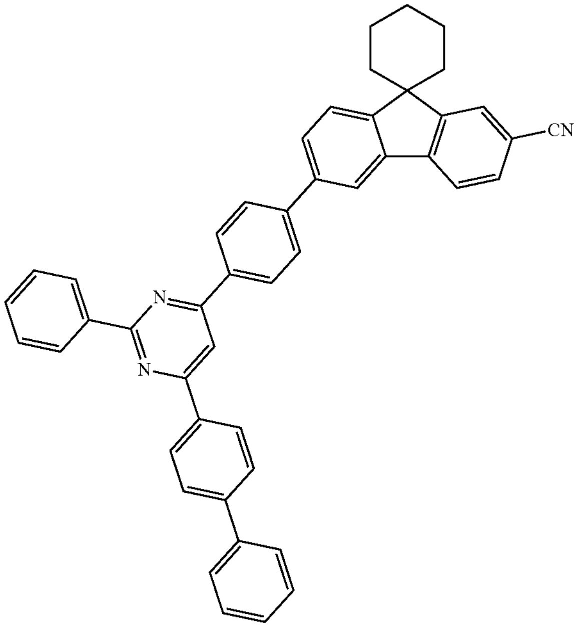
C-60
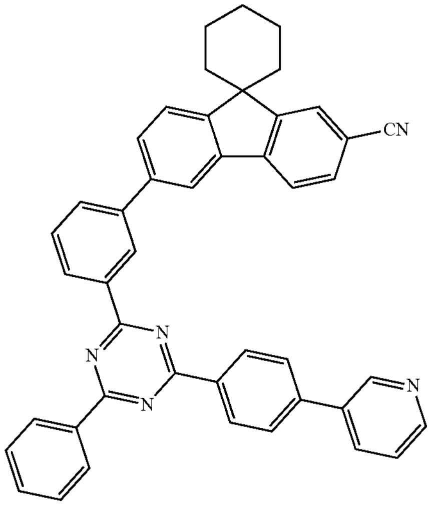

-continued
C-61
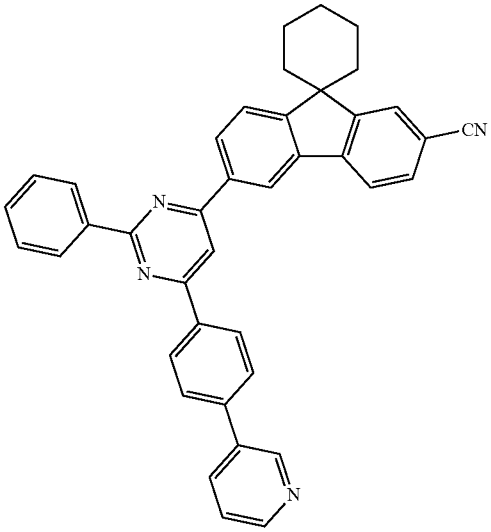
-continued
C-63
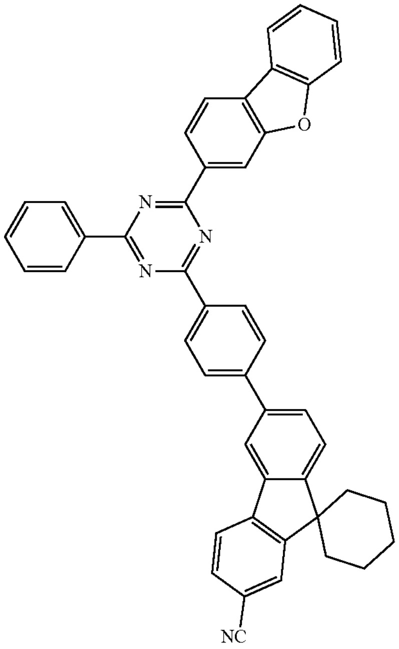
C-62
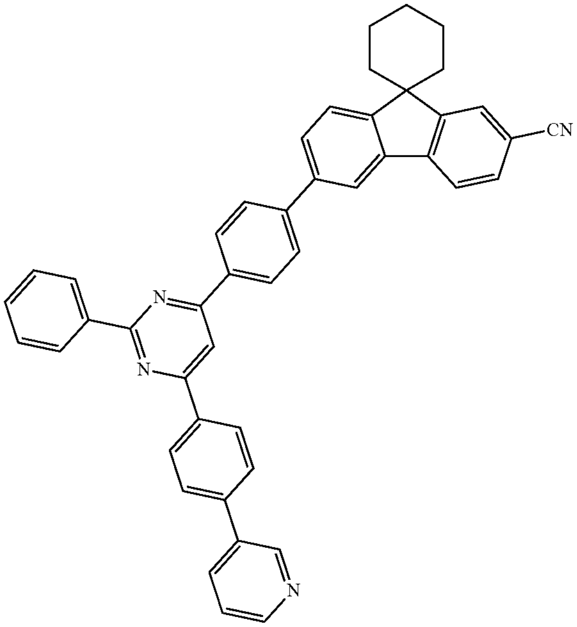
C-64
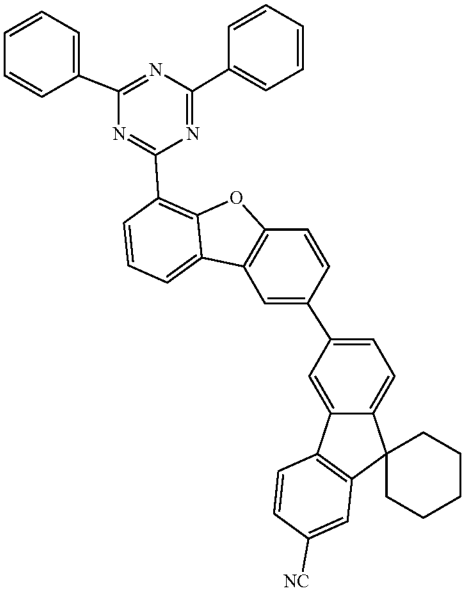

-continued
C-65
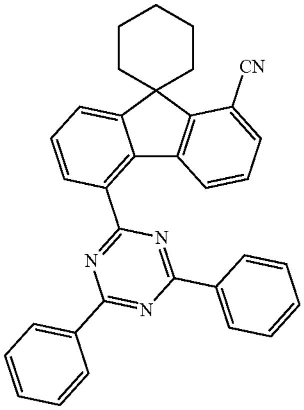
C-66
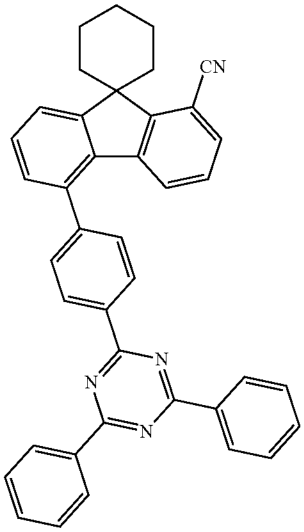
C-67
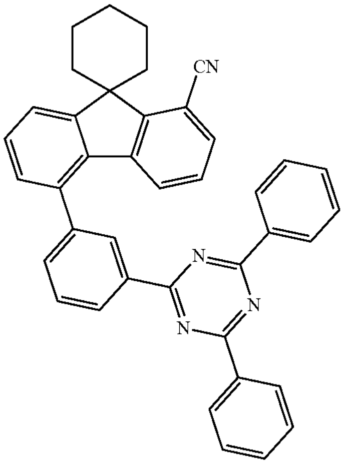
-continued
C-68
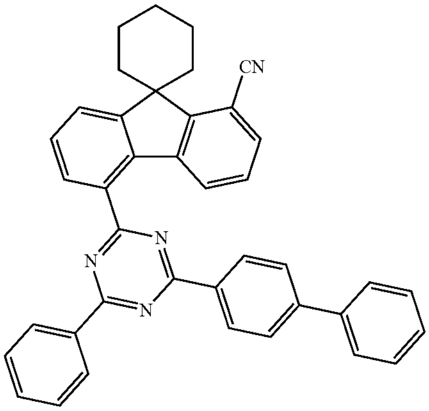
C-69
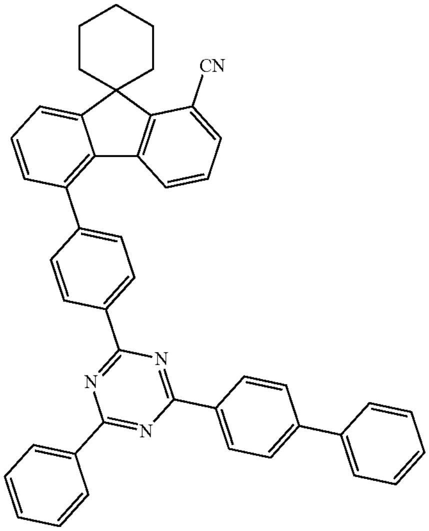
C-70
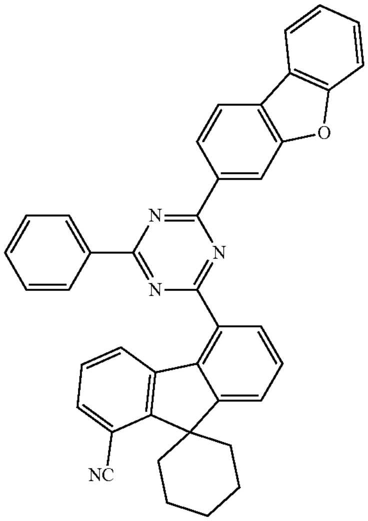

C-71
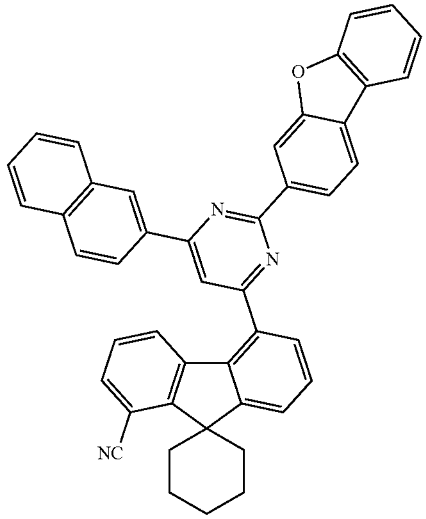
C-72
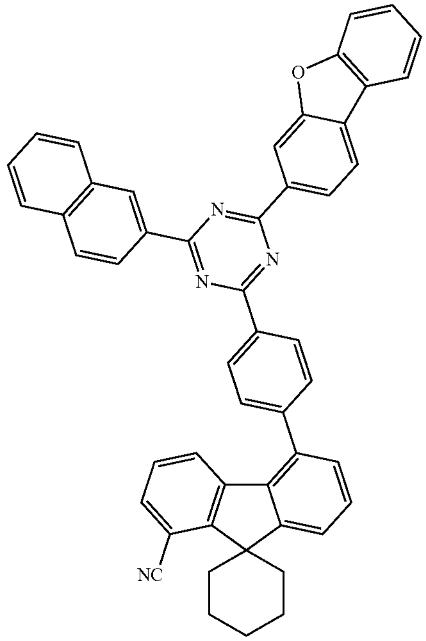
C-73
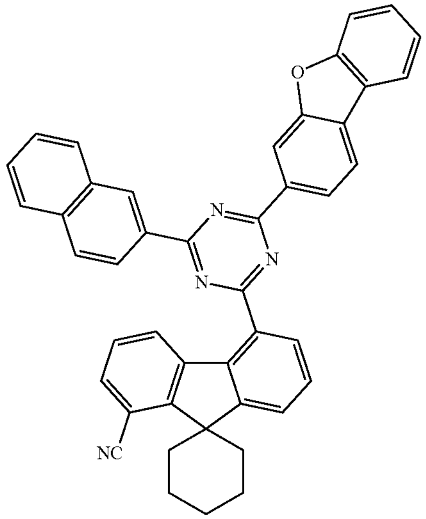
C-74
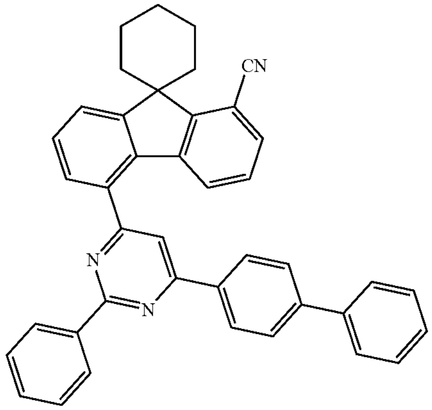
C-75
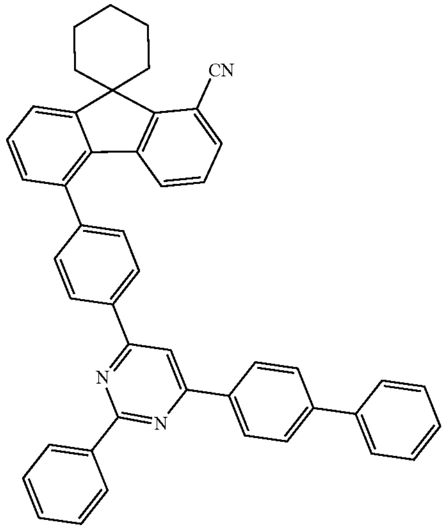

-continued
C-76
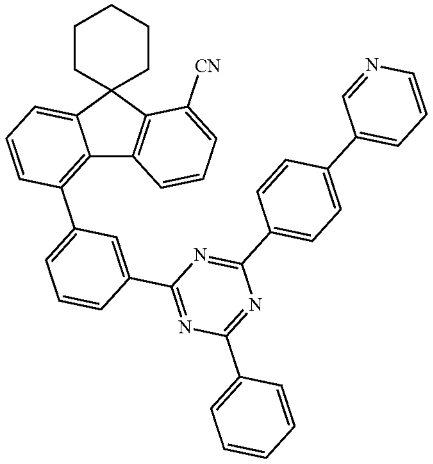
C-77
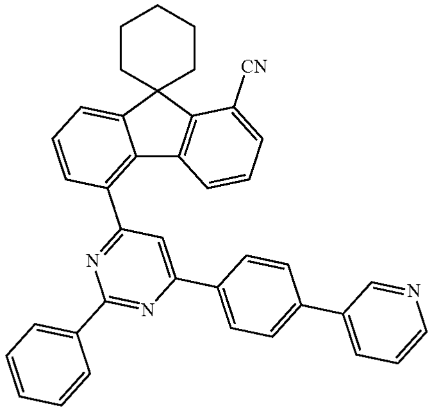
C-78
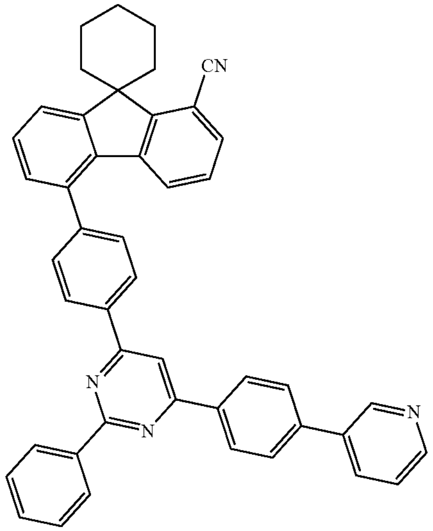
-continued
C-79
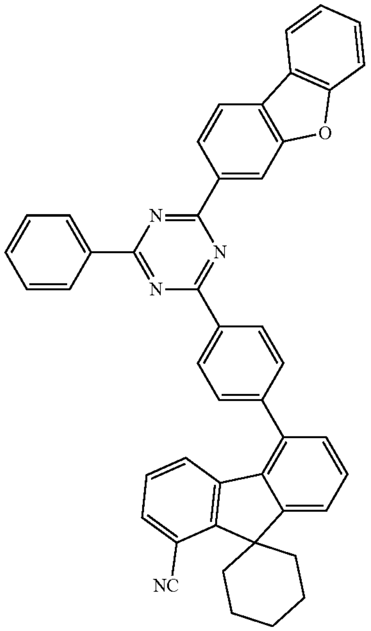
C-80
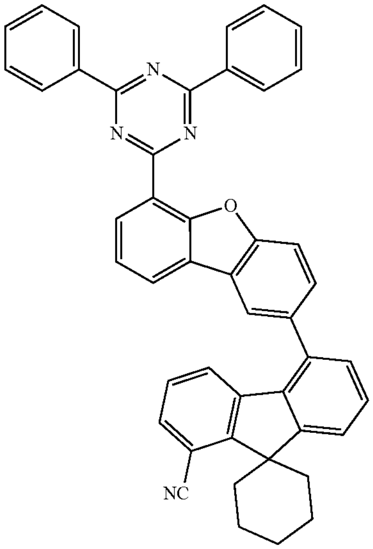
C-81
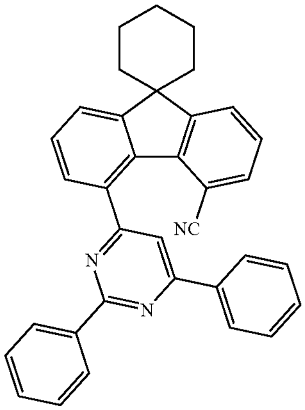

-continued
C-82
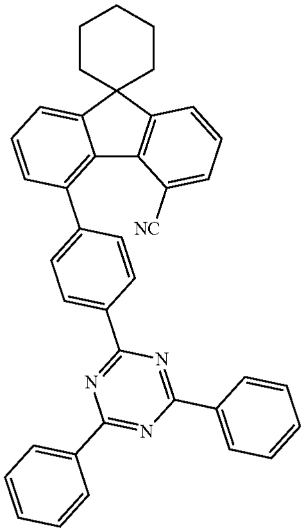
C-83
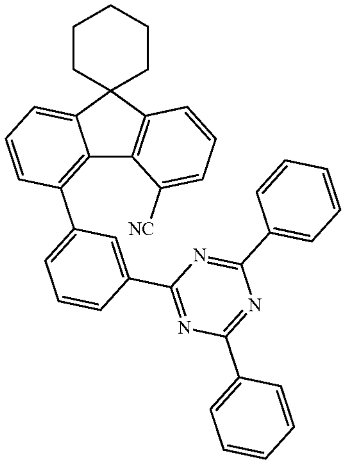
C-84
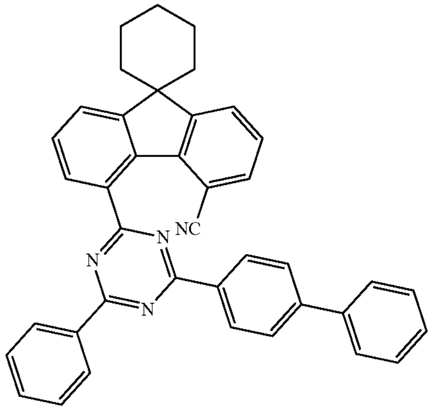
-continued
C-85
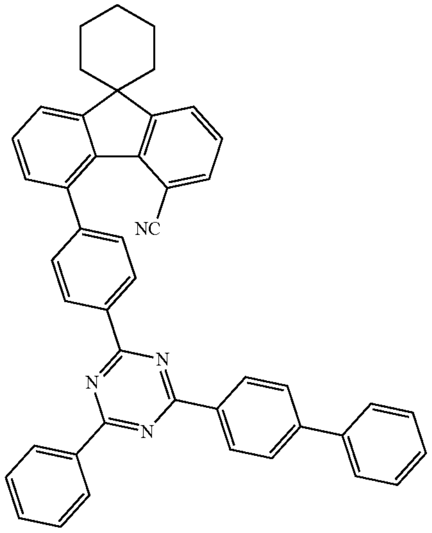
C-86
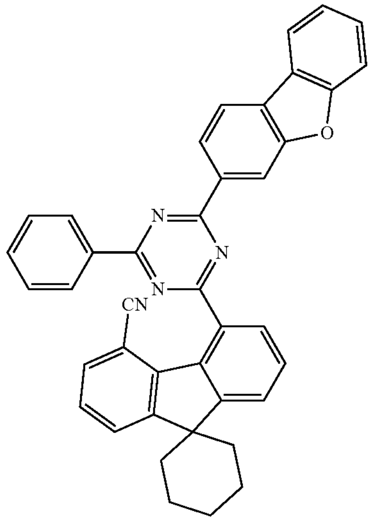
C-87
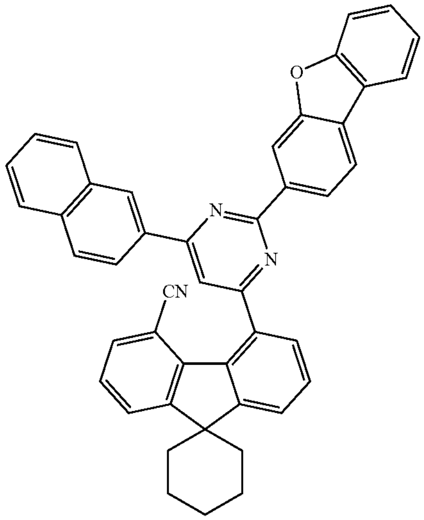

-continued
C-88
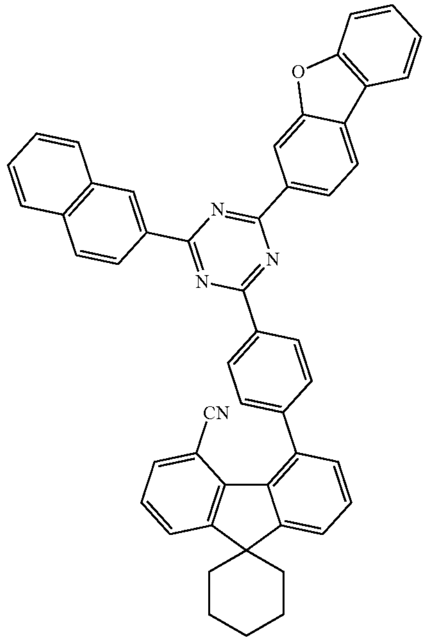
C-89
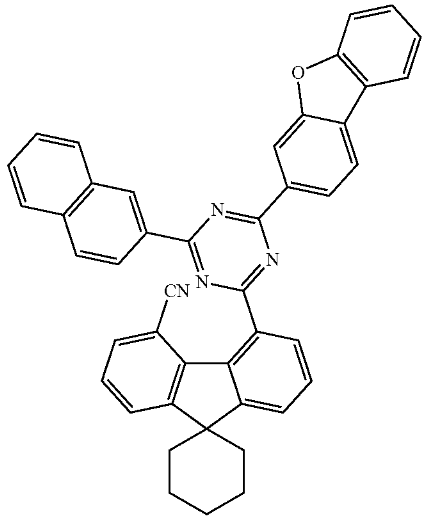
C-90
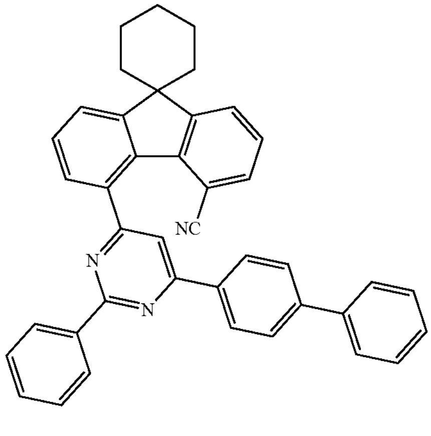
-continued
C-91
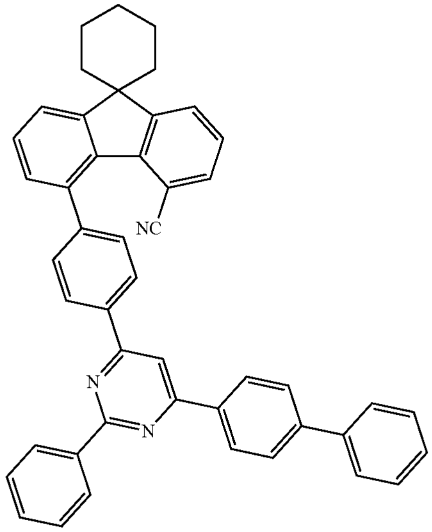
C-92
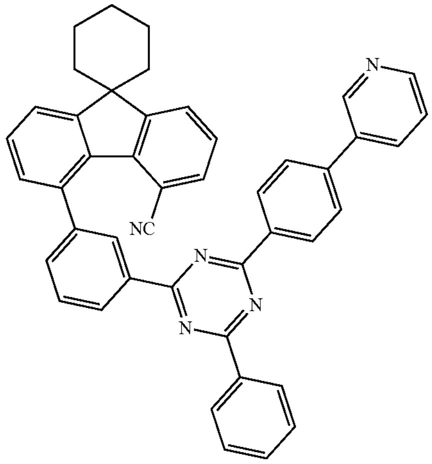
C-93
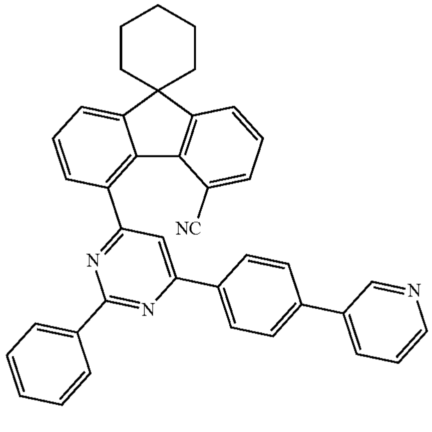

-continued
C-94
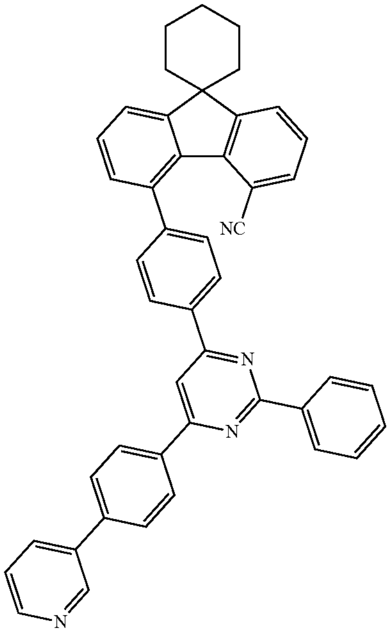
C-95
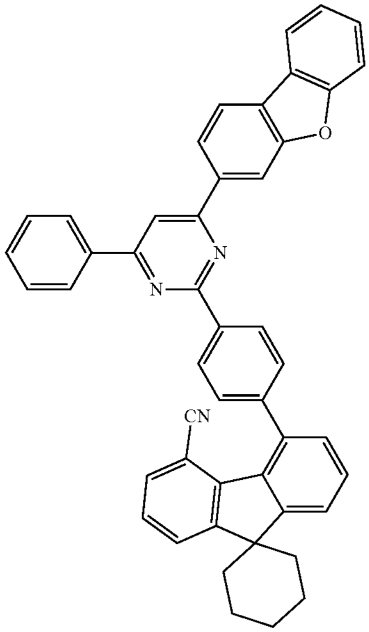
-continued
C-96
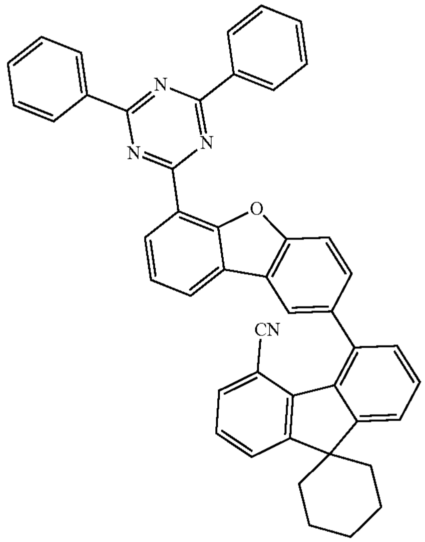
C-97
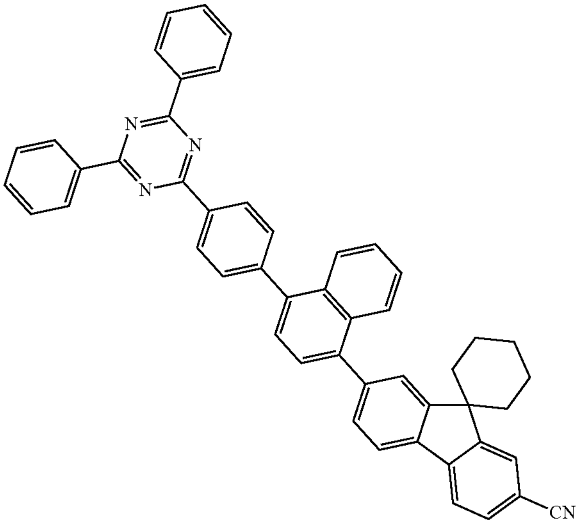
C-98
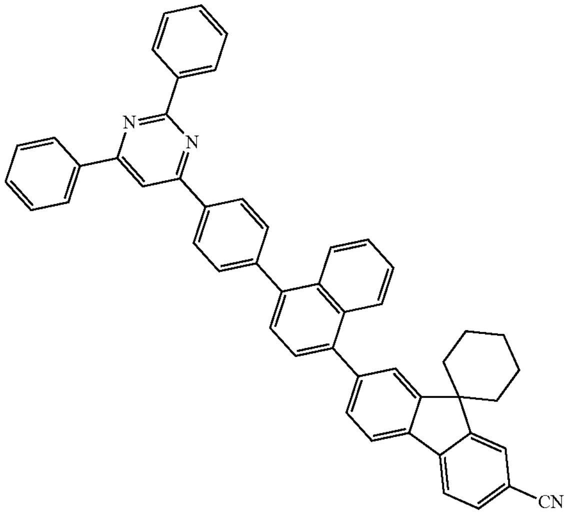

C-99
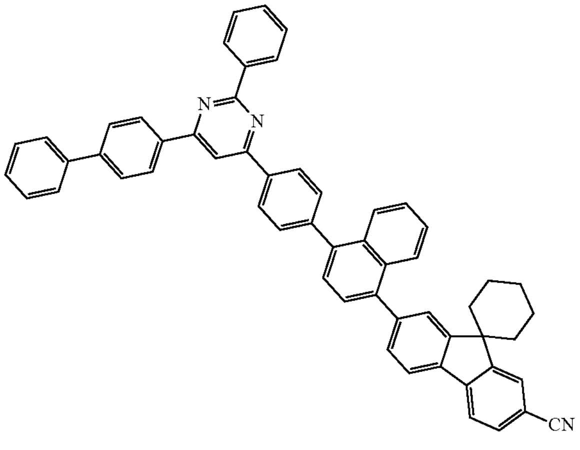
C-100
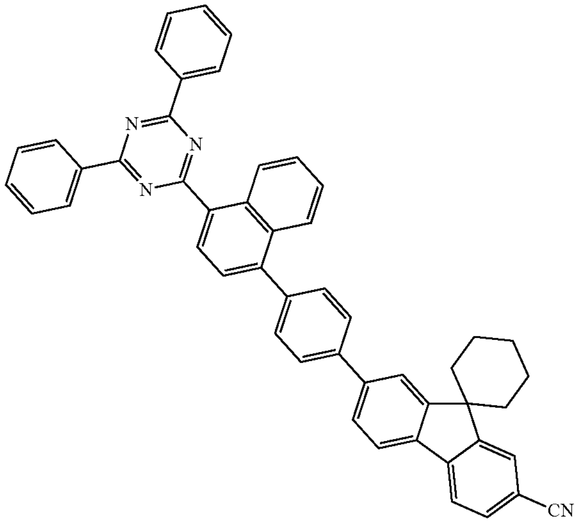
C-101
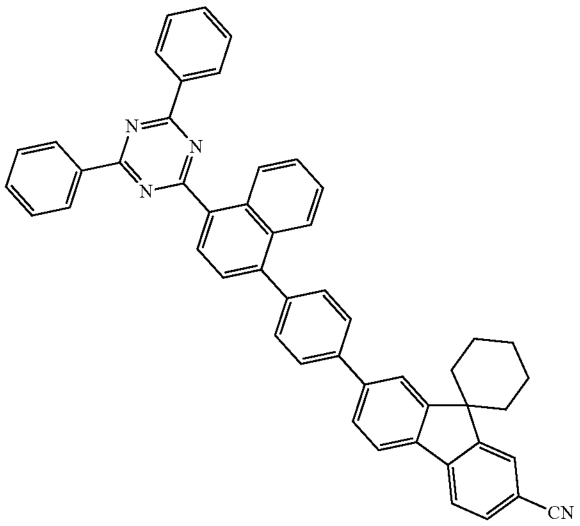
C-102
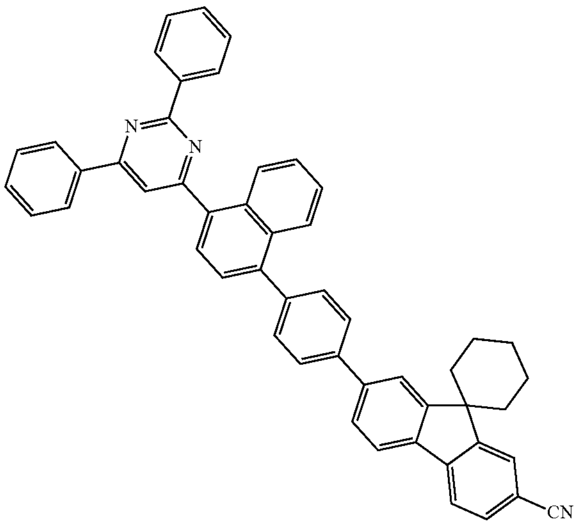
C-103
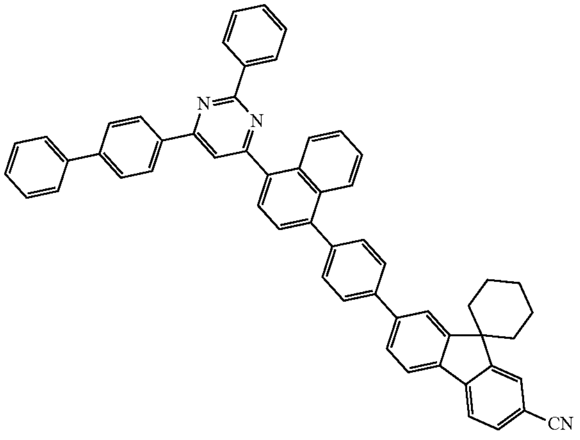
C-104
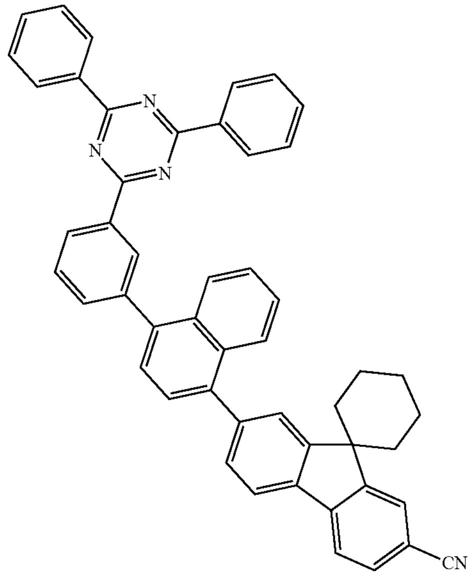

-continued
C-105
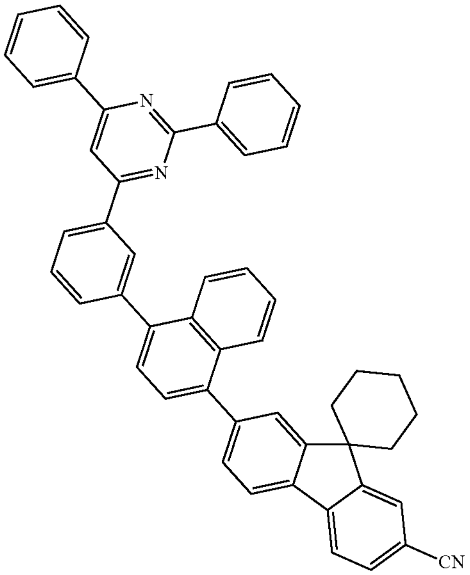
C-106
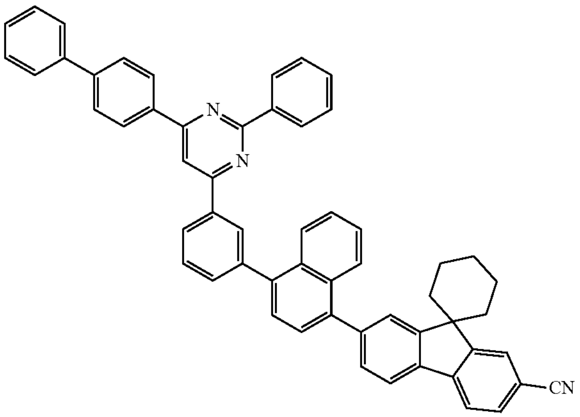
C-107
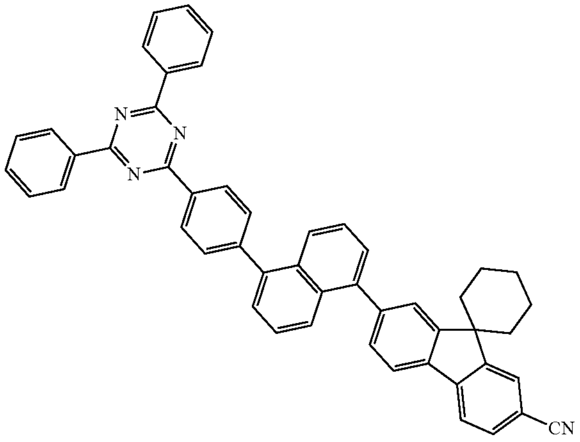
-continued
C-108
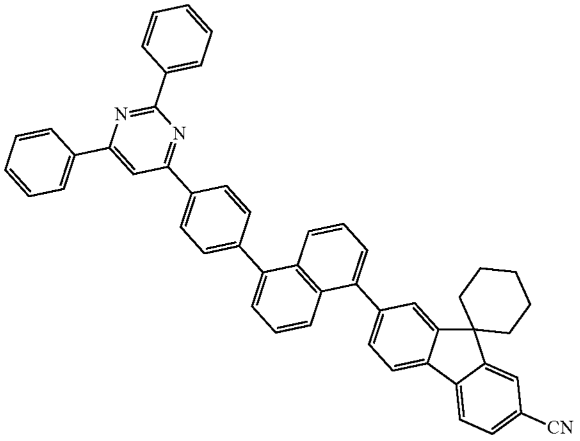
C-109
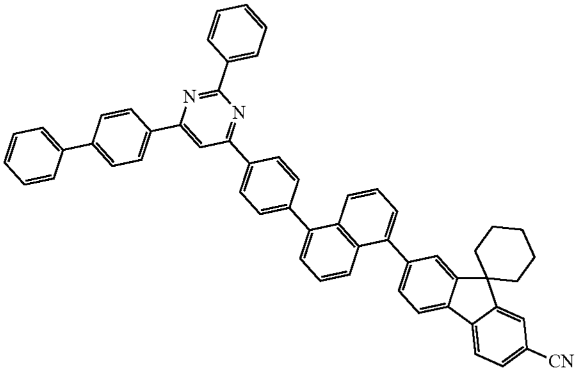
C-110
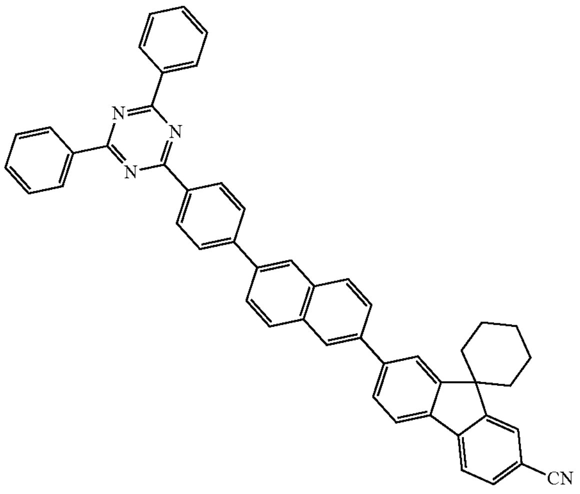

-continued
C-111
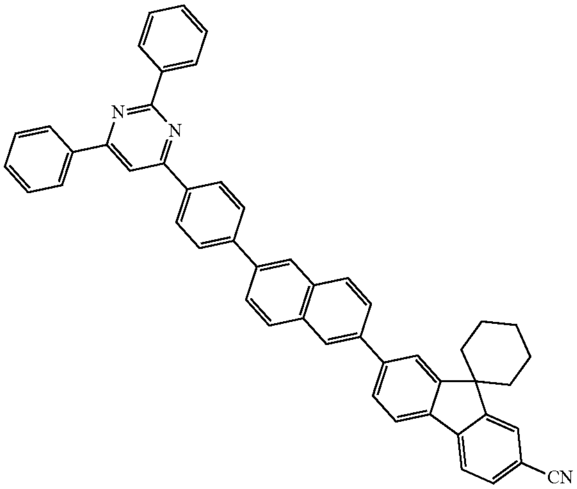
C-112
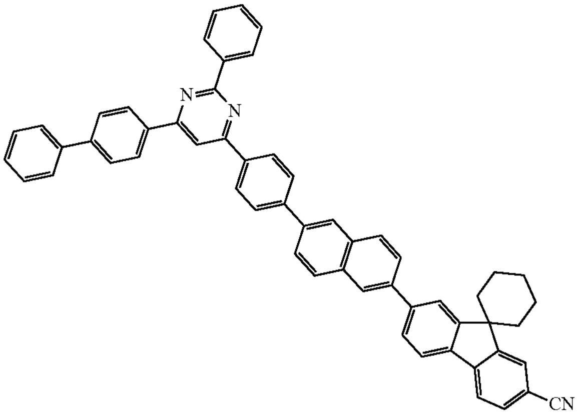
C-113
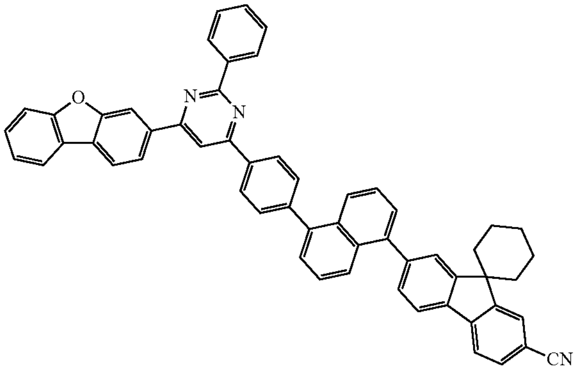
-continued
C-114
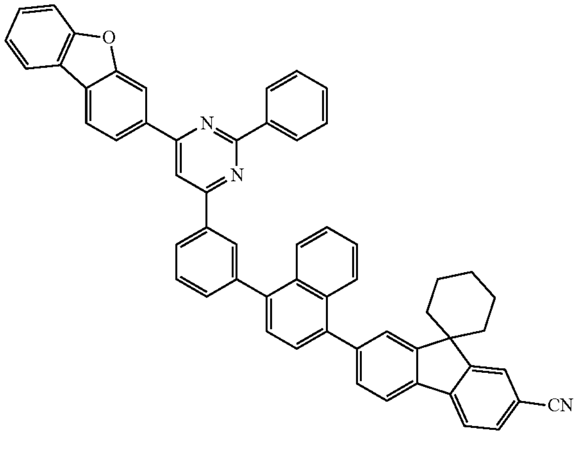
C-115
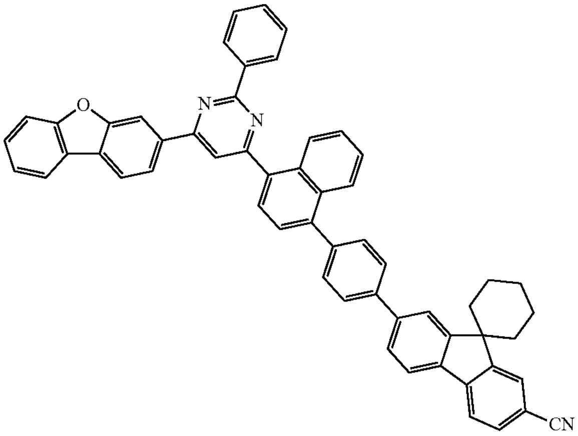
C-116
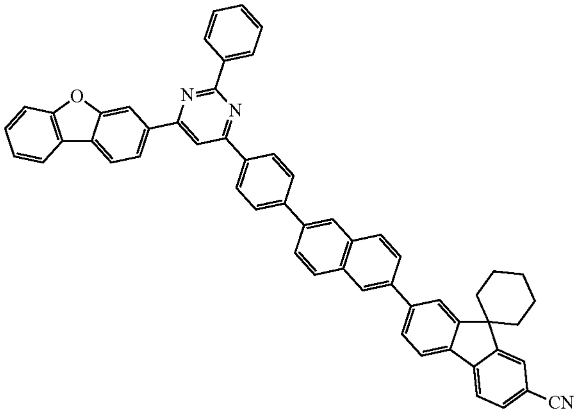

-continued

C-117

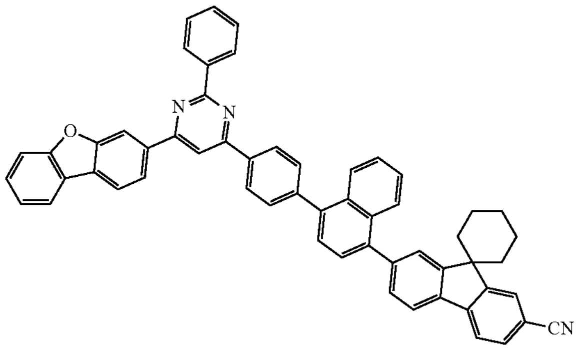

As used herein, “alkyl” refers to a monovalent substituent derived from a linear or branched chain saturated hydrocarbon having 1 to 40 carbon atoms. Examples of such alkyl may include, but are not limited to, methyl, ethyl, propyl, isobutyl, sec-butyl, pentyl, iso-amyl, hexyl or the like.

As used herein, “alkenyl” refers to a monovalent substituent derived from a linear or branched chain unsaturated hydrocarbon having 2 to 40 carbon atoms, having at least one carbon-carbon double bond. Examples of such alkenyl may include, but are not limited to, vinyl, allyl, isopropenyl, 2-butenyl or the like.

As used herein, “alkynyl” refers to a monovalent substituent derived from a linear or branched chain unsaturated hydrocarbon having 2 to 40 carbon atoms, having at least one carbon-carbon triple bond. Examples of such alkynyl may include, but are not limited to, ethynyl, 2-propynyl or the like.

As used herein, “aryl” refers to a monovalent substituent derived from a $C_6$ to $C_{40}$ aromatic hydrocarbon which is in a structure with a single ring or two or more rings combined with each other. In addition, a form in which two or more rings are pendant (e.g., simply attached) to or fused with each other may also be included. Examples of such aryl may include, but are not limited to, phenyl, naphthyl, phenanthryl, anthryl or the like.

As used herein, “heteroaryl” refers to a monovalent substituent derived from a monoheterocyclic or polyheterocyclic aromatic hydrocarbon having 5 to 60 nuclear atoms. In such an embodiment, one or more carbons in the ring, preferably one to three carbons, are substituted with a heteroatom such as N, O, S or Se. In addition, a form in which two or more rings are pendant to or fused with each other may be included and a form fused with an aryl group may be included. Examples of such heteroaryl may include, but are not limited to, a 6-membered monocyclic ring including, for example, pyridyl, pyrazinyl, pyrimidinyl, pyridazinyl and triazinyl; a polycyclic ring including, for example, phenoxathienyl, indolinzinyl, indolyl purinyl, quinolyl, benzothiazole, and carbazolyl; 2-furanyl; N-imidazolyl; 2-isoxazolyl; 2-pyridinyl; 2-pyrimidinyl or the like.

As used herein, “aryloxy” is a monovalent substituent represented by RO—, where R refers to aryl having 5 to 40 carbon atoms. Examples of such aryloxy may include, but are not limited to, phenyloxy, naphthyloxy, diphenyloxy or the like.

As used herein, “alkyloxy” refers to a monovalent substituent represented by R'O—, where R' refers to alkyl having 1 to 40 carbon atoms. Such alkyloxy may include a linear, branched or cyclic structure. Examples of such alkyloxy may include, but are not limited to, methoxy, ethoxy, n-propoxy, 1-propoxy, t-butoxy, n-butoxy, pentoxy or the like.

As used herein, “arylamine” refers to an amine substituted with an aryl group having 6 to 40 carbon atoms, in which case at least two aryl groups may be included and may be the same as or different from each other.

As used herein, “heteroarylarylamine” refers to an amine substituted with an aryl group having 6 to 40 carbon atoms and a heteroaryl group having 5 to 40 nuclear atoms.

As used herein, “heteroarylamine” refers to an amine substituted with at least two heteroaryl groups having 5 to 40 nuclear atoms, in which case the heteroaryl groups may be the same or different from each other.

As used herein, “cycloalkyl” refers to a monovalent substituent derived from a monocyclic or polycyclic non-aromatic hydrocarbon having 3 to 40 carbon atoms. Examples of such cycloalkyl may include, but are not limited to, cyclopropyl, cyclopentyl, cyclohexyl, norbornyl, adamantine or the like.

As used herein, “heterocycloalkyl” refers to a monovalent substituent derived from a non-aromatic hydrocarbon having 3 to 40 nuclear atoms, where one or more carbons in the ring, preferably one to three carbons, are substituted with a heteroatom such as N, O, S or Se. Examples of such heterocycloalkyl may include, but are not limited to, morpholine, piperazine or the like.

As used herein, “alkylsilyl” refers to silyl in which substitution with alkyl having 1 to 40 carbon atoms has been made, and “arylsilyl” refers to silyl in which substitution with aryl having 5 to 40 carbon atoms has been made.

As used herein, the term “fused ring (e.g., condensed ring)” refers to a fused aliphatic ring, a fused aromatic ring, a fused heteroaliphatic ring, a fused heteroaromatic ring, or a combination thereof.

<Electron Transport Layer Material>

The present invention provides an electron transport layer including the compound represented by Chemical Formula 1.

The electron transport layer (ETL) serves to move electrons injected from the cathode to an adjacent layer, specifically a light emitting layer.

The compound represented by Chemical Formula 1 may be used solely as an electron transport layer (ETL) material, or may be used in combination with an electron transport layer material known in the art. It may preferably be used solely.

The electron transport layer material that may be used in combination with the compound of Chemical Formula 1 includes an electron transport material commonly known in the art. Non-limiting examples of applicable electron transport materials may include oxazole-based compounds, isoxazole-based compounds, triazole-based compounds, isothiazole-based compounds, oxadiazole-based compounds, thiadiazole-based compounds, perylene-based compounds, aluminum complexes (e.g., tris(8-quinolinolato)-aluminium ($Alq_3$), BAlq, SAlq, $Almq_3$), gallium complexes (e.g., Gaq'2OPiv, Gaq'2OAc, 2(Gaq'2)), etc. These may be used solely or two or more types may be used in combination.

In the present invention, when the compound of Chemical Formula 1 and the material for the electron transport layer are used in combination, a mixing ratio thereof is not particularly limited, and may be appropriately adjusted within a range known in the art.

<Electron Transport Auxiliary Layer Material>

In addition, the present invention provides an auxiliary electron transport layer including the compound represented by Chemical Formula 1.

The electron transport auxiliary layer is disposed between the light emitting layer and the electron transport layer and serves to substantially prevent diffusion of excitons or holes generated in the light emitting layer into the electron transport layer.

The compound represented by Chemical Formula 1 may be used solely as an electron transport auxiliary layer material, or may be combined with an electron transport layer material known in the art. It may preferably be used solely.

The electron transport auxiliary layer material that may be used in combination with the compound of Chemical Formula 1 includes an electron transport material commonly known in the art. For example, the electron transport auxiliary layer may include an oxadiazole derivative, a triazole derivative, a phenanthroline derivative (e.g., BCP), a heterocyclic derivative containing nitrogen, and the like.

In the present invention, when the compound of Chemical Formula 1 and the material for the electron transport auxiliary layer are used in combination, a mixing ratio thereof is not particularly limited, and may be appropriately adjusted within a range known in the art.

<Organic Electroluminescent Device>

The present invention provides an organic electroluminescent ("EL") device including the compound represented by Chemical Formula 1.

More specifically, the organic EL device according to the present invention includes an anode (e.g., a positive electrode), a cathode (e.g., a negative electrode), and one or more organic layers disposed between the anode and the cathode, and at least one of the one or more organic layers includes the compound represented by Chemical Formula 1. In such an embodiment, the compound may be used solely or as a combination of two or more kinds thereof.

The one or more organic layers may be any one or more of a hole injection layer, a hole transport layer, a light emitting layer, a light emitting auxiliary layer, an electron transport layer, an electron transport auxiliary layer, and an electron injection layer, and at least one of the organic layers may include the compound represented by Chemical Formula 1. Specifically, the organic layer including the compound represented by Chemical Formula 1 preferably is a light-emitting layer (more specifically, a phosphorescent light-emitting host material), an electron transport layer, or an electron transport auxiliary layer.

The light emitting layer of the organic EL device according to the present invention may include a host material and a dopant material, and in such a case, may include the compound of Chemical Formula 1 as the host material. In addition, the light emitting layer of the present invention may include a compound known in the art other than the compound represented by Chemical Formula 1 as a host.

When the compound represented by Chemical Formula 1 is included as a material for the light emitting layer of the organic EL device, preferably a phosphorescent host material of blue, green, and red colors, a binding force between holes and electrons in the light emitting layer increases, so the efficiency (luminous efficiency and power efficiency), lifespan, luminance and driving voltage of the organic EL device may be improved. Specifically, the compound represented by Chemical Formula 1 may preferably be included in the organic EL device as a green and/or red phosphorescent host, a fluorescent host, or a dopant material. In particular, the compound represented by Chemical Formula 1 of the present invention preferably is a green phosphorescent exciplex N-type host material of the light-emitting layer having high efficiency.

The structure of the organic EL device of the present invention is not particularly limited, but a non-limiting example thereof may be a structure in which a substrate, an anode, a hole injection layer, a hole transport layer, a light emitting auxiliary layer, a light emitting layer, an electron transport auxiliary layer, an electron transport layer, an electron transport layer and a cathode are sequentially stacked. In such an embodiment, at least one of the hole injection layer, the hole transport layer, the light emitting auxiliary layer, the light emitting layer, the electron transport auxiliary layer, the electron transport layer and the electron transport layer may include the compound represented by Chemical Formula 1. Preferably, the light emitting layer, and more preferably, the phosphorescent host may include the compound represented by Chemical Formula 1. In such an embodiment, an electron injection layer may be further stacked on the electron transport layer.

In addition, the structure of the organic EL device of the present invention may have a structure in which an insulating layer or an adhesive layer is inserted at an interface between the electrode and the organic layer.

The organic EL device of the present invention may be prepared by materials and methods known in the art, except that the one or more organic layers include the compound represented by Chemical Formula 1.

The organic layer may be formed by a vacuum deposition (evaporation) method or a solution coating method. Examples of the solution coating method may include, but are not limited to, spin coating, dip coating, doctor blading, inkjet printing, thermal transfer or the like.

The substrate used in Preparing the organic EL device of the present invention is not particularly limited, but silicon wafers, quartz, glass plates, metal plates, plastic films, sheets or the like may be used.

In addition, any anode material known in the art may be used as a material of the anode without limitation. For example, examples thereof may include, but is not limited to, a metal such as vanadium, chromium, copper, zinc, and gold or an alloy thereof; metal oxides such as zinc oxide, indium oxide, indium tin oxide (ITO), or indium zinc oxide (IZO); combination of oxide with metal such as ZnO:Al or $SnO_2$:Sb; conductive polymers such as polythiophene, poly (3-methylthiophene), poly [3,4-(ethylene-1,2-dioxy)thiophene] (PEDT), polypyrrole or polyaniline; and carbon black or the like.

In addition, any cathode material known in the art may be used as a material of the cathode without limitation. For example, examples thereof may include, but is not limited to, a metal such as magnesium, calcium, sodium, potassium, titanium, indium, yttrium, lithium, gadolinium, aluminum, silver, tin, or lead or an alloy thereof; a multi-layered material such as LiF/Al or $LiO_2$/Al or the like.

In addition, a material of the hole injection layer, the hole transport layer, the electron injection layer, and the electron transport layer is not particularly limited and conventional materials known in the art may be used without limitation.

Hereinafter, the present invention will be described in detail with reference to the following embodiments. However, the following embodiments are merely to illustrate the invention, and the present invention is not limited to the following embodiments.

Preparation Examples 1 to 14

[Preparation Example 1] Synthesis of 2-chloro-4-(dibenzo[b,d]furan-3-yl)-6-phenyl-1,3,5-triazine

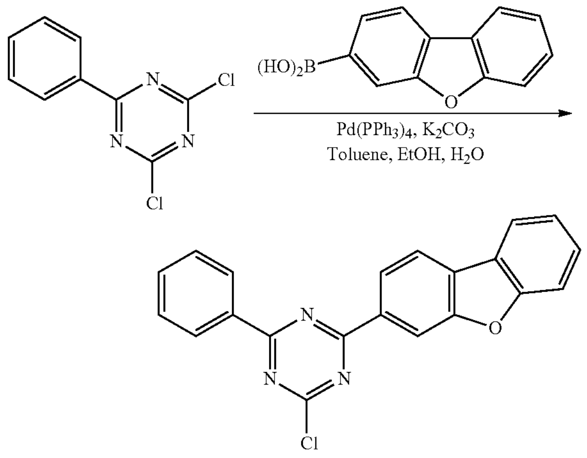

2,4-dichloro-6-phenyl-1,3,5-triazine (50.0 g, 221.18 mmol), 2-chloro-4-(dibenzo[b,d]furan-3-yl)-6-phenyl-1,3,5-triazine (46.89 g, 221.18 mmol), $Pd(PPh_3)_4$ (12.78 g, 11.06 mmol), and $K_2CO_3$ (91.71 g, 663.54 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 2-chloro-4-(dibenzo[b,d]furan-3-yl)-6-phenyl-1,3,5-triazine (56.98 g, yield 72%) was obtained using column chromatography.

$^1$H-NMR: δ 7.50 (t, 3H), 8.36 (d, 2H), 7.31 (s, 1H), 7.39 (s, 1H), 7.82 (s, 1H), 7.98 (s, 1H), 8.03 (s, 1H), 7.54 (s, 1H), 7.76 (s, 1H)

[LCMS]: 357

[Preparation Example 2] Synthesis of 2-([1,1'-biphenyl]-4-yl)-4-chloro-6-(dibenzo[b,d]furan-3-yl)-1,3,5-triazine

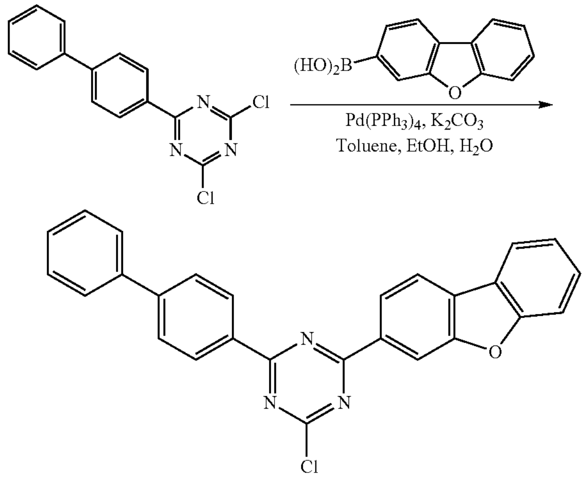

2-([1,1'-biphenyl]-4-yl)-4,6-dichloro-1,3,5-triazine (50.0 g, 165.48 mmol), 2-chloro-4-(dibenzo[b,d]furan-3-yl)-6-phenyl-1,3,5-triazine (35.08 g, 212.01 mmol), $Pd(PPh_3)_4$ (9.56 g, 8.27 mmol), and $K_2CO_3$ (68.61 g, 496.43 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 2-([1,1'-biphenyl]-4-yl)-4-chloro-6-(dibenzo[b,d]furan-3-yl)-1,3,5-triazine (71.80 g, yield 72%) was obtained using column chromatography.

$^1$H-NMR: δ 7.76 (s, 1H), 7.54 (s, 1H), 8.03 (s, 1H), 7.98 (s, 1H), 7.82 (s, 1H), 7.39 (s, 1H), 7.31 (s, 1H), 7.96 (s, 1H), 7.25 (d, 2H), 7.75 (d, 2H), 7.96 (s, 1H), 7.49 (d, 2H), 7.41 (s, 1H)

[LCMS]: 433

[Preparation Example 3] Synthesis of 4-chloro-2-(dibenzo[b,d]furan-3-yl)-6-(naphthalen-2-yl)pyrimidine

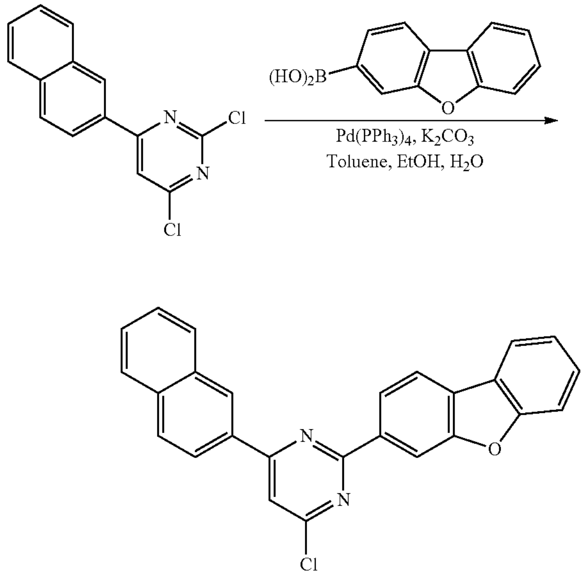

2,4-dichloro-6-(naphthalen-2-yl)pyrimidine (50.0 g, 181.73 mmol), 2-chloro-4-(dibenzo[b,d]furan-3-yl)-6-phenyl-1,3,5-triazine (38.53 g, 212.01 mmol), $Pd(PPh_3)_4$ (10.5 g, 9.09 mmol), and $K_2CO_3$ (75.35 g, 545.2 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 4-chloro-2-(dibenzo[b,d]furan-3-yl)-6-(naphthalen-2-yl)pyrimidine (73.94 g, yield 72%) was obtained using column chromatography.

$^1$H-NMR: δ 7.76 (s, 1H), 7.54 (s, 1H), 8.03 (s, 1H), 7.98 (d, sH), 7.03 (s, 1H), 7.82 (s, 1H), 7.39 (s, 1H), 7.31 (s, 1H), 8.46 (s, 1H), 8.06 (d, 2H), 8.00 (s, 1H), 7.61 (s, 1H), 7.59 (s, 1H)

[LCMS]: 433

[Preparation Example 4] Synthesis of 2-chloro-4-(dibenzo[b,d]furan-3-yl)-6-(naphthalen-2-yl)-1,3,5-triazine

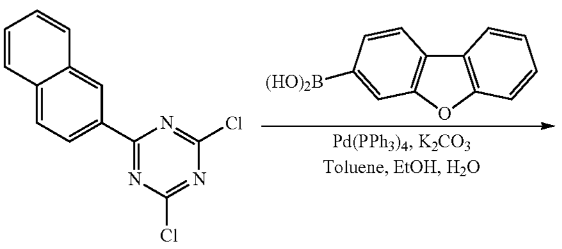

-continued

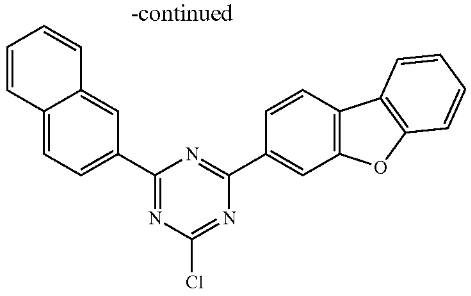

2,4-dichloro-6-(naphthalen-2-yl)-1,3,5-triazine (50.0 g, 181.08 mmol), 2-chloro-4-(dibenzo[b,d]furan-3-yl)-6-phenyl-1,3,5-triazine (38.39 g, 181.08 mmol), $Pd(PPh_3)_4$ (10.46 g, 9.05 mmol), and $K_2CO_3$ (75.08 g, 543.24 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 2-chloro-4-(dibenzo[b,d]furan-3-yl)-6-(naphthalen-2-yl)-1,3,5-triazine (73.86 g, yield 72%) was obtained using column chromatography.

$^1$H-NMR: δ 7.76 (s, 1H), 7.54 (s, 1H), 7.98 (d, sH), 7.03 (s, 1H), 7.82 (s, 1H), 7.39 (s, 1H), 7.31 (s, 1H), 8.46 (s, 1H), 8.06 (d, 2H), 8.00 (s, 1H), 7.61 (s, 1H), 7.59 (s, 1H)

[LCMS]: 407

[Preparation Example 5] Synthesis of 2-(4-chlorophenyl)-4-(dibenzo[b,d]furan-3-yl)-6-(naphthalen-2-yl)-1,3,5-triazine

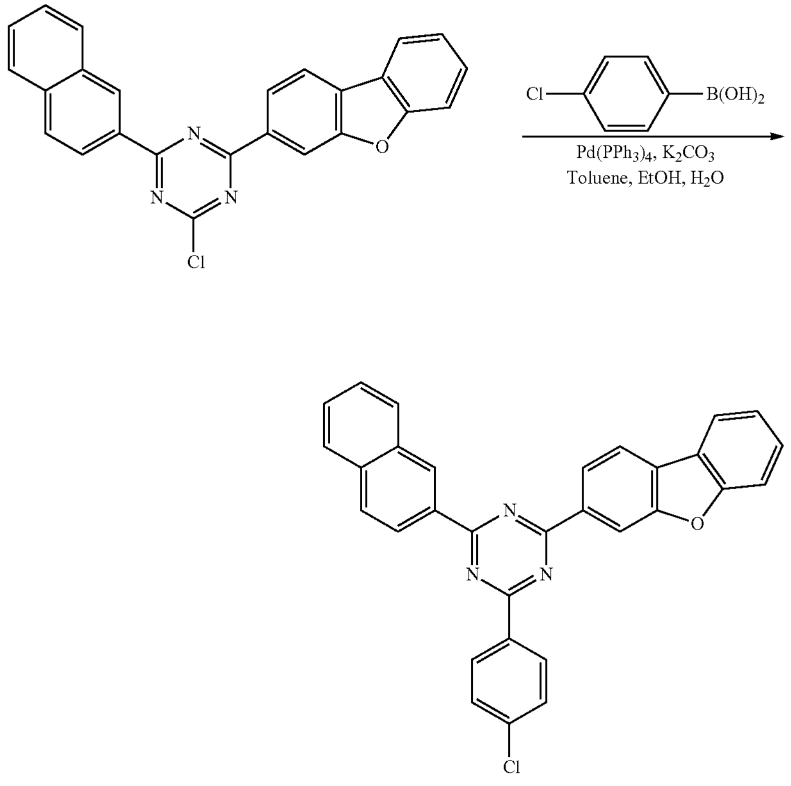

2-chloro-4-(dibenzo[b,d]furan-3-yl)-6-(naphthalen-2-yl)-1,3,5-triazine (50.0 g, 122.59 mmol), 2-chloro-4-(dibenzo[b,d]furan-3-yl)-6-phenyl-1,3,5-triazine (25.99 g, 122.59 mmol), $Pd(PPh_3)_4$ (7.08 g, 6.13 mmol), and $K_2CO_3$ (50.83 g, 367.77 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 2-(4-chlorophenyl)-4-(dibenzo[b,d]furan-3-yl)-6-(naphthalen-2-yl)-1,3,5-triazine (59.33 g, yield 72%) was obtained using column chromatography.

$^1$H-NMR: δ 7.76 (s, 1H), 7.54 (s, 1H), 7.98 (d, sH), 7.03 (s, 1H), 7.82 (s, 1H), 7.39 (s, 1H), 7.31 (s, 1H), 8.46 (s, 1H), 8.06 (d, 2H), 8.00 (s, 1H), 7.61 (s, 1H), 7.59 (s, 1H), 8.25 (d, 2H), 7.51 (d, 2H)

[LCMS]: 483

[Preparation Example 6] Synthesis of 4-chloro-2-phenyl-6-(4-(pyridin-3-yl)phenyl)pyrimidine

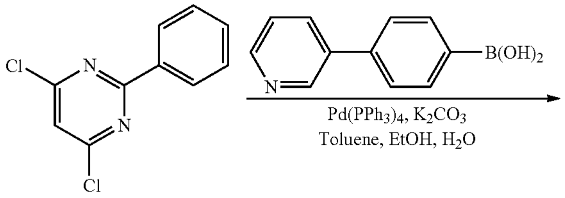

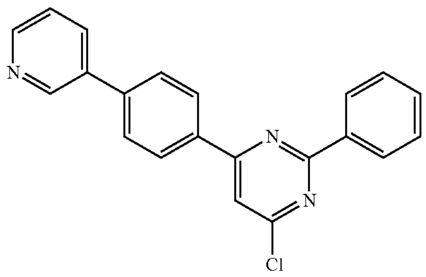

4,6-dichloro-2-phenylpyrimidine (50.0 g, 222.15 mmol), (4-(pyridin-3-yl)phenyl)boronic acid (44.21 g, 222.15 mmol), $Pd(PPh_3)_4$ (12.84 g, 11.11 mmol), and $K_2CO_3$ (92.11 g, 666.46 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 4-chloro-2-phenyl-6-(4-(pyridin-3-yl)phenyl)pyrimidine (76.40 g, yield 72%) was obtained using column chromatography.

$^1$H-NMR: δ 9.24 (s, 1H), 8.70 (s, 1H), 7.03 (s, 1H), 7.57 (s, 1H), 8.34 (s, 1H), 8.42 (s, 1H), 8.30 (d, 2H), 7.25 (d, 2H), 8.36 (s, 1H), 7.50 (t, 3H)

[LCMS]: 343

[Preparation Example 7] Synthesis of 2-chloro-4-phenyl-6-(4-(pyridin-3-yl)phenyl)-1,3,5-triazine

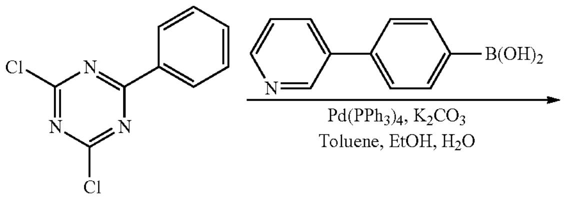

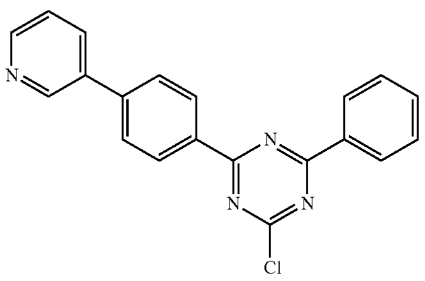

2,4-dichloro-6-phenyl-1,3,5-triazine (50.0 g, 222.18 mmol), (4-(pyridin-3-yl)phenyl)boronic acid (44.02 g, 222.18 mmol), $Pd(PPh_3)_4$ (12.78 g, 11.06 mmol), and $K_2CO_3$ (91.71 g, 663.54 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 2-chloro-4-phenyl-6-(4-(pyridin-3-yl)phenyl)-1,3,5-triazine (76.26 g, yield 72%) was obtained using column chromatography.

$^1$H-NMR: δ 9.24 (s, 1H), 8.70 (s, 1H), 7.57 (s, 1H), 8.34 (s, 1H), 8.42 (s, 1H), 8.30 (d, 2H), 7.25 (d, 2H), 8.36 (s, 1H), 7.50 (t, 3H)

[LCMS]: 344

[Preparation Example 8] Synthesis of 4-(4-chlorophenyl)-2-phenyl-6-(4-(pyridin-3-yl)phenyl)pyrimidine

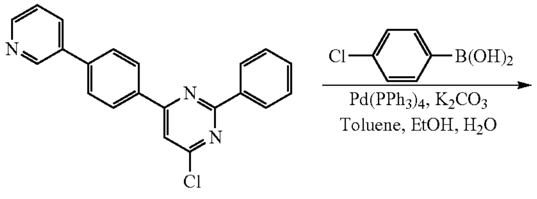

-continued

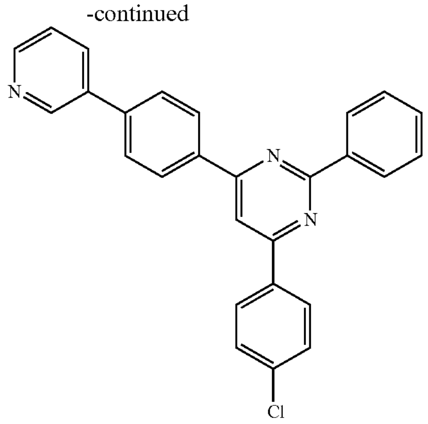

4-chloro-2-phenyl-6-(4-(pyridin-3-yl)phenyl)pyrimidine (50.0 g, 145.43 mmol), (4-chlorophenyl)boronic acid (22.74 g, 145.43 mmol), $Pd(PPh_3)_4$ (8.4 g, 7.27 mmol), and $K_2CO_3$ (60.3 g, 436.29 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 4-(4-chlorophenyl)-2-phenyl-6-(4-(pyridin-3-yl)phenyl)pyrimidine (61.07 g, yield 72%) using column chromatography %) was obtained using column chromatography.

$^1$H-NMR: δ 9.24 (s, 1H), 8.70 (s, 1H), 7.57 (s, 1H), 8.34 (s, 1H), 8.42 (s, 1H), 8.30 (d, 2H), 7.25 (d, 2H), 8.36 (s, 1H), 7.50 (t, 3H), 7.97 (d, 2H), 7.60 (d, 2H)

[LCMS]: 419

[Preparation Example 9] Synthesis of 2-(4-chlorophenyl)-4-phenyl-6-(4-(pyridin-3-yl)phenyl)-1,3,5-triazine

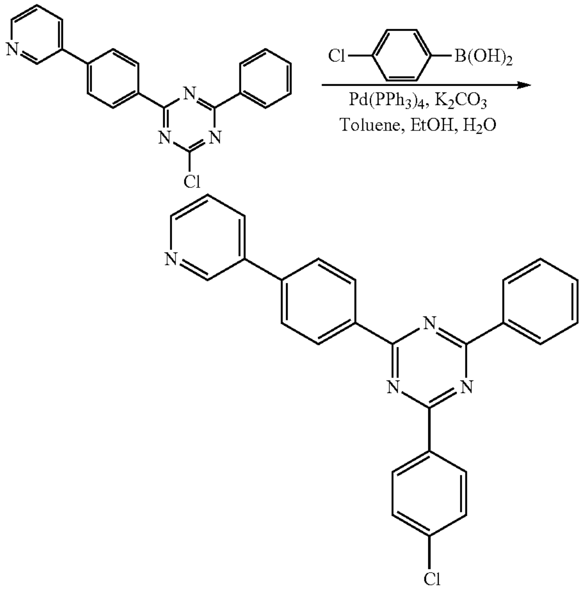

2-chloro-4-phenyl-6-(4-(pyridin-3-yl)phenyl)-1,3,5-triazine (50.0 g, 145.01 mmol), (4-chlorophenyl)boronic acid (22.68 g, 145.01 mmol), $Pd(PPh_3)_4$ (8.38 g, 7.25 mmol), and $K_2CO_3$ (60.13 g, 435.03 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 2-(4-chlorophenyl)-4-phenyl-6-(4-(pyridin-3-yl)phenyl)-1,3,5-triazine (61.04 g, yield 72%) was obtained using column chromatography.

$^1$H-NMR: δ 9.24 (s, 1H), 8.70 (s, 1H), 8.34 (s, 1H), 8.42 (s, 1H), 8.30 (d, 2H), 7.25 (d, 2H), 8.36 (s, 1H), 7.50 (t, 3H), 7.97 (d, 2H), 7.60 (d, 2H)

[LCMS]: 420

[Preparation Example 10] Synthesis of 4-(8-chlorodibenzo[b,d]furan-4-yl)-2,6-diphenylpyrimidine

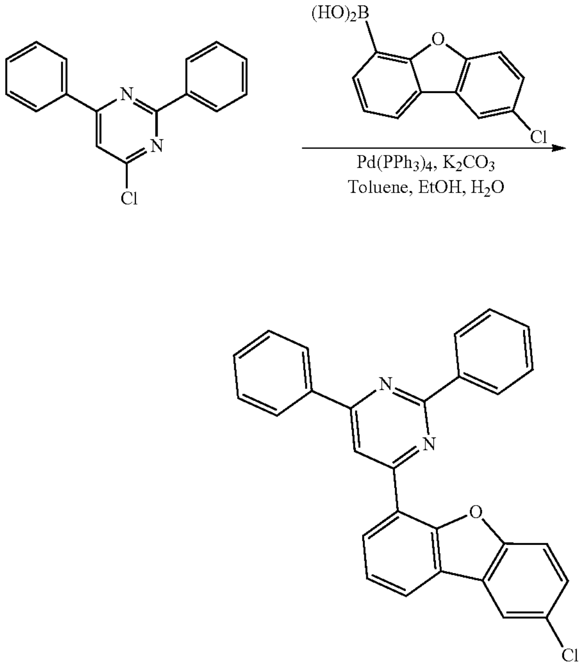

4-chloro-2,6-diphenylpyrimidine (50.0 g, 187.46 mmol), (8-chlorodibenzo[b,d]furan-4-yl)boronic acid (46.2 g, 187.46 mmol), $Pd(PPh_3)_4$ (10.83 g, 9.37 mmol), and $K_2CO_3$ (77.72 g, 562.37 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 4-(8-chlorodibenzo[b,d]furan-4-yl)-2,6-diphenylpyrimidine (61.04 g, yield 72%) was obtained using column chromatography.

$^1$H-NMR: δ 7.54 (s, 1H), 7.50 (s, 1H), 8.08 (s, 1H), 8.23 (s, 1H), 7.74 (s, 1H), 7.20 (s, 1H), 7.51 (s, 1H), 8.35 (s, 1H), 7.94 (d, 2H), 8.35 (s, 1H), 7.50 (t, 3H), 7.55 (d, 2H), 7.49 (s, 1H)

[LCMS]: 432

[Preparation Example 11] Synthesis of 2-(8-chlorodibenzo[b,d]furan-4-yl)-4,6-diphenyl-1,3,5-triazine

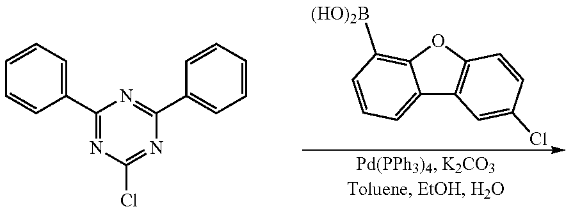

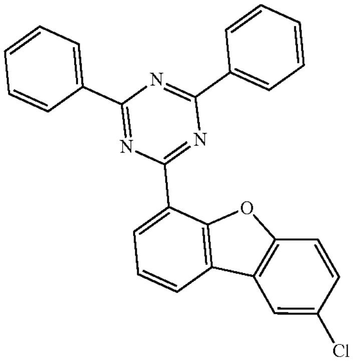

2-chloro-4,6-diphenyl-1,3,5-triazine (50.0 g, 186.76 mmol), (8-chlorodibenzo[b,d]furan-4-yl)boronic acid (46.03 g, 186.76 mmol), $Pd(PPh_3)_4$ (10.79 g, 9.34 mmol), and $K_2CO_3$ (77.44 g, 560.29 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 2-(8-chlorodibenzo[b,d]furan-4-yl)-4,6-diphenyl-1,3,5-triazine (61.04 g, yield 72%) was obtained using column chromatography.

$^1$H-NMR: δ 7.54 (s, 1H), 8.08 (s, 1H), 8.23 (s, 1H), 7.74 (s, 1H), 7.20 (s, 1H), 7.51 (s, 1H), 8.35 (s, 1H), 7.94 (d, 2H), 8.35 (s, 1H), 7.50 (t, 3H), 7.55 (d, 2H), 7.49 (s, 1H)

[LCMS]: 433

[Preparation Example 12] Synthesis of 4-(8-chlorodibenzo[b,d]furan-4-yl)-6-(dibenzo[b,d]furan-3-yl)-2-phenylpyrimidine

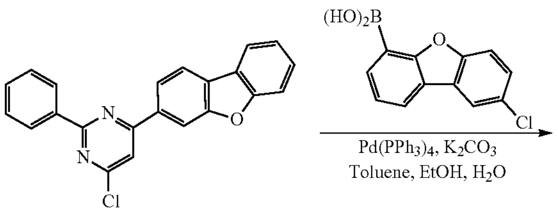

-continued

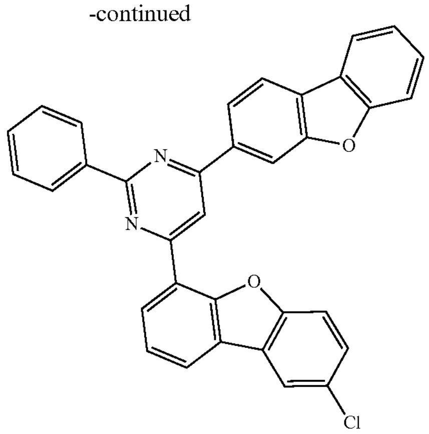

4-chloro-6-(dibenzo[b,d]furan-3-yl)-2-phenylpyrimidine (50.0 g, 140.13 mmol), (8-chlorodibenzo[b,d]furan-4-yl) boronic acid (34.54 g, 140.13 mmol), $Pd(PPh_3)_4$ (8.1 g, 7.01 mmol), and $K_2CO_3$ (58.1 g, 420.39 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 4-(8-chlorodibenzo[b,d]furan-4-yl)-6-(dibenzo[b,d]furan-3-yl)-2-phenylpyrimidine (73.29 g, yield 72%) was obtained using column chromatography.

$^1$H-NMR: δ 7.54 (s, 1H), 8.08 (s, 1H), 8.23 (s, 1H), 7.31 (s, 1H), 7.98 (d, 2H), 7.74 (s, 1H), 7.20 (s, 1H), 7.51 (s, 1H), 8.35 (s, 1H), 7.94 (d, 2H), 8.35 (s, 1H), 7.50 (t, 3H), 7.55 (d, 2H), 7.49 (s, 1H)

[LCMS]: 522

[Preparation Example 13] Synthesis of 2-(8-chlorodibenzo[b,d]furan-4-yl)-4-(dibenzo[b,d]furan-3-yl)-6-phenyl-1,3,5-triazine

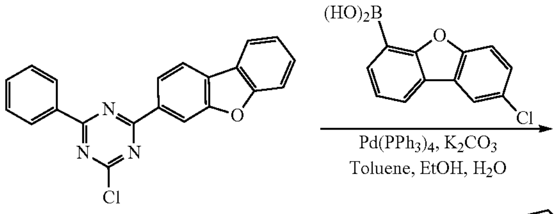

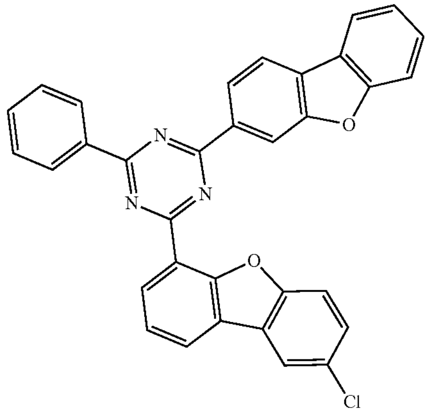

2-chloro-4-(dibenzo[b,d]furan-3-yl)-6-phenyl-1,3,5-triazine (50.0 g, 139.74 mmol), (8-chlorodibenzo[b,d]furan-4-yl)boronic acid (34.44 g, 139.74 mmol), $Pd(PPh_3)_4$ (8.07 g, 6.99 mmol), and $K_2CO_3$ (57.94 g, 419.23 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 2-(8-chlorodibenzo[b,d]furan-4-yl)-4-(dibenzo[b,d]furan-3-yl)-6-phenyl-1,3,5-triazine (73.22 g, yield 72%) was obtained using column chromatography.

$^1$H-NMR: δ 7.54 (s, 1H), 8.08 (s, 1H), 8.23 (s, 1H), 7.31 (s, 1H), 7.98 (d, 2H), 7.74 (s, 1H), 7.20 (s, 1H), 7.51 (s, 1H), 8.35 (s, 1H), 7.94 (d, 2H), 7.50 (t, 3H), 7.55 (d, 2H), 7.49 (s, 1H)

[LCMS]: 523

[Preparation Example 14] Synthesis of 2-([1,1'-biphenyl]-4-yl)-4-(4-chlorophenyl)-6-(dibenzo[b,d]furan-3-yl)-1,3,5-triazine

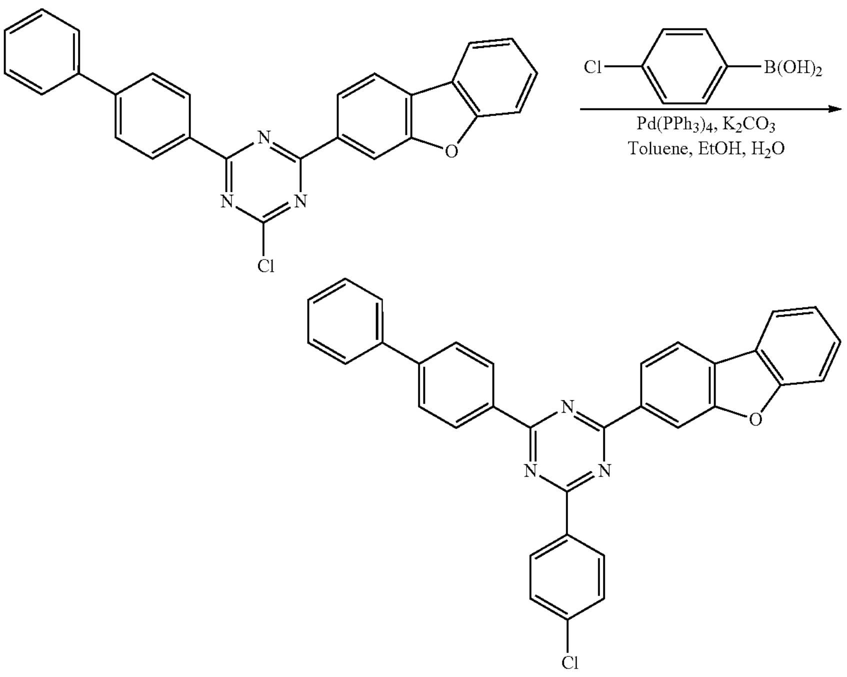

2-([1,1'-biphenyl]-4-yl)-4-chloro-6-(dibenzo[b,d]furan-3-yl)-1,3,5-triazine (50.0 g, 115.23 mmol), (4-chlorophenyl) boronic acid (18.02 g, 115.23 mmol), $Pd(PPh_3)_4$ (6.66 g, 5.76 mmol), and $K_2CO_3$ (47.78 g, 345.7 mmol) were added to toluene, ethanol, and $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound 2-([1,1'-biphenyl]-4-yl)-4-(4-chlorophenyl)-6-(dibenzo[b,d]furan-3-yl)-1,3,5-triazine (42.31 g, yield 72%) was obtained using column chromatography.

$^1$H-NMR: δ 7.76 (s, 1H), 7.54 (s, 1H), 8.03 (s, 1H), 7.98 (s, 1H), 7.82 (s, 1H), 7.39 (s, 1H), 7.31 (s, 1H), 7.96 (s, 1H), 7.25 (d, 2H), 7.75 (d, 2H), 7.96 (s, 1H), 7.49 (d, 2H), 7.41 (s, 1H), 8.25 (d, 2H), 7.51 (d, 2H)

[LCMS]: 509

Synthesis Examples 1 to 32

[Synthesis Example 1] Synthesis of compound A-1

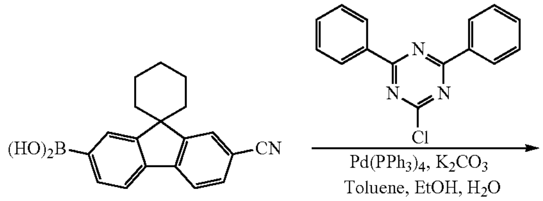

-continued

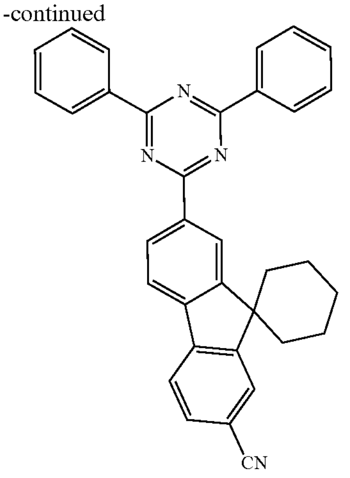

A-1

(2'-cyanospiro[cyclohexane-1,9'-fluoren]-7'-yl)boronic acid (10 g, 32.98 mmol), 2-chloro-4,6-diphenyl-1,3,5-triazine (8.83 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-1 (11.65 g, yield 72%) was obtained using column chromatography.

[LCMS]: 490

[Synthesis Example 2] Synthesis of Compound A-2

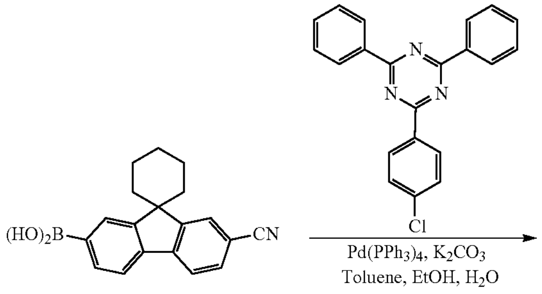

-continued

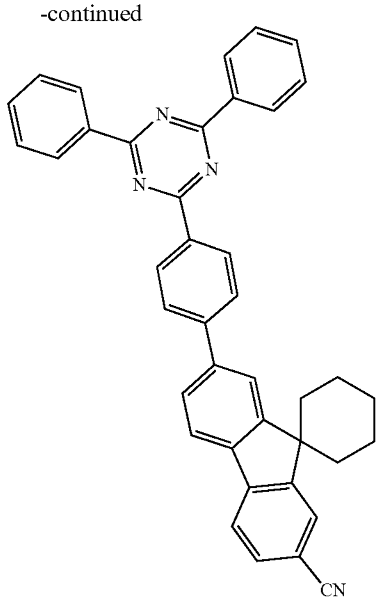

A-2

(2'-cyanospiro[cyclohexane-1,9'-fluoren]-7'-yl)boronic acid (10 g, 32.98 mmol), 2-chloro-4,6-diphenyl-1,3,5-triazine (11.34 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-2 (13.22 g, yield 72%) was obtained using column chromatography.

[LCMS]: 566

[Synthesis Example 3] Synthesis of Compound A-3

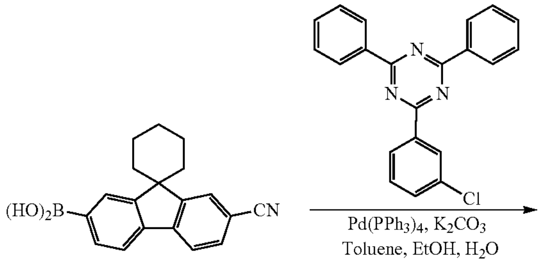

-continued

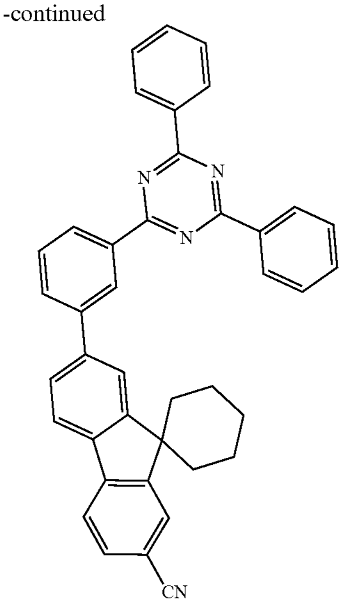

A-3

(2'-cyanospiro[cyclohexane-1,9'-fluoren]-7'-yl)boronic acid (10 g, 32.98 mmol), 2-(3-chlorophenyl)-4,6-diphenyl-1,3,5-triazine (11.34 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-3 (13.22 g, yield 72%) was obtained using column chromatography.

[LCMS]: 566

[Synthesis Example 4] Synthesis of Compound A-5

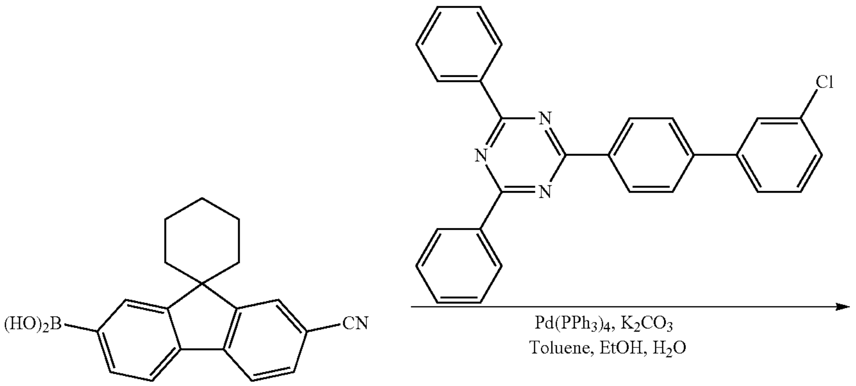

-continued

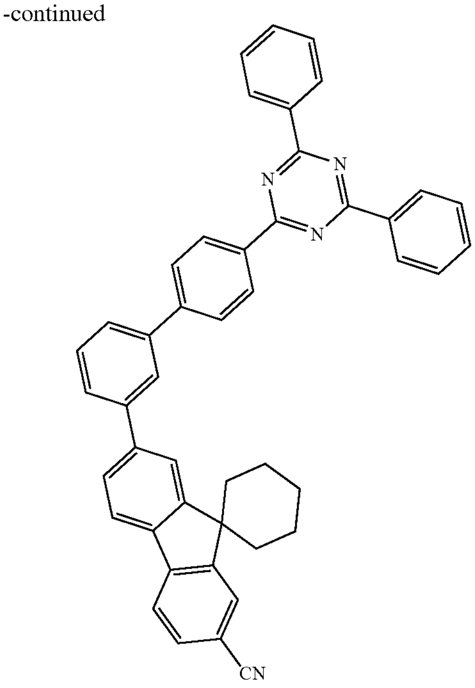

A-5

(2'-cyanospiro[cyclohexane-1,9'-fluoren]-7'-yl)boronic acid (10 g, 32.98 mmol), 2-(3'-chloro-[1,1'-biphenyl]-4-yl)-4,6-diphenyl-1,3,5-triazine (13.85 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-5 (15.27 g, yield 72%) was obtained using column chromatography.

[LCMS]: 642

[Synthesis Example 5] Synthesis of Compound A-17

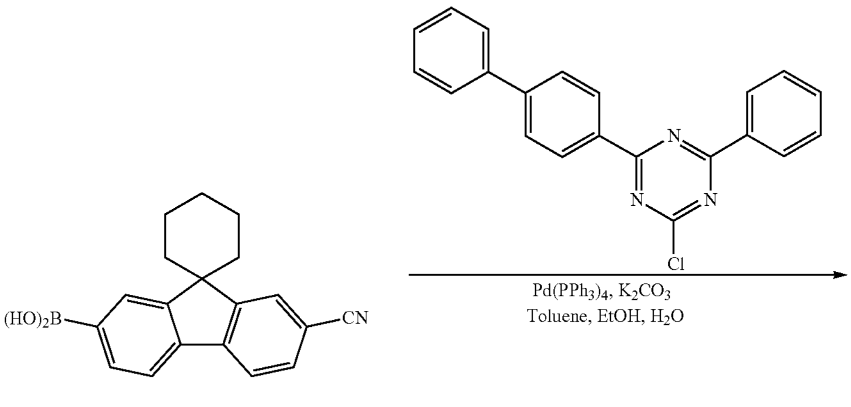

-continued

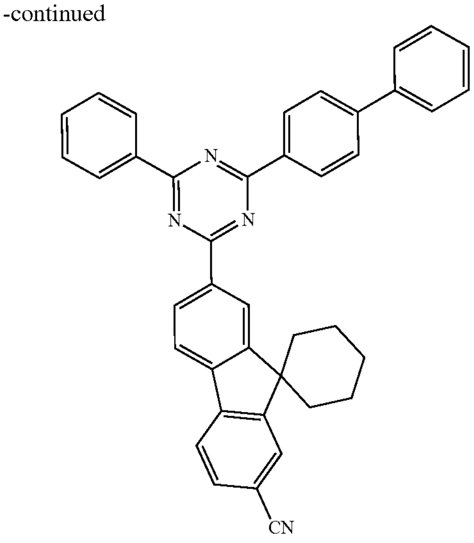

A-17

(2'-cyanospiro[cyclohexane-1,9'-fluoren]-7'-yl)boronic acid (10 g, 32.98 mmol), 2-([1,1'-biphenyl]-4-yl)-4-chloro-6-phenyl-1,3,5-triazine (11.34 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-17 (13.44 g, yield 72%) was obtained using column chromatography.

[LCMS]: 566

[Synthesis Example 6] Synthesis of Compound A-18

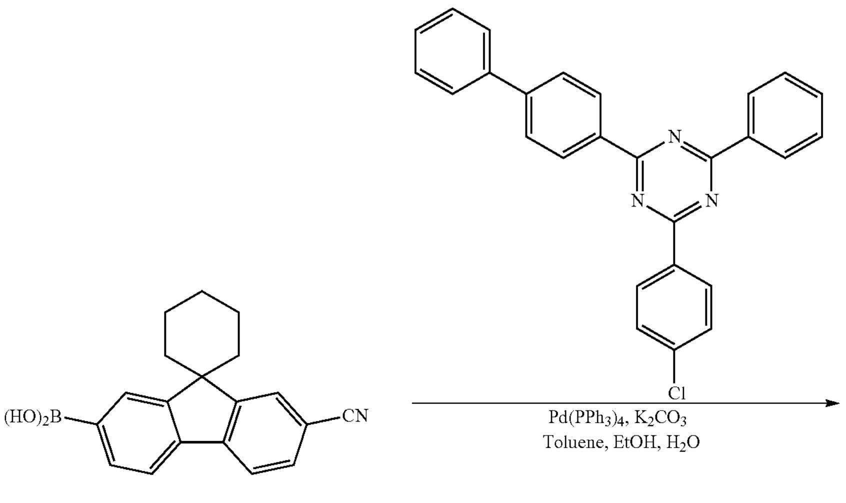

-continued

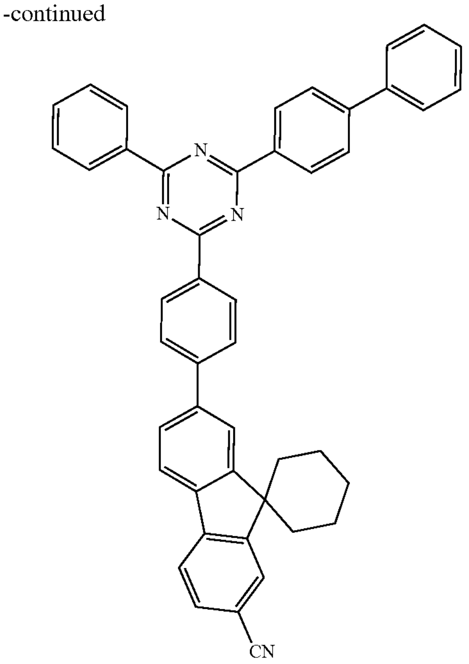

A-18

(2'-cyanospiro[cyclohexane-1,9'-fluoren]-7'-yl)boronic acid (10 g, 32.98 mmol), 2-([1,1'-biphenyl]-4-yl)-4-(4-chlorophenyl)-6-phenyl-1,3,5-triazine (13.85 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-18 (15.27 g, yield 72%) was obtained using column chromatography.

[LCMS]: 642

[Synthesis Example 7] Synthesis of Compound A-19

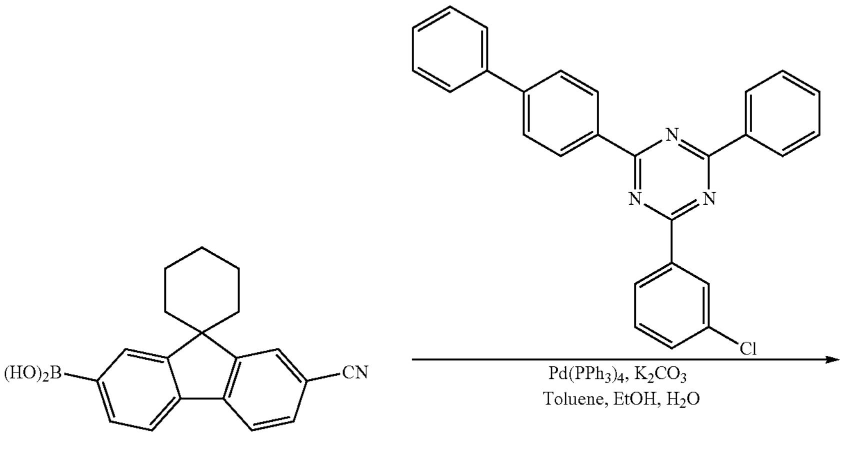

-continued

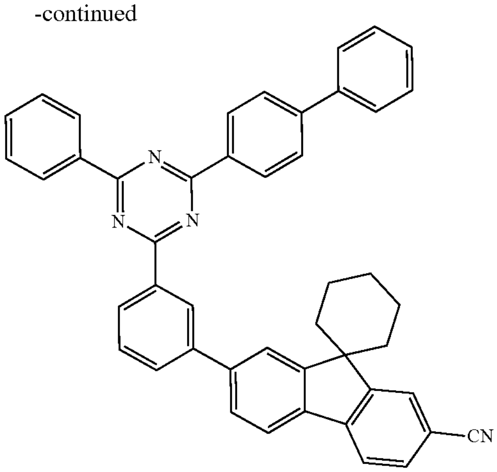

A-19

(2'-cyanospiro[cyclohexane-1,9'-fluoren]-7'-yl)boronic acid (10 g, 32.98 mmol), 2-([1,1'-biphenyl]-4-yl)-4-(3-chlorophenyl)-6-phenyl-1,3,5-triazine (13.85 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-19 (15.27 g, yield 72%) was obtained using column chromatography.

[LCMS]: 642

[Synthesis Example 8] Synthesis of Compound A-22

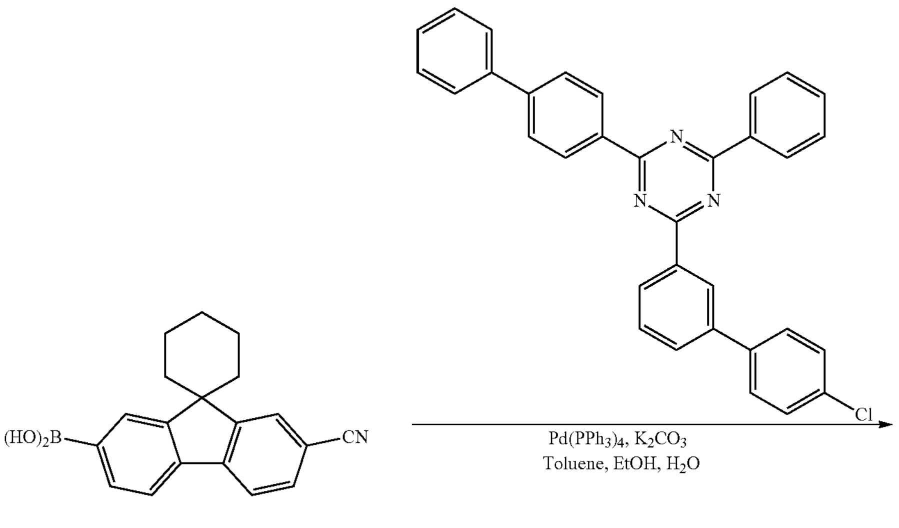

-continued

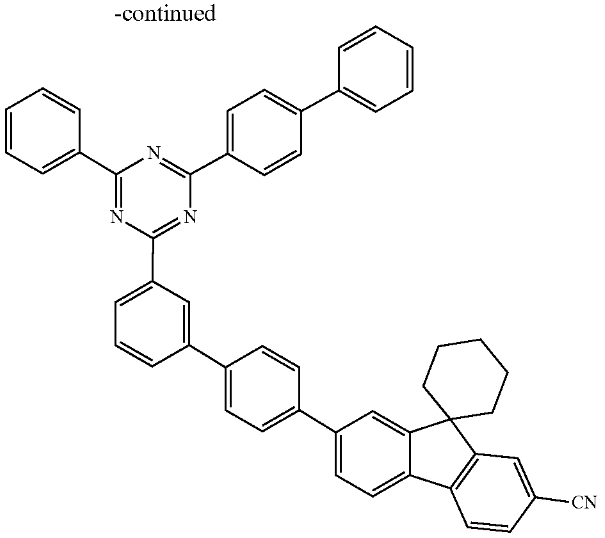

A-22

(2'-cyanospiro[cyclohexane-1,9'-fluoren]-7'-yl)boronic acid (10 g, 32.98 mmol), 2-([1,1'-biphenyl]-4-yl)-4-(4'-chloro-[1,1'-biphenyl]-3-yl)-6-phenyl-1,3,5-triazine (16.36 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-22 (17.07 g, yield 72%) was obtained using column chromatography.

[LCMS]: 718

[Synthesis Example 9] Synthesis of Compound A-33

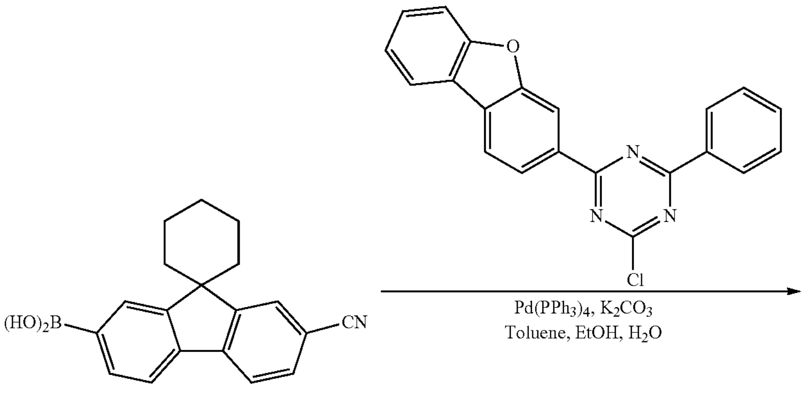

-continued

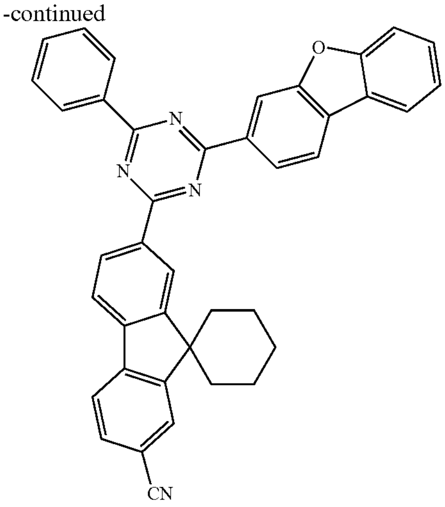

A-33

(2'-cyanospiro[cyclohexane-1,9'-fluoren]-7'-yl)boronic acid (10 g, 32.98 mmol), the target compound of Preparation Example 1 (11.8 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-33 (13.79 g, yield 72%) was obtained using column chromatography.

[LCMS]: 580

[Synthesis Example 10] Synthesis of Compound A-35

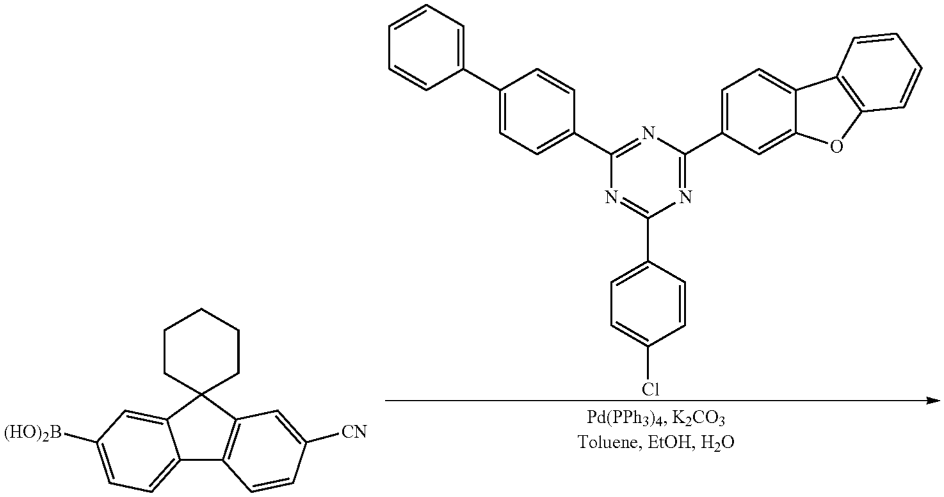

-continued

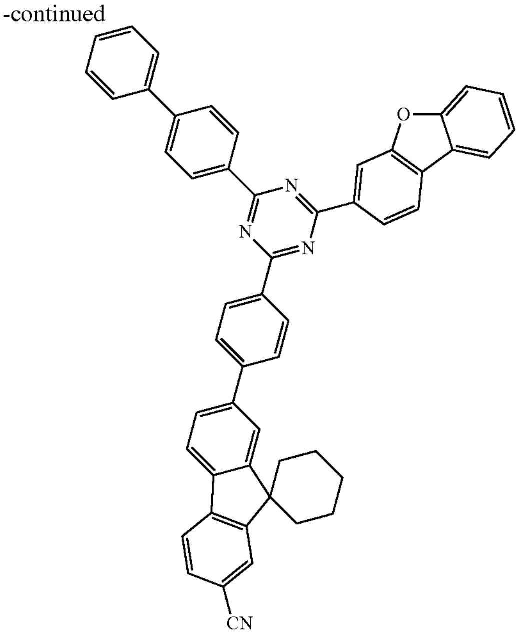

A-35

(2'-cyanospiro[cyclohexane-1,9'-fluoren]-7'-yl)boronic acid (10 g, 32.98 mmol), the target compound of Preparation Example 14 (16.82 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-35 (17.41 g, yield 72%) was obtained using column chromatography.

[LCMS]: 732

[Synthesis Example 11] Synthesis of Compound A-44

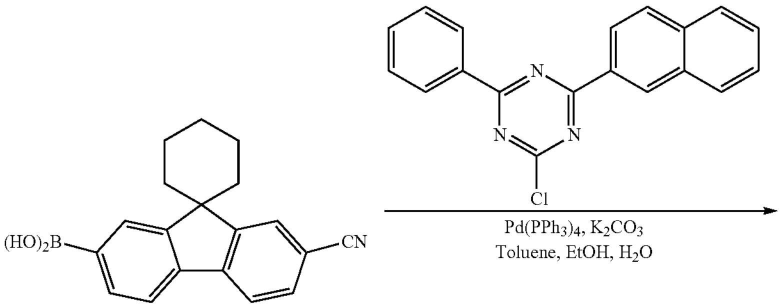

-continued

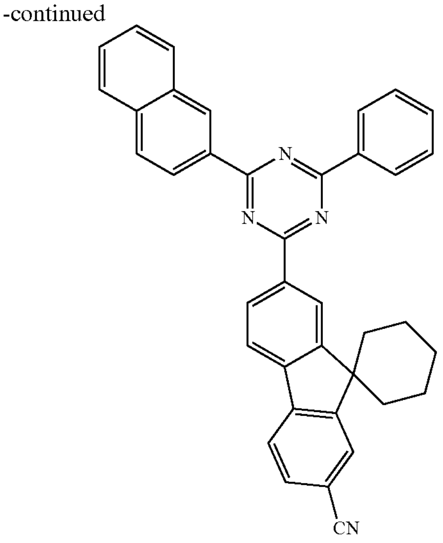

A-44

(2'-cyanospiro[cyclohexane-1,9'-fluoren]-7'-yl)boronic acid (10 g, 32.98 mmol), 2-chloro-4-(naphthalen-2-yl)-6-phenyl-1,3,5-triazine (10.48 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-44 (12.84 g, yield 72%) was obtained using column chromatography.

[LCMS]: 540

[Synthesis Example 12] Synthesis of Compound A-46

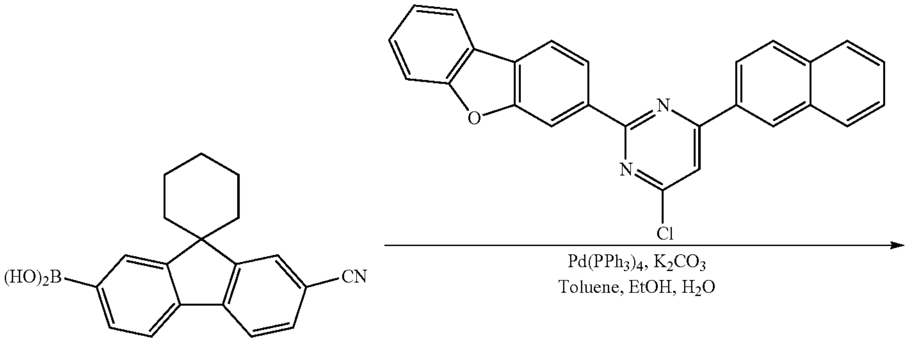

-continued

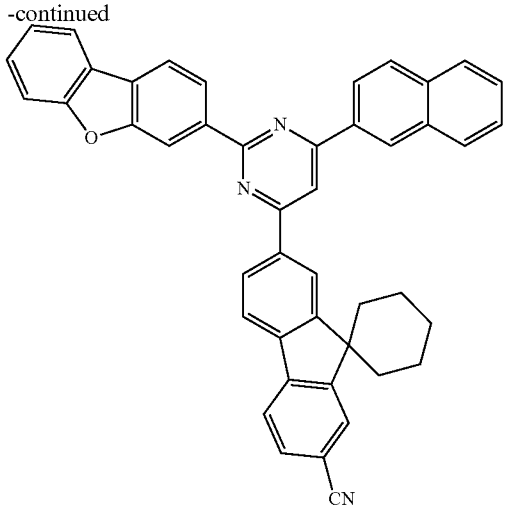

A-46

(2'-cyanospiro[cyclohexane-1,9'-fluoren]-7'-yl)boronic acid (10 g, 32.98 mmol), the target compound of Preparation Example 3 (13.42 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-46 (14.96 g, yield 72%) was obtained using column chromatography.

[LCMS]: 629

[Synthesis Example 13] Synthesis of Compound A-57

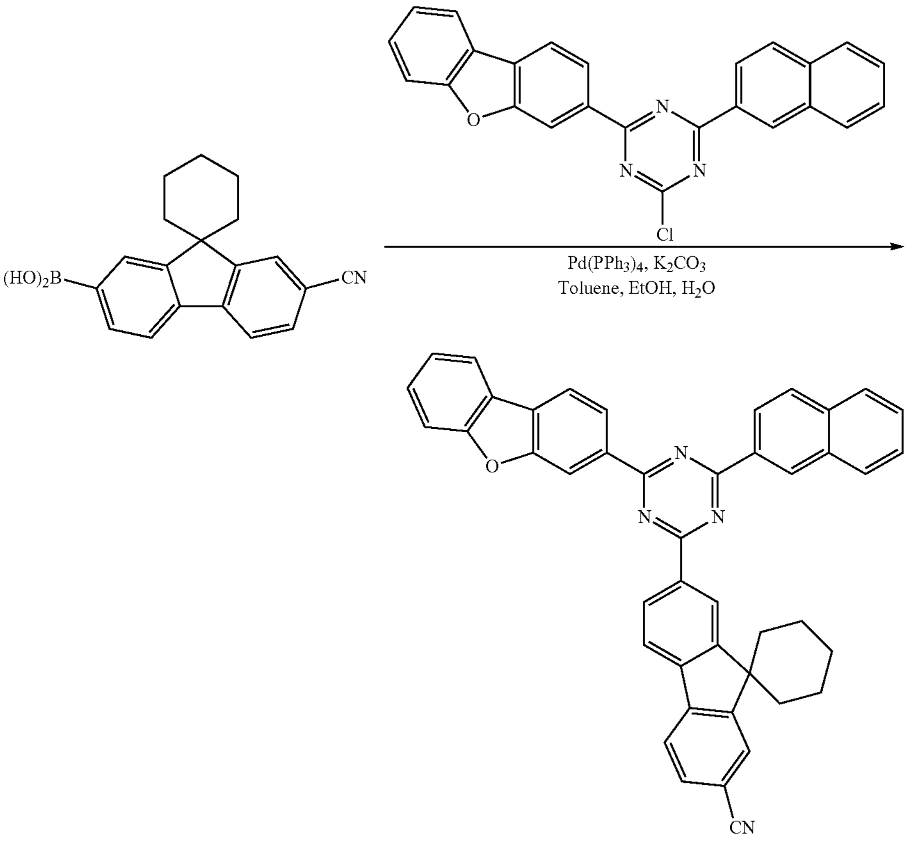

A-57

(2'-cyanospiro[cyclohexane-1,9'-fluoren]-7'-yl)boronic acid (10 g, 32.98 mmol), the target compound of Preparation Example 4 (13.45 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-57 (14.98 g, yield 72%) was obtained using column chromatography.

[LCMS]: 630

[Synthesis Example 14] Synthesis of Compound A-51

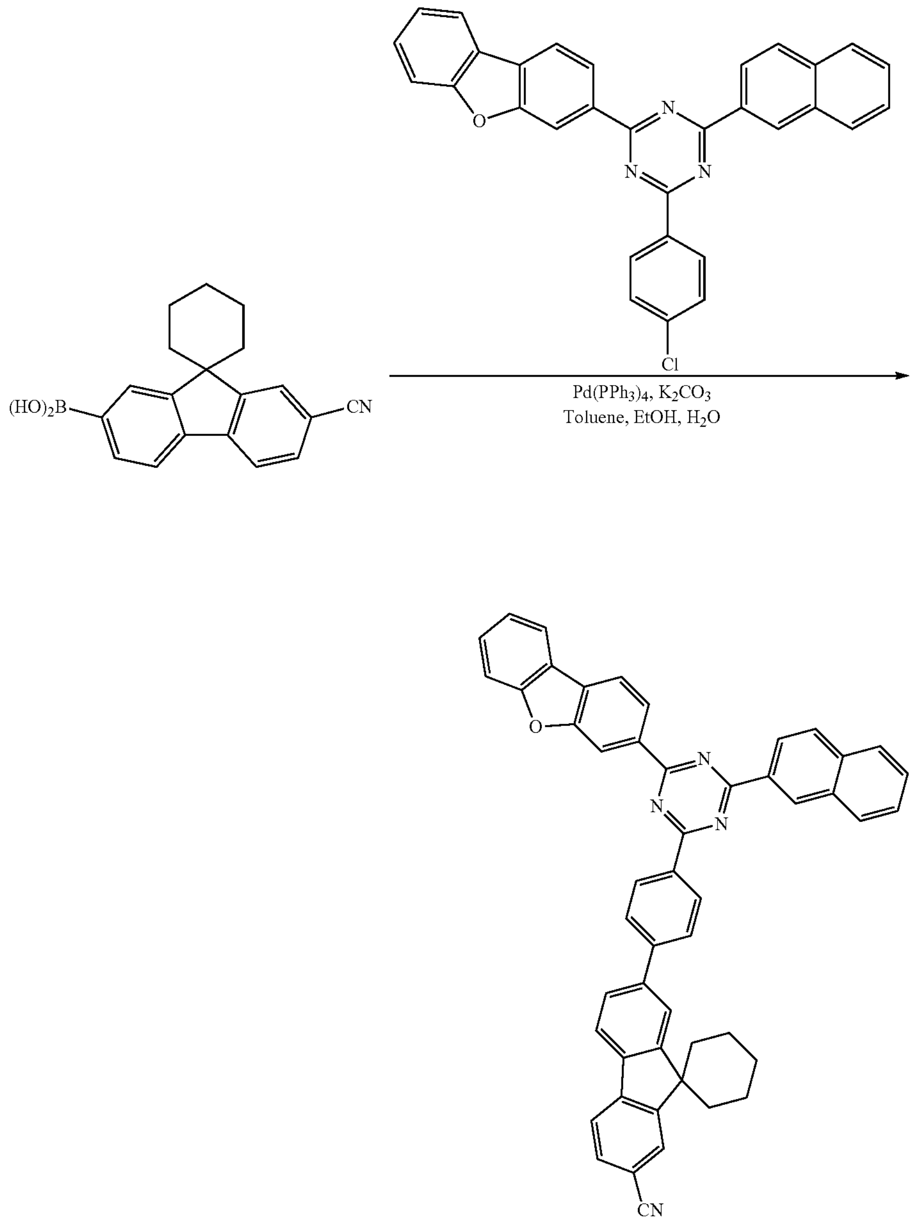

A-51

(2'-cyanospiro[cyclohexane-1,9'-fluoren]-7'-yl)boronic acid (10 g, 32.98 mmol), the target compound of Preparation Example 5 (15.96 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound A-51 (16.79 g, yield 72%) was obtained using column chromatography.

[LCMS]: 706

[Synthesis Example 15] Synthesis of Compound B-1

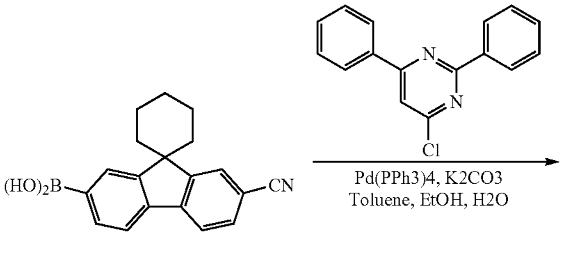

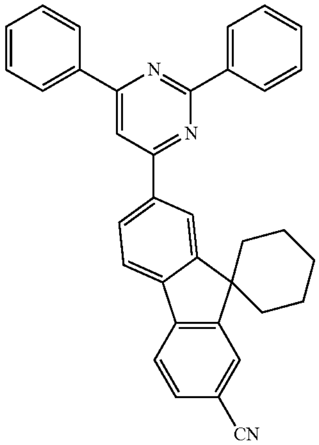

B-1

(2'-cyanospiro[cyclohexane-1,9'-fluoren]-7'-yl)boronic acid (10 g, 32.98 mmol), 4-chloro-2,6-diphenylpyrimidine (8.8 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-1 (11.63 g, yield 72%) was obtained using column chromatography.

[LCMS]: 489

[Synthesis Example 16] Synthesis of Compound B-2

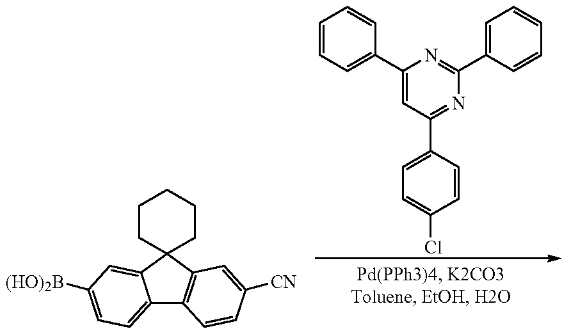

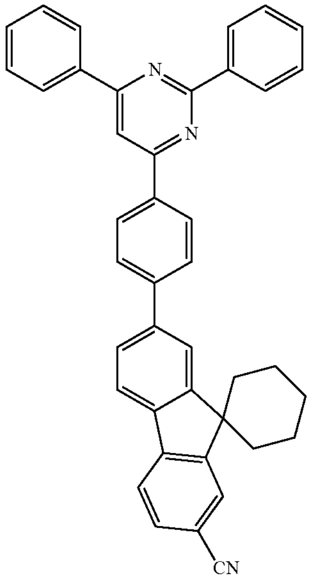

B-2

(2'-cyanospiro[cyclohexane-1,9'-fluoren]-7'-yl)boronic acid (10 g, 32.98 mmol), 4-(4-chlorophenyl)-2,6-diphenylpyrimidine (11.31 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-2 (13.44 g, yield 72%) was obtained using column chromatography.

[LCMS]: 565

[Synthesis Example 17] Synthesis of Compound B-17
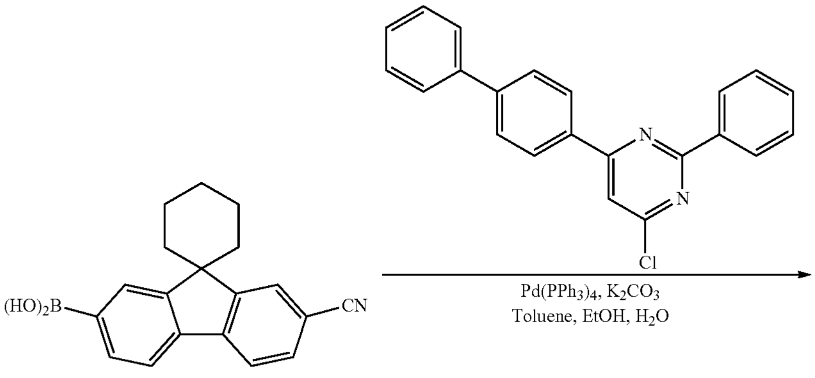
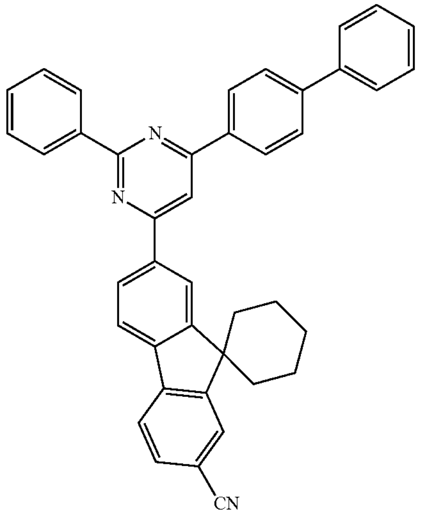
B-17

(2'-cyanospiro[cyclohexane-1,9'-fluoren]-7'-yl)boronic acid (10 g, 32.98 mmol), 4-([1,1'-biphenyl]-4-yl)-6-chloro-2-phenylpyrimidine (11.28 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-17 (13.41 g, yield 72%) was obtained using column chromatography.

[LCMS]: 564

[Synthesis Example 18] Synthesis of Compound B-18

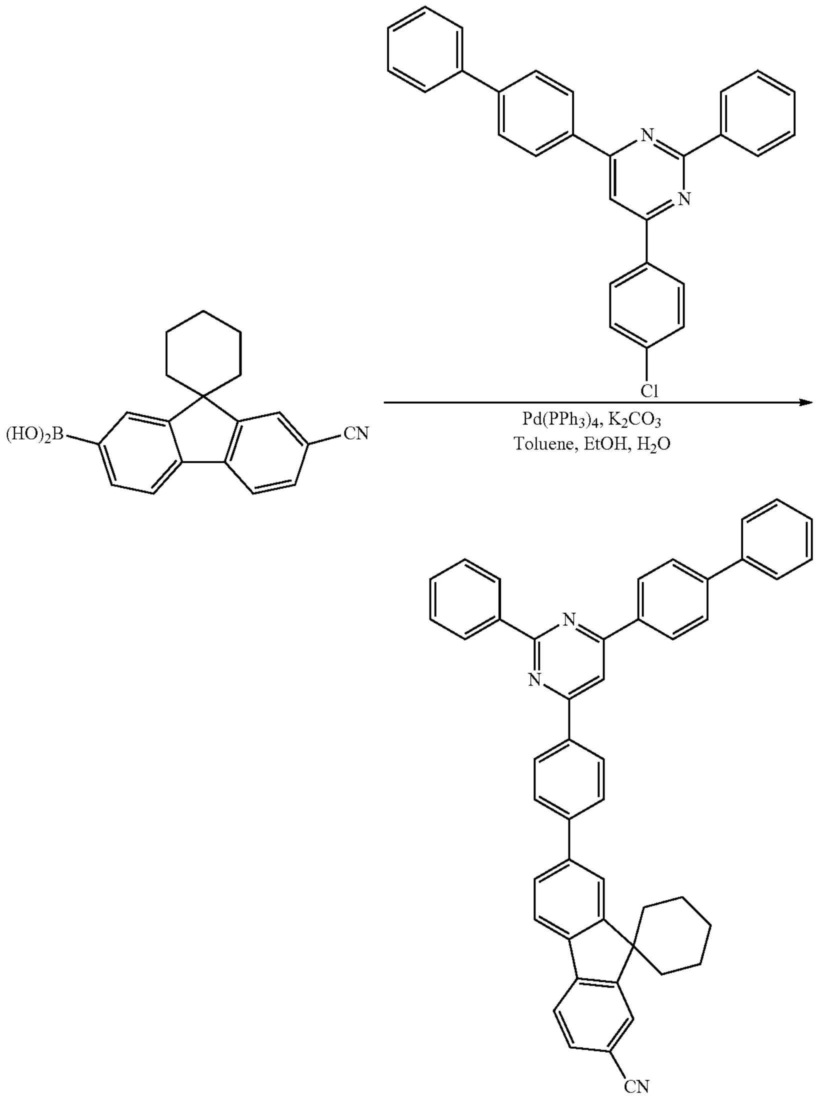

B-18

(2'-cyanospiro[cyclohexane-1,9'-fluoren]-7'-yl)boronic acid (10 g, 32.98 mmol), 4-([1,1'-biphenyl]-4-yl)-6-(4-chlorophenyl)-2-phenylpyrimidine (13.82 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-18 (15.24 g, yield 72%) was obtained using column chromatography.

[LCMS]: 641

[Synthesis Example 19] Synthesis of Compound B-34
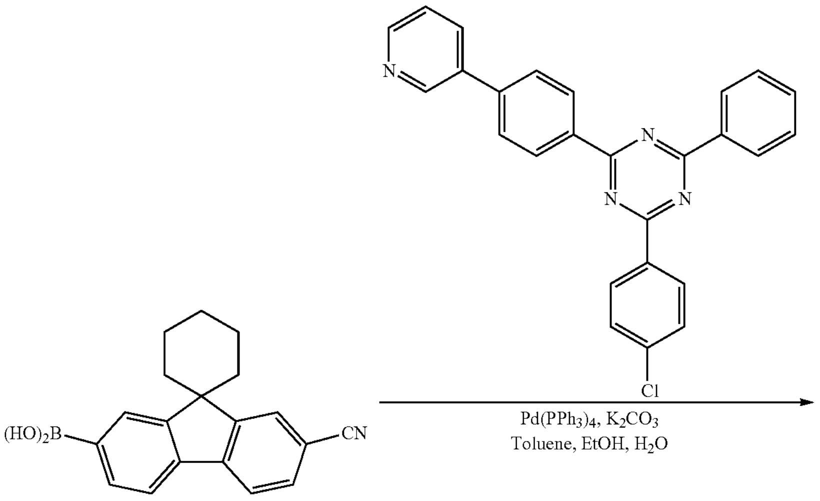
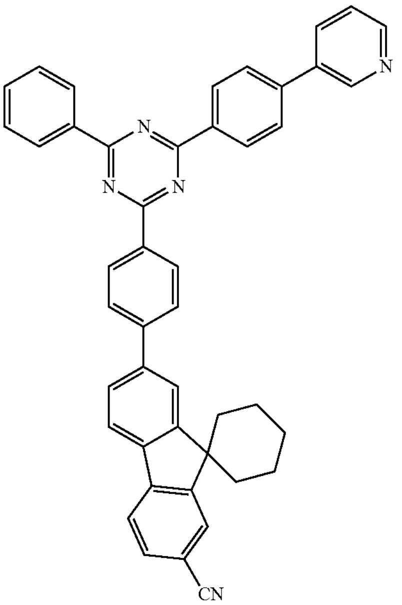
B-34

(2'-cyanospiro[cyclohexane-1,9'-fluoren]-7'-yl)boronic acid (10 g, 32.98 mmol), the target compound of Preparation Example 9 (13.88 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-34 (15.29 g, yield 72%) was obtained using column chromatography.

[LCMS]: 643

[Synthesis Example 20] Synthesis of Compound B-33

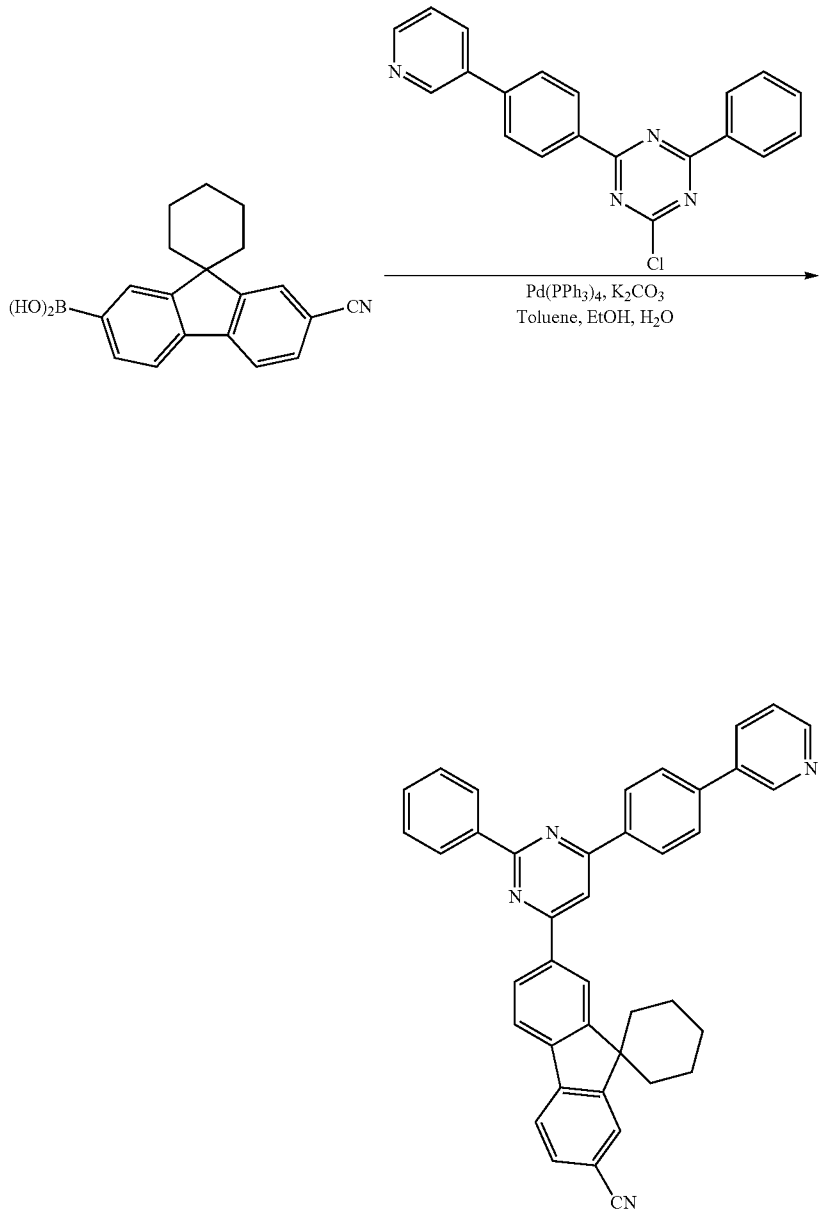

B-33

(2'-cyanospiro[cyclohexane-1,9'-fluoren]-7'-yl)boronic acid (10 g, 32.98 mmol), the target compound of Preparation Example 7 (11.37 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-33 (13.48 g, yield 72%) was obtained using column chromatography.

[LCMS]: 567

[Synthesis Example 21] Synthesis of Compound B-35

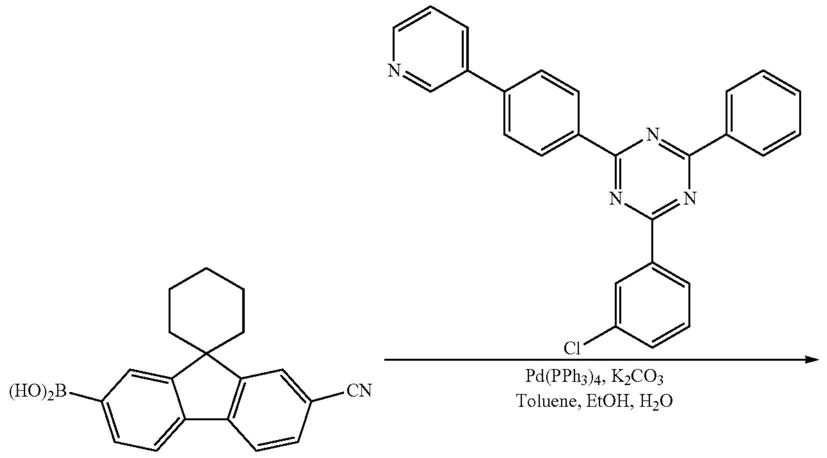

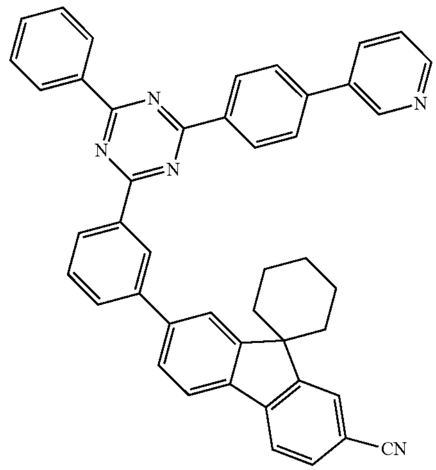

B-35

(2'-cyanospiro[cyclohexane-1,9'-fluoren]-7'-yl)boronic acid (10 g, 32.98 mmol), 2-(3-chlorophenyl)-4-phenyl-6-(4-(pyridin-3-yl)phenyl)-1,3,5-triazine (13.85 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-35 (15.25 g, yield 72%) was obtained using column chromatography.

[LCMS]: 642

[Synthesis Example 22] Synthesis of Compound B-49

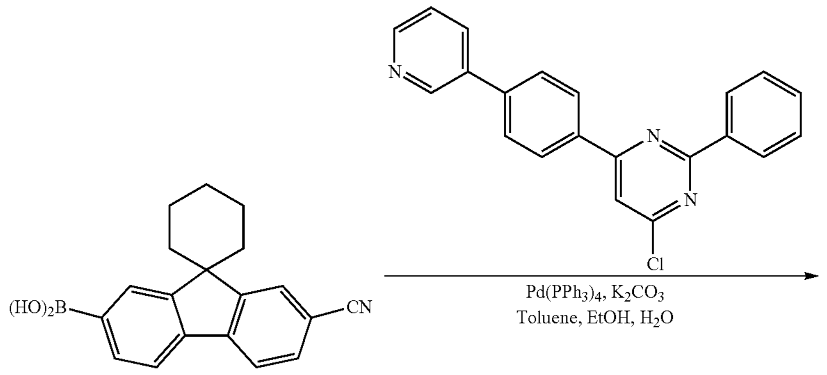

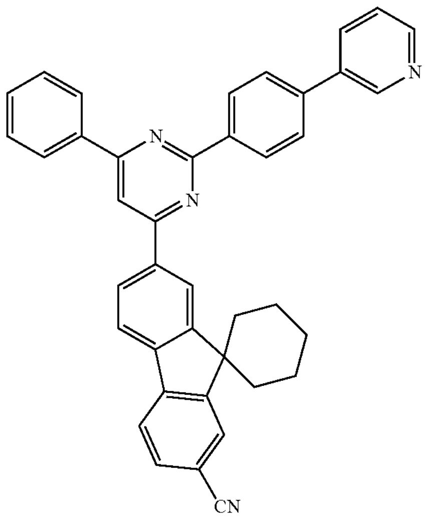

B-49

(2'-cyanospiro[cyclohexane-1,9'-fluoren]-7'-yl)boronic acid (10 g, 32.98 mmol), the target compound of Preparation Example 6 (11.31 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-49 (13.44 g, yield 72%) was obtained using column chromatography.

[LCMS]: 566

[Synthesis Example 23] Synthesis of Compound B-50

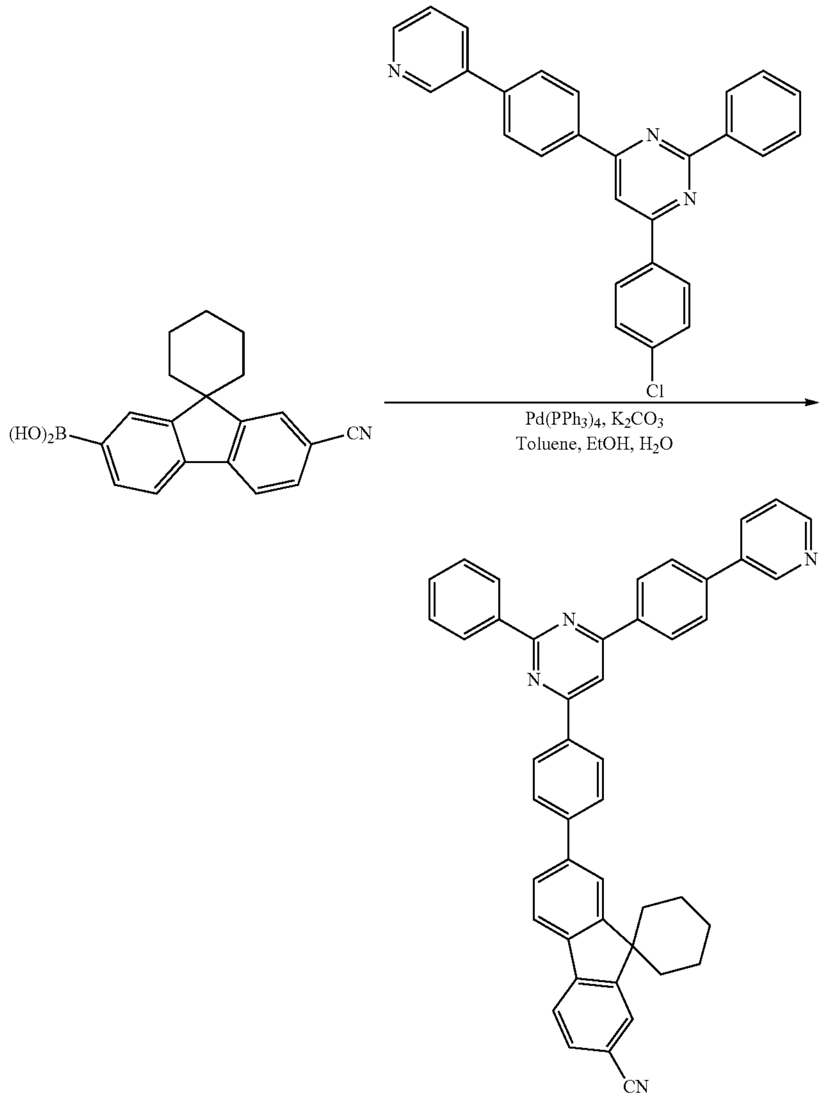

B-50

(2'-cyanospiro[cyclohexane-1,9'-fluoren]-7'-yl)boronic acid (10 g, 32.98 mmol), the target compound of Preparation Example 8 (13.82 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-50 (15.25 g, yield 72%) was obtained using column chromatography.

[LCMS]: 642

[Synthesis Example 24] Synthesis of Compound B-67
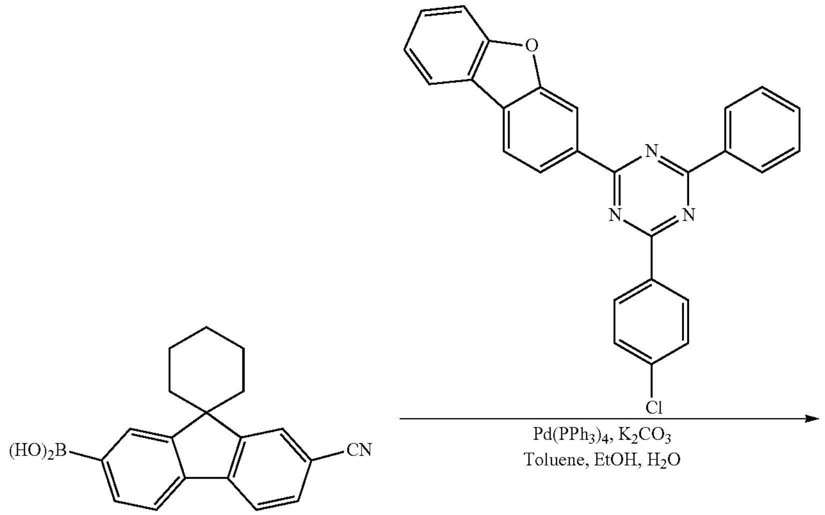
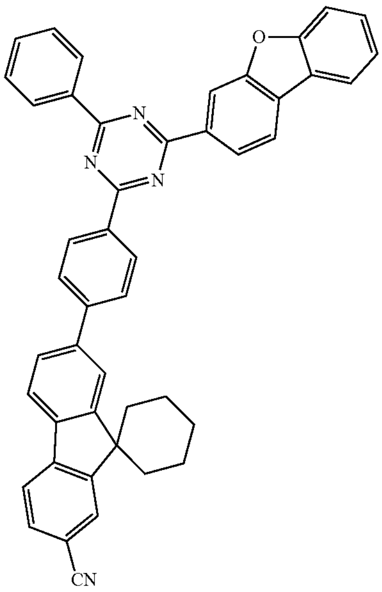
B-67

(2'-cyanospiro[cyclohexane-1,9'-fluoren]-7'-yl)boronic acid (10 g, 32.98 mmol), 2-(4-chlorophenyl)-4-(dibenzo[b, d]furan-3-yl)-6-phenyl-1,3,5-triazine (14.31 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-67 (15.60 g, yield 72%) was obtained using column chromatography.

[LCMS]: 656

[Synthesis Example 25] Synthesis of Compound B-82

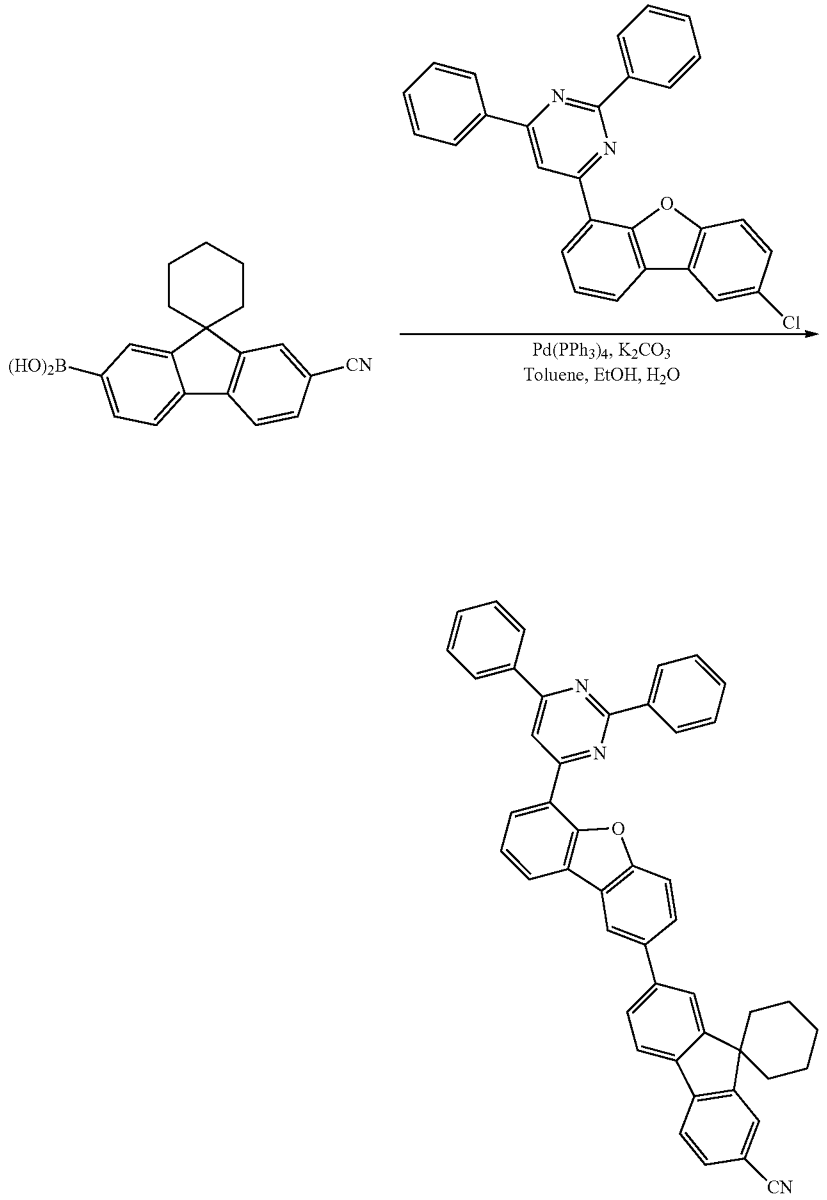

B-82

(2'-cyanospiro[cyclohexane-1,9'-fluoren]-7'-yl)boronic acid (10 g, 32.98 mmol), the target compound of Preparation Example 10 (14.28 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-82 (15.57 g, yield 72%) was obtained using column chromatography.

[LCMS]: 655

[Synthesis Example 26] Synthesis of Compound B-83

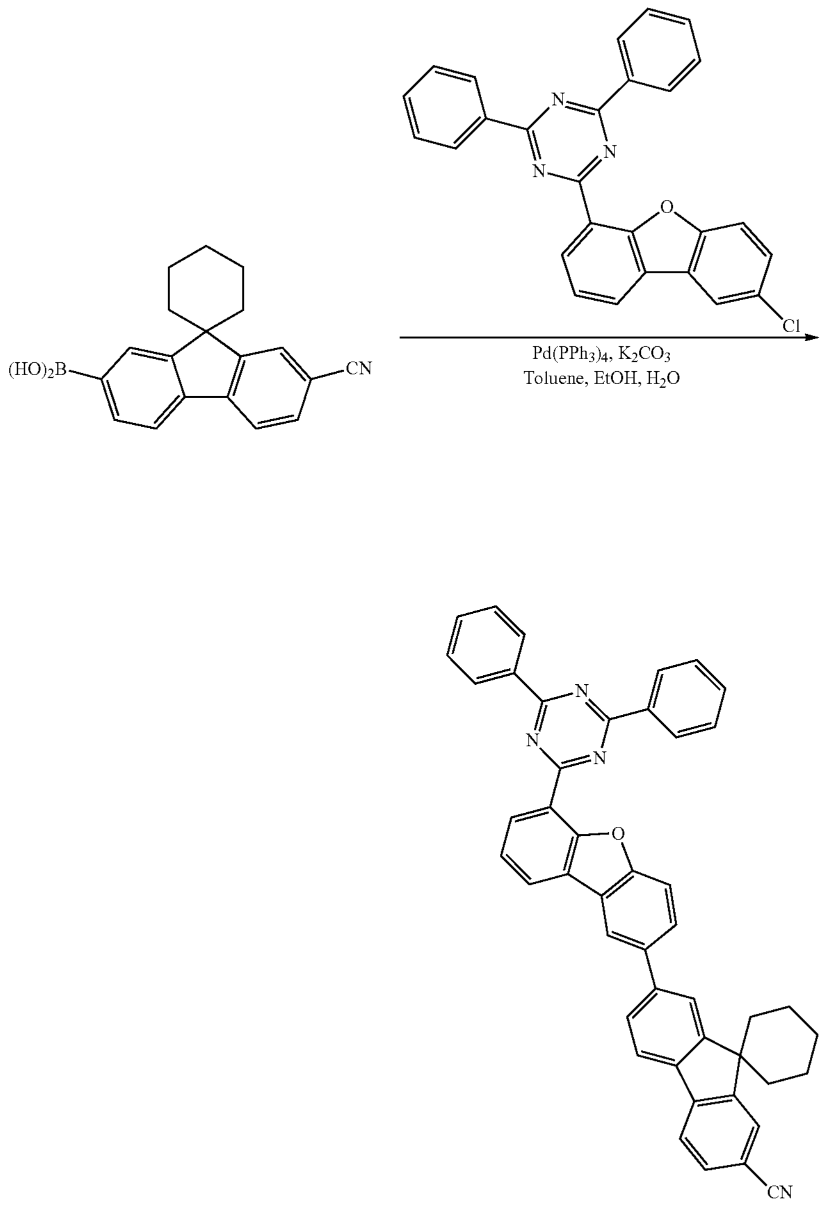

B-83

(2'-cyanospiro[cyclohexane-1,9'-fluoren]-7'-yl)boronic acid (10 g, 32.98 mmol), the target compound of Preparation Example 11 (14.31 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-83 (15.57 g, yield 72%) was obtained using column chromatography.

[LCMS]: 656

[Synthesis Example 27] Synthesis of Compound B-88

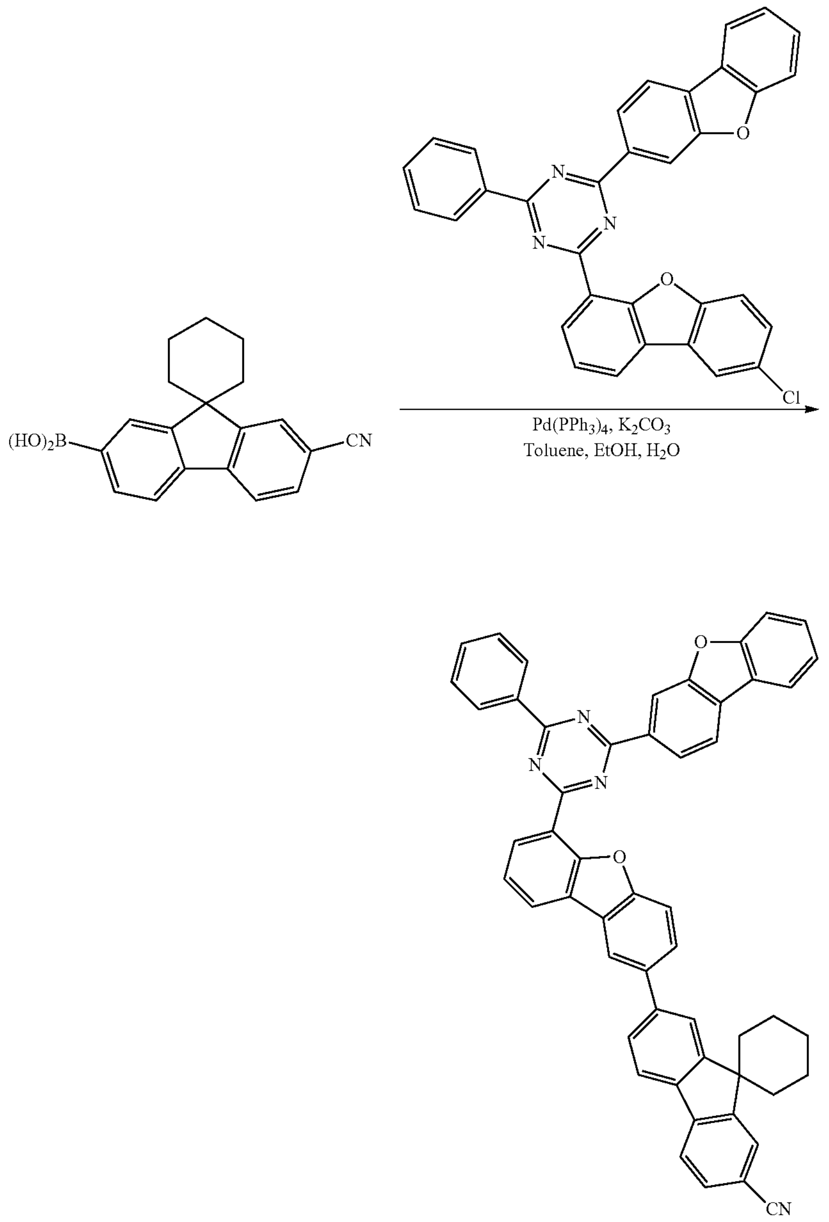

B-88

(2'-cyanospiro[cyclohexane-1,9'-fluoren]-7'-yl)boronic acid (10 g, 32.98 mmol), the target compound of Preparation Example 13 (17.28 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-88 (17.74 g, yield 72%) was obtained using column chromatography.

[LCMS]: 746

[Synthesis Example 28] Synthesis of Compound B-89

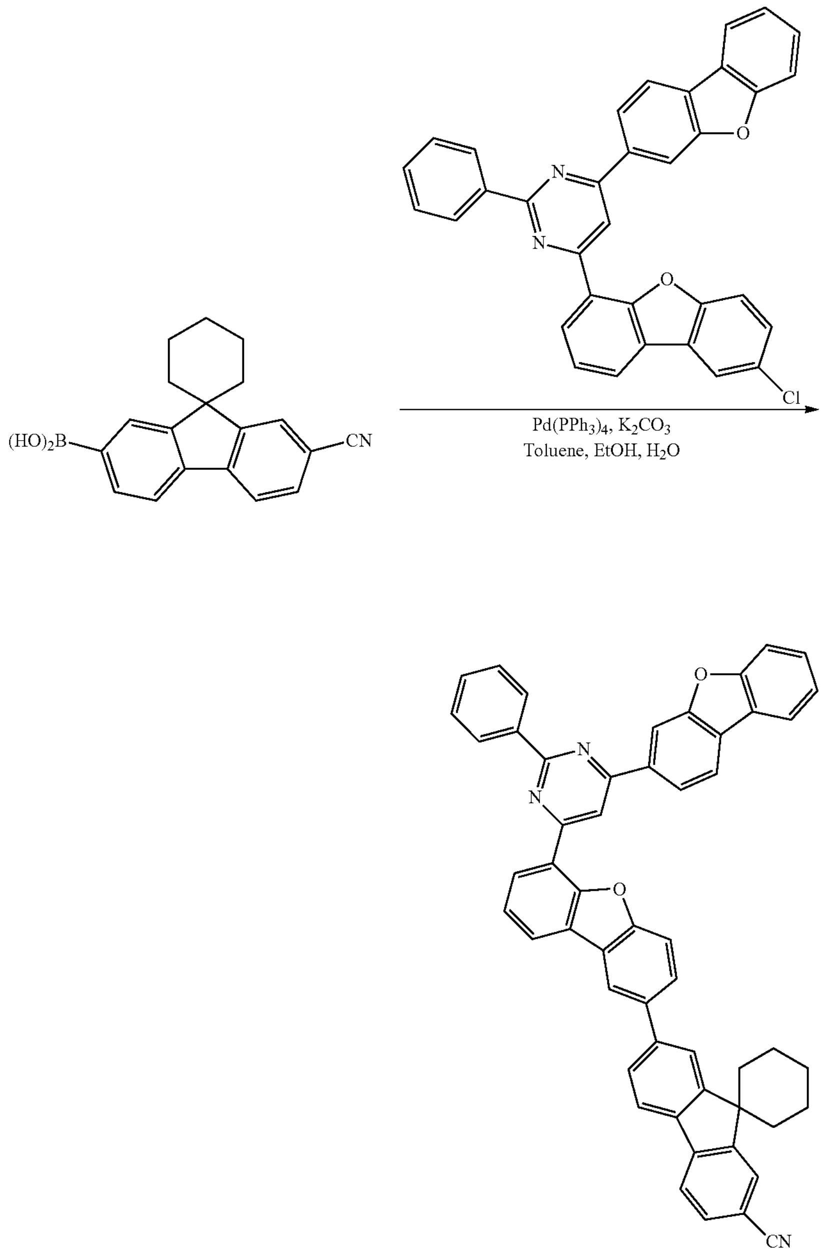

B-89

(2'-cyanospiro[cyclohexane-1,9'-fluoren]-7'-yl)boronic acid (10 g, 32.98 mmol), the target compound of Preparation Example 12 (17.25 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-89 (17.74 g, yield 72%) was obtained using column chromatography.

[LCMS]: 745

[Synthesis Example 29] Synthesis of Compound B-362

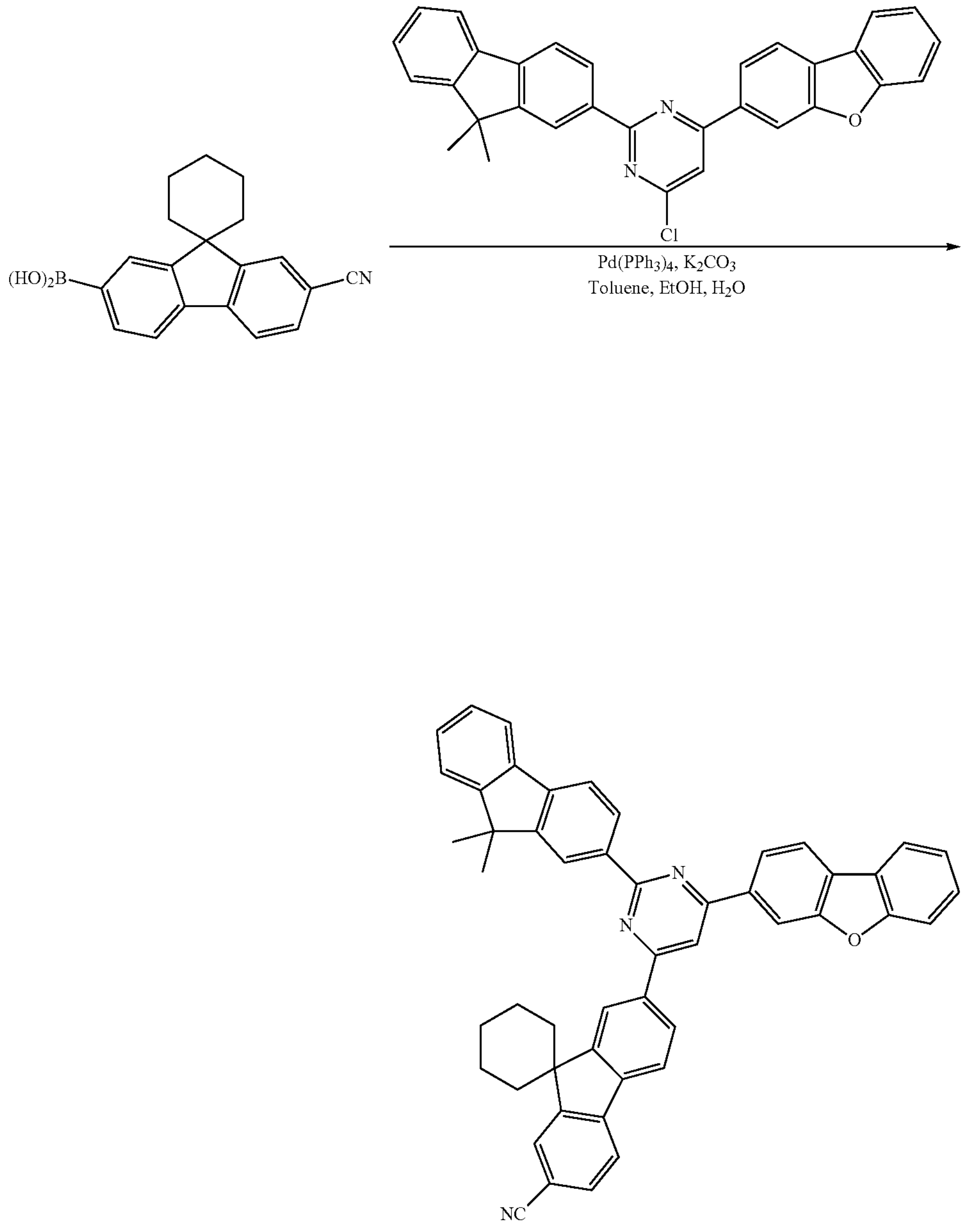

B-362

(2'-cyanospiro[cyclohexane-1,9'-fluoren]-7'-yl)boronic acid (10 g, 32.98 mmol), 4-chloro-6-(dibenzo[b,d]furan-3-yl)-2-(9,9-dimethyl-9H-fluoren-2-yl)pyrimidine (15.60 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-362 (22.39 g, yield 72%) was obtained using column chromatography.

[LCMS]: 695

[Synthesis Example 30] Synthesis of Compound B-363

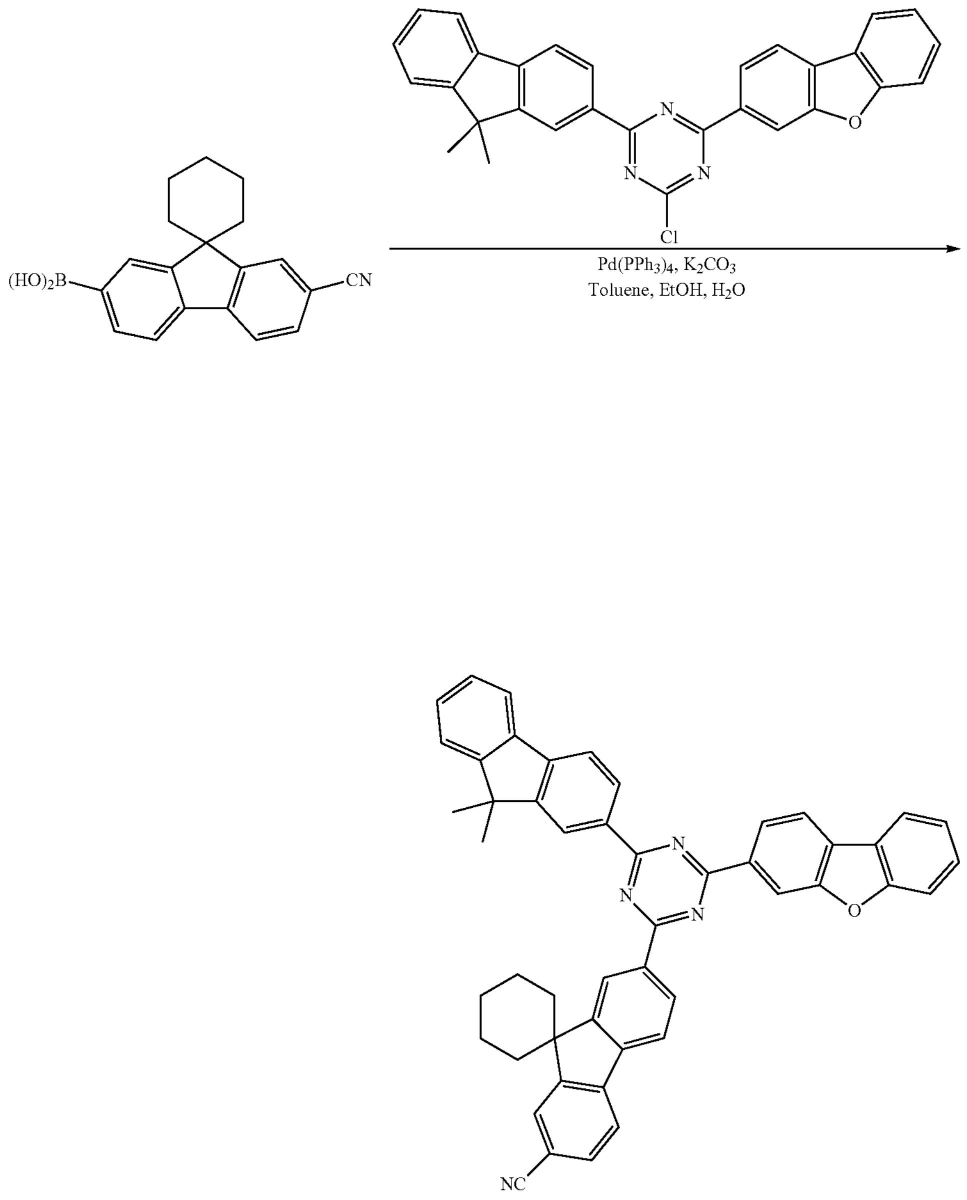

B-363

(2'-cyanospiro[cyclohexane-1,9'-fluoren]-7'-yl)boronic acid (10 g, 32.98 mmol), 2-chloro-4-(dibenzo[b,d]furan-3-yl)-6-(9,9-dimethyl-9H-fluoren-2-yl)-1,3,5-triazine (15.63 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-363 (16.55 g, yield 72%) was obtained using column chromatography.

[LCMS]: 696

[Synthesis Example 31] Synthesis of Compound B-365

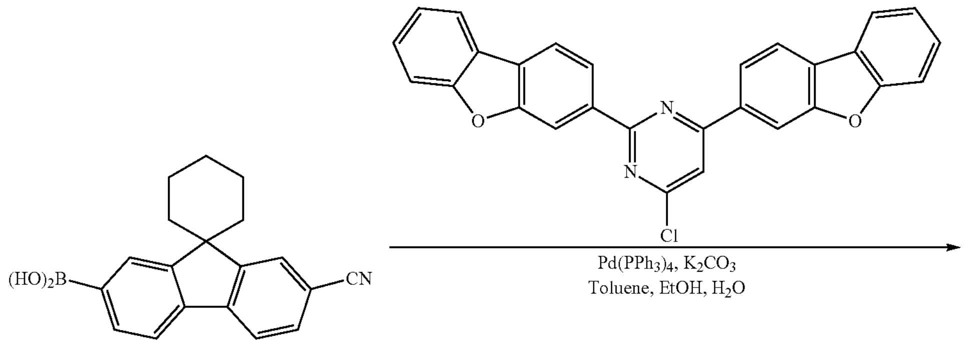

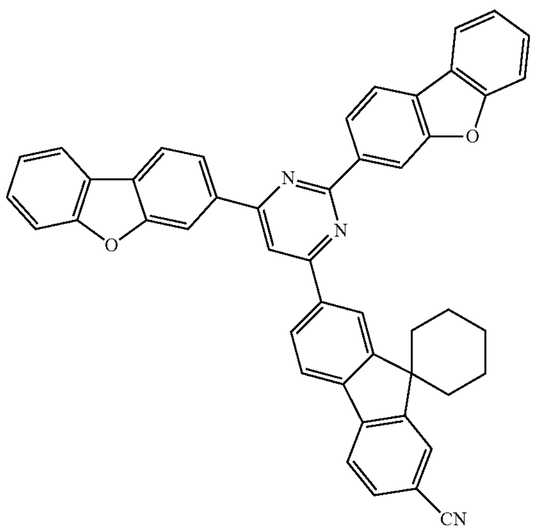

B-365

(2'-cyanospiro[cyclohexane-1,9'-fluoren]-7'-yl)boronic acid (10 g, 32.98 mmol), 4-chloro-2,6-bis(dibenzo[b,d]furan-3-yl)pyrimidine (14.74 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-365 (15.91 g, yield 72%) was obtained using column chromatography.

[LCMS]: 669

[Synthesis Example 32] Synthesis of Compound B-370

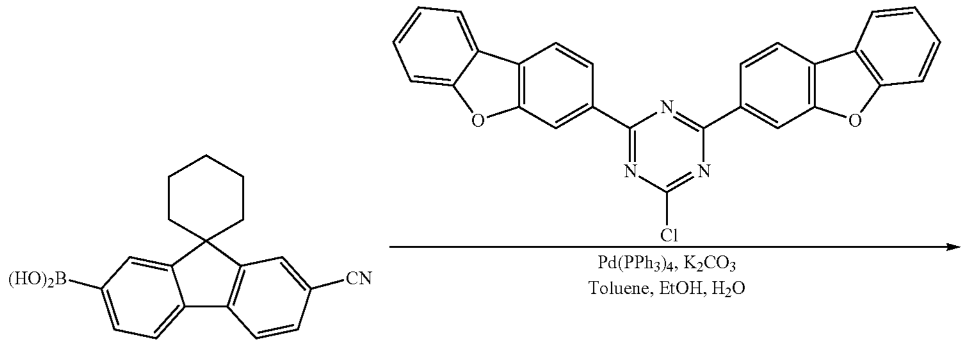

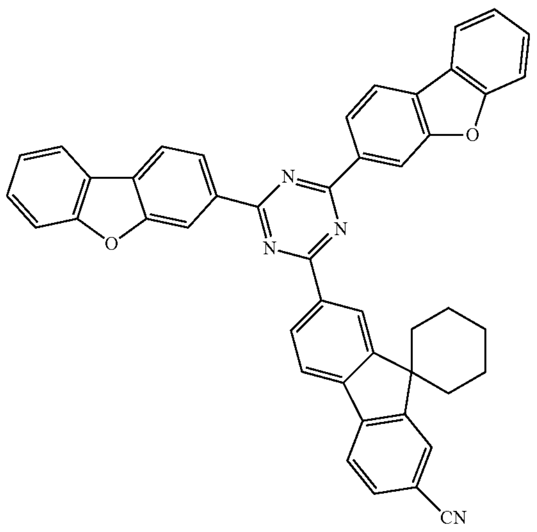

B-370

(2'-cyanospiro[cyclohexane-1,9'-fluoren]-7'-yl)boronic acid (10 g, 32.98 mmol), 2-chloro-4,6-bis(dibenzo[b,d]furan-3-yl)-1,3,5-triazine (14.77 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound B-370 (15.93 g, yield 72%) was obtained using column chromatography.

[LCMS]: 670

[Synthesis Example 33] Synthesis of Compound C-97

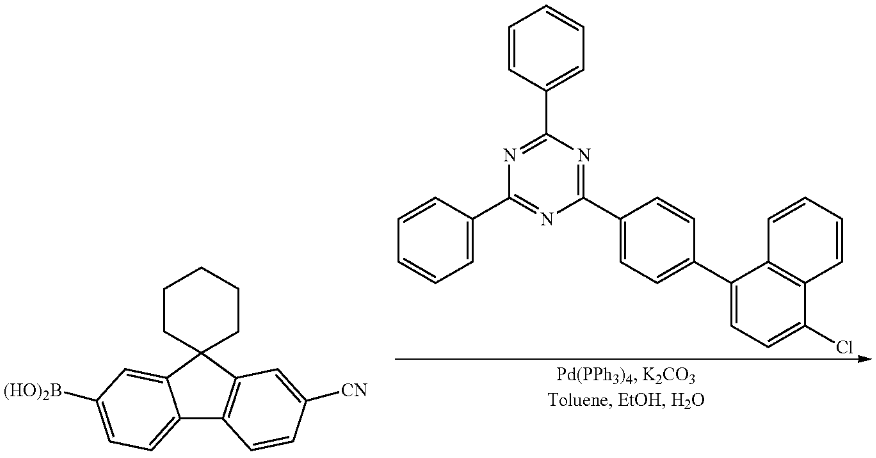

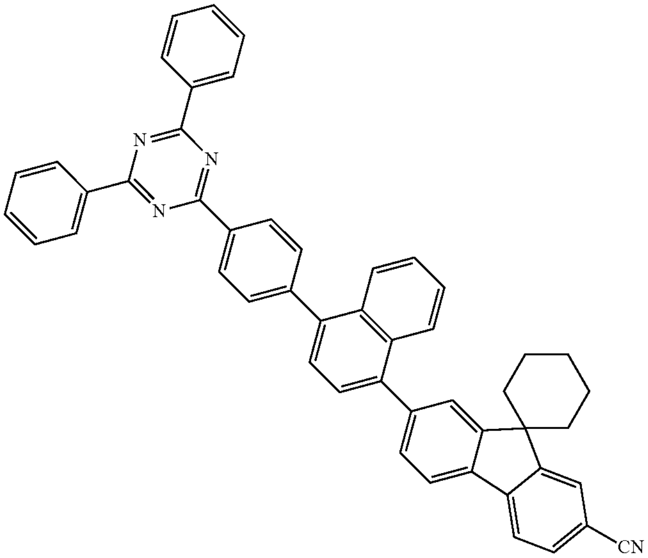

C-97

(2'-cyanospiro[cyclohexane-1,9'-fluoren]-7'-yl)boronic acid (10 g, 32.98 mmol), 2-(4-(4-chloronaphthalen-1-yl) phenyl)-4,6-diphenyl-1,3,5-triazine (15.50 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound C-97 (16.43 g, yield 72%) was obtained using column chromatography.

[LCMS]: 692

[Synthesis Example 34] Synthesis of Compound C-99

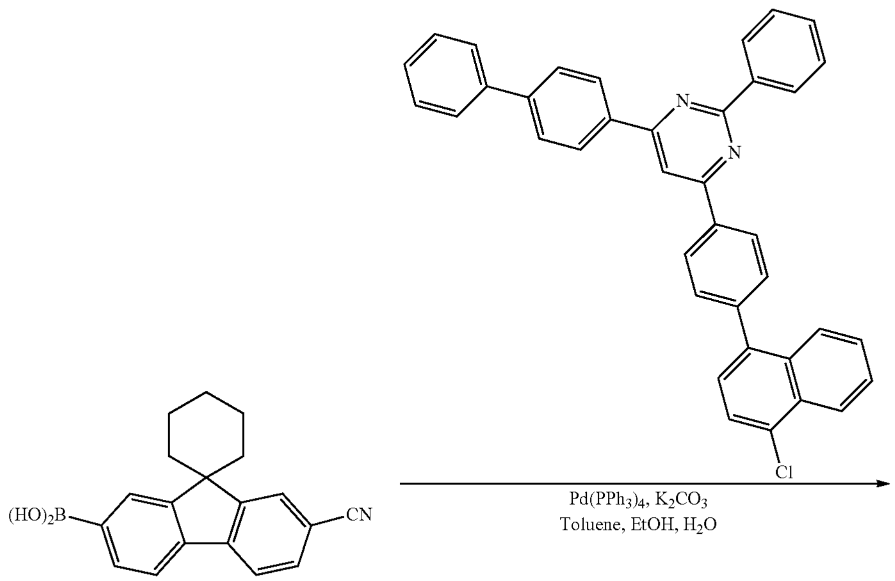

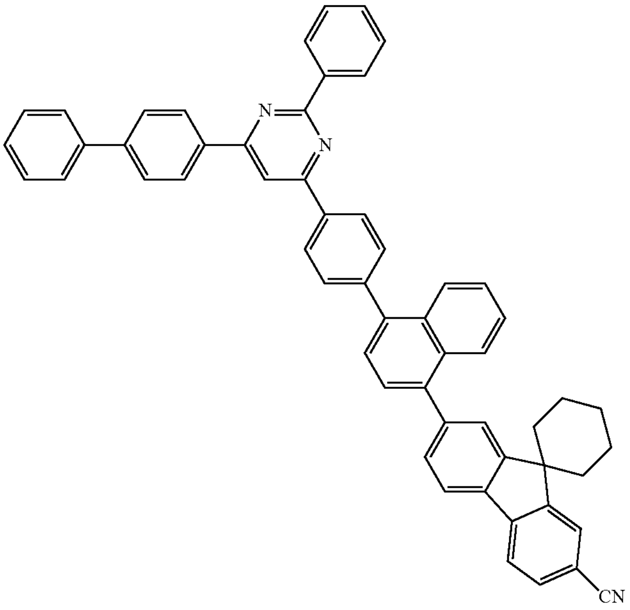

C-99

(2'-cyanospiro[cyclohexane-1,9'-fluoren]-7'-yl)boronic acid (10 g, 32.98 mmol), 4-([1,1'-biphenyl]-4-yl)-6-(4-(4-chloronaphthalen-1-yl)phenyl)-2-phenylpyrimidine (17.98 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound C-99 (18.24 g, yield 72%) was obtained using column chromatography.

[LCMS]: 767

[Synthesis Example 35] Synthesis of Compound C-101

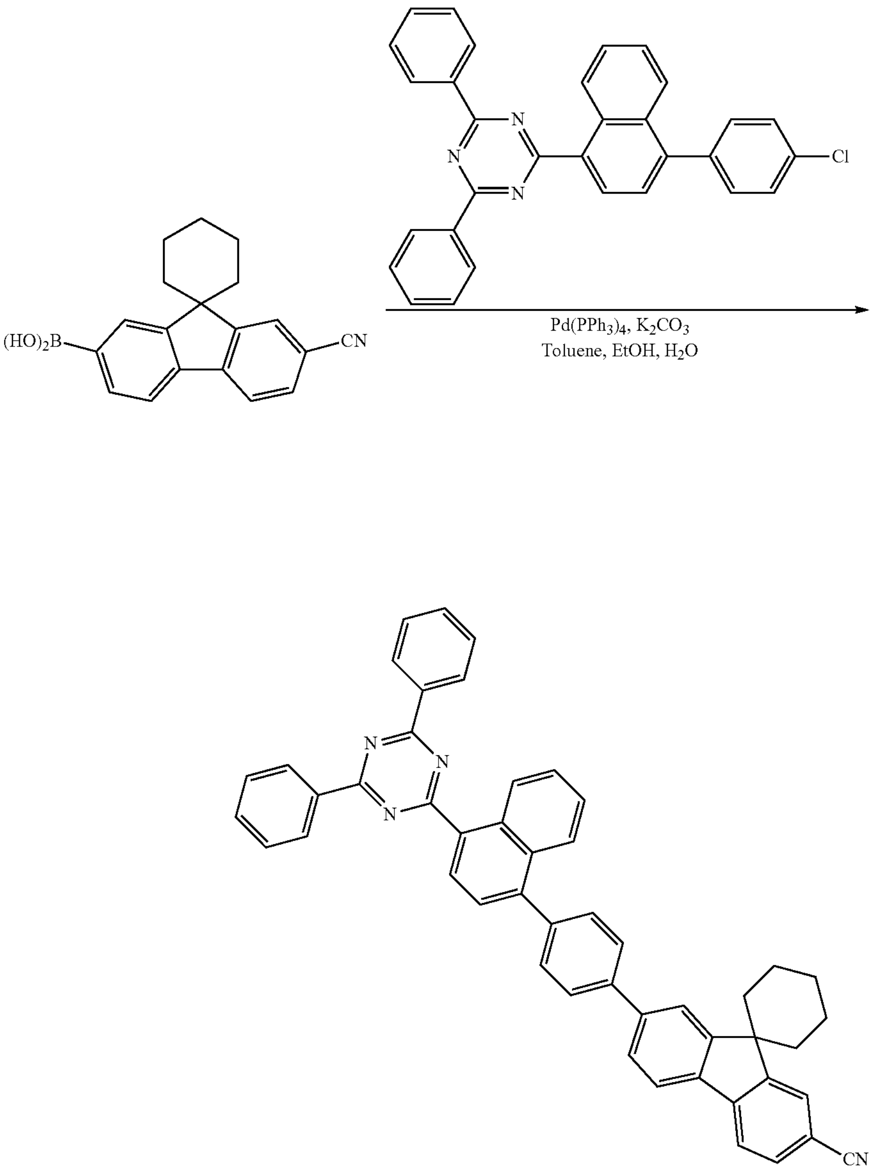

C-101

(2'-cyanospiro[cyclohexane-1,9'-fluoren]-7'-yl)boronic acid (10 g, 32.98 mmol), 2-(4-(4-chlorophenyl)naphthalen-1-yl)-4,6-diphenyl-1,3,5-triazine (15.5 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound C-101 (16.43 g, yield 72%) was obtained using column chromatography.

[LCMS]: 692

[Synthesis Example 36] Synthesis of Compound C-103

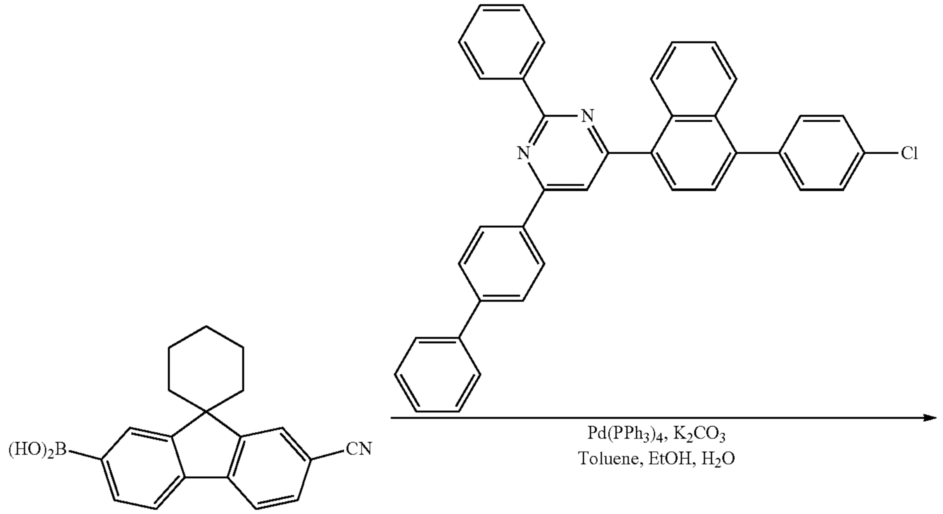

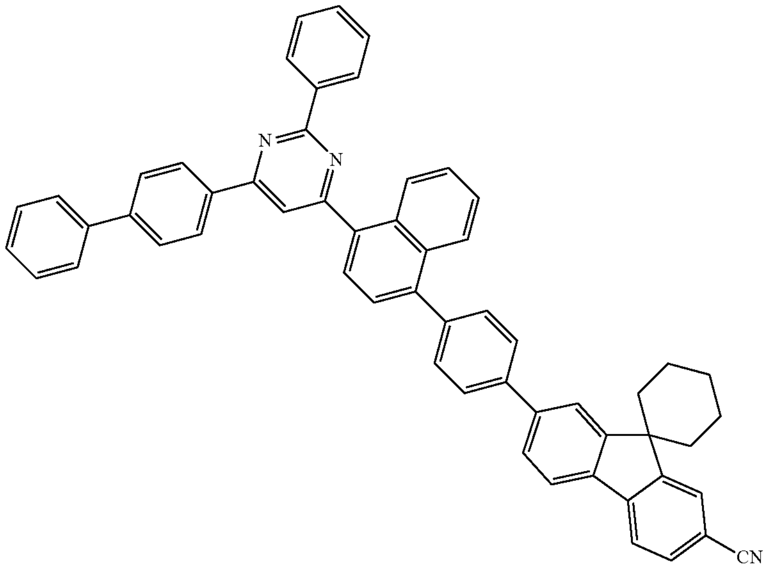

C-103

(2'-cyanospiro[cyclohexane-1,9'-fluoren]-7'-yl)boronic acid (10 g, 32.98 mmol), 4-([1,1'-biphenyl]-4-yl)-6-(4-(4-chlorophenyl)naphthalen-1-yl)-2-phenylpyrimidine (17.98 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound C-103 (18.24 g, yield 72%) was obtained using column chromatography.

[LCMS]: 767

[Synthesis Example 37] Synthesis of Compound C-117

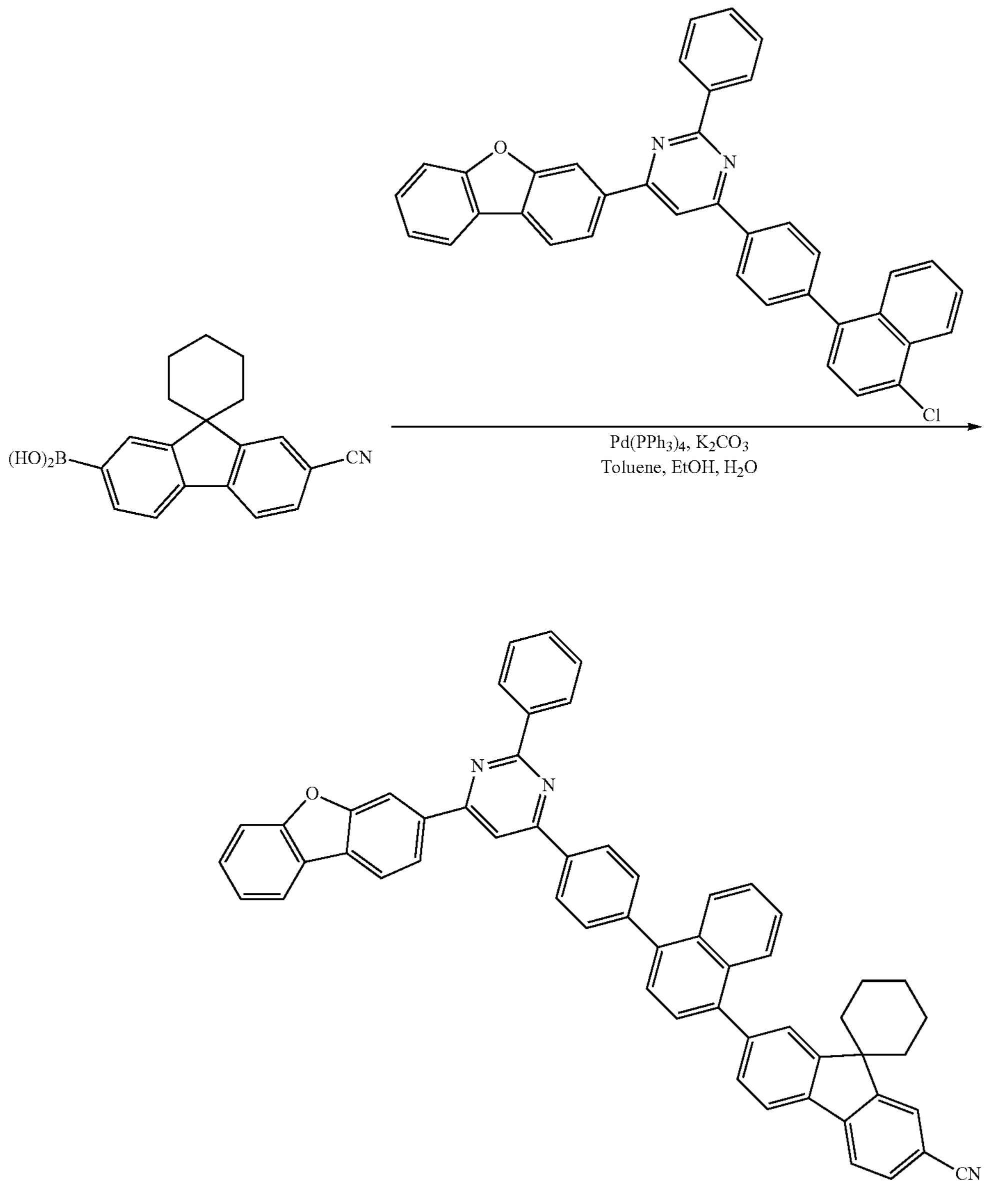

C-117

(2'-cyanospiro[cyclohexane-1,9'-fluoren]-7'-yl)boronic acid (10 g, 32.98 mmol), 4-(4-(4-chloronaphthalen-1-yl)phenyl)-6-(dibenzo[b,d]furan-3-yl)-2-phenylpyrimidine (18.44 g, 32.98 mmol), $Pd(PPh_3)_4$ (1.91 g, 1.65 mmol), and $K_2CO_3$ (13.68 g, 98.95 mmol) were added to 200 ml of toluene, 50 ml of EtOH, and 50 ml of $H_2O$, and the mixture was heated and refluxed for 12 hours. After completion of the reaction, extraction was performed with methylene chloride, $MgSO_4$ was added, and the mixture was filtered. After removing a solvent of the filtered organic layer, a target compound C-117 (18.57 g, yield 72%) was obtained using column chromatography.

[LCMS]: 781

[Embodiments 1 to 6] Preparation of Green Organic EL Device

Compounds A-1, A-5, A-17, B-2, B-17, and B-35 synthesized in Synthesis Examples were subjected to high-purity sublimation purification in a conventionally known method, and then green organic EL devices were prepared as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone, methanol, and the like, dried, transferred to a UV OZONE cleaner (Power sonic 405, Hwasin Tech), then cleaned using UV for 5 minutes, and then transferred to a vacuum evaporator.

On the ITO transparent electrode prepared as above, m-MTDATA (60 nm)/TCTA (80 nm)/respective compounds of A-1, A-5, A-17, B-2, B-17, B-35+10% $Ir(ppy)_3$ (30 nm)/BCP (10 nm)/$Alq_3$ (30 nm)/LiF (1 nm)/Al (200 nm) were stacked in the order, and thus organic EL devices were prepared.

The structures of m-MTDATA, TCTA, $Ir(ppy)_3$, CBP, BCP, and compounds A to D as used herein are each as follows.

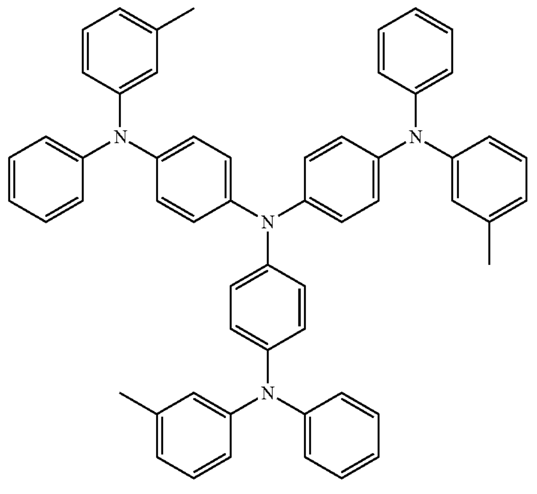

m-MTDATA

-continued

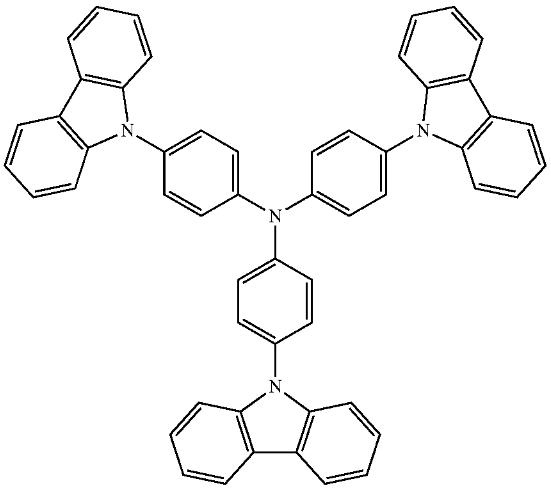

TCTA

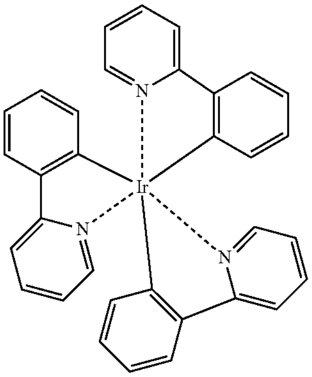

$Ir(ppy)_3$

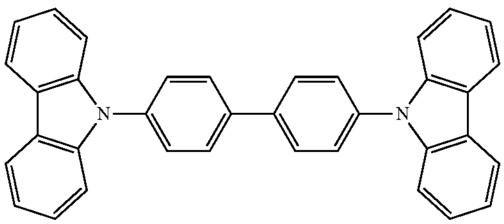

CBP

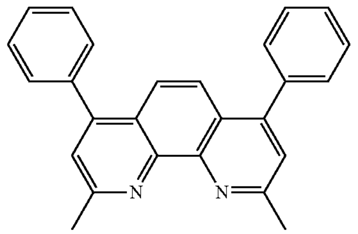

BCP

-continued

A

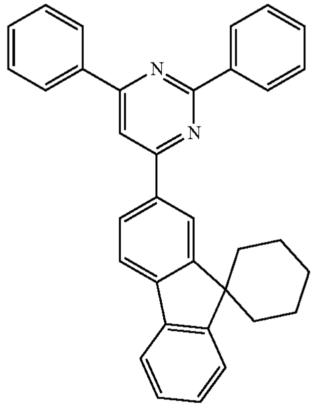

B

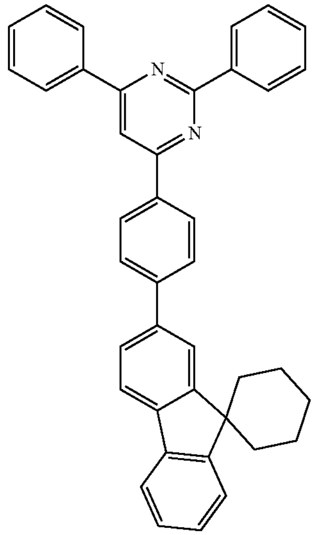

C

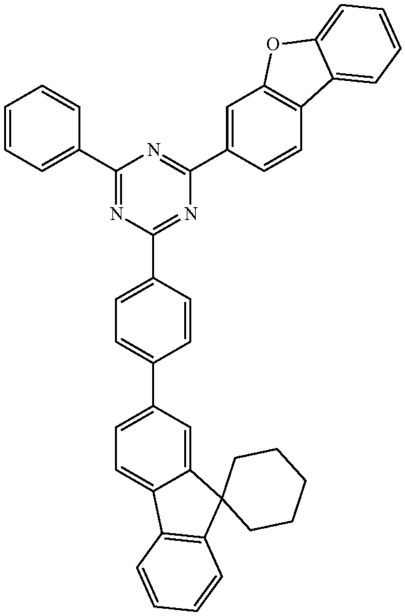

-continued

D

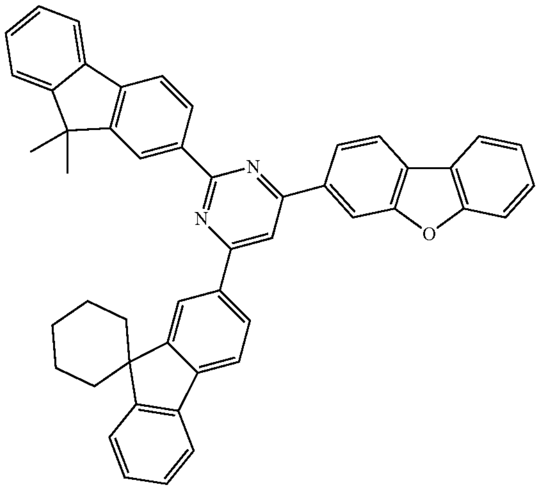

[Comparative Example 1] Preparation of Green Organic EL Device

A green organic EL device of Comparative Example 1 was prepared in the same manner as in Embodiment 1, except that CBP was used instead of Compound A-1 as a light-emitting host material in forming of the light-emitting layer.

[Comparative Example 2] Preparation of Green Organic EL Device

A green organic EL device of Comparative Example 2 was prepared in the same manner as in Embodiment 1, except that Compound A was used instead of Compound A-1 as a light-emitting host material in forming of the light-emitting layer.

[Comparative Example 3] Preparation of Green Organic EL Device

A green organic EL device of Comparative Example 3 was prepared in the same manner as in Embodiment 1, except that Compound B was used instead of Compound A-1 as a light-emitting host material in forming of the light-emitting layer.

[Comparative Example 4] Preparation of Green Organic EL Device

A green organic EL device of Comparative Example 4 was prepared in the same manner as in Embodiment 1, except that Compound C was used instead of Compound A-1 as a light-emitting host material in forming of the light-emitting layer.

[Comparative Example 5] Preparation of Green Organic EL Device

A green organic EL device of Comparative Example 5 was prepared in the same manner as in Embodiment 1, except that Compound D was used instead of Compound A-1 as a light-emitting host material in forming of the light-emitting layer.

Evaluation Example 1

For each of the green organic EL devices prepared in Embodiments 1 to 6 and Comparative Examples 1 to 5, a driving voltage, a current efficiency and an emission peak (e.g., electroluminescence peak (EL peak)) at a current density of mA/cm 2 were measured and the results are shown in Table 1 below.

TABLE 1

| Sample | Host | Driving voltage (V) | EL Peak (nm) | Current efficiency (cd/A) |
|---|---|---|---|---|
| Embodiment 1 | A-1 | 5.43 | 515 | 44.2 |
| Embodiment 2 | A-5 | 5.53 | 516 | 42.3 |
| Embodiment 3 | A-17 | 5.44 | 518 | 49.2 |
| Embodiment 4 | B-2 | 5.53 | 517 | 44.8 |
| Embodiment 5 | B-17 | 5.34 | 516 | 45.2 |
| Embodiment 6 | B-35 | 5.69 | 516 | 43.6 |
| Comp. Ex. 1 | CBP | 6.52 | 516 | 38.2 |
| Comp. Ex. 2 | A | 6.53 | 517 | 37.2 |
| Comp. Ex. 3 | B | 6.51 | 516 | 36.3 |
| Comp. Ex. 4 | C | 6.55 | 515 | 38.2 |
| Comp. Ex. 5 | D | 6.47 | 514 | 37.9 |

As shown in Table 1, it was appreciated that the green organic EL devices of Embodiments 1 to 6 in which Compounds A-1, A-5, A-17, B-2, B-17, and B-35 of the present invention were used in the light-emitting layer exhibited more excellent performance in terms of the device efficiency and the driving voltage, as compared to the green organic EL device of Comparative Example 1 in which conventional CBP was used and as compared to the green organic EL devices of Comparative Examples 2 to 5 in which Compounds A to D which do not include a cyano group were used.

[Embodiments 7 to 21] Preparation of Blue Organic EL Devices

Compounds A-3 to A-57, B-50 to B-370, and C-97 to C-117 synthesized in Synthesis Examples were subjected to high-purity sublimation purification in a conventionally known method, and then blue organic EL devices were prepared as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech) cleaned for 5 minutes using UV, and then transferred to a vacuum evaporator.

On the ITO transparent electrode prepared as above, DS-205 (Doosan Electronics Co., Ltd., 80 nm)/NPB (15 nm)/ADN+5% DS-405 (Doosan Electronics Co., Ltd., 30 nm)/respective Compounds A-3 to A-57, B-50 to B-370, and C-97 to C-117 (30 nm)/LiF (1 nm)/Al (200 nm) were stacked in the order, and thus organic EL devices were prepared.

[Comparative Example 6] Preparation of Blue Organic EL Device

A blue organic EL device according to Comparative Example 6 was prepared in the same manner as in Embodiment 7, except that $Alq_3$ was used instead of Compound A-3 as an electron transport layer material.

[Comparative Example 7] Preparation of Blue Organic EL Device

A blue organic EL device according to Comparative Example 7 was prepared in the same manner as in Embodiment 7, except that Compound A was used instead of Compound A-3 as an electron transport layer material.

[Comparative Example 8] Preparation of Blue Organic EL Device

A blue organic EL device according to Comparative Example 8 was prepared in the same manner as in Embodiment 7, except that Compound B was used instead of Compound A-3 as an electron transport layer material.

[Comparative Example 9] Preparation of Blue Organic EL Device

A blue organic EL device according to Comparative Example 9 was prepared in the same manner as in Embodiment 7, except that Compound C was used instead of Compound A-3 as an electron transport layer material.

[Comparative Example 10] Preparation of Blue Organic EL Device

A blue organic EL device according to Comparative Example 10 was prepared in the same manner as in Embodiment 7, except that Compound D was used instead of Compound A-3 as an electron transport layer material.

[Comparative Example 11] Preparation of Blue Organic EL Device

A blue organic EL device according to Comparative Example 11 was prepared in the same manner as in Embodiment 7, except that Compound A-3 was not used as an electron transport layer material.

For example, structures of NPB, ADN, $Alq_3$, Compounds A to D used in Embodiments 7 to 21 and Comparative Examples 6 to 11 are as follows.

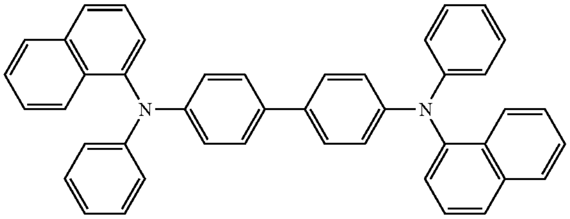

NPB

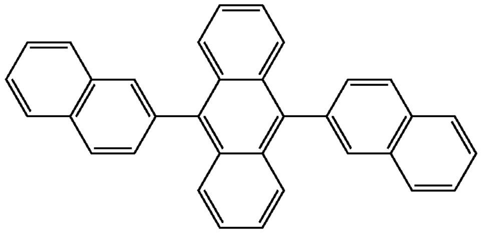

ADN

-continued

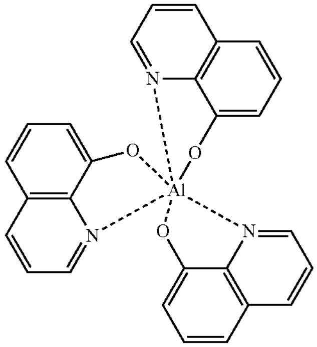

Alq3

A

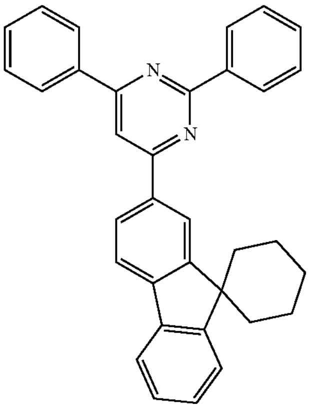

B

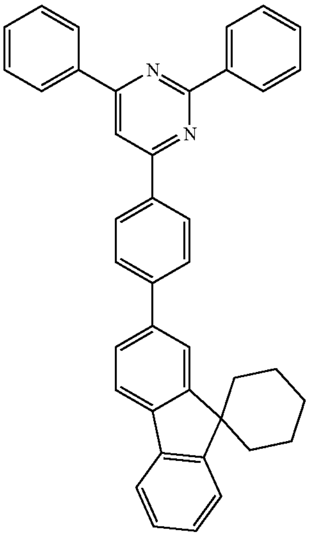

-continued

C

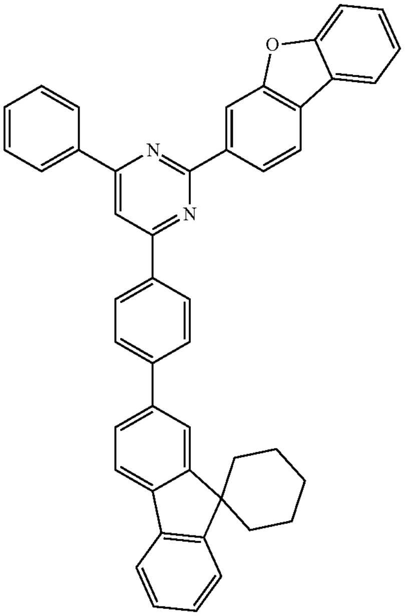

D

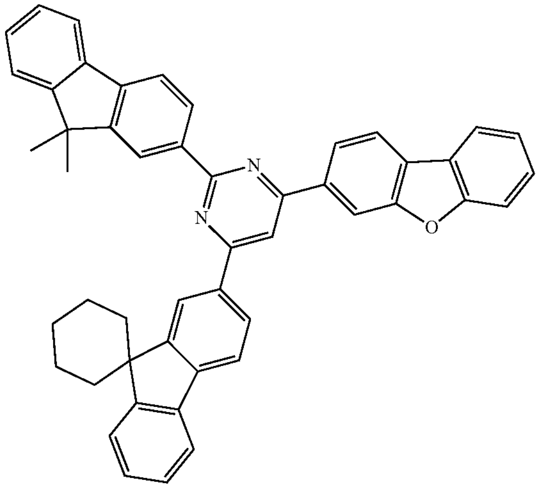

Evaluation Example 2

For each of the blue organic EL devices prepared in Embodiments 7 to 21 and Comparative Examples 6 to 11, a driving voltage, a current efficiency and an EL peak at a current density of 10 mA/cm 2 were measured and the results are shown in Table 2 below.

TABLE 2

| Sample | Electron transport layer material | Driving voltage (V) | EL peak (nm) | Current efficiency (cd/A) |
|---|---|---|---|---|
| Embodiment 7 | A-3 | 3.6 | 456 | 6.6 |
| Embodiment 8 | A-44 | 3.7 | 456 | 6.5 |
| Embodiment 9 | A-57 | 3.7 | 458 | 6.6 |

TABLE 2-continued

| Sample | Electron transport layer material | Driving voltage (V) | EL peak (nm) | Current efficiency (cd/A) |
|---|---|---|---|---|
| Embodiment 10 | B-50 | 4.1 | 453 | 6.5 |
| Embodiment 11 | B-67 | 3.8 | 456 | 6.8 |
| Embodiment 12 | B-82 | 4.0 | 457 | 6.6 |
| Embodiment 13 | B-362 | 3.6 | 455 | 6.6 |
| Embodiment 14 | B-363 | 3.8 | 457 | 6.6 |
| Embodiment 15 | B-365 | 4.0 | 452 | 6.4 |
| Embodiment 16 | B-370 | 3.7 | 456 | 6.8 |
| Embodiment 17 | C-97 | 3.7 | 456 | 6.7 |
| Embodiment 18 | C-99 | 3.9 | 456 | 6.6 |
| Embodiment 19 | C-101 | 3.8 | 456 | 6.5 |
| Embodiment 20 | C-103 | 3.7 | 458 | 6.5 |
| Embodiment 21 | C-117 | 4.0 | 452 | 6.4 |
| Comp. Ex. 6 | $Alq_3$ | 4.7 | 459 | 5.6 |
| Comp. Ex. 7 | A | 4.8 | 458 | 5.4 |
| Comp. Ex. 8 | B | 4.7 | 459 | 5.5 |
| Comp. Ex. 9 | C | 4.9 | 458 | 5.6 |
| Comp. Ex. 10 | D | 4.8 | 457 | 5.5 |
| Comp. Ex. 11 | — | 4.8 | 460 | 6.2 |

As shown in Table 2, it was appreciated that the blue organic EL devices of Embodiments 7 to 21 in which the compounds of the present invention were used as the electron transport layer material exhibited excellent performance in terms of the driving voltage, the EL peak and the current efficiency of the device, as compared to the blue organic EL device of Comparative Example 6 in which conventional $Alq_3$ was used as an electron transport layer material; the blue organic EL devices of Comparative Examples 7 to 10 in which Compounds A to D were used as electron transport layer materials, respectively; and the blue organic EL device of Comparative Example 11 in which the electron transport layer is not included.

[Embodiments 22 to 37] Preparation of Blue Organic EL Devices

Compounds A-2 to A-51, and B-1 to B-89 synthesized in Synthesis Examples were subjected to high-purity sublimation purification in a conventionally known method, and then blue organic EL devices were prepared as follows.

First, a glass substrate thin-film-coated with indium tin oxide (ITO) to a thickness of 1500 Å was washed with distilled water ultrasonically. After washing with distilled water was completed, the glass substrate was ultrasonically cleaned with a solvent, such as isopropyl alcohol, acetone and methanol, dried, transferred to a UV OZONE cleaner (Power sonic 405, Hwasin Tech) cleaned for 5 minutes using UV, and then transferred to a vacuum evaporator.

On the ITO transparent electrode prepared as above, DS-205 (Doosan Electronics Co., Ltd., 80 nm)/NPB (15 nm)/ADN+5% DS-405 (Doosan Electronics Co., Ltd., 30 nm)/respective Compounds A-2 to A-51 and B-1 to B-89 (5 nm)/$Alq_3$ (25 nm)/LiF (1 nm)/Al (200 nm) were stacked in the order, and thus organic EL devices were prepared.

In such a case, structures of NPB, ADN, $Alq_3$, Compounds A to D used are as follows.

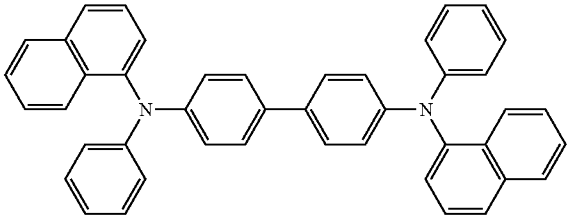

NPB

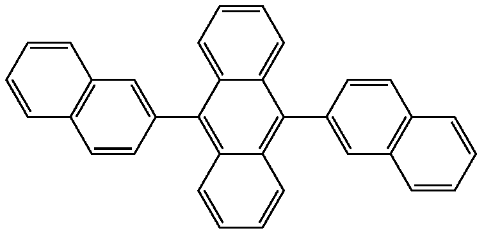

ADN

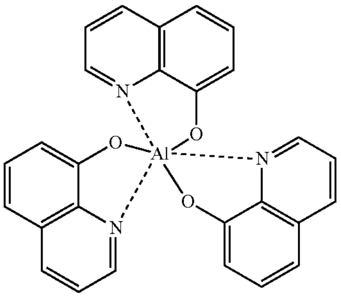

Alq3

A

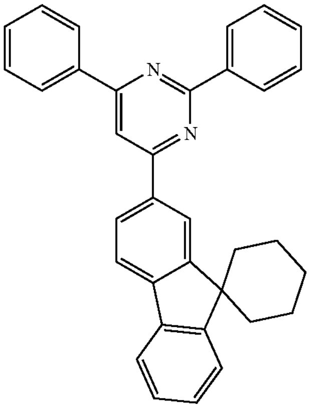

-continued

B

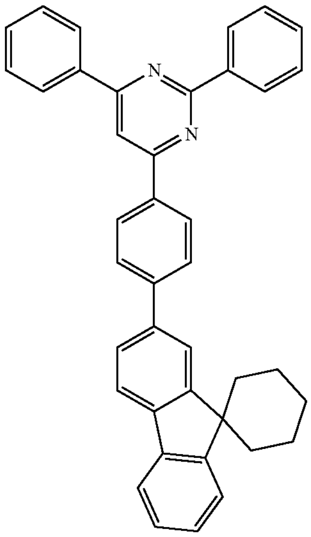

C

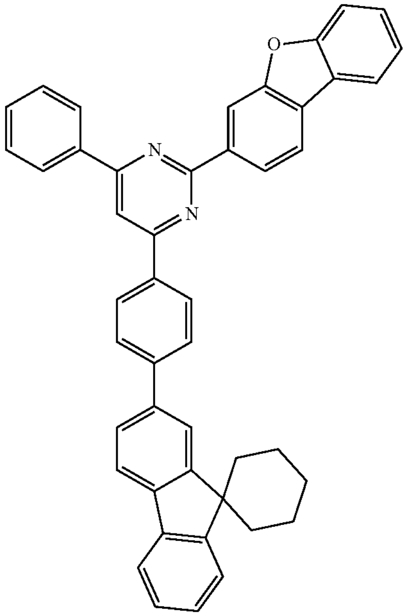

-continued

D

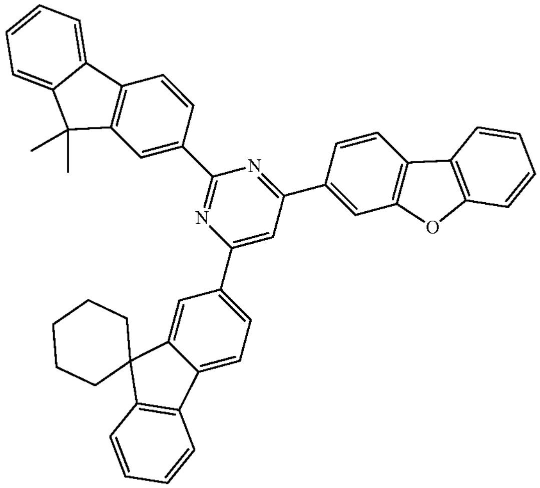

[Comparative Example 12] Preparation of Blue Organic EL Device

A blue organic EL device according to Comparative Example 12 was prepared in the same manner as in Embodiment 22, except that Compound A-2 which was used as an electron transport auxiliary layer material in Embodiment 22 was not used, and $Alq_3$, which is an electron transport layer material, was deposited to 30 nm instead of 25 nm.

[Comparative Example 13] Preparation of Blue Organic EL Device

A blue organic EL device according to Comparative Example 13 was prepared in the same manner as in Embodiment 22, except that Compound A was used instead of Compound A-2 which was used as an electron transport auxiliary layer material in Embodiment 22.

[Comparative Example 14] Preparation of Blue Organic EL Device

A blue organic EL device according to Comparative Example 14 was prepared in the same manner as in Embodiment 22, except that Compound B was used instead of Compound A-2 which was used as an electron transport auxiliary layer material in Embodiment 22.

[Comparative Example 15] Preparation of Blue Organic EL Device

A blue organic EL device according to Comparative Example 15 was prepared in the same manner as in Embodiment 22, except that Compound C was used instead of Compound A-2 which was used as an electron transport auxiliary layer material in Embodiment 22.

[Comparative Example 16] Preparation of Blue Organic EL Device

A blue organic EL device according to Comparative Example 16 was prepared in the same manner as in Embodiment 22, except that Compound D was used instead of Compound A-2 which was used as an electron transport auxiliary layer material in Embodiment 22.

Evaluation Example 3

For each of the blue organic EL devices prepared in Embodiments 22 to 37 and Comparative Examples 12 to 16, a driving voltage, an emission wavelength, and a current efficiency at a current density of 10 mA/cm 2 were measured and the results are shown in Table 3 below.

TABLE 3

| Sample | Electron transport auxiliary layer | Driving voltage (V) | EL peak (nm) | Current efficiency (cd/A) |
|---|---|---|---|---|
| Embodiment 22 | A-2 | 3.5 | 450 | 8.5 |
| Embodiment 23 | A-18 | 3.6 | 450 | 8.8 |
| Embodiment 24 | A-19 | 3.2 | 452 | 8.6 |
| Embodiment 25 | A-22 | 3.8 | 451 | 9.0 |
| Embodiment 26 | A-33 | 3.6 | 450 | 9.2 |
| Embodiment 27 | A-35 | 4.0 | 450 | 8.5 |
| Embodiment 28 | A-46 | 3.8 | 452 | 8.3 |
| Embodiment 29 | A-51 | 3.3 | 452 | 8.6 |
| Embodiment 30 | B-1 | 3.8 | 451 | 9.0 |
| Embodiment 31 | B-18 | 3.6 | 450 | 9.2 |
| Embodiment 32 | B-33 | 4.0 | 450 | 8.5 |
| Embodiment 33 | B-34 | 3.8 | 452 | 8.4 |
| Embodiment 34 | B-49 | 3.5 | 450 | 8.6 |
| Embodiment 35 | B-83 | 3.5 | 450 | 8.8 |
| Embodiment 36 | B-88 | 3.3 | 452 | 8.6 |
| Embodiment 37 | B-89 | 3.4 | 452 | 8.9 |
| Comp. Ex. 12 | — | 4.8 | 457 | 5.8 |
| Comp. Ex. 13 | A | 4.7 | 456 | 6.0 |
| Comp. Ex. 14 | B | 4.8 | 455 | 5.9 |
| Comp. Ex. 15 | C | 4.9 | 454 | 5.8 |
| Comp. Ex. 16 | D | 4.6 | 455 | 5.9 |

As shown in Table 3, it was appreciated that the blue organic EL devices of Embodiments 22 to 37 in which the compounds of the present invention were used as the electron transport auxiliary layer material exhibited excellent performance in terms of the current efficiency and the driving voltage of the device, as compared to the blue organic EL device of Comparative Example 12 in which an electron transport layer including $Alq_3$ was included and an electron transport auxiliary layer is not included; and the blue organic EL devices of Comparative Examples 13 to 16 in which Compounds A to D which do not include a cyano group were used as the electron transport auxiliary layer material, respectively.

What is claimed is:

1. A compound represented by the following Chemical Formula 1:

[Chemical Formula 1]

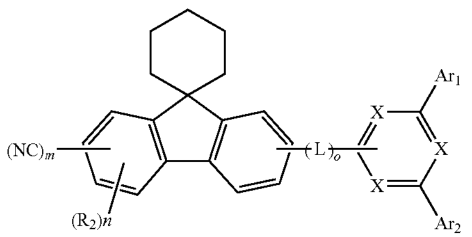

wherein in Chemical Formula 1, a plurality of X are the same as or different from each other, each independently being $C(R_1)$ or N, wherein at least two of the plurality of X are N, $R_1$ and $R_2$ are the same as or different from each other, each independently being selected from: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ monoarylphosphinyl group, a $C_6$ to $C_{60}$ diarylphosphinyl group, a $C_6$ to $C_{60}$ arylamine group, a $C_5$ to $C_{60}$ arylheteroarylamine group, and a heteroarylamine group having 5 to 60 nuclear atoms, m is an integer in a range from 0 to 2, n is an integer in a range from 0 to 4, L is a single bond, or is selected from: a $C_6$ to $C_{18}$ arylene group and a heteroarylene group having 5 to 18 nuclear atoms, o is an integer in a range from 0 to 3, $Ar_1$ and $Ar_2$ are the same as or different from each other, each independently being selected from: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphinyl group, a $C_6$ to $C_{60}$ monoarylphosphinyl group, a $C_6$ to $C_{60}$ diarylphosphinyl group, a $C_6$ to $C_{60}$ arylamine group, a $C_5$ to $C_{60}$ arylheteroarylamine group, and a heteroarylamine group having 5 to 60 nuclear atoms, and the arylene group and the heteroarylene group of L; the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $Ar_1$ to $Ar_2$ and $R_1$ to $R_2$ are each independently substituted or unsubstituted with one or more substituents of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, a $C_6$ to $C_{60}$ arylamine group, a $C_5$ to $C_{60}$ arylheteroarylamine group, and a heteroarylamine group having 5 to 60 nuclear atoms, and when the substituents are plural in number, the substituents are the same as or different from each other, and m is 1 or more; or at least one of the substituent of $Ar_1$ and the substituent of $Ar_2$ is a cyano group.

2. The compound of claim 1, wherein m is 0 or 1, and $R_2$ is selected from: hydrogen, a $C_6$ to $C_{60}$ aryl group, and a heteroaryl group having 5 to 60 nuclear atoms.

3. The compound of claim 1, wherein L is a single bond, or a moiety represented by any one of the following Chemical Formulas 2 and 3:

[Chemical Formula 2]

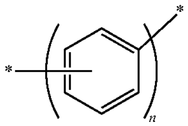

[Chemical Formula 3]

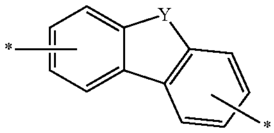

wherein in Chemical Formula 2 or 3,

* represents a site where a bond is made with Chemical Formula 1,

Y is selected from: $C(R_3)_2$, $NR_3$, O, S and Se, $R_3$ are the same as or different from each other, each independently being selected from: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphinyl group, a $C_6$ to $C_{60}$ monoarylphosphinyl group, a $C_6$ to $C_{60}$ diarylphosphinyl group, a $C_6$ to $C_{60}$ arylamine group, a $C_5$ to $C_{60}$ arylheteroarylamine group, and a heteroarylamine group having 5 to 60 nuclear atoms, and n is an integer in a range from 1 to 3.

4. The compound of claim 1, wherein L is a $C_6$ to $C_{18}$ arylene group selected from the group consisting of linkers represented by the following structural formulas:

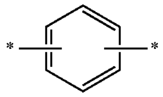
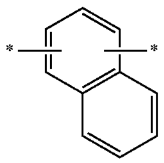
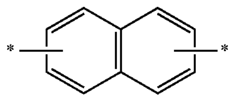
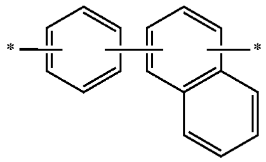
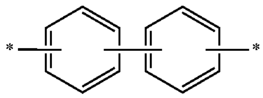
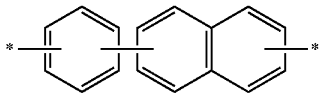
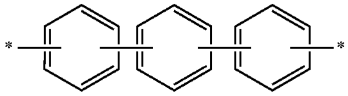
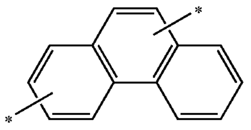
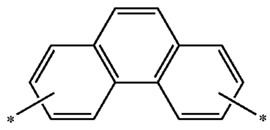
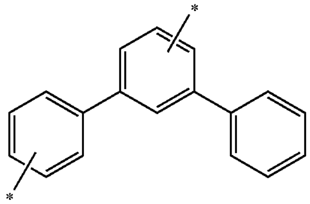
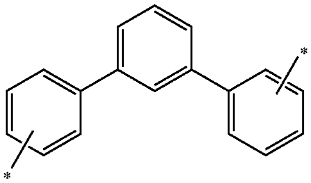
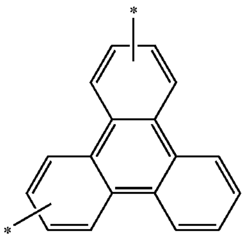

wherein in the above structural formulas, * represents a site where a bond is made with Chemical Formula 1.

5. The compound of claim 1, wherein L is a heteroarylene group having 5 to 18 nuclear atoms selected from the group consisting of linkers represented by the following structural formulas:

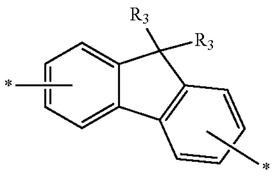
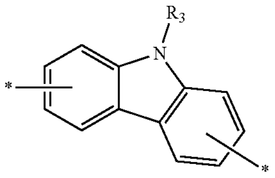

-continued

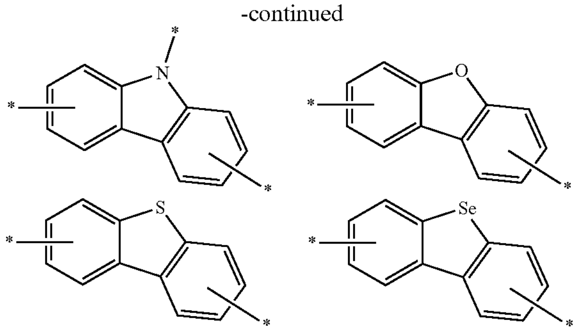

wherein in the above structural formulas, * represents a site where a bond is made with Chemical Formula 1, and $R_3$ are the same as or different from each other, each independently being selected from: hydrogen, a $C_1$ to $C_{40}$ alkyl group, a $C_6$ to $C_{60}$ aryl group, a heteroaryl group having 5 to 60 nuclear atoms.

6. The compound of claim 1, wherein

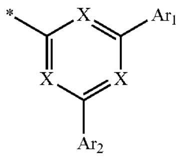

is selected from substituents represented by the following Chemical Formulas A-1 to A-3:

A-1

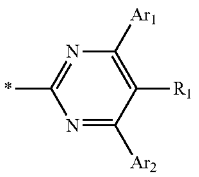

A-2

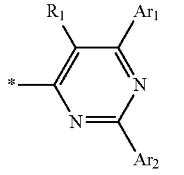

A-3

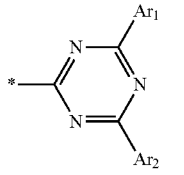

wherein in the above Chemical Formulas A-1 to A-3, $R_1$, $Ar_1$, and $Ar_2$ are each as defined in claim 1.

7. The compound of claim 1, wherein $Ar_1$ and $Ar_2$ are the same as or different from each other, each independently being selected from: a $C_6$ to $C_{60}$ aryl group and a heteroaryl group having 5 to 60 nuclear atoms, and the aryl group and the heteroaryl group of $Ar_1$ and $Ar_2$ are each independently substituted or unsubstituted with one or more substituents of: hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, a $C_6$ to $C_{60}$ arylamine group, a $C_5$ to $C_{60}$ arylheteroarylamine group, and a heteroarylamine group having 5 to 60 nuclear atoms, and when the substituents are plural in number, the substituents are the same as or different from each other.

8. The compound of claim 1, wherein at least one of $Ar_1$ and $Ar_2$ is a $C_6$ to $C_{18}$ aryl group, and the aryl group is substituted with a nitrogen-containing heteroaromatic ring containing at least one nitrogen.

9. The compound of claim 1, wherein the compound represented by Chemical Formula 1 is represented by any one of the following Chemical Formulas 4 to 7:

[Chemical Formula 4]

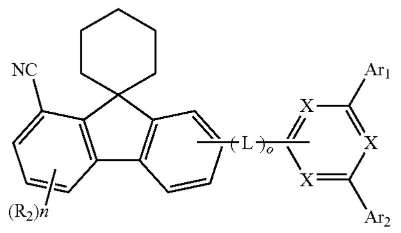

[Chemical Formula 5]

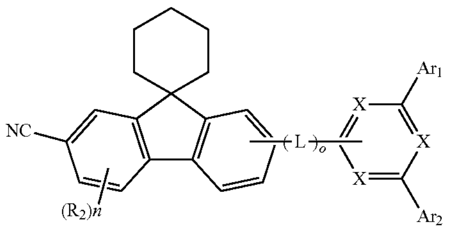

[Chemical Formula 6]

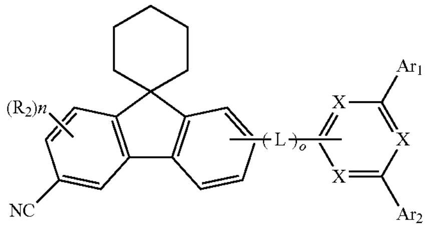

-continued

[Chemical Formula 7]

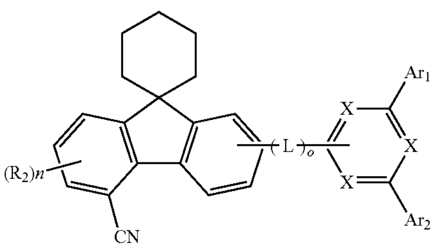

in Chemical Formulas 4 to 7,

X, L, $Ar_1$, $Ar_2$, $R_2$, n and o are each as defined in claim 1.

10. The compound of claim 1, wherein the compound represented by Chemical Formula 1 is represented by any one of the following Chemical Formulas 8 to 11:

[Chemical Formula 8]

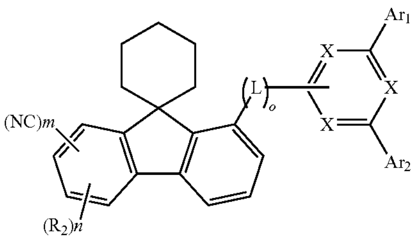

[Chemical Formula 9]

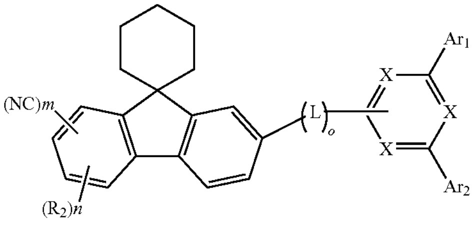

[Chemical Formula 10]

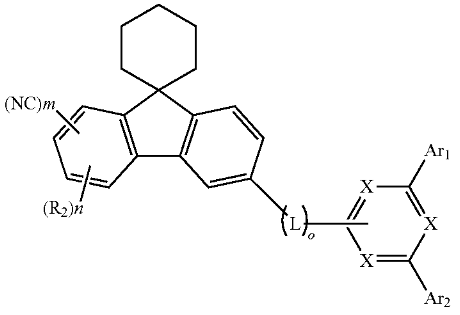

-continued

[Chemical Formula 11]

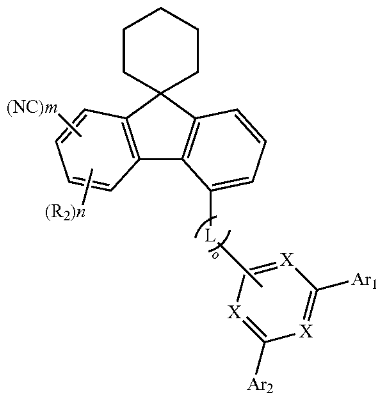

wherein in Chemical Formulas 8 to 11,

X, L, $Ar_1$, $Ar_2$, $R_2$, m, n and o are each as defined in claim 1.

11. The compound of claim 1, wherein the compound represented by Chemical Formula 1 is represented by any one of the following Chemical Formulas 12 to 15:

[Chemical Formula 12]

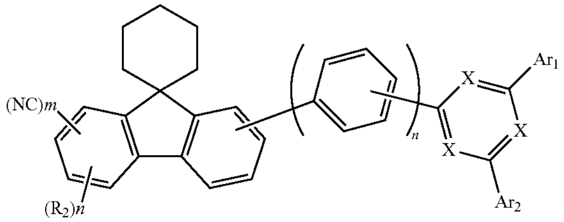

[Chemical Formula 13]

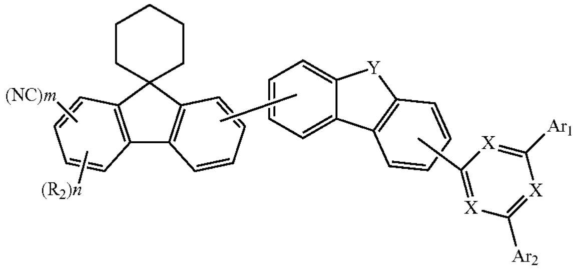

[Chemical Formula 14]

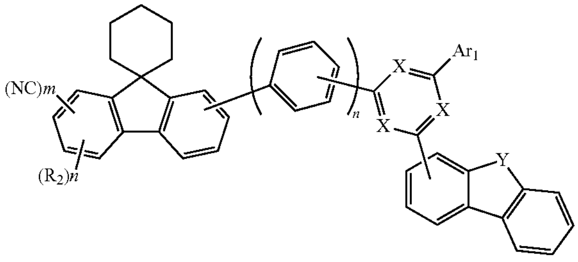

-continued

[Chemical Formula 15]

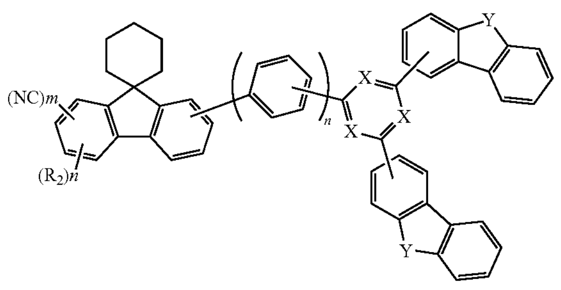

wherein in Chemical Formulas 12 to 15,

X, $Ar_1$, $Ar_2$, $R_2$, m, and n are each as defined in claim 1,

Y is selected from: $C(R_3)_2$, $NR_3$, O, S, and Se, and $R_3$ are the same as or different from each other, each independently being selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphinyl group, a $C_6$ to $C_{60}$ monoarylphosphinyl group, a $C_6$ to $C_{60}$ diarylphosphinyl group, a $C_6$ to $C_{60}$ arylamine group, a $C_5$ to $C_{60}$ arylheteroarylamine group, and a heteroarylamine group having 5 to 60 nuclear atoms.

12. The compound of claim 1, wherein the compound represented by Chemical Formula 1 (m≥1) is represented by any one of the following Chemical Formulas 12A to 15A:

[Chemical Formula 12A]

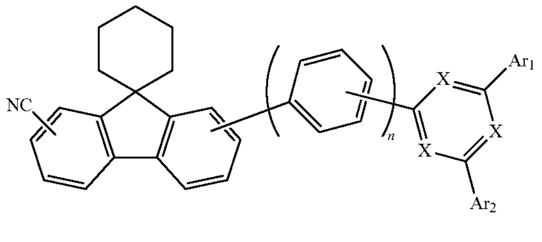

[Chemical Formula 13A]

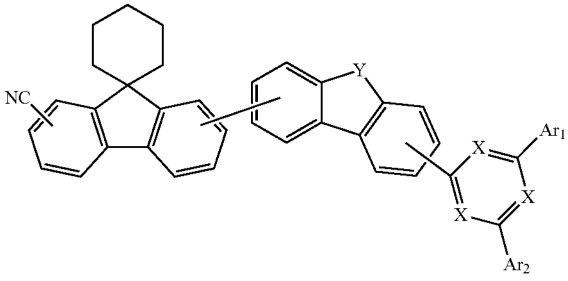

-continued

[Chemical Formula 14A]

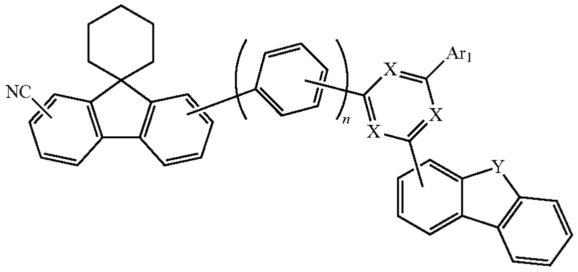

[Chemical Formula 15A]

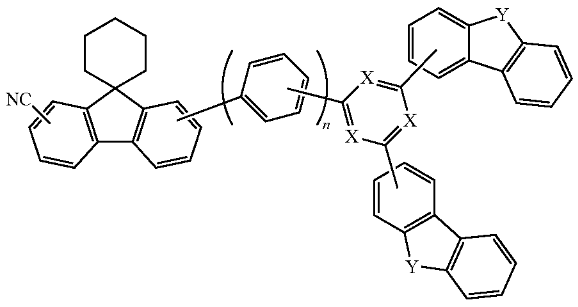

wherein in Chemical Formulas 12A to 15A,

X, $Ar_1$, $Ar_2$ and n are each as defined in claim 1, and

Y is selected from: $C(R_3)_2$, $NR_3$, O, S, and Se, and $R_3$ are the same as or different from each other, each independently being selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphinyl group, a $C_6$ to $C_{60}$ monoarylphosphinyl group, a $C_6$ to $C_{60}$ diarylphosphinyl group, a $C_6$ to $C_{60}$ arylamine group, a $C_5$ to $C_{60}$ arylheteroarylamine group, and a heteroarylamine group having 5 to 60 nuclear atoms.

13. The compound of claim 1, wherein the compound in which at least one of the substituent of $Ar_1$ and the substituent $Ar_2$ is a cyano group is represented by any one of the following Chemical Formulas 16 to 18:

[Chemical Formula 16]

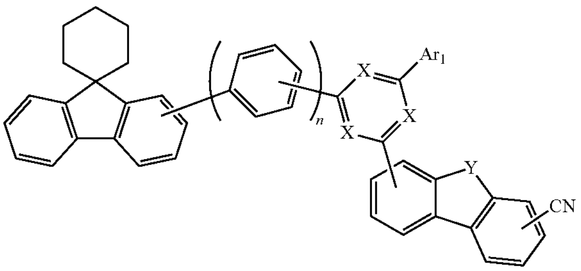

-continued

[Chemical Formula 17]

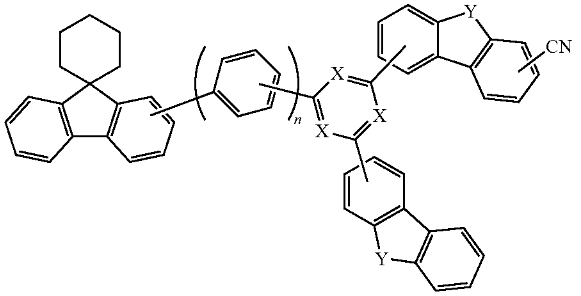

[Chemical Formula 18]

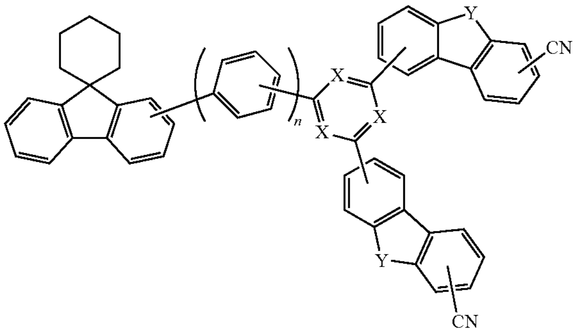

wherein in Chemical Formulas 16 to 18,

X, $Ar_1$ and n are each as defined in claim 1,

Y is selected from: $C(R_3)_2$, $NR_3$, O, S, and Se, and $R_3$ are the same as or different from each other, each independently being selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_3$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphinyl group, a $C_6$ to $C_{60}$ monoarylphosphinyl group, a $C_6$ to $C_{60}$ diarylphosphinyl group, a $C_6$ to $C_{60}$ arylamine group, a $C_5$ to $C_{60}$ arylheteroarylamine group, and a heteroarylamine group having 5 to 60 nuclear atoms.

14. The compound of claim 1, wherein the compound represented by Chemical Formula 1 is a material of a light-emitting layer, an electron transport layer, or an electron transport auxiliary layer.

15. An organic electroluminescent device comprising:

an anode;

a cathode; and one or more organic layers disposed between the anode and the cathode, wherein at least one of the one or more organic layers comprises the compound according to claim 1.

16. The organic electroluminescent device of claim 15, wherein the organic layer comprising the compound is selected from: a light-emitting layer, a light-emitting auxiliary layer, an electron transport layer, and an electron transport auxiliary layer.

17. The organic electroluminescent device of claim 16, wherein the light-emitting layer comprises a host and a dopant, and the host comprises the compound represented by Chemical Formula 1.

* * * * *